US012790612B2

(12) United States Patent
Gao et al.

(10) Patent No.: US 12,790,612 B2
(45) Date of Patent: Nov. 10, 2026

(54) DEAMINASE-BASED RNA SENSORS

(71) Applicant: The Board of Trustees of the Leland Stanford Junior University, Stanford, CA (US)

(72) Inventors: Xiaojing Gao, Stanford, CA (US); Kristjan Eerik Kaseniit, Stanford, CA (US); Noa Katz, Stanford, CA (US); Natalie S. Kolber, Stanford, CA (US); Eric Wolfsberg, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 56 days.

(21) Appl. No.: 18/814,161

(22) Filed: Aug. 23, 2024

(65) Prior Publication Data

US 2025/0019706 A1 Jan. 16, 2025

Related U.S. Application Data

(63) Continuation of application No. PCT/US2023/063245, filed on Feb. 24, 2023.

(60) Provisional application No. 63/313,423, filed on Feb. 24, 2022.

(51) Int. Cl.
*C12N 15/113* (2010.01)
*C12N 9/78* (2006.01)

(52) U.S. Cl.
CPC .............. *C12N 15/113* (2013.01); *C12N 9/78* (2013.01); *C12N 2310/531* (2013.01)

(58) Field of Classification Search
CPC .. C12N 15/113; C12N 9/78; C12N 2310/531; C12Q 2521/539; C12Q 2525/301; C12Q 1/6813; C12Q 2563/107; C12Q 2521/301; C12Y 305/04004
See application file for complete search history.

(56) References Cited

U.S. PATENT DOCUMENTS 4,797,368 A 1/1989 Carter et al.
5,139,941 A 8/1992 Muzyczka et al.
6,566,118 B1 5/2003 Atkinson et al.
6,596,535 B1 7/2003 Carter
6,989,264 B2 1/2006 Atkinson et al.
6,995,006 B2 2/2006 Atkinson et al.
10,988,763 B2 4/2021 Turunen et al.
11,274,300 B2 3/2022 Aalto et al.
11,479,575 B2 10/2022 Fraley et al.
11,649,454 B2 5/2023 Turunen et al.
2017/0191057 A1 7/2017 Jamieson et al.
2019/0032141 A1 1/2019 Weiss et al.
2019/0218552 A1 7/2019 Turunen et al.
2020/0263180 A1 8/2020 Mali et al.
2021/0009972 A1 1/2021 Zhang et al.
2021/0079393 A1 3/2021 Boudet et al.
2021/0238597 A1 8/2021 Turunen et al.
2021/0355494 A1 11/2021 Wei et al.
2022/0010333 A1 1/2022 Mali et al.
2022/0098587 A1 3/2022 Yuan et al.
2022/0307020 A1 9/2022 Yuan et al.
2023/0123513 A1 4/2023 Jiang et al.
2023/0183689 A1 6/2023 Bose
2023/0242906 A1 8/2023 Levanon et al.
2023/0399635 A1 12/2023 Savva et al.

FOREIGN PATENT DOCUMENTS

CA 3127243 A1 * 7/2020 ........... C12N 15/113
EP 0488528 A1 6/1992
WO WO1991018088 A1 11/1991
WO WO1993009239 A1 5/1993
WO WO-9411523 A2 * 5/1994 ............ C12N 15/65
WO WO1999011764 A2 3/1999
WO WO1999041258 A1 8/1999
WO WO2006073496 A2 7/2006

(Continued)

OTHER PUBLICATIONS

Kaseniit et al. “Modular and programmable RNA sensing using ADAR editing in living cells” Nat. Biotech. (2022) 41: 482-487 . (bioRxiv preprint doi: https://doi.org/10.1101/2022.01.28.478207; this version posted Jan. 29, 2022 (Year: 2022).*
Zhao et al. “RNA-responsive elements for eukaryotic translational control” Nat. Biotech. (2022) 40: 539-545 (Year: 2022).*
Daniel at al. “RNA editing of non-coding RNA and its role in gene regulation” Biochimie (2015) 117 :22-27. (Year: 2015).*
Diaz de Arce et al. “Complete motif analysis of sequence requirements for translation initiation at non-AUG start codons” Nucleic Acids Research (2018) vol. 46, No. 2: 985-994. (Year: 2018).*
Garncarz et al (A high throughput screen to identify enhancers of ADAR-mediated RNA-editing; RNA Biology, 2013, 10(2):192-204; IDS received on Oct. 17, 2024; IDS Cite No. 13) (Year: 2013).*

(Continued)

*Primary Examiner* — Neil P Hammell
*Assistant Examiner* — Qiwen Su-Tobon
(74) *Attorney, Agent, or Firm* — Bret E. Field; Bozicevic, Field & Francis LLP

(57) ABSTRACT

RNA editing tools for use in systems designed to measure RNA in vivo and manipulate specific cell types are disclosed herein. An RNA sensor system comprising a) a single-stranded RNA (ssRNA) sensor comprising a stop codon and a payload; optionally wherein the ssRNA sensor further comprises a normalizing gene; and b) an adenosine deaminase acting on RNA (ADAR) deaminase; wherein the sensor is capable of binding to a ssRNA target to form a double-stranded RNA (dsRNA) duplex that becomes a substrate for the ADAR deaminase; wherein the substrate comprises a mispairing within the stop codon; and wherein the mispairing is editable by the ADAR deaminase, which editing can effectively remove the stop codon so as to enable translation and expression of the payload. A method of quantifying ribonucleic acid (RNA) levels using the RNA sensor system is also disclosed.

28 Claims, 44 Drawing Sheets

Specification includes a Sequence Listing.

(56) References Cited

FOREIGN PATENT DOCUMENTS

| | | | | | |
|---|---|---|---|---|---|
| WO | WO2015022335 | A1 | | 2/2015 | |
| WO | WO2019070704 | A1 | | 4/2019 | |
| WO | WO-2019071048 | A1 | * | 4/2019 | ........... C12N 15/102 |
| WO | WO2022003684 | A1 | | 1/2022 | |
| WO | WO2022007803 | A1 | | 1/2022 | |
| WO | WO2022091100 | A1 | | 5/2022 | |
| WO | WO2022103852 | A1 | | 5/2022 | |
| WO | WO2022140264 | A1 | | 6/2022 | |
| WO | WO2022248879 | A1 | | 12/2022 | |
| WO | WO-2022266117 | A2 | * | 12/2022 | ........... C12N 15/635 |
| WO | WO2023020574 | A1 | | 2/2023 | |
| WO | WO2023077135 | A1 | | 5/2023 | |
| WO | WO2023077138 | A1 | | 5/2023 | |
| WO | WO2023164630 | A1 | | 8/2023 | |

OTHER PUBLICATIONS

Bantel-Schaal et al., Human Adeno-Associated Virus Type 5 Is Only Distantly Related to Other Known Primate Helper-Dependent Parvoviruses, J. Viral., 73(2): 939-947 (1999).
Biswas et al., MS2-TRIBE Evaluates Both Protein-RNA Interactions and Nuclear Organization of Transcription by RNA Editing, iScience, 23(7): 101318 (Jul. 24, 2020).
Bitter et al., Expression and secretion vectors for yeast, Methods Enzymol, 153:516-44 (1987).
Chen et al., Vancomycin analogues active against vanA-resistant strains inhibit bacterial transglycosylase without binding substrate, PNAS, 100(10):5658-5663 (Apr. 24, 2003).
Cox et al., RNA Editing with CRISPR-Cas13, Science., 358(6366):1019-1027 (Nov. 24, 2017).
Dabrowski et al., Translational readthrough potential of natural termination codons in eucaryotes—The impact of RNA sequence, RNA Biol, 12(9):950-8 (2015).
Danan-Gotthold et al., Promoting RNA editing by ADAR attraction, Genome Biol., 18(1):196 (Oct. 23, 2017).
Dykstra et al., Engineering synthetic RNA devices for cell control, Nature Reviews Genetics, 23:215-228 (Apr. 2022).
Fukuda et al., Construction of a guide-RNA for site-directed RNA mutagenesis utilising intracellular A-to-I RNA editing, Scientific Reports vol. 7, Article No. 41478 (2017).
Gabay et al., Landscape of adenosine-to-inosine RNA recoding across human tissues, Nat Commun, 13(1):1184 (Mar. 4, 2022).
Gallo et al., ADAR RNA editing in human disease; more to it than meets the I, Hum Genet., 136(9):1265-1278 (Sep. 2017).
Gao et al., Driver Fusions and Their Implications in the Development and Treatment of Human Cancers, Cell Rep, 23(1):227-238.e3 (Apr. 3, 2018).
Garncarz et al., A high-throughput screen to identify enhancers of ADAR-mediated RNA-editing, RNA Biol, 10(2):192-204 (Feb. 2013).
Gatsiou et al., Adenosine-to-Inosine RNA Editing in Health and Disease, Antioxid Redox Signal, 29(9):846-863 (Sep. 20, 2018).
Goodman et al., ADAR proteins: structure and catalytic mechanism, Curr Top Microbiol Immunol, 353:1-33 (2012).
Groves et al., Computing in mammalian cells with nucleic acid strand exchange, Nat Nanotechnol, 11(3):287-294 (Mar. 2016).
Han et al., Programmable siRNA pro-drugs that activate RNAi activity in response to specific cellular RNA biomarkers, Mol Ther Nucleic Acids, 27:797-809 (Jan. 3, 2022).
Hochrein et al., High-Performance Allosteric Conditional Guide RNAs for Mammalian Cell-Selective Regulation of CRISPR/Cas, ACS Synthetic Biology, 10(5):964-971 (2021).
Hou et al., Lipid nanoparticles for mRNA delivery, Nature Reviews Materials, 6:1078-1094 (2021).
Hur, Double-Stranded RNA Sensors and Modulators in Innate Immunity, Annu Rev Immunol, 37:349-375 (Apr. 26, 2019).
Kaseniit et al., Modular, programmable RNA sensing using ADAR editing in living cells, Nature Biotechnology, 41:482-487 (2023).
Katrekar et al., Comprehensive interrogation of the ADAR2 deaminase domain for engineering enhanced RNA editing activity and specificity, eLife, 11:e75555 (Jan. 19, 2022).
Katrekar et al., In vivo RNA editing of point mutations via RNA-guided adenosine deaminases, Nat Methods, 16(3):239-242 (Mar. 2019).
Kotin et al., Site-specific integration by adeno-associated virus, Proc Natl Acad Sci U S A, 87(6):2211-5 (Mar. 1990).
Kulkarni et al., Beyond bulk: a review of single cell transcriptomics methodologies and applications, Curr Opin Biotechnol, 58:129-136 (Aug. 2019) .
Kuruma et al., The PURE system for the cell-free synthesis of membrane proteins, Nat Protoc, 10(9):1328-44 (Sep. 2015).
Kuttan et al., Mechanistic insights into editing-site specificity of ADARs, Proc Natl Acad Sci U S A, 109(48):E3295-304 (Nov. 27, 2012).
Labanieh et al., Programming CAR-T cells to kill cancer, Nature Biomedical Engineering, 2:377-391 (2018).
Lavickova et al., A Simple, Robust, and Low-Cost Method to Produce the PURE Cell-Free System, ACS Synth Biol, 8(2):455-462 (Feb. 15, 2019).
Lin et al., Building Endogenous Gene Connections through RNA Self-Assembly Controlled CRISPR/Cas9 Function, J Am Chem Soc, 143(47):19834-19843 (Dec. 1, 2021).
Loughran et al., Avoidance of reporter assay distortions from fused dual reporters, RNA N. Y. N 23, 1285-1289 (2017).
Luo et al., Genetic Dissection of Neural Circuits: A Decade of Progress, Neuron, 98(2):256-281 (Apr. 18, 2018).
Matthews et al., Structures of human ADAR2 bound to dsRNA reveal base-flipping mechanism and basis for site selectivity, Nat Struct Mol Biol, 23(5):426-33 (May 2016).
Merkle et al., Precise RNA editing by recruiting endogenous ADARs with antisense oligonucleotides, Nature Biotechnology, 37:133-138 (2019).
Qian et al., Programmable RNA sensing for cell monitoring and manipulation, Nature, 610:713-721 (Oct. 2022).
Qu et al., Programmable RNA editing by recruiting endogenous ADAR using engineered RNAs, Nature Biotechnology, 37:1059-1069 (2019).
Reautschnig et al., CLUSTER guide RNAs enable precise and efficient RNA editing with endogenous ADAR enzymes in vivo, Nat Biotechnol, 40(5):759-768 (May 2022).
Rodriguez et al., The growing and glowing toolbox of fluorescent and photoactive proteins, Trends Biochem Sci, 42(2): 111-129 (Feb. 2017).
Samulski et al., Targeted integration of adeno-associated virus (AAV) into human chromosome 19, EMBO J, 10(12):3941-50 (Dec. 1991).
Scholefield et al., Prime editing—an update on the field, Gene Ther, 28(7-8):396-401 (Aug. 2021).
Starostina et al., Construction and Immunogenicity of Modified mRNA-Vaccine Variants Encoding Influenza Virus Antigens, Vaccines (Basel), 9(5):452 (May 3, 2021).
Szymczak-Workman et al., Design and construction of 2A peptide-linked multicistronic vectors, Cold Spring Harb Protoc, 2012(2):199-204 (Feb. 1, 2012).
Uzonyi et al., Deciphering the principles of the RNA editing code via large-scale systematic probing, Mol Cell, 81(11):2374-2387 (Jun. 3, 2021).
Wang et al., Adenosine Deaminases That Act on RNA (ADARs), Enzymes, 41:215-268 (2017).
Waterman et al., Comparison of biosequences, Adv. Appl. Math., 2, 482-489 (1981).
Xie et al., Logic integration of mRNA signals by an RNAi-based molecular computer, Nucleic Acids Res, 38(8):2692-701 (May 2010).
Xie et al., Multi-input RNAi-based logic circuit for identification of specific cancer cells, Science, 333(6047):1307-11 (Sep. 2, 2011).
Yeh et al., ATP-independent bioluminescent reporter variants to improve in vivo imaging, ACS Chem Biol, 14(5):959-965 (May 17, 2019).

(56) References Cited

OTHER PUBLICATIONS

Ying et al., Activatable CRISPR Transcriptional Circuits Generate Functional RNA for mRNA Sensing and Silencing, Angew Chem Int Ed Engl, 59(42):18599-18604 (Oct. 12, 2020).
Yoshikawa et al., Mutant p53 R248Q but not R248W enhances in vitro invasiveness of human lung cancer NCI-H1299 cells, Biomed. Res. 31, 401-411 (2010).
Zhang et al., PowerBLAST: a new network BLAST application for interactive or automated sequence analysis and annotation, Genome Res, 7(6):649-56 (Jun. 1997).
Zhao et al., RNA-responsive elements for eukaryotic translational control, Nature Biotechnology 40(4):1-7 (Apr. 2022).
Gommans et al., A mammalian reporter system for fast and quantitative detection of intracellular A-to-I RNA editing levels, Anal Biochem. Apr. 15, 2010; 399(2): 230-236.

* cited by examiner

*Density contours shown for mCherry+ cells only (>1e5) Trend-lines show percentile-binned averages and are repeated in the last pane.*

Number of expanded sensor candidates (3' UTR, split 3' UTR, CDS, split CDS + 3' UTR) for mouse transcripts

(a) 0% Ψ

(b) 100% Ψ

(c) 25% Ψ

*Density contours shown for mCherry+ cells only (>1e5)*
*Trend-lines show percentile-binned averages and are repeated in the last pane.*

Example stem-loop variants

DEAMINASE-BASED RNA SENSORS

CROSS-REFERENCE TO RELATED APPLICATIONS

This application is a continuation of PCT Application No. PCT/US2023/063245 filed Feb. 24, 2023, which application claims priority pursuant to 35 U.S.C. § 119 (e) to the filing date of U.S. Provisional Application Ser. No. 63/313,423 filed Feb. 24, 2022, the disclosures of which applications are herein incorporated by reference.

GOVERNMENT RIGHTS

This invention was made with Government support under contract 1656518 awarded by the National Science Foundation and under contract EB027723 awarded by the National Institutes of Health. The Government has certain rights in the invention.

REFERENCE TO AN ELECTRONIC SEQUENCE LISTING

The contents of the electronic sequence listing (STAN-1939_S22-045_SEQ_LIST.xml; Size: 12,737 bytes; and Date of Creation: Aug. 12, 2024) is herein incorporated by reference in its entirety.

INTRODUCTION

Single-cell transcriptomics often serve as the de facto way to define cell types and states, but targeting cells based on their RNA profile has remained challenging. RNA sense-response systems would for example enable the identification and destruction of harmful cells (e.g., in the contexts of cancer and autoimmune disorders), or the experimental manipulation of specific cells in a complex environment (e.g., the nervous and the immune systems). Available RNA sensing technologies are limited to miRNAs, or require careful design around functional RNA structures such as ribozymes, guide RNAs or internal ribosome entry sites. For the latter, an additional confounding factor is the cell's natural response to double-stranded RNA (dsRNA). dsRNA editing by adenosine deaminases acting on RNA (ADARs) allows for the editing of specific RNAs.

Provided herein are methods and kits for detecting target RNAs and expressing proteins in target cells utilizing ADAR editing.

SUMMARY

The present disclosure provides a method for expressing a protein in a target cell, the method comprising combining the target cell with a sensor RNA comprising the following: (ia) a first nucleotide sequence comprising a sensor nucleotide sequence that is reverse complementary to the target RNA wherein the sensor nucleotide sequence comprises a stem-loop sequence comprising one or more editable codons, or (ib) a first nucleotide sequence comprising a sensor nucleotide sequence that is reverse complementary to the 3' UTR of the target RNA, wherein the sensor nucleotide sequence comprises one or more editable codons, and (ii) a second nucleotide sequence encoding a first cleavage domain, and (iii) a third nucleotide sequence encoding an output protein; wherein the target RNA is present in the target cell.

The present disclosure provides a method for detecting a target RNA, the method including (a) combining the biological sample with a sensor RNA including the following: (i) a first nucleotide sequence encoding a marker protein, (ii) a second nucleotide sequence including a sensor nucleotide sequence that is reverse complementary to the 3' UTR of the target RNA, wherein the sensor nucleotide sequence includes a stop codon, (iii) a third nucleotide sequence encoding a second cleavage domain, and (iv) a fourth nucleotide sequence encoding an output protein; (b) assaying for the presence of the output protein in the biological sample.

The present disclosure also provides method for detecting a target RNA in a biological sample, the method including: (a) combining the biological sample with a sensor RNA including the following: (i) a first nucleotide sequence including a stem-loop sequence including one or more stop codons, (ii) a second nucleotide sequence including a sensor nucleotide sequence that is reverse complementary to the target RNA, (iii) a third nucleotide sequence encoding a first cleavage domain, and (iv) a fourth nucleotide sequence encoding an output protein; and (b) assaying for the presence of the output protein in the biological sample.

The present disclosure provides a method for detecting a target RNA in a biological sample, the method comprising: (a) combining the biological sample with a sensor RNA comprising the following: (i) a first nucleotide sequence comprising a sensor nucleotide sequence that is reverse complementary to the target RNA, wherein the sensor nucleotide sequence comprises a start codon and (ii) a second nucleotide sequence encoding an output protein; and (b) assaying for the presence of the output protein in the biological sample.

The present disclosure provides a method for detecting a target RNA in a biological sample, the method comprising: (a) combining the biological sample with a sensor RNA comprising the following: (i) a first nucleotide sequence comprising a sensor nucleotide sequence that is reverse complementary to the target RNA, wherein the sensor nucleotide sequence comprises an AUA sequence and (ii) a second nucleotide sequence encoding an output protein; and (b) assaying for the presence of the output protein in the biological sample.

Kits for practicing the subject methods are also provided.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1A:
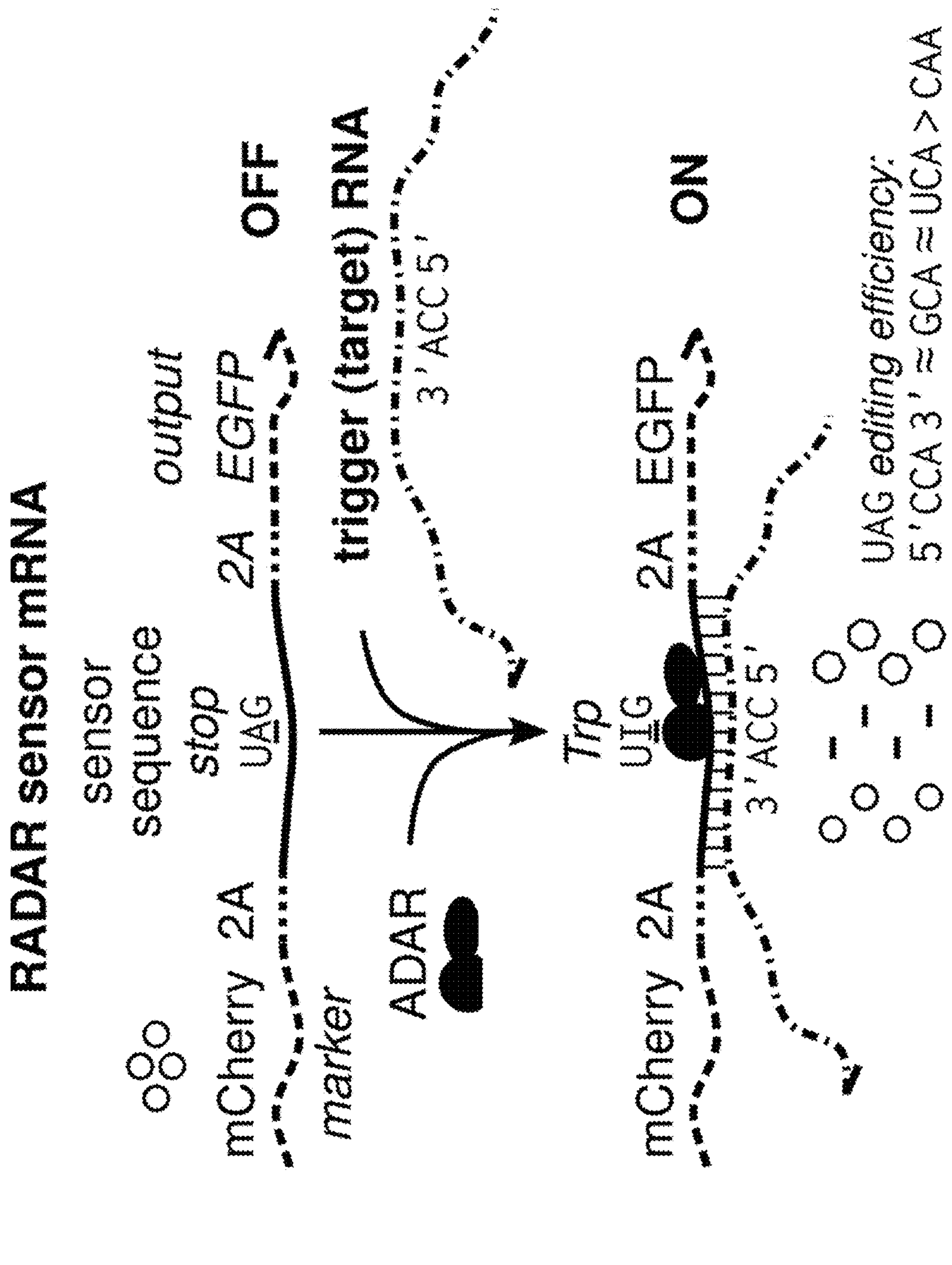
FIGS. 1A-1L. Modular live RNA sensing using ADAR editing. 1A) RADAR expresses an output protein once an input RNA has bound the sensor sequence, triggering an edit of an upstream stop codon by ADAR. 1B) Sensor 1 detects transfected trigger (target RNA) 1, but not the nonmatching trigger 2 in human cells and is enhanced by ADAR1p150 as assayed by flow cytometry. 1C) RADAR output is strongly correlated to input amount. 1D) Cre recombinase as an alternative output. The reporter is turned on by Cre-mediated inversion, with lower reporter amounts corresponding to higher activation fold ratios. 1E) RADAR detects a genomically integrated, doxycycline-induced trigger. 1F) RADAR detects a subsequence within a natural 3' UTR. 1G) RADAR detects an endogenous heat shock induced gene via 3' UTR sensor or an endogenously expressed gene, modulated by siRNA knockdown. 1H) Sensor can be reduced to 72 bp. 1I) The "split" design allows detection of a smaller core sequence. 1J) Detecting a trigger sequence within a CDS. 1K) RADAR is compatible with 85% of the genome. 1L) Enhancing RADAR using an engineered ADAR that only binds the sensor mRNA via MS2-MCP interactions. The chimeric ADAR does not enhance editing of the MS2-free sensor. The MS2 can be placed in the 3' UTR of the sensor or proximal to the dsRNA forming sensor region. In all figures, unless otherwise noted, we report the mean output fluorescence intensity in cells gated for high transfection efficiency (relative within the given experiment). Each dot represents one biological replicate and the horizontal lines indicate the mean of data in each group. Significance determined by Bonferroni-corrected two-tailed Student t-test.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It must be noted that as used herein and in the appended claims, the singular forms "a", "an", and "the" include plural referents unless the context clearly dictates otherwise. For example, the term "a RNA sensor" refers to one or more RNA sensors, i.e., a single RNA sensor and multiple RNA sensors. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer including purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

By "hybridizable" or "complementary" or "substantially complementary" it is meant that a nucleic acid (e.g. RNA, DNA) contains a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine/adenosine) (A) pairing with thymidine/thymidine (T), A pairing with uracil/uridine (U), and guanine/guanosine) (G) pairing with cytosine/cytidine (C). Inosine (I) bases pair with cytosine/cytidine. In addition, for hybridization between two RNA molecules (e.g., dsRNA), and for hybridization of a DNA molecule with an RNA molecule (e.g., when a DNA target nucleic acid base pairs with a guide RNA, etc.): G can also base pair with U. For example, G/U base-pairing is partially responsible for the degeneracy (i.e., redundancy) of the genetic code in the context of tRNA anti-codon base-pairing with codons in mRNA. Thus, in the context of this disclosure, a G (e.g., of a protein-binding segment (e.g., dsRNA duplex) of a guide RNA molecule; of a target nucleic acid (e.g., target DNA or RNA) base pairing with a sensor RNA) is considered complementary to both a U and to C. For example, when a G/U base-pair can be made at a given nucleotide position of a protein-binding segment (e.g., dsRNA duplex) of a sensor RNA molecule, the position is not considered to be non-complementary, but is instead considered to be complementary.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more).

It is understood that the sequence of a polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure, a 'bulge', and the like). A polynucleotide can include 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. The remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a protein, a cell, or an organism, refers to a nucleic acid, protein, cell, or organism that is found in nature. For example, a polypeptide or polynucleotide sequence that is present in an organism (including viruses) that can be isolated from a source in nature and which has not been intentionally modified by a human in the laboratory is naturally occurring.

The term "exogenous" as used herein as applied to a nucleic acid or a protein refers to a nucleic acid or protein that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell. As used herein, the term "endogenous polypeptide" refers to a polypeptide that is normally found in and/or produced by a given bacterium, organism, or cell in nature.

"Recombinant," as used herein, means that a particular nucleic acid or protein is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA containing the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms.

Thus, e.g., the term "recombinant" nucleic acid or "recombinant" protein refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" or "vector" is meant a recombinant nucleic acid, generally recombinant DNA, which has been generated for the purpose of the expression and/or propagation of a nucleotide sequence(s) of interest, or is to be used in the construction of other recombinant nucleotide sequences.

The term "transformation" or "transfection" refers to a permanent or transient genetic change induced in a cell following introduction of a nucleic acid (i.e., DNA and/or RNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e., in vitro, ex vivo, or in vivo). A general discussion of these methods can be found in Ausubel et al, Short Protocols in Molecular Biology, 3rd ed., Wiley & Sons, 1995.

The terms "regulatory region" and "regulatory elements", used interchangeably herein, refer to transcriptional and translational control sequences, such as promoters, enhancers, polyadenylation signals, terminators, protein degradation signals, translational start and stop codons, translation initiation sites, splice enhancer/donor/branch/acceptor sites, and the like, that provide for and/or regulate expression of a coding sequence and/or production of an encoded polypeptide in a host cell. As used herein, a "promoter sequence" or "promoter" is a DNA regulatory region capable of binding/recruiting RNA polymerase (e.g., via a transcription initiation complex) and initiating transcription of a downstream (3' direction) sequence (e.g., a protein coding ("coding") or non-protein-coding ("non-coding") sequence. A promoter can be a constitutively active promoter (e.g., a promoter that is constitutively in an active/"ON" state), it may be an inducible promoter (e.g., a promoter whose state, active/"ON" or inactive/"OFF", is controlled by an external stimulus, e.g., the presence of a particular temperature, compound, or protein), it may be a spatially restricted promoter (e.g., tissue specific promoter, cell type specific promoter, etc.), and/or it may be a temporally restricted promoter (e.g., the promoter is in the "ON" state or "OFF" state during specific stages of embryonic development or during specific stages of a biological process, e.g., hair follicle cycle in mice).

"Operably linked" refers to a juxtaposition wherein the components so described are in a relationship permitting them to function in their intended manner. For instance, a promoter is operably linked to a nucleotide sequence (e.g., a protein coding sequence, e.g., a sequence encoding an mRNA; a non protein coding sequence, e.g., a sequence encoding a Shh protein; and the like) if the promoter affects its transcription and/or expression.

The term "adenosine deaminase acting on RNA" or "ADAR" refers to an enzyme that catalyze the hydrolytic C6 deamination of adenosine (A) to produce inosine (I) in RNA substrates that are double stranded. ADARs preferentially edit double stranded RNAs at sites of mismatches where mismatches containing adenosines and cytosines are editing more efficiently than other mismatches. Editing by ADARs results in nucleotide substitution in RNA, because the purine I generated as the result of the deamination reaction is recognized as G instead of A, both by ribosomes during translational decoding of mRNA and by RNA-dependent polymerases during RNA replication. The term "ADAR" encompasses any know type of ADAR such as ADAR1 (ADAR) or ADAR2 (ADARB2).

As used herein "ADAR1" refers to an adenosine deaminase acting on RNA that catalyze the hydrolytic C6 deamination of adenosine (A) to produce inosine (I) in RNA substrates that are double stranded. ADAR1 has 2 main isoforms, p150 and p110. The term "ADAR1" encompasses ADAR1 from various species. Amino acid sequences of ADAR1 from various species are publicly available. See, e.g., GenBank Accession Nos. NP_001102 (*Homo sapiens* ADAR1 p150), NP_001180424.1 (*Homo sapiens* ADAR1 p110), NP_001139768 (*Mus musculus* ADAR1 p150), NP_001033676 (*Mus musculus* ADAR1 p110). The term "ADAR1" as used herein also encompasses fragments, fusion proteins, and variants (e.g., variants having one or more amino acid substitutions, addition, deletions, and/or insertions) that retain ADAR1 enzymatic activity.

As used herein "ADAR2" refers to an adenosine deaminase acting on RNA that catalyze the hydrolytic C6 deamination of adenosine (A) to produce inosine (I) in RNA substrates that are double stranded. ADAR2 is exclusively localized to the nucleus. The term "ADAR2" encompasses ADAR2 from various species. Amino acid sequences of ADAR2 from various species are publicly available. See, e.g., GenBank Accession Nos. NP_056648.1 (*Homo sapiens* ADAR2), NP_001020008.1 (*Mus musculus* ADAR2), AC052474.1 (*Doryteuthis opalescens* ADAR2). The term "ADAR2" as used herein also encompasses fragments, fusion proteins, and variants (e.g., variants having one or more amino acid substitutions, addition, deletions, and/or insertions) that retain ADAR2 enzymatic activity.

The term "sample" as used herein relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). In certain embodiments of the method, the sample includes a cell. In some instances of the method, the cell is in vitro. In some instances of the method, the cell is in vivo.

The term "biological sample" encompasses a clinical sample or a non-clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's sample cell, e.g., a sample containing polynucleotides and/or polypeptides that is obtained from a patient's sample cell (e.g., a cell lysate or other cell extract containing polynucleotides and/or polypeptides); and a sample containing sample cells from a patient. A biological sample containing a sample cell from a patient can also include normal, non-diseased cells. A biological sample may be from a plant or an animal. The biological sample may also be from any species. In certain embodiments of the method, the biological sample includes a cell. In some instances of the method, the cell is in vitro. In some instances of the method, the cell is in vivo.

The term "editable codon" as used herein refers to a 3 nucleotide sequence that is editable by an ADAR protein or a derivative thereof. The codon may be a start codon, a stop codon or an AUA codon. The codon contains a sequence that contains an adenosine base. In general, in the methods disclosed herein, the editable codon is a start codon that is edited to become a non-start codon, a stop codon that is edited to become a non-stop codon, or a non-start codon (i.e., AUA) that is edited to become a start codon.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

In further describing the subject invention, methods for detecting a target RNA described first in greater detail. Next, methods of expressing a target protein of interest are described. Kits are also described.

Methods for Detecting a Target RNA

As summarized above, methods are provided for detecting a target RNA in a biological sample, the method including (a) combining the biological sample with a sensor RNA and (b) assaying for the presence of an output protein associated with the detection with the target RNA. In some embodiments, the biological sample is a cell.

The target RNA may be any RNA. For example, the target RNA includes, without limitation, mRNA, long non-coding RNA, transfer RNA, ribosomal RNA, small RNAs such as microRNA, small interfering RNA, small nucleolar RNAs, etc. In some embodiments, the target RNA may differentially expressed in different tissues cell types, or cell states and the detecting of the target RNA may be used to identify tissue types, cell types or cell states. In some embodiments, the target RNA may be a genetic variant of gene. In these instances, the genetic variant may be predictive of a disease or susceptible to a disease such as an oncogenic mutation or a genetic variant associated with increased susceptibility to a pathogen. In some embodiments, the methods of the present disclosure may be used to detect point mutations that are associated with the development of a disease such as cancer, neurodegenerative disease, an autoimmune disease, etc. In some embodiments, the methods of the present disclosure are capable of detecting small indels, single nucleotide polymorphisms (SNPs) or variant, multi-nucleotide variant or dinucleotide variant, etc. In some embodiments, the methods of the present disclosure are capable of detecting and distinguishing copy number variants within and between biological samples. The target RNA may also be a gene fusion which may be predictive of cancer in general or a specific type of cancer. The target RNA may also be a specific splice variant (isoform) of a gene.

In some embodiments, the sensor RNA includes the following: (i) a first nucleotide sequence encoding a marker protein, (ii) a second nucleotide sequence encoding a first cleavage domain, (iii) a third nucleotide sequence including a sensor nucleotide sequence that is reverse complementary to the target RNA, wherein the sensor nucleotide sequence includes one or more stop codons, (iv) a fourth nucleotide sequence encoding a second cleavage domain, and (v) a fifth nucleotide sequence encoding an output protein.

In some embodiments, the sensor RNA includes the following: (i) a first nucleotide sequence encoding a marker protein, (ii) a second nucleotide sequence encoding a cleavage domain (iii) a third nucleotide sequence including a sensor nucleotide sequence that is reverse complementary to the 3' UTR of the target RNA, wherein the sensor nucleotide sequence includes one or more stop codons, (iv) a fourth nucleotide sequence encoding a second cleavage domain, and (v) a fifth nucleotide sequence encoding an output protein.

In some embodiments, the sensor RNA includes the following: (i) a first nucleotide sequence containing a stem-loop sequence containing one or more stop codons (ii) a second nucleotide sequence containing a sensor nucleotide sequence that is reverse complementary to the target RNA, (iii) a third nucleotide sequence encoding a cleavage domain, and (iv) a fourth nucleotide sequence encoding an output protein.

In some embodiments, the sensor RNA includes the following: (i) a first nucleotide sequence containing a sensor nucleotide sequence that is reverse complementary to the target RNA wherein the sensor nucleotide sequence contains a stem-loop sequence containing one or more stop codons, (ii) a second nucleotide sequence encoding a cleavage domain, and (iii) a third nucleotide sequence encoding an output protein.

In some embodiments, the sensor RNA includes the following: (i) a first nucleotide sequence containing a sensor nucleotide sequence that is reverse complementary to the target RNA, (ii) a second nucleotide sequence containing a stem-loop sequence containing one or more stop codons (iii) a third nucleotide sequence encoding a cleavage domain, and (iv) a fourth nucleotide sequence encoding an output protein.

In some embodiments, the sensor RNA has one or more stop codons containing at least 1 base that is mismatched with 1) a sequence within the stem loop opposite the stop codon or 2) a sequence in the target RNA. The at least 1 base that is mismatched is generally not more than 2 bases that are mismatched. In an embodiment, the sensor RNA has one or more stop codons containing only 1 base that is mismatched with 1) a sequence within the stem loop opposite the stop codon or 2) a sequence in the target RNA. In some embodiments, the sensor RNA does not have any mismatched bases.

In certain embodiments, the sensor RNA contains the first nucleotide sequence to the third, fourth or fifth nucleotide sequences in order (i.e., the fifth nucleotide sequence follows the fourth nucleotide sequence which follows the third nucleotide sequence which follows the second nucleotide sequence which follows the first nucleotide sequence). In some embodiments, the sensor RNA contains the first nucleotide sequence to the third, fourth or fifth nucleotide sequence that are not in order described above.

The sensor RNA of the present disclosure contains a sensor nucleotide sequence or a stem-loop sequence containing one or more stop codons which is followed by a nucleotide sequence encoding an output protein. In some embodiments, the sensor RNA contains one or more stop codons that contain at least 1 base that is mismatched with the target RNA or the sequence within the stem-loop. In some embodiments, the sensor RNA does not contain any mismatches with the target RNA. In the presence of the target RNA, the sensor nucleotide sequence of the sensor RNA hybridizes to the target RNA thereby forming a double stranded RNA molecule that can recruit an ADAR protein. The double stranded RNA can contain a stop codon with or without mismatches, or a stop codon could be within the stem-loop of the sensor RNA. An ADAR protein then edits the adenosine base within the stop codon(s) of the sensor RNA to an inosine base. This editing removes the stop codon(s) which then allows the output protein to be produced from the sensor RNA within the biological sample.

When the sensor RNA contains a nucleotide sequence containing a stem-loop sequence comprising a stop codon, any stem-loop sequence may be used. In some embodiments, the stem loop contains natural editing sites. Natural editing sites are sites within nucleotide sequences which are edited in nature. Natural editing sites are known in the art and have been described in, for example, Gabay et al. (Nat Commun. 2022 Mar. 4; 13(1):1184) which is specifically incorporated by reference herein. Examples of natural editing sites include, without limitation, editing sites found in GRIA2, GRIA3, IGFBP7, NEIL1, FLNA, GRIK2, CDK13, GABRA3, GLI1, SPEG, HTR2C, GRIA4, CYFIP2, CADPS, CADPS, RICTOR, COG3, GRIK1, COPA, HBE1, SON, FLNB, MAGEL2, NOVA1, PNMT, WASH1, LAT, DACT3, FXYD5, ZNF717, ZNF551 CAPS1, etc. Natural editing sites are also disclosed in Table 1 below. In some embodiments, the stem-loop sequence is a GluR-B stem-loop or a modified variant thereof. In some embodiments, the stem contains a natural editing site while the loop is a synthetic sequence. In some embodiments, the sequence of the stem is altered compared to the natural editing site by the addition or removal of nucleotides in order to add or remove mismatches. In some embodiments, the sequence alteration adds or removes additional stop codons In some embodiments, the stem-loop sequence contains a CAPS1 derived stem-loop according to:

CAAGGUCAAUGAGGAGAUGUACAUAGAAAUA-CAAUCCUGUGUACAUCUUCUAGCAU GACC-CAC (SEQ ID NO: 1; CAPS1 variant 2). In some embodiments, the stem-loop sequence contains a CAPS1 derived stem-loop according to:

CAAGGUCAAUGAGGAGAUGUACAUAAUA-CAAUGUGUACAUCUUCUAGCAUGACCCA C (SEQ ID NO: 2; CAPS1 variant 3). In some embodiments, the stem-loop sequence contains a GLI1 derived stem-loop according to:

CCCAACCUCUGUCUACUCAC-CACAGCCCCCCAGCAUCACUGUGAAUGCUGC-CAUGGA UGCUAGAGGGCUACAG-GAAGAGCCAGAAGUUGG (SEQ ID NO: 3; GLI1 variant 4). In some embodiments, the stem-loop sequence contains a GLI1 derived stem-loop according to:

CUCACCACAGCCCCCCAGCAUCACU-GUGAAUGCUGCCAUGGAUGCUAGAGGGC-UACA GGA (SEQ ID NO: 4; GLI1 variant 5). In some embodiments, the stem-loop sequence contains a GABRA3 derived stem-loop according to:

AAGUGGCAUAUGCGACGGCCAUGGACUGGUU-CAUAGCCGUCUGUUAUGCCU (SEQ ID NO: 5; GABRA3 variant 6). In some embodiments, the stem-loop sequence contains a GABRA3 derived stem-loop according to:

UGGCAUAUGCGACGGCCAUGGACUGGUU-CAUAGCCGUCUGUUAUG (SEQ ID NO: 6; GABRA3 variant 7). In some embodiments, the stem-loop sequence contains a GLURB derived stem-loop according to:

CAUUAAGGUGGGUGGAAUAGUAUACAA-AGUAUCCCACCUACCCUGAUG (SEQ ID NO: 7; GLURB variant 8). In some embodiments, the stem-loop sequence contains a GLURB derived stem-loop according to:

CAUUAAGGUGGGUGGAAUAGUAUACAA-AGUAUCCCACCUACCCCGAUG (SEQ ID NO: 8; GLURB variant 9). In some embodiments, the stem-loop sequence comprises GLURB derived stem-loop according to:

UCCGUUUAGGUGGGUGGAAUAGUAAUACAA-AGUAUCCCACCUACCCAGACG (SEQ ID NO: 9; GLURB variant 1).

TABLE 1

Natural editing sites

| local genome sequence context | chromosome | position | strand | gene | maximum native editing levels | editing location in transcripts |
|---|---|---|---|---|---|---|
| CAG | chr4 | 1.57E+08 | + | GRIA2 | 0.997 | NM_001083620.1, exon11, c.A1679G, p.Q560R; NM_001083619.1, exon11, c.A1820G, p.Q607R; NM_000826.3, exon11, c.A1820G, p.Q607R |
| AAG | chrX | 1.23E+08 | + | GRIA3 | 0.982 | NM_000828.4, exon13, c.A2323G, p.R775G; NM_007325.4, exon13, c.A2323G, p.R775G |
| AAG | chr4 | 57110068 | − | IGFBP7 | 0.963 | NM_001553.2, exon1, c.A284G, p.K95R; NM_001253835.1, exon1, c.A284G, p.K95R |
| AAG | chr4 | 1.57E+08 | + | GRIA2 | 0.960 | NM_001083620.1, exon13, c.A2149G, p.R717G; NM_001083619.1, exon13, c.A2290G, p.R764G; NM_000826.3, exon13, c.A2290G, p.R764G |
| AAA | chr15 | 75353745 | + | NEIL1 | 0.958 | NM_024608.3, exon6, c.A725G, p.K242R; NM_001256552.1, exon6, c.A983G, p.K328R |
| CAG | chrX | 1.54E+08 | − | FLNA | 0.943 | NM_001110556.1, exon43, c.A7022G, p.Q2341R; NM_001456.3, exon42, c.A6998G, p.Q2333R |
| CAG | chr6 | 1.02E+08 | + | GRIK2 | 0.897 | NM_001166247.1, exon12, c.A1862G, p.Q621R; NM_021956.4, exon12, c.A1862G, p.Q621R; NM_175768.3, exon12, c.A1862G, p.Q621R |
| CAG | chr7 | 39950949 | + | CDK13 | 0.896 | NM_003718.4, exon1, c.A308G, p.Q103R; NM_031267.3, exon1, c.A308G, p.Q103R |
| AAG | chr15 | 75353746 | + | NEIL1 | 0.887 | NM_024608.3, exon6, c.A726G, p.K242K; NM_001256552.1, exon6, c.A984G, p.K328K |

TABLE 1-continued

| Natural editing sites | | | | | | |
|---|---|---|---|---|---|---|
| local genome sequence context | chromosome | position | strand | gene | maximum native editing levels | editing location in transcripts |
| ATAGC | chrX | 1.52E+08 | − | GABRA3 | 0.846 | NM_000808.3, exon9, c.A1026G, p.I342M |
| CTAGA | chr12 | 57470841 | + | GLI1 | 0.844 | NM_001160045.1, exon10, c.A1717G, p.R573G;<br>NM_001167609.1, exon11, c.A1978G, p.R660G;<br>NM_005269.2, exon12, c.A2101G, p.R701G |
| TAC | chr6 | 1.02E+08 | + | GRIK2 | 0.833 | NM_001166247.1, exon11, c.A1712G, p.Y571C;<br>NM_021956.4, exon11, c.A1712G, p.Y571C;<br>NM_175768.3, exon11, c.A1712G, p.Y571C |
| CAG | chr2 | 2.19E+08 | + | SPEG | 0.829 | NM_005876.4, exon30, c.A6139G, p.S2047G |
| AAT | chrX | 1.15E+08 | + | HTR2C | 0.826 | NM_001256760.2, exon6, c.A466G, p.I156V;<br>NM_000868.3, exon5, c.A466G, p.I156V |
| AAG | chr11 | 1.06E+08 | + | GRIA4 | 0.825 | NM_001077243.2, exon14, c.A2293G, p.R765G;<br>NM_000829.3, exon14, c.A2293G, p.R765G |
| TTAAG | chr5 | 1.57E+08 | + | CYFIP2 | 0.800 | NM_014376.3, exon10, c.A958G, p.K320E;<br>NM_001291721.1, exon9, c.A880G, p.K294E;<br>NM_001291722.1, exon10, c.A958G, p.K320E;<br>NM_001037333.2, exon10, c.A958G, p.K320E |
| TGAGG | chr3 | 62438132 | − | CADPS | 0.767 | NM_003716.3, exon28, c.A3749G, p.E1250G;<br>NM_183393.2, exon25, c.A3512G, p.E1171G;<br>NM_183394.2, exon26, c.A3632G, p.E1211G |
| CAG | chr5 | 38949393 | − | RICTOR | 0.702 | NM_001285439.1, exon32, c.A4171G, p.R1391G |
| TAT | chrX | 1.15E+08 | + | HTR2C | 0.691 | NM_001256760.2, exon6, c.A478G, p.I160V;<br>NM_000868.3, exon5, c.A478G, p.I160V |
| AAT | chr13 | 45516263 | + | COG3 | 0.690 | NM_031431.3, exon17, c.A1903G, p.I635V |
| CAG | chr21 | 29581430 | − | GRIK1 | 0.666 | NM_001320618.1, exon10, c.A1490G, p.Q497R;<br>NM_000830.4, exon13, c.A1907G, p.Q636R;<br>NM_001320621.1, exon10, c.A1436G, p.Q479R;<br>NM_175611.2, exon12, c.A1862G, p.Q621R;<br>NM_001320616.1, exon13, c.A1907G, p.Q636R |
| ATATT | chr1 | 1.6E+08 | − | COPA | 0.625 | NM_001098398.1, exon6, c.A490G, p.I164V;<br>NM_004371.3, exon6, c.A490G, p.I164V |
| AAG | chr11 | 5269810 | − | HBE1 | 0.624 | NM_005330.3, exon1, c.A81G, p.E27E |
| CTAGG | chr21 | 33550969 | + | SON | 0.622 | NM_138927.2, exon3, c.A1738G, p.R580G;<br>NM_001291411.1, exon3, c.A1738G, p.R580G;<br>NM_032195.2, exon3, c.A1738G, p.R580G |
| AAT | chrX | 1.15E+08 | + | HTR2C | 0.616 | NM_001256760.2, exon6, c.A473G, p.N158S;<br>NM_000868.3, exon5, c.A473G, p.N158S |
| CAG | chr3 | 58156074 | + | FLNB | 0.605 | NM_001457.3, exon41, c.A6887G, p.Q2296R;<br>NM_001164319.1, exon40, c.A6815G, p.Q2272R;<br>NM_001164317.1, exon42, c.A6980G, p.Q2327R;<br>NM_001164318.1, exon41, c.A6854G, p.Q2285R |
| CAG | chr15 | 23646169 | − | MAGEL2 | 0.595 | NM_019066.4, exon1, c.A1574G, p.Q525R |
| GTAGC | chr14 | 26448324 | − | NOVA1 | 0.566 | NM_002515.2, exon5, c.A1159G, p.S387G;<br>NM_006489.2, exon4, c.A1087G, p.S363G |
| ATACG | chrX | 1.15E+08 | + | HTR2C | 0.563 | NM_001256760.2, exon6, c.A468G, p.I156M;<br>NM_000868.3, exon5, c.A468G, p.I156M |
| GTAGT | chr17 | 39670276 | + | PNMT | 0.555 | NM_002686.4, exon3, c.A736G, p.S246G |
| CAG | chr9 | 18481 | − | WASH1 | 0.554 | NM_182905.4, exon3, c.A161G, p.Q54R |
| CAG | chr7 | 39950745 | + | CDK13 | 0.539 | NM_003718.4, exon1, c.A104G, p.Q35R;<br>NM_031267.3, exon1, c.A104G, p.Q35R |
| CAG | chr16 | 28984887 | + | LAT | 0.525 | NM_001014989.1, exon1, c.A26G, p.Q9R |
| CAG | chr19 | 46649480 | − | DACT3 | 0.524 | NM_145056.2, exon4, c.A892G, p.S298G;<br>NM_001301046.1, exon4, c.A217G, p.S73G |
| TTATG | chr3 | 58156064 | + | FLNB | 0.415 | NM_001457.3, exon41, c.A6877G, p.M2293V<br>NM_001164319.1, exon40, c.A6805G, p.M2269V;<br>NM_001164317.1, exon42, c.A6970G, p.M2324V;<br>NM_001164318.1, exon41, c.A6844G, p.M2282V |
| TGAGA | chr19 | 35166329 | + | FXYD5 | 0.362 | NM_001320912.1, exon8, c.A491G, p.E164G |
| CTATG | chr3 | 75736912 | − | ZNF717 | 0.322 | NM_001290209.1, exon5, c.A2561G, p.Y854C;<br>NM_001290208.1, exon5, c.A2711G, p.Y904C;<br>NM_001128223.2, exon5, c.A2711G, p.Y904C |
| GAATG | chr19 | 57686495 | + | ZNF551 | 0.124 | NM_138347.4, exon3, c.A220G, p.M74V;<br>NM_001270938.1, exon3, c.A136G, p.M46V |

When the sensor RNA contains a nucleotide sequence containing a stem-loop sequence containing a stop codon, the length of the stem-loop may have a limit. For example, the stem-loop may be 50 bp or less, 40 bp or less, 30 bp or less or 20 bp or less. In an embodiment, the length of the stem-loop is 18-50 bps.

Sensor RNAs containing a nucleotide sequence containing a stem-loop sequence containing an editable codon have certain advantages relative to sensor RNAs that do not contain such a stem-loop sequence, such as those disclosed in International Application PCT/US2022/033459. This is due to ADAR having separate domains for RNA editing (catalytic domain) and dsRNA binding. First, sensor RNAs containing a nucleotide sequence containing a stem-loop sequence containing an editable codon decouples the sequence that is being edited (e.g., a stop codon) from the sequence that recruits the ADAR protein (i.e., the dsRNA segment that is formed when the sensor nucleotide sequence hybridizes to the target RNA). Generally, if the editable codon in the sensor RNA is a UAG (stop codon) and there is only one mismatch in the stop codon relative to the target RNA then the target RNA should have a CCA sequence (or a sequence that is reverse complementary to a different stop codon having one mismatch with the stop codon). The presence of the CCA sequence (or an equivalent sequence for a different editable codon) potentially limits the number of possible target RNAs. Requiring a specific sequence (such as CCA or an equivalent sequence) to be present in the target RNA can be limiting because it restricts which subsequence a sensor could be created against; for example, a CCA or equivalent sequence may only present in highly structured parts of the target RNA, may only be present in the coding sequence, or may be present in protein-bound sections of a target RNA, all of which may contribute to lower availability for sensor-target hybridization, reducing efficiency. With a sensor containing a stem-loop, the range of suitable subsequences is greatly increased, so problematic target RNA subsequences can be avoided and efficient ones utilized instead. In some embodiments where gene fusions or splice variants are to be distinguished, flexibility in target RNA subsequence choice is needed, and is provided by the stem-loop design. Second, while ADAR editing is largely sequence-agnostic, there are some minor biases primarily driven by the catalytic domain which extend beyond the editable codon. Biases driven by the catalytic domain are known in the art and have been described by, for example, Kuttan et al. (Proc Natl Acad Sci USA. 2012 Nov. 27; 109(48):E3295-304) which is specifically incorporated by reference herein. Editing sites in the sensor RNA may be dictated by the target RNA which precludes optimization of the editing site (i.e., the stop or non-stop codons of the present disclosure). By separating out the editing site from the sensor nucleotide sequence that hybridizes to the target RNA, to the editing site and the sensor nucleotide sequence can be optimized separately.

In some embodiments, the sensor RNA contains a non-start codon in place of a stop codon. In these embodiments, the sensor RNA contains the following: (i) a first nucleotide sequence containing a sensor nucleotide sequence that is reverse complementary to the target RNA, wherein the sensor nucleotide sequence contains a non-start codon (e.g. AUA) that contains at least 1 base that is mismatched with the target RNA sequence, (ii) a second nucleotide sequence encoding a second cleavage domain, and (iii) a third nucleotide sequence encoding an output protein. In the presence of the target RNA, the sensor RNA hybridizes to the target RNA thereby forming a double stranded RNA molecule containing one or more base mismatches within the non-start codon or elsewhere. An ADAR protein then edits the adenosine base within the non-start codon (e.g., AUA to AUI) of the sensor RNA to an inosine base. This editing converts the non-start codon to a start codon which then allows the output protein to be produced from the sensor RNA within the biological sample.

In some embodiments, the sensor RNA has a start codon in place of a stop codon. In these embodiments, the sensor RNA has the following: (i) a first nucleotide sequence having a sensor nucleotide sequence that is reverse complementary to the target RNA, wherein the sensor nucleotide sequence has a start codon (e.g. AUG) that has at least 1 base that is mismatched with the target RNA sequence and (ii) a second nucleotide sequence encoding an output protein wherein the sequence encoding the output protein has a start codon. In the presence of the target RNA, the sensor RNA hybridizes to the target RNA thereby forming a double stranded RNA molecule having one or more base mismatches within the start codon or elsewhere. An ADAR protein then edits the adenosine base within the start codon (e.g., AUG to IUG) of the sensor RNA to an inosine base. This editing converts the start codon to a non-start codon which then allows the output protein to be produced from the sensor RNA within the biological sample. Prior to editing, the presence of the first start codon within the sensor nucleotide sequence represents an upstream reading frame which suppresses the expression of the downstream reading frame. After editing, the upstream reading frame is removed allowing the downstream reading frame to be expressed which produces the output protein.

When the sensor RNA contains a start codon in place of a stop codon, the upstream reading frame as described above may have particular features. In some embodiments, the length of the upstream reading frame is shorter than the downstream reading frame. In some embodiments, the length of the upstream reading frame is longer than the downstream reading frame. In an embodiment, the length of the upstream reading frame is about the same length of the downstream reading frame.

In some embodiments, the sensor RNA contains a start codon in place of a stop codon. In these embodiments, the sensor RNA contains the following: (i) a first nucleotide sequence containing a sensor nucleotide sequence that is reverse complementary to the target RNA, wherein the sensor nucleotide sequence contains a start codon (e.g., AUG) that contains at least 1 base that is mismatched with the target RNA sequence and (ii) a second nucleotide sequence encoding an output protein. In the presence of the target RNA, the sensor RNA hybridizes to the target RNA thereby forming a double stranded RNA molecule containing one or more base mismatches within the start codon or elsewhere. An ADAR protein then edits the adenosine base within the start codon (e.g., AUG to IUG) of the sensor RNA to an inosine base. This editing converts the start codon to a non-start codon which then prevents the production of the output protein. In this embodiment, the output protein is only produced in the absence of the target RNA.

In some embodiments, the sensor RNA includes splice sites prior to the output protein. In these embodiments, the ADAR protein edits a codon at the splice thereby removing the splice site leading to the production of the output protein. In some embodiments, the ADAR protein edits a non-splice site converting it into a splice site thereby inactivating the production of the output protein.

In some cases, it is desired to reduce the immunogenicity of the sensor RNA. Methods of reducing the immunogenicity of RNAs are known in the art such and have been described by, for example, Starostina et al. (Vaccines (Basel). 2021 May 3; 9(5):452) which is specifically incorporated by reference herein. In general, methods of reducing the immunogenicity of a sensor RNA involves the incorporation of modified ribonucleic acids into the sensor RNA. Modified ribonucleic acids that find use in the present disclosure includes, without limitation, methylcytosine, pseudouridine, methyladenosine, etc. In some embodiments, the methylcytosine is 5-methylcytosine. In some embodiments, the pseudouridine is N1-methyl-pseudouridine. In some embodiments, the methyladenosine is a N6-methyladenosine. In some embodiments, the methyladenosine is a N1-methyladenosine. In some embodiments, a portion of the nucleotides present in the sensor RNA are composed of modified ribonucleic acids. For instance, a portion of the uridines in the sensor RNA are replaced with pseudouridines. When the uridines of the sensor RNA are replaced with pseudouridines, a certain percentage of the uridines are replaced with pseudouridines. For instance, about 1-10%, about 10-20%, about 20-30%, about 30-40%, about 40-50%, about 50-60%, about 60-70%, about 70-80%, 80-90% or greater than 90% of the uridines are replaced with pseudouridines. In an embodiment, 75% or less of the uridines in the sensor RNAs are replaced with pseudouridines. In an embodiment, the sensor sequence does not have pseudouridines.

When a sensor RNA contains pseudouridines, the pseudouridine(s) may be in specific locations. In some embodiments, the pseudouridine(s) are not adjacent to adenosines that are the targets of ADAR editing. In some embodiments, the pseudouridine(s) are not contained in the sensor sequence that hybridizes with a target RNA. When a sensor RNA contains pseudouridines, the sensor may contain a particular stop codon. In some embodiments, the stop codon used is UGA. When the UGA stop codon is used, the adenosine in the UGA may be followed by a specific nucleotide. In some embodiments, the adenosine in the UGA is followed by guanosine such the nucleotide sequence is UGAG.

In some embodiments, the sensor nucleotide sequence includes bases that are mismatched with adenosine bases within the target RNA that are not within a start or stop codon. In some embodiments, the mismatched bases prevent the editing of adenosines that are not within the stop or start codons.

In some embodiments, the sensor nucleotide sequence includes one or more editing inducing elements (EIEs). Suitable EIEs that find use in the present disclosure are disclosed within Uzonyi et al. (Mol Cell. 2021 Jun. 3; 81(11):2374-2387) and Danan-Gotthold et al. (Genome Biol. 2017 Oct. 23; 18(1):196).

A marker protein of the present disclosure may be any marker protein that is useful for the detection of the presence of a sensor mRNA within a biological sample. For instance, the marker protein may be a fluorescent protein or a luminescent protein. Non-limiting examples of useful fluorescent proteins include but are not limited to GFP, EBFP, Azurite, Cerulean, mCFP, Turquoise, ECFP, mKeima-Red, TagCFP, AmCyan, mTFP, TurboGFP, TagGFP, EGFP, TagYFP, EYFP, Topaz, Venus, mCitrine, TurboYFP, mOrange, TurboRFP, tdTomato, TagRFP, dsRed2, mRFP, mCherry, mPlum mRaspberry, mScarlet, etc. Examples of luminescent proteins, include without limitation, Cypridinia luciferase, *Gaussia* luciferase, *Renilla* luciferase, Phontinus luciferase, *Luciola* luciferase, *Pyrophorus* luciferase, *Phrixothrix* luciferase, etc. In some embodiments, the marker protein may be the first half of the output protein. In these embodiments, the sequence encoding the marker protein produces the first half of the output which may be non-functional without the second half of the output protein in the absence of the target RNA. In the presence of the target RNA, the second half of the output protein is produced. When the second half of the output protein is produced in the presence of the first half of the output protein, the two halves are then able to form a functional output protein. In these embodiments, the first half of the output protein is the N-terminus of the output protein and the second half of the output protein is the C-terminus of the output protein.

In certain embodiments, the sensor RNA includes a nucleotide sequences that encodes a cleavage domain. Cleavage domains that find use in the present disclosure include without limitation, HIV-1 protease cleavage domain, TEV cleavage domain, preScission protease cleavage domain, HCV protease cleavage domain, RecA cleavage domain, self-cleaving domain, etc. When a self-cleaving domain is used then the self-cleaving domain may be a 2A self-cleaving domain. 2A self-cleaving domains that find use in the present disclosure include T2A, P2A, E2A and F2A which are described in Szymczak-Workman et al. (Cold Spring Harb Protoc. 2012 Feb. 1; 2012(2):199-204). In some embodiments, the sensor RNA includes a first and a second cleavage domain. When the sensor RNA includes a first and a second cleavage domain, the cleavage domains may be of the same type or they may be of a different type. For instance, the first cleavage domain may be a P2A self-cleaving domain and the second cleavage domain may also be a P2A self-cleaving domain or the first cleavage domain may be a P2A self-cleaving domain and the second cleavage domain may also be a T2A self-cleaving domain or any combination thereof.

The sensor nucleotide sequence of the present disclosure may be reverse complementary to any region of the target RNA. In certain embodiments, the sensor nucleotide sequence is reverse complementary to the 3' UTR of the target RNA. In some embodiments, the sensor nucleotide sequence is reverse complementary to the 5' UTR of the target RNA. In certain embodiments, the sensor nucleotide sequence is reverse complementary to the coding sequence of the target RNA. In some embodiments, the sensor nucleotide sequence is reverse complementary to an exon of the target RNA. In some embodiments, the sensor nucleotide sequence is reverse complementary to an intron of the target RNA. In some embodiments, the sensor nucleotide sequence is reverse complementary to two separate non-contiguous regions of the same target RNA. For instance, the sensor nucleotide sequence may be reverse complementary to two separate regions of the 5' UTR of the target RNA, to two separate regions of the coding sequence of the target RNA, to two separate regions of the 5' UTR of the target RNA, to a region in the 5' UTR and a region in the coding sequence of the target RNA, to a region in the coding sequence and a region in the 3' UTR of the target RNA, or to a region in the 5' UTR and a region in the 3' UTR of the target RNA. In some embodiments, the sensor RNA is reverse complimentary to two or more distinct target RNAs.

Figure 4A:
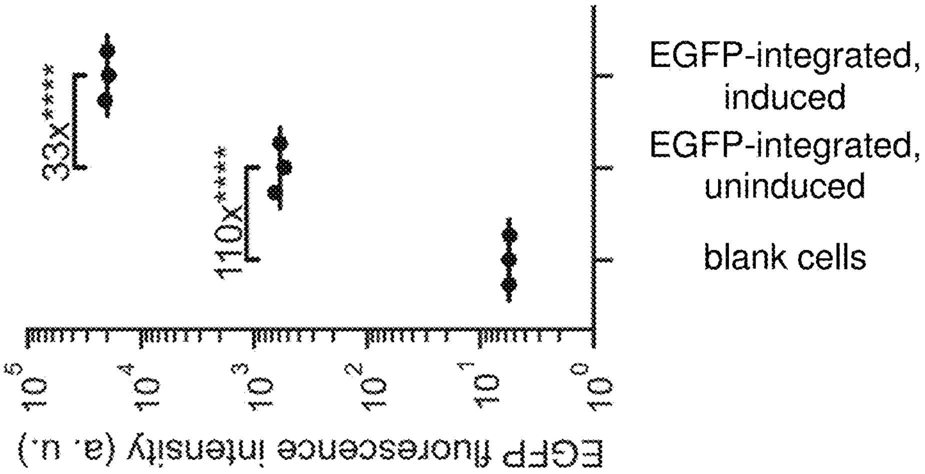
FIGS. 4A-4I. 4A) The inducible trigger shows imperfect repression, as EGFP is detected even when inducer is not present. Parental (no EGFP) or inducible-EGFP-integrated cells were transfected with an unrelated sensor (mTagBFP2 transfection marker, mCherry output) and ADAR1-p150 to measure the average EGFP expression. 4B) Calibration curve with varying amounts of plasmid DNA of construct used to generate the inducible-EGFP-integrated cell line. Orange and blue (two replicates) overlapping appears grey in the plot. 4C) Estimated number of the average mRNA molecules per cell in the inducible-EGFP-integrated cells, either with or without inducer. 4D) A trigger sequence in the CDS performs more poorly compared to the same exact sequence placed into the 3' UTR. 4E) 3' UTR sensor has no significant effect on trigger protein expression (EGFP fluorescence). 4F) The sensor for a CDS sequence has marginal effect on the trigger mRNA protein expression (EGFP fluorescence reduced 1.14-fold). 4G) Incremental benefits of updated sensor designs to the % of genes with at least one, six, or 51 sensor candidates, compared to just 90 bp 3' UTR sensors. 4H) Mouse transcriptome analysis using the expanded set of sensor designs. 4I) RADAR sensor for a split trigger is much more strongly triggered when the split parts are on the same transcript ("1:2"), rather than separate transcripts ("1,2"), suggesting that gene fusions may be detected with the split design.
Figure 4B:
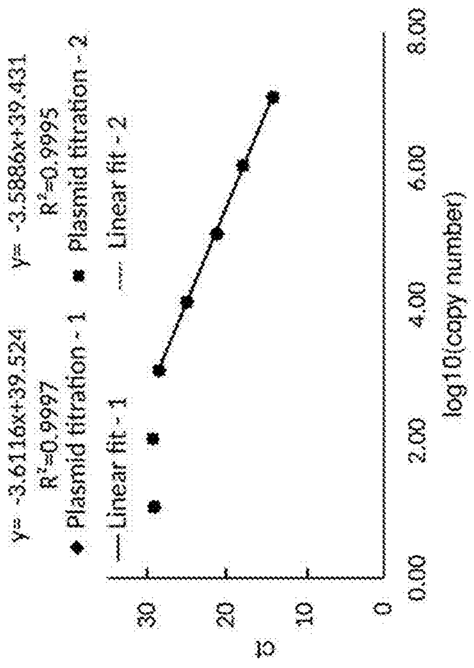
Figure 4C:
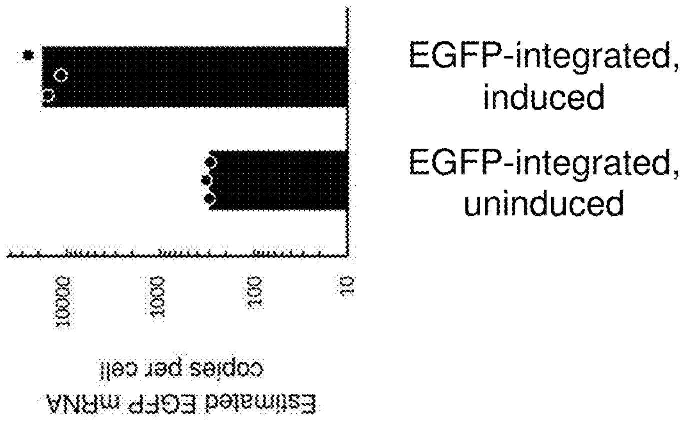
Figure 4D:
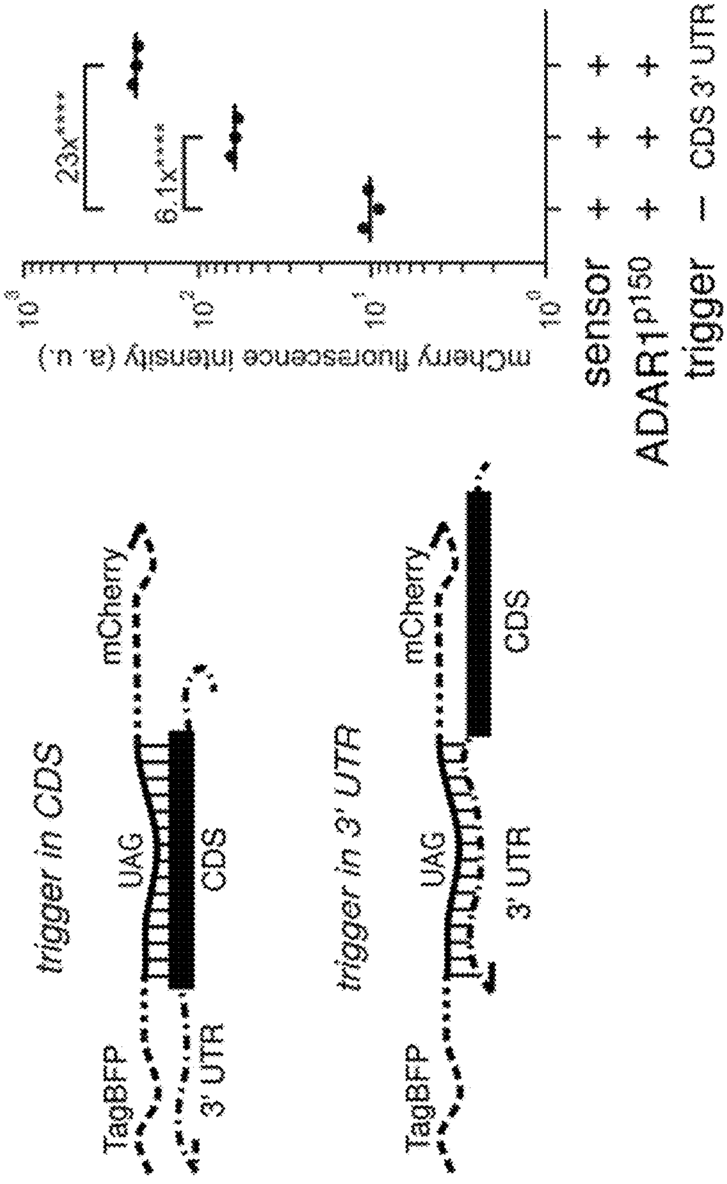

Sensor RNAs that have sensor nucleotide sequences that are reverse complimentary to the 3' or 5' UTR have certain advantages relative to sensor RNAs that are reverse complementary to coding sequences (CDS), such as those disclosed in International Application PCT/US2022/033459. First, ADAR editing is more efficient in the UTR when compared CDS because translating ribosomes may destabilize dsRNA. The increased efficiency is shown in FIG. 4D. Second, RADAR is less likely to interfere with the production of the protein encoded by the target RNA because 1) dsRNA formation in the UTR rather than the CDS will not affect the translation ribosome, and 2) any bystander editing that occur in the UTR of the target RNA is less likely to cause detrimental outcomes because the coding sequence would not be edited.

The sensor nucleotide sequence of the present disclosure may be any length determined necessary for sufficient specificity to the target RNA. For instance the sensor nucleotide sequence could be less than about 50 nucleotides, from about 50 to 60, about 60 to 70, about 70 to 80, about 80 to 90, about 90 to 100, about 100 to 110, about 110 to 120, about 120 to 130, about 130 to 140, about 140 to 150, about 150 to 160, about 160 to 170, about 170 to 180, about 180 to 190, about 190 to 200, about 200 to 210, about 210 to 220, about 220 to 230, about 230 to 240, about 240 to 250, about 250 to 260, about 260 to 270, about 270 to 280, about 280 to 290, about 290 to 300, about 300 to 310, about 310 to 320, about 320 to 330, about 330 to 340, about 340 to 350, about 350 to 360, about 360 to 370, about 370 to 380, about 380 to 390, about 390 to 400, about 400 to 410, about 410 to 420, about 420 to 430, about 430 to 440, about 440 to 450, about 450 to 460, about 460 to 470, about 470 to 480, about 480 to 490, about 490 to 500 or greater than 500 nucleotides in length.

When the sensor nucleotide sequence is reverse complementary to two non-contiguous regions within a target RNA, the distance between the two non-contiguous regions of the target may be any length. For instance, the distance between the two non-contiguous regions of the target may be less than about 50 nucleotides, from about 50 to 60, about 60 to 70, about 70 to 80, about 80 to 90, about 90 to 100, about 100 to 150, about 150 to 200, about 200 to 250, about 250 to 300, about 300 to 350, about 350 to 400, about 400 to 450, about 450 to 500 or greater than 500 nucleotides.

When the sensor nucleotide sequence is reverse complimentary to two non-contiguous regions within the target RNA, the nucleotide sequence of the sensor nucleotide that is reverse complementary to the first region of the two non-contiguous regions with the target RNA may be any length. For instance, the nucleotide sequence of the sensor nucleotide that is reverse complementary to the first region of the two non-contiguous regions may be less than about 20 nucleotides, from about 20 to 30, about 30 to 40, about 40 to 50, about 50 to 60, about 60 to 70, about 70 to 80, about 80 to 90, about 90 to 100, about 100 to 110, about 110 to 120, about 120 to 130, about 130 to 140, about 140 to 150, about 150 to 160, about 160 to 170, about 170 to 180, about 180 to 190, about 190 to 200, about 200 to 210, about 210 to 220, about 220 to 230, about 230 to 240, about 240 to 250, about 250 to 260, about 260 to 270, about 270 to 280, about 280 to 290, about 290 to 300, about 300 to 310, about 310 to 320, about 320 to 330, about 330 to 340, about 340 to 350, about 350 to 360, about 360 to 370, about 370 to 380, about 380 to 390, about 390 to 400, about 400 to 410, about 410 to 420, about 420 to 430, about 430 to 440, about 440 to 450, about 450 to 460, about 460 to 470, about 470 to 480, about 480 to 490, about 490 to 500 or greater than 500 nucleotides in length.

When the sensor nucleotide sequence is reverse complimentary to two non-contiguous regions with the target RNA, the nucleotide sequence of the sensor nucleotide that is reverse complementary to the second region of the two non-contiguous regions with the target RNA may be any length. For instance, the nucleotide sequence of the sensor nucleotide that is reverse complementary to the second region of the two non-contiguous regions may be less than about 20 nucleotides, from about 20 to 30, about 30 to 40, about 40 to 50, about 50 to 60, about 60 to 70, about 70 to 80, about 80 to 90, about 90 to 100, about 100 to 110, about 110 to 120, about 120 to 130, about 130 to 140, about 140 to 150, about 150 to 160, about 160 to 170, about 170 to 180, about 180 to 190, about 190 to 200, about 200 to 210, about 210 to 220, about 220 to 230, about 230 to 240, about 240 to 250, about 250 to 260, about 260 to 270, about 270 to 280, about 280 to 290, about 290 to 300, about 300 to 310, about 310 to 320, about 320 to 330, about 330 to 340, about 340 to 350, about 350 to 360, about 360 to 370, about 370 to 380, about 380 to 390, about 390 to 400, about 400 to 410, about 410 to 420, about 420 to 430, about 430 to 440, about 440 to 450, about 450 to 460, about 460 to 470, about 470 to 480, about 480 to 490, about 490 to 500 or greater than 500 nucleotides in length.

The sensor nucleotide sequence or the stem-loops of the present disclosure may include any stop or start codon including an adenosine residue. For example, the stop codon of the sensor nucleotide sequence may be UAG, UAA, or UGA. In general, the stop codons of the present disclosure are in-frame with the coding sequence of the output protein such that the output protein is produced when the stop codon is edited.

The output protein of the present disclosure may be any output protein desired. Examples of the output protein of the present disclosure include, without limitation, a fluorescent protein, a genomic modification protein, a transcription factor, a killing factor, a toxin, an antigen, a T cell receptor, an enzyme, a therapeutic protein, a cytokine, a chemokine, a growth factor, a signaling peptide, a chimeric antigen receptor (CAR), etc. The output proteins may be secreted, transmembrane or membrane-tethered. When output proteins are to be trafficked to specific locations within the biological sample then the coding sequence of the output protein is preceded by a nucleotide sequence encoding the appropriate signal peptide such as those described in Owji et al. (Eur J Cell Biol. 2018 August; 97(6):422-441).

When the output protein is a genomic modification protein, the genomic modification proteins may include, without limitation, CRE recombinase or variants thereof, meganucleases or variants thereof, Zinc-finger nucleases or variants thereof, CRISPR/Cas-9 nuclease or variants thereof, a modified Cas9 nickase fused to a reverse-transcriptase (i.e., genomic modification protein used in prime editing), TAL effector nucleases or variants thereof, etc. Methods of prime editing are known in the art and have been described in, for example, Scholefield et al (Gene Ther. 2021 August; 28(7-8):396-401) which is specifically incorporated by reference herein.

When the output protein is a transcription factor, the transcription factor may include, without limitation, jun, fos, max, mad, serum response factor (SRF), AP-1, AP2, myb, MyoD, myogenin, ETS-box containing proteins, TFE3, E2F, ATF1, ATF2, ATF3, ATF4, ZF5, NFAT, CREB, 5 HNF4, C/EBP, SP1, CCAAT-box binding proteins, interferon regulation factor (IRF-1), Wilms tumor protein, ETS-binding protein, STAT, GATA-box binding proteins, e.g., GAT A-3, and the forkhead family of winged helix proteins.

When the output protein is a killing factor, the killing factor may include, without limitation, tumor necrosis factor alpha (TNFa), Fas ligand (FasL), a caspase such as caspase 1, caspase 2, caspase 3, caspase 4, caspase 5, caspase 6, caspase 7, caspase 8, caspase 9, caspase 10, caspase 11, caspase 12, caspase 13 or a variant thereof, etc.

When the output protein is a therapeutic protein, the therapeutic protein of may include, without limitation, hormones and growth and differentiation factors including, without limitation, insulin, glucagon, growth hormone (GH), parathyroid hormone (PTH), growth hormone releasing factor (GHRF), follicle stimulating hormone (FSH), luteinizing hormone (LH), human chorionic gonadotropin (hCG), vascular endothelial growth factor (VEGF), angioproteinetins, angiostatin, granulocyte colony stimulating factor (GCSF), erythroproteinetin (EPO), connective tissue growth factor (CTGF), basic fibroblast growth factor (bFGF), acidic fibroblast growth factor (aFGF), epidermal growth factor (EGF), transforming growth factor .alpha. (TGFa), platelet-derived growth factor (PDGF), insulin growth factors I and II (IGF-1 and IGF-11), any one of the transforming growth factor 13-superfamily, including TGFI3, activins, inhibins, or any of the bone morphogenic proteins (BMP) including BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

When the output protein is a cytokine, the cytokine may include, without limitation IL-1-like, IL-1α, IL-1β, IL-1RA, IL-18, CD132, IL-2, IL-4, IL-7, IL-9, IL-13, CD1243, 132, IL-15, CD131, IL-3, IL-5, GM-CSF, IL-6-like, IL-6, IL-11, G-CSF, IL-12, LIF, OSM, IL-10-like, IL-10, IL-20, IL-14, IL-16, IL-17, IFN-α, IFN-β, IFN-γ, CD154, LT-β, TNF-α, TNF-β, 4-1BBL, APRIL, CD70, CD153, CD178, GITRL, LIGHT, OX40L, TALL-1, TRAIL, TWEAK, TRANCE, TGF-β1, TGF-β2, TGF-β3, Epo, Tpo, Flt-3L, SCF, M-CSF, MSP, etc.

When the output protein is a chemokine, the chemokine may include, without limitation XCL1, XCL2, CCL1, CCL2, CCL3, CCL4, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CXCL1, CXCL2, CXCL3, CXCL4, CXCL5, CXCL6, CXCL7, CXCL8, CXCL9, CXCL10, CXCL11, CXCL12, CXCL13, CXCL14, CX3CL1, etc.

In certain embodiments, when the output polypeptide is a CAR, the extracellular binding domain of the CAR has a single chain antibody. The single-chain antibody may be a monoclonal single-chain antibody, a chimeric single-chain antibody, a humanized single-chain antibody, a fully human single-chain antibody, and/or the like. In one non-limiting example, the single chain antibody is a single chain variable fragment (scFv). Suitable CAR extracellular binding domains include those described in Labanieh et al. (2018 *Nature Biomedical Engineering* 2:377-391) which is specifically incorporated by reference herein. In some embodiments, the extracellular binding domain of the CAR is a single-chain version (e.g., an scFv version) of an antibody approved by the United States Food and Drug Administration and/or the European Medicines Agency (EMA) for use as a therapeutic antibody, e.g., for inducing antibody-dependent cellular cytotoxicity (ADCC) of certain disease-associated cells in a patient, etc. Non-limiting examples of single-chain antibodies which may be employed when the protein of interest is a CAR include single-chain versions (e.g., scFv versions) of Adecatumumab, Ascrinvacumab, Cixutumumab, Conatumumab, Daratumumab, Drozitumab, Duligotumab, Durvalumab, Dusigitumab, Enfortumab, Enoticumab, Figitumumab, Ganitumab, Glembatumumab, Intetumumab, Ipilimumab, Iratumumab, Icrucumab, Lexatumumab, Lucatumumab, Mapatumumab, Narnatumab, Necitumumab, Nesvacumab, Ofatumumab, Olaratumab, Panitumumab, Patritumab, Pritumumab, Radretumab, Ramucirumab, Rilotumumab, Robatumumab, Seribantumab, Tarextumab, Teprotumumab, Tovetumab, Vantictumab, Vesencumab, Votumumab, Zalutumumab, Flanvotumab, Altumomab, Anatumomab, Arcitumomab, Bectumomab, Blinatumomab, Detumomab, Ibritumomab, Minretumomab, Mitumomab, Moxetumomab, Naptumomab, Nofetumomab, Pemtumomab, Pintumomab, Racotumomab, Satumomab, Solitomab, Taplitumomab, Tenatumomab, Tositumomab, Tremelimumab, Abagovomab, Igovomab, Oregovomab, Capromab, Edrecolomab, Nacolomab, Amatuximab, Bavituximab, Brentuximab, Cetuximab, Derlotuximab, Dinutuximab, Ensituximab, Futuximab, Girentuximab, Indatuximab, Isatuximab, Margetuximab, Rituximab, Siltuximab, Ublituximab, Ecromeximab, Abituzumab, Alemtuzumab, Bevacizumab, Bivatuzumab, Brontictuzumab, Cantuzumab, Cantuzumab, Citatuzumab, Clivatuzumab, Dacetuzumab, Demcizumab, Dalotuzumab, Denintuzumab, Elotuzumab, Emactuzumab, Emibetuzumab, Enoblituzumab, Etaracizumab, Farletuzumab, Ficlatuzumab, Gemtuzumab, Imgatuzumab, Inotuzumab, Labetuzumab, Lifastuzumab, Lintuzumab, Lorvotuzumab, Lumretuzumab, Matuzumab, Milatuzumab, Nimotuzumab, Obinutuzumab, Ocaratuzumab, Otlertuzumab, Onartuzumab, Oportuzumab, Parsatuzumab, Pertuzumab, Pinatuzumab, Polatuzumab, Sibrotuzumab, Simtuzumab, Tacatuzumab, Tigatuzumab, Trastuzumab, Tucotuzumab, Vandortuzumab, Vanucizumab, Veltuzumab, Vorsetuzumab, Sofituzumab, Catumaxomab, Ertumaxomab, Depatuxizumab, Ontuxizumab, Blontuvetmab, Tamtuvetmab, or an antigen-binding variant thereof.

The output protein may further include a tag to be used to detect the protein following its production. For instance, the tag may include, without limitation, a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like.

In some embodiments, the detecting is quantitative or qualitative. For instance, the detecting of the target RNA may be correlated with the quantity of the output protein produced. In some embodiments, the quantity of the output protein relative to the quantitative of target RNA may be linear. In some embodiments, the quantity of the output protein relative to the quantitative of target RNA may be logarithmic. The methods of the present disclosure are capable of quantitatively detecting changes in the expression of specific genes through the detection of the target RNA. For instance, the methods are capable of detecting about a 2 fold, 3 fold, 4 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 5000 fold, 10,000 fold, 50,000 fold, 100,000 fold, or greater than a 100,000 fold change in the target RNA.

Aspects of this disclosure include assaying for the presence of the output protein in a biological sample. In some embodiments, the assaying for the output protein may contain using immunoblotting. In some embodiments, the assaying contains using microscopy. When the assaying contains microscopy the output protein may be conjugated to a fluorescent or luminescent protein or the output protein may be a fluorescent or luminescent protein. In some embodiments, the assaying for the presence of the output protein contains using flow cytometry. When the assaying includes flow cytometry, fluorescence activating cell sorting may be used.

The methods of the present disclosure also contain combining the biological sample with the sensor RNA. The combining can be done using any convenient method known in the art. In some embodiments, the combining includes transfecting the biological sample with a recombinant vector containing the sensor RNA. When the biological sample is transfected with the recombinant vector, the recombinant vector includes, without limitation, a plasmid, a viral vector, a cosmid an artificial chromosome, etc. In some embodiments, the combining contains contacting the biological sample with a lipid nanoparticle containing the sensor RNA. Lipid nanoparticles has been described in the art such as Hou et al. (Nat Rev Mater. 2021; 6(12):1078-1094).

When transfection of a biological sample such as a cell is desired, vectors, such as plasmids viral vectors, cosmids or artificial chromosomes, may be employed to engineer the cell to express the sensor RNA, as desired. Protocols of interest include those described in published PCT application WO1999/041258, the disclosure of which protocols are herein incorporated by reference.

Depending on the nature of the cell and/or expression construct, protocols of interest may include electroporation, particle gun technology, calcium phosphate precipitation, direct microinjection, viral infection and the like. The choice of method is generally dependent on the type of cell being transformed and the circumstances under which the transformation is taking place (i.e., in vitro, ex vivo, or in vivo). A general discussion of these methods can be found in Ausubel, et al, Short Protocols in Molecular Biology, 3rd ed., Wiley & Sons, 1995. In some embodiments, lipofectamine and calcium mediated gene transfer technologies are used. After the subject nucleic acids have been introduced into a cell, the cell may be incubated, normally at 37° C., sometimes under selection, for a period of about 1-24 hours in order to allow for the expression of the sensor RNA. In mammalian target cells, a number of viral-based expression systems may be utilized to express the sensor RNA(s). In cases where an adenovirus is used as an expression vector, the sensor RNA sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the chimeric protein in infected hosts. (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see Bittner et al., Methods in Enzymol. 153:51-544 (1987)).

In some embodiments, the viral vector is a recombinant adeno-associated virus (AAV) vector. AAV vectors are DNA viruses of relatively small size that can integrate, in a stable and site specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The application of AAV as a vector for gene therapy has been rapidly developed in recent years. Wild-type AAV can infect, with a comparatively high titer, dividing or non-dividing cells, or tissues of mammal, including human, and also can integrate into in human cells at specific site (on the long arm of chromosome 19) (Kotin et al, Proc. Natl. Acad. Sci. U.S.A., 1990. 87: 2211-2215; Samulski et al, EMBO J., 1991. 10: 3941-3950 the disclosures of which are hereby incorporated by reference herein in their entireties). AAV vector without the rep and cap genes loses specificity of site-specific integration, but may still mediate long-term stable expression of exogenous genes. AAV vector exists in cells in two forms, wherein one is episomic outside of the chromosome; another is integrated into the chromosome, with the former as the major form. Moreover, AAV has not been found to be associated with any human disease, nor any change of biological characteristics arising from the integration has been observed. There are sixteen serotypes of AAV reported in literature, respectively named AAV1, AAV2, AAV3, AAV4, AAV5, AAV6, AAV7, AAV8, AAV9, AAV10, AAV11, AAV12, AAV13, AAV14, AAV15, and AAV16, wherein AAV5 is originally isolated from humans (Bantel-Schaal, and H. zur Hausen. Virology, 1984. 134: 52-63), while AAV1-4 and AAV6 are all found in the study of adenovirus (Ursula Bantel-Schaal, Hajo Delius and Harald zur Hausen. J. Viral., 1999. 73: 939-947).

AAV vectors may be prepared using any convenient methods. Adeno-associated viruses of any serotype are suitable (See, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p 5-14, Rudder Arnold, London, U K (2006); and D E Bowles, J E Rabinowitz, R J Samulski "The Genus Dependovirus" (J R Kerr, S F Cotmore. M E Bloom, R M Linden, C R Parrish, Eds.) p 15-23, Rudder Arnold, London, UK (2006), the disclosures of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Preparation of hybrid vectors is described in, for example, PCT Application No. PCTIUS2005/027091, the disclosure of which is herein incorporated by reference in its entirety. The use of viral vectors derived from the AAVs for transferring genes in vitro and in vivo has been described (See e.g., International Patent Application Publication Nos: 91/18088 and WO 93/09239; U.S. Pat. Nos. 4,797,368, 6,596,535, and 5,139,941; and European Patent No: 0488528, all of which are herein incorporated by reference in their entirety). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the invention are encapsidated into a virus particle (e.g., AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the invention includes a recombinant virus particle (recombinant because it contains a recombinant polynucleotide) comprising any of the vectors described herein. Methods of producing such particles are known in the art and are described in U.S. Pat. No. 6,596,535.

When the biological sample is transfected with a recombinant vector including the sensor RNA, the sensor RNA is operably linked to a promoter. Suitable promoters of the present disclosure include, without limitation, a SFFV promoter, a hEF1a, a CMV promotor or a variant thereof, an inducible promoter, a CMV-tetO promoter, a tissue or cell specific promoter, etc.

In some aspects of the present disclosure, the sensor RNA includes one or more MS2 hairpins. In some embodiments, the sensor RNA includes more than one MS2 hairpin. For example, the sensor RNA may include two or more, three or more, four or more, five or more, six or more, seven or more, eight or more, nine or more, ten more, or more than ten. In some aspects, the sensor RNA include one or more TAR RNA elements. For example, the sensor RNA may include two or more, three or more, four or more, five or more, six or more, seven or more, eight or more, nine or more, ten more, or more than ten. In some aspects, the sensor RNA include one or more BoxB stem-loop. For example, the sensor RNA may include two or more, three or more, four or more, five or more, six or more, seven or more, eight or more, nine or more, ten more, or more than ten. In some aspects, the sensor RNA includes MS2 hairpins and BoxB stem loops, MS2 hairpins and TAR RNA elements, or BoxB stem-loops and TAR RNA elements.

In some embodiments, the method of detecting a target RNA further contains combining the biological sample with an ADAR protein or a coding sequence thereof. The ADAR protein may be any ADAR protein from any species. For instance, the ADAR protein may include without limitation, an ADAR (ADAR1), an ADAR p110, an ADAR p150, an ADAR2, an engineered ADAR protein such as a protein containing a deaminase domain of ADAR2 or a variant thereof and a MS2 RNA binding protein (MCP), an engineered ADAR protein that lacks a nuclear localization sequence, an engineered ADAR protein containing a nuclear export sequence, an engineered ADAR protein containing one or more dsRNA binding domains from one or more distinct ADAR proteins, an engineered ADAR protein containing a TAR RNA binding protein, an engineered ADAR protein containing a Lambda N peptide, a split engineered ADAR protein wherein the N and C terminus of the deaminase domain are produced separately and the two halves binding to one another in the presence of the target RNA, etc. Suitable engineered ADAR proteins have been described in Katrekar et al. (Nat Methods. 2019 March; 16(3):239-242.), Biswas et al. (iScience. 2020 Jul. 24; 23(7):101318), Matthews et al. (Nat Struct Mol Biol. 2016 May; 23(5):426-33), Cox et al. (Science. 2017 Nov. 24; 358(6366):1019-1027) or Kuttan et al. (Proc Natl Acad Sci USA. 2012 Nov. 27; 109(48):E3295-304). Split engineered ADAR proteins are described in Katrekar et al. (Elife. 2022 Jan. 19; 11:e75555). When the sensor RNA contains a start codon in place of a stop codon, a particular ADAR protein may be used. In some embodiments, the ADAR protein is ADAR2 when the sensor RNA contains a start codon in place of a stop codon.

In some embodiments, RNA editing proteins other than ADARs are used. For instance, proteins of the apolipoprotein B mRNA editing enzyme, catalytic polypeptide-like (APOBEC) family may be used. Examples of suitable APOBEC proteins include, without limitation, APOBEC1, APOBEC2, APOBEC3A, APOBEC3B, APOBEC3C, APOBEC3D, APOBEC3F, APOBEC3G, APOBEC3H, APOBEC4, etc.

In some embodiments, the sensor RNA further contains a nucleotide sequence containing a cleavage domain followed by a nucleotide sequence encoding any of the ADAR proteins described above wherein the nucleotide sequence containing the cleavage domain is after the nucleotide sequence encoding the output protein. In some embodiments, an ADAR protein is used instead of a marker protein as the first nucleotide sequence.

In some embodiments, the sensor RNA further contains a nucleotide sequence encoding a second sensor nucleotide sequence that is reverse complementary to a second target RNA wherein the sensor nucleotide sequence contains a second stop codon wherein the sequences of the first and second target RNAs are different. In some embodiments, the stop codon that contains at least 1 base that is mismatched with the second target RNA sequence. In some embodiments, the sensor RNA further contains a nucleotide sequence encoding a second sensor nucleotide sequence that is reverse complementary to a second target RNA wherein the sensor nucleotide sequence contains a start codon. In some embodiments, the sensor RNA further contains a nucleotide sequence encoding a second sensor nucleotide sequence that is reverse complementary to a second target RNA wherein the sensor nucleotide sequence contains a non-start codon that can be edited to a start codon. In some embodiments, the stop, start or non-start codon contains at least 1 base that is mismatched with the second target RNA sequence. In some embodiments, the stop, start or non-start codon is contained with a stem-loop sequence contained in the second sensor nucleotide sequence. In some embodiments, the biological sample is combined with two or more sensor RNAs that detect two or more distinct target RNAs.

In some embodiments, the method of detecting a target RNA further contains combining the biological sample with a protein that specifically localizes the sensor RNA to the location of the target RNA. For examples, a protein that specifically localizes the sensor RNA to the location of the target RNA may be a dCas9 or a dCas13 protein that has a guide RNA directed to the genomic locus corresponding to the target RNA (in the case of dCas9) or the target RNA directly (in the case of dCas13). In some embodiments, the dCas9 or dCas13 is engineered to be linked to a MCP, a TAR RNA binding protein or a Lambda N peptide.

Methods for Expressing a Protein in a Target Cell

As summarized above, methods are provided for expressing a protein in a target cell, the methods including combining a cell with a sensor RNA as described above, wherein the target RNA is present in the target cell.

The target RNA to which the sensor RNA hybridizes is, in some instances, determined by the target cell. In some embodiments, the target cell is a cell that is in a particular disease state. In these instances, the target cell includes a target RNA that is specific to the disease state or is in a higher abundance in cells that are in a particular disease state such as a cancerous cell. The cell may be in any disease state. In some embodiments, the target cell is a particular cell type. In these instances, the target cell includes a target RNA that is specific to the cell type or is in a higher abundance in cells that are a particular cell type. The cell may be any cell type.

Cells of any origin are candidate cells for combining with a sensor RNA of the present disclosure. Non-limiting examples of candidate cell types include connective tissue elements such as fibroblast, skeletal tissue (bone and cartilage), skeletal, cardiac and smooth muscle, epithelial tissues (e.g., liver, lung, breast, skin, bladder and kidney), neural cells (glia and neurons), endocrine cells (adrenal, pituitary, pancreatic islet cells), bone marrow cells, melanocytes, and many different types of hematopoetic cells. Suitable cells can also be cells representative of a specific body tissue from a subject. The types of body tissues include, but are not limited, to blood, muscle, nerve, brain, heart, lung, liver, pancreas, spleen, thymus, esophagus, stomach, intestine, kidney, testis, ovary, hair, skin, bone, breast, uterus, bladder, spinal cord and various kinds of body fluids.

Cells suitable for use in a subject method include cells of a variety of subject hosts. Generally, such subject hosts are "mammals" or "mammalian", where these terms are used broadly to describe organisms which are within the class mammalia, including the orders carnivore (e.g., dogs and cats), rodentia (e.g., mice, guinea pigs and rats), and primates (e.g., humans, chimpanzees and monkeys). In many aspects, the subject host will be a human. In certain embodiments, the subject host is a plant.

In certain embodiments, the method for expressing a target protein in a target cell further includes combining the biological sample with an ADAR protein or a coding sequence thereof. The ADAR protein may be any ADAR protein from any species. For instance, the ADAR protein may include without limitation, an ADAR (ADAR1), an ADAR p110, an ADAR p150, an ADAR2, an engineered ADAR protein such as a protein including a deaminase domain of ADAR2 or a variant thereof and a MS2 RNA binding protein MCP, etc. Suitable engineered ADAR proteins have been described in Katrekar et al. (Nat Methods. 2019 March; 16(3):239-242.), Biswas et al. (iScience. 2020 Jul. 24; 23(7):101318), Matthews et al. (Nat Struct Mol Biol. 2016 May; 23(5):426-33), Cox et al. (Science. 2017 Nov. 24; 358(6366):1019-1027) or Kuttan et al. (Proc Natl Acad Sci USA. 2012 Nov. 27; 109(48):E3295-304).

The methods for expressing a protein in a target cell include combining the target cell with the sensor RNA. The combining can be done using any convenient method known in the art. In some embodiments, the combining includes transfecting the biological sample with a recombinant vector including the sensor RNA. When the biological sample is transfected with the recombinant vector, the recombinant vector includes, without limitation, a plasmid, a viral vector, a cosmid an artificial chromosome, etc. In some embodiments, the combining includes contacting the biological sample with a lipid nanoparticle including the sensor RNA. Lipid nanoparticles has been described in the art such as Hou et al. (Nat Rev Mater. 2021; 6(12):1078-1094).

When transfection of a biological sample such as a cell is desired, vectors, such as plasmids viral vectors, cosmids or artificial chromosomes, may be employed to engineer the cell to express the sensor RNA, as desired.

The protein expressed in the target cell is the output protein encoded by the sensor RNA. The output protein of the sensor RNA may be any of the output proteins described above. In some embodiments, the output protein treats the disease or condition associated with the target RNA in the target cell.

In some embodiments, the methods of the present disclosure can be used to produce a target protein in the absences of a cell. In these embodiments, a cell-free system includes the biological sample, the sensor RNA and the ADAR protein. The biological sample may include any target RNA. For example, the biological sample may be a sample including viral matter such as viral RNA wherein detection of the viral RNA leads to production of the output protein. Suitable cell-free systems include those described by Kuruma et al. (Nat Protoc. 2015 September; 10(9):1328-44) and Lavickova et al. (ACS Synth Biol. 2019 Feb. 15; 8(2):455-462).

Methods for Treating a Disease or Condition

Methods for expressing a protein in a target cell may also be used to treat an individual for a disease or a condition. In the methods disclosed herein, the protein for expression in a target cell may promote the survival of the target cell or may promote the death of the cell. For instance, if the disease or condition is associated with a cell that is infected by a pathogen or a cancer cell then it may be desirable for the promotion of the death of such cells. In embodiments in which the death of the target cell is desired, output protein encoded by the sensor RNA may be any output protein that promotes the death of the cell. Output protein that promote the death of the cell include, without limitation, a toxin, tumor necrosis factor alpha (TNFa), Fas ligand (FasL), a caspase such as caspase 1, caspase 2, caspase 3, caspase 4, caspase 5, caspase 6, caspase 7, caspase 8, caspase 9, caspase 10, caspase 11, caspase 12, caspase 13 or a variant thereof, etc.

In addition, if the disease or condition is associated with a cell that is infected by a pathogen or a cancer cell it may also be desirable to activate an immune cell to target the infected cell or cancer cell. Immune cells generally include white blood cells (leukocytes) which are derived from hematopoietic stem cells (HSC) produced in the bone marrow. Immune cells also include, e.g., lymphocytes (T cells, B cells, natural killer (NK) cells) and myeloid-derived cells (neutrophil, eosinophil, basophil, monocyte, macrophage, dendritic cells). T cells include all types of immune cells expressing CD3 including T-helper cells ($CD4^+$ cells), cytotoxic T-cells ($CD8^+$ cells), T-regulatory cells (Treg) and gamma-delta T cells. Cytotoxic cells include $CD8^+$ T cells, natural-killer (NK) cells, and neutrophils, which cells are capable of mediating cytotoxicity responses.

In embodiments in which the activation of immune cell is desired, the target RNA that the sensor RNA is directed to may be a target RNA that is specifically expressed in an immune cell. In embodiments in which the activation of immune cell is desired, the sensor RNA may contain a sequence that encodes an output protein that activates or modulates the activity of the immune cell. Non-limiting examples of output proteins that activate immune cells include a chimeric antigen receptor, such as those described above, or a cytokine such as IL-1-like, IL-1α, IL-10, IL-1RA, IL-18, CD132, IL-2, IL-4, IL-7, IL-9, IL-13, CD1243, 132, IL-15, CD131, IL-3, IL-5, GM-CSF, IL-6-like, IL-6, IL-11, G-CSF, IL-12, LIF, OSM, IL-10-like, IL-10, IL-20, IL-14, IL-16, IL-17, IFN-α, IFN-β, IFN-γ, CD154, LT-β, TNF-α, TNF-β, 4-1BBL, APRIL, CD70, CD153, CD178, GITRL, LIGHT, OX40L, TALL-1, TRAIL, TWEAK, TRANCE, TGF-β1, TGF-β2, TGF-β3, Epo, Tpo, Flt-3L, SCF, M-CSF, MSP, etc.

If the disease or condition is associated with the expression of a non-functional protein, a reduced functioning protein or a protein that has an aberrant activity in a disease state relative to a non-disease state then it may be desirable to have a sensor RNA that is targeted to the diseased cells where, upon contact with the diseased cell that contains the target RNA, the cell produces the output protein where the output protein is a fully functional form of the protein that is non-functioning, has reduced functionality or has aberrant functions.

If the disease or condition is associated with the degradation of a tissue it may be desirable to promote the growth or regrowth of said tissue. In embodiments in which the disease or condition is associated with tissue degradation it may be desirable to have a sensor RNA that is targeted to the diseased cells where, upon contact with the diseased cell that contains the target RNA, the cell produces the output protein that promotes the growth or regrowth of the tissue. Non-limiting examples of output proteins that promote the growth or regrowth of the tissue include hormones and growth and differentiation factors including, without limitation, insulin, glucagon, growth hormone (GH), parathyroid hormone (PTH), growth hormone releasing factor (GHRF), follicle stimulating hormone (FSH), luteinizing hormone (LH), human chorionic gonadotropin (hCG), vascular endothelial growth factor (VEGF), angioproteinetins, angiostatin, granulocyte colony stimulating factor (GCSF), erythroproteinetin (EPO), connective tissue growth factor (CTGF), basic fibroblast growth factor (bFGF), acidic fibroblast growth factor (aFGF), epidermal growth factor (EGF), transforming growth factor .alpha. (TGFa), platelet-derived growth factor (PDGF), insulin growth factors I and II (IGF-1 and IGF-11), any one of the transforming growth factor 13-superfamily, including TGFI3, activins, inhibins, or any of the bone morphogenic proteins (BMP) including BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Given the diversity of cellular activities that may be modulated through the use of the subject sensor RNA, the instant methods of treatment may be utilized for a variety of applications. As non-limiting examples, the instant methods may find use in a treatment directed to a variety of diseases including but not limited to e.g., *Acanthamoeba* infection, *Acinetobacter* infection, Adenovirus infection, ADHD (Attention Deficit/Hyperactivity Disorder), AIDS (Acquired Immune Deficiency Syndrome), ALS (Amyotrophic Lateral Sclerosis), Alzheimer's Disease, Amebiasis, Intestinal (*Entamoeba histolytica* infection), Anaplasmosis, Human, Anemia, *Angiostrongylus* Infection, Animal-Related Diseases, *Anisakis* Infection (Anisakiasis), Anthrax, Aortic Aneurysm, Aortic Dissection, Arenavirus Infection, Arthritis (e.g., Childhood Arthritis, Fibromyalgia, Gout, Lupus (SLE) (Systemic lupus erythematosus), Osteoarthritis, Rheumatoid Arthritis, etc.), *Ascaris* Infection (Ascariasis), *Aspergillus* Infection (Aspergillosis), Asthma, Attention Deficit/Hyperactivity Disorder, Autism, Avian Influenza, B virus Infection (Herpes B virus), *B. cepacia* infection (*Burkholderia cepacia* Infection), Babesiosis (*Babesia* Infection), Bacterial Meningitis, Bacterial Vaginosis (BV), *Balamuthia* infection (*Balamuthia mandrillaris* infection), *Balamuthia mandrillaris* infection, Balantidiasis, *Balantidium* Infection (Balantidiasis), *Baylisascaris* Infection, *Bilharzia*, Birth Defects, Black Lung (Coal Workers' Pneumoconioses), *Blastocystis hominis* Infection, *Blastocystis* Infection, Blastomycosis, Bleeding Disorders, Blood Disorders, Body Lice (*Pediculus humanus* corporis), *Borrelia burgdorferi* Infection, Botulism (*Clostridium* botulinim), Bovine Spongiform Encephalopathy (BSE), Brainerd Diarrhea, Breast Cancer, Bronchiolitis, Bronchitis, *Brucella* Infection (Brucellosis), Brucellosis, *Burkholderia cepacia* Infection (*B. cepacia* infection), *Burkholderia mallei, Burkholderia pseudomallei* Infection, *Campylobacter* Infection (Campylobacteriosis), Campylobacteriosis, Cancer (e.g., Colorectal (Colon) Cancer, Gynecologic Cancers, Lung Cancer, Prostate Cancer, Skin Cancer, etc.), *Candida* Infection (Candidiasis), Candidiasis, Canine Flu, Capillaria Infection (Capillariasis), Capillariasis, Carbapenem resistant *Klebsiella pneumonia* (CRKP), Cat Flea Tapeworm, Cercarial Dermatitis, Cerebral Palsy, Cervical Cancer, Chagas Disease (*Trypanosoma cruzi* Infection), Chickenpox (Varicella Disease), Chikungunya Fever (CHIKV), Childhood Arthritis, German Measles (Rubella Virus), Measles, Mumps, Rotavirus Infection, *Chlamydia* (*Chlamydia trachomatis* Disease), *Chlamydia pneumoniae* Infection, *Chlamydia trachomatis* Disease, Cholera (*Vibrio cholerae* Infection), Chronic Fatigue Syndrome (CFS), Chronic Obstructive Pulmonary Disease (COPD), Ciguatera Fish Poisoning, Ciguatoxin, Classic Creutzfeldt-Jakob Disease, Clonorchiasis, *Clonorchis* Infection (Clonorchiasis), *Clostridium* botulinim, *Clostridium difficile* Infection, *Clostridium perfringens* infection, *Clostridium tetani* Infection, Clotting Disorders, CMV (Cytomegalovirus Infection), Coal Workers' Pneumoconioses, Coccidioidomycosis, Colorectal (Colon) Cancer, Common Cold, Conjunctivitis, Cooleys Anemia, COPD (Chronic Obstructive Pulmonary Disease), *Corynebacterium diphtheriae* Infection, *Coxiella burnetii* Infection, Creutzfeldt-Jakob Disease, CRKP (Carbapenem resistant *Klebsiella pneumonia*), Crohn's Disease, Cryptococcosis, Cryptosporidiosis, *Cryptosporidium* Infection (Cryptosporidiosis), *Cyclospora* Infection (Cyclosporiasis), Cyclosporiasis, Cysticercosis, Cystoisospora Infection (Cystoisosporaiasis), Cystoisosporaiasis, Cytomegalovirus Infection (CMV), Dengue Fever (DF), Dengue Hemorrhagic Fever (DHF), Dermatophytes, Dermopathy, Diabetes, Diamond Blackfan Anemia (DBA), *Dientamoeba fragilis* Infection, Diphtheria (*Corynebacterium diphtheriae* Infection), Diphyllobothriasis, *Diphyllobothrium* Infection (Diphyllobothriasis), *Dipylidium* Infection, Dog Flea Tapeworm, Down Syndrome (Trisomy 21), Dracunculiasis, Dwarf Tapeworm (*Hymenolepis* Infection), *E. coli* Infection (*Escherichia coli* Infection), Ear Infection (Otitis Media), Eastern Equine Encephalitis (EEE), Ebola Hemorrhagic Fever, Echinococcosis, Ehrlichiosis, Elephantiasis, Encephalitis (Mosquito-Borne and Tick-Borne), *Entamoeba histolytica* infection, *Enterobius vermicularis* Infection, Enterovirus Infections (Non-Polio), Epidemic Typhus, Epilepsy, Epstein-Barr Virus Infection (EBV Infection), *Escherichia coli* Infection, Extensively Drug-Resistant TB (XDR TB), *Fasciola* Infection (Fascioliasis), *Fasciolopsis* Infection (Fasciolopsiasis), Fibromyalgia, Fifth Disease (Parvovirus B19 Infection), Flavorings-Related Lung Disease, Folliculitis, Food-Related Diseases, *Clostridium perfringens* infection, Fragile X Syndrome, *Francisella tularensis* Infection, Genital Candidiasis (Vulvovaginal Candidiasis (VVC)), Genital Herpes (Herpes Simplex Virus Infection), Genital Warts, German Measles (Rubella Virus), Giardia Infection (Giardiasis), Glanders (*Burkholderia mallei*), *Gnathostoma* Infection, Gnathostomiasis (*Gnathostoma* Infection), Gonorrhea (*Neisseria gonorrhoeae* Infection), Gout, Granulomatous amebic encephalitis (GAE), Group A Strep Infection (GAS) (Group A Streptococcal Infection), Group B Strep Infection (GBS) (Group B Streptococcal Infection), Guinea Worm Disease (Dracunculiasis), Gynecologic Cancers (e.g., Cervical Cancer, Ovarian Cancer, Uterine Cancer, Vaginal and Vulvar Cancers, etc.), H1N1 Flu, *Haemophilus influenzae* Infection (Hib Infection), Hand, Foot, and Mouth Disease (HFMD), Hansen's Disease, Hantavirus Pulmonary Syndrome (HPS), Head Lice (*Pediculus humanus* capitis), Heart Disease (Cardiovascular Health), Heat Stress, Hemochromatosis, Hemophilia, Hendra Virus Infection, Herpes B virus, Herpes Simplex Virus Infection, Heterophyes Infection (Heterophyiasis), Hib Infection (*Haemophilus influenzae* Infection), High Blood Pressure, *Histoplasma capsulatum* Disease, Histoplasmosis (*Histoplasma capsulatum* Disease), Hot Tub Rash (*Pseudomonas* dermatitis Infection), HPV Infection (Human Papillomavirus Infection), Human Ehrlichiosis, Human Immunodeficiency Virus, Human Papillomavirus Infection (HPV Infection), *Hymenolepis* Infection, Hypertension, Hyperthermia, Hypothermia, Impetigo, Infectious Mononucleosis, Inflammatory Bowel Disease (IBD), Influenza, Avian Influenza, H1N1 Flu, Pandemic Flu, Seasonal Flu, Swine Influenza, Invasive Candidiasis, Iron Overload (Hemochromatosis), *Isospora* Infection (Isosporiasis), Japanese Encephalitis, Jaundice, *K. pneumoniae* (*Klebsiella pneumoniae*), Kala-Azar, Kawasaki Syndrome (KS), Kernicterus, *Klebsiella pneumoniae* (*K. pneumoniae*), La Crosse Encephalitis (LAC), La Crosse Encephalitis virus (LACV), Lassa Fever, Latex Allergies, Lead Poisoning, Legionnaires' Disease (Legionellosis), *Leishmania* Infection (Leishmaniasis), Leprosy, Leptospira Infection (Leptospirosis), Leptospirosis, Leukemia, Lice, *Listeria* Infection (Listeriosis), Listeriosis, Liver Disease and Hepatitis, *Loa* Infection, Lockjaw, Lou Gehrig's Disease, Lung Cancer, Lupus (SLE) (Systemic lupus erythematosus), Lyme Disease (*Borrelia burgdorferi* Infection), Lymphatic Filariasis, Lymphedema, Lymphocytic Choriomeningitis (LCMV), Lymphogranuloma venereum Infection (LGV), Malaria, Marburg Hemorrhagic Fever, Measles, Melioidosis (*Burkholderia pseudomallei* Infection), Meningitis (Meningococcal Disease), Meningococcal Disease, Methicillin Resistant *Staphylococcus aureus* (MRSA), Micronutrient Malnutrition, Microsporidia Infection, Molluscum Contagiosum, Monkey B virus, Monkeypox, Morgellons, Mosquito-Borne Diseases, Mucormycosis, Multidrug-Resistant TB (MDR TB), Mumps, *Mycobacterium abscessus* Infection, *Mycobacterium avium* Complex (MAC), *Mycoplasma pneumoniae* Infection, Myiasis, *Naegleria* Infection (Primary Amebic Meningoencephalitis (PAM)), Necrotizing Fasciitis, Neglected Tropical Diseases (NTD), *Neisseria gonorrhoeae* Infection, Neurocysticercosis, New Variant Creutzfeldt-Jakob Disease, Newborn Jaundice (Kernicterus), Nipah Virus Encephalitis, Nocardiosis, Non-Polio Enterovirus Infections, Nonpathogenic (Harmless) Intestinal Protozoa, Norovirus Infection, Norwalk-like Viruses (NLV), Novel H1N1 Flu, Onchocerciasis, *Opisthorchis* Infection, Oral Cancer, Orf Virus, Oropharyngeal Candidiasis (OPC), Osteoarthritis (OA), Osteoporosis, Otitis Media, Ovarian Cancer, Pandemic Flu, Paragonimiasis, *Paragonimus* Infection (Paragonimiasis), Parasitic Diseases, Parvovirus B19 Infection, *Pediculus humanus* capitis, *Pediculus humanus* corporis, Pelvic Inflammatory Disease (PID), Peripheral Arterial Disease (PAD), Pertussis, Phthiriasis, Pink Eye (Conjunctivitis), Pinworm Infection (*Enterobius vermicularis* Infection), Plague (*Yersinia pestis* Infection), *Pneumocystis jirovecii* Pneumonia, Pneumonia, Polio Infection (Poliomyelitis Infection), Pontiac Fever, Prion Diseases (Transmissible spongiform encephalopathies (TSEs)), Prostate Cancer, *Pseudomonas* dermatitis Infection, Psittacosis, Pubic Lice (Phthiriasis), Pulmonary Hypertension, Q Fever (*Coxiella burnetii* Infection), Rabies, Raccoon Roundworm Infection (*Baylisascaris* Infection), Rat-Bite Fever (RBF) (*Streptobacillus moniliformis* Infection), Recreational Water Illness (RWI), Relapsing Fever, Respiratory Syncytial Virus Infection (RSV), Rheumatoid Arthritis (RA), *Rickettsia rickettsii* Infection, Rift Valley Fever (RVF), Ringworm (Dermatophytes), Ringworm in Animals, River Blindness (Onchocerciasis), Rocky Mountain Spotted Fever (RMSF) (*Rickettsia rickettsii* Infection), Rotavirus Infection, RVF (Rift Valley Fever), RWI (Recreational Water Illness), *Salmonella* Infection (*Salmonellosis*), Scabies, Scarlet Fever, Schistosomiasis (*Schistosoma* Infection), Seasonal Flu, Severe Acute Respiratory Syndrome, Sexually Transmitted Diseases (STDs) (e.g., Bacterial Vaginosis (BV), *Chlamydia*, Genital Herpes, Gonorrhea, Human Papillomavirus Infection, Pelvic Inflammatory Disease, Syphilis, Trichomoniasis, HIV/AIDS, etc.), *Shigella* Infection (Shigellosis), Shingles (Varicella Zoster Virus (VZV)), Sickle Cell Disease, Single Gene Disorders, Sinus Infection (Sinusitus), Skin Cancer, Sleeping Sickness (African Trypanosomiasis), Smallpox (Variola Major and Variola Minor), Sore Mouth Infection (Orf Virus), Southern Tick-Associated Rash Illness (STARI), Spina *Bifida* (Myelomeningocele), Sporotrichosis, Spotted Fever Group *Rickettsia* (SFGR), St. Louis Encephalitis, *Staphylococcus aureus* Infection, *Streptobacillus moniliformis* Infection, Streptococcal Diseases, *Streptococcus pneumoniae* Infection, Stroke, *Strongyloides* Infection (Strongyloidiasis), Sudden Infant Death Syndrome (SIDS), Swimmer's Itch (Cercarial Dermatitis), Swine Influenza, Syphilis (*Treponema pallidum* Infection), Systemic lupus erythematosus, Tapeworm Infection (*Taenia* Infection), Testicular Cancer, Tetanus Disease (*Clostridium tetani* Infection), Thrush (Oropharyngeal Candidiasis (OPC)), Tickborne Relapsing Fever, Tickborne Diseases (e.g., Anaplasmosis, Babesiosis, Ehrlichiosis, Lyme Disease, Tourette Syndrome (TS), Toxic Shock Syndrome (TSS), Toxocariasis (*Toxocara* Infection), Toxoplasmosis (*Toxoplasma* Infection), Trachoma Infection, Transmissible spongiform encephalopathies (TSEs), Traumatic Brain Injury (TBI), Trichinellosis (Trichinosis), Trichomoniasis (*Trichomonas* Infection), Tuberculosis (TB) (*Mycobacterium tuberculosis* Infection), Tularemia (*Francisella tularensis* Infection), Typhoid Fever (*Salmonella typhi* Infection), Uterine Cancer, Vaginal and Vulvar Cancers, Vancomycin-Intermediate/Resistant *Staphylococcus aureus* Infections (VISA/VRSA), Vancomycin-resistant Enterococci Infection (VRE), Variant Creutzfeldt-Jakob Disease (vCJD), Varicella-Zoster Virus Infection, Variola Major and Variola Minor, *Vibrio cholerae* Infection, *Vibrio parahaemolyticus* Infection, *Vibrio vulnificus* Infection, Viral Gastroenteritis, Viral Hemorrhagic Fevers (VHF), Viral Hepatitis, Viral Meningitis (Aseptic Meningitis), Von Willebrand Disease, Vulvovaginal Candidiasis (VVC), West Nile Virus Infection, Western Equine Encephalitis Infection, Whipworm Infection (Trichuriasis), Whitmore's Disease, Whooping Cough, Xenotropic Murine Leukemia Virus-related Virus Infection, Yellow Fever, *Yersinia pestis* Infection, Yersiniosis (*Yersinia enterocolitica* Infection), Zoonotic Hookworm, Zygomycosis, and the like.

In some instances, methods of treatment utilizing one or more sensor RNAs of the instant disclosure may find use in treating a cancer. Cancers, the treatment of which may include the use of one or more proteolytically cleavable polypeptides of the instant disclosure, will vary and may include but are not limited to e.g., Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, etc.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sézary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenström Macroglobulinemia, Wilms Tumor, and the like.

Compositions

Also compositions for practicing the methods are described in the present disclosure. In general, subject compositions may have sensor RNA as described above in addition to a pharmaceutically acceptable excipient. In some embodiments, the subject compositions contain a secondary agent for treating any of the diseases or conditions described above.

Compositions of the present disclosure can be administered by any suitable means, including topical, oral, parenteral, intrapulmonary, and intranasal. Parenteral infusions include intramuscular, intravenous (bolus or slow drip), intraarterial, intraperitoneal, intrathecal or subcutaneous administration. An agent can be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the disclosure, by such means as depot injections or erodible implants.

As noted above, sensor RNA can be formulated with an a pharmaceutically acceptable carrier (one or more organic or inorganic ingredients, natural or synthetic, with which a subject agent is combined to facilitate its application). A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

The composition may be administered in a unit dosage form and may be prepared by any methods well known in the art. Such methods include combining agent with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Depending on the individual and condition being treated and on the administration route, the active agent may be administered in dosages of 0.01 mg to 500 mg/kg body weight per day, e.g., about 20 mg/day for an average person. Dosages will be appropriately adjusted for pediatric formulation.

In some embodiments, the composition is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the composition may further include a preservative. Suitable preservatives include, but are not limited to, a benzyl alcohol, phenol, chlorobutanol, benzalkonium chloride, and the like. In many cases, the composition is stored at about 4° C. Pharmaceutical compositions may also be lyophilized, in which case they generally include cryoprotectants such as sucrose, trehalose, lactose, maltose, mannitol, and the like. Lyophilized formulations can be stored over extended periods of time, even at ambient temperatures.

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The compositions of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

As described above, the composition may also contain a secondary agent for treatment of any of the diseases or condition described above. When the disease or condition is cancer, the secondary agent may be a chemotherapeutic agent. Chemotherapeutic agents that find use in the present disclosure include, without limitation, Abitrexate (Methotrexate Injection), Abraxane (Paclitaxel Injection), Adcetris (Brentuximab Vedotin Injection), Adriamycin (Doxorubicin), Adrucil Injection (5-FU (fluorouracil)), Afinitor (Everolimus), Afinitor Disperz (Everolimus), Alimta (PEMET EXED), Alkeran Injection (Melphalan Injection), Alkeran Tablets (Melphalan), Aredia (Pamidronate), Arimidex (Anastrozole), Aromasin (Exemestane), Arranon (Nelarabine), Arzerra (Ofatumumab Injection), Avastin (Bevacizumab), Bexxar (Tositumomab), BiCNU (Carmustine), Blenoxane (Bleomycin), Bosulif (Bosutinib), Busulfex Injection (Busulfan Injection), Campath (Alemtuzumab), Camptosar (Irinotecan), Caprelsa (Vandetanib), Casodex (Bicalutamide), CeeNU (Lomustine), CeeNU Dose Pack (Lomustine), Cerubidine (Daunorubicin), Clolar (Clofarabine Injection), Cometriq (Cabozantinib), Cosmegen (Dactinomycin), CytosarU (Cytarabine), Cytoxan (Cytoxan), Cytoxan Injection (Cyclophosphamide Injection), Dacogen (Decitabine), DaunoXome (Daunorubicin Lipid Complex Injection), Decadron (Dexamethasone), DepoCyt (Cytarabine Lipid Complex Injection), Dexamethasone Intensol (Dexamethasone), Dexpak Taperpak (Dexamethasone), Docefrez (Docetaxel), Doxil (Doxorubicin Lipid Complex Injection), Droxia (Hydroxyurea), DTIC (Decarbazine), Eligard (Leuprolide), Ellence (Ellence (epirubicin)), Eloxatin (Eloxatin (oxaliplatin)), Elspar (Asparaginase), Emcyt (Estramustine), Erbitux (Cetuximab), Erivedge (Vismodegib), Erwinaze (Asparaginase *Erwinia chrysanthemi*), Ethyol (Amifostine), Etopophos (Etoposide Injection), Eulexin (Flutamide), Fareston (Toremifene), Faslodex (Fulvestrant), Femara (Letrozole), Firmagon (Degarelix Injection), Fludara (Fludarabine), Folex (Methotrexate Injection), Folotyn (Pralatrexate Injection), FUDR (FUDR (floxuridine)), Gemzar (Gemcitabine), Gilotrif (Afatinib), Gleevec (Imatinib Mesylate), Gliadel Wafer (Carmustine wafer), Halaven (Eribulin Injection), Herceptin (Trastuzumab), Hexalen (Altretamine), Hycamtin (Topotecan), Hycamtin (Topotecan), Hydrea (Hydroxyurea), lclusig (Ponatinib), Idamycin PFS (Idarubicin), Ifex (Ifosfamide), Inlyta (Axitinib), Intron A alfab (Interferon alfa-2a), Iressa (Gefitinib), Istodax (Romidepsin Injection), Ixempra (Ixabepilone Injection), Jakafi (Ruxolitinib), Jevtana (Cabazitaxel Injection), Kadcyla (Ado-trastuzumab Emtansine), Kyprolis (Carfilzomib), Leukeran (Chlorambucil), Leukine (Sargramostim), Leustatin (Cladribine), Lupron (Leuprolide), Lupron Depot (Leuprolide), Lupron DepotPED (Leuprolide), Lysodren (Mitotane), Marqibo Kit (Vincristine Lipid Complex Injection), Matulane (Procarbazine), Megace (Megestrol), Mekinist (Trametinib), Mesnex (Mesna), Mesnex (Mesna Injection), Metastron (Strontium-89 Chloride), Mexate (Methotrexate Injection), Mustargen (Mechlorethamine), Mutamycin (Mitomycin), Myleran (Busulfan), Mylotarg (Gemtuzumab Ozogamicin), Navelbine (Vinorelbine), Neosar Injection (Cyclophosphamide Injection), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Oncaspar (Pegaspargase), Oncovin (Vincristine), Ontak (Denileukin Diftitox), Onxol (Paclitaxel Injection), Panretin (Alitretinoin), Paraplatin (Carboplatin), Perjeta (Pertuzumab Injection), Platinol (Cisplatin), Platinol (Cisplatin Injection), PlatinolAQ (Cisplatin), PlatinolAQ (Cisplatin Injection), Pomalyst (Pomalidomide), Prednisone Intensol (Prednisone), Proleukin (Aldesleukin), Purinethol (Mercaptopurine), Reclast (Zoledronic acid), Revlimid (Lenalidomide), Rheumatrex (Methotrexate), Rituxan (Rituximab), RoferonA alfaa (Interferon alfa-2a), Rubex (Doxorubicin), Sandostatin (Octreotide), Sandostatin LAR Depot (Octreotide), Soltamox (Tamoxifen), Sprycel (Dasatinib), Sterapred (Prednisone), Sterapred DS (Prednisone), Stivarga (Regorafenib), Supprelin LA (Histrelin Implant), Sutent (Sunitinib), Sylatron (Peginterferon Alfa-2b Injection (Sylatron)), Synribo (Omacetaxine Injection), Tabloid (Thioguanine), Taflinar (Dabrafenib), Tarceva (Erlotinib), Targretin Capsules (Bexarotene), Tasigna (Decarbazine), Taxol (Paclitaxel Injection), Taxotere (Docetaxel), Temodar (Temozolomide), Temodar (Temozolomide Injection), Tepadina (Thiotepa), Thalomid (Thalidomide), TheraCys BCG (BCG), Thioplex (Thiotepa), TICE BCG (BCG), Toposar (Etoposide Injection), Torisel (Temsirolimus), Treanda (Bendamustine hydrochloride), Trelstar (Triptorelin Injection), Trexall (Methotrexate), Trisenox (Arsenic trioxide), Tykerb (lapatinib), Valstar (Valrubicin Intravesical), Vantas (Histrelin Implant), Vectibix (Panitumumab), Velban (Vinblastine), Velcade (Bortezomib), Vepesid (Etoposide), Vepesid (Etoposide Injection), Vesanoid (Tretinoin), Vidaza (Azacitidine), Vincasar PFS (Vincristine), Vincrex (Vincristine), Votrient (Pazopanib), Vumon (Teniposide), Wellcovorin IV (Leucovorin Injection), Xalkori (Crizotinib), Xeloda (Capecitabine), Xtandi (Enzalutamide), Yervoy (Ipilimumab Injection), Zaltrap (Ziv-aflibercept Injection), Zanosar (Streptozocin), Zelboraf (Vemurafenib), Zevalin (Ibritumomab Tiuxetan), Zoladex (Goserelin), Zolinza (Vorinostat), Zometa (Zoledronic acid), Zortress (Everolimus), Zytiga (Abiraterone), Nimotuzumab and immune checkpoint inhibitors such as nivolumab, pembrolizumab/MK-3475, pidilizumab and AMP-224 targeting PD-1; and BMS-935559, MEDI4736, MPDL3280A and MSB0010718C targeting PD-L1 and those targeting CTLA-4 such as ipilimumab.

When the disease or condition is associated with an infection, the secondary agent may be an antibiotic. Antibiotics that find use in the present disclosure include, without limitation, antibiotics with the classes of aminoglycosides; carbapenems; and the like; penicillins, e.g. penicillin G, penicillin V, methicillin, oxacillin, carbenicillin, nafcillin, ampicillin, etc. penicillins in combination with β-lactamase inhibitors, cephalosporins, e.g. cefaclor, cefazolin, cefuroxime, moxalactam, etc.; tetracyclines; cephalosporins; quinolones; lincomycins; macrolides; sulfonamides; glycopeptides including the anti-infective antibiotics vancomycin, teicoplanin, telavancin, ramoplanin and decaplanin. Derivatives of vancomycin include, for example, oritavancin and dalbavancin (both lipoglycopeptides). Telavancin is a semi-synthetic lipoglycopeptide derivative of vancomycin (approved by FDA in 2009). Other vancomycin analogs are disclosed, for example, in WO 2015022335 A1 and Chen et al. (2003) PNAS 100(10): 5658-5663, each herein specifically incorporated by reference. Non-limiting examples of antibiotics include vancomycin, linezolid, azithromycin, daptomycin, colistin, eperezolid, fusidic acid, rifampicin, tetracyclin, fidaxomicin, clindamycin, lincomycin, rifalazil, and clarithromycin.

Kits

Also provided are kits for practicing the methods described in the present disclosure. In general, subject kits may contain a sensor RNA as described above. The sensor RNA may be contained in a lipid nanoparticle or the sensor RNA may be within a recombinant vector as described above. In some cases, the kit further contains an ADAR protein or a coding sequence thereof. When the kit contains a coding sequence of the ADAR it may be in a recombinant vector as described above. When the kit contains the ADAR protein or the coding sequence thereof, the ADAR protein may be any ADAR protein described above.

In some cases, the kit may further contain a positive and/or negative control. The positive control may be in the form of a biological sample containing the target RNA, a sensor RNA containing an edited codon (i.e., a stop codon that has been edited to be a non-stop codon or a start codon edited to be a non-start codon or a non-start codon edited to be a start codon) or a sensor RNA containing the nucleotide sequence of the target RNA. The negative control may be in the form of a biological sample that does not contain the target RNA.

A subject kit can include any combination of components for performing the methods of the present disclosure. The components of a subject kit can be present as a mixture or can be separate entities. In some cases, components are present as a lyophilized mixture. In some cases, the components are present as a liquid mixture. Components of a subject kit can be in the same or separate containers, in any combination.

The subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a remote site.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1

A RADAR sensor is inspired by recent advances in RNA editing (Katrekar, D. et al. (2019) *Nat. Methods* 16, 239-242; Qu, L. et al. (2019) *Nat. Biotechnol.* 37, 1059-1069; Merkle, T. et al. (2019) *Nat. Biotechnol.* 37, 133-138; Reautschnig, P. et al. (2022) *Nat. Biotechnol.* 1-10), and consists of three parts (FIG. 1A): a marker coding sequence; a sensor sequence reverse complementary to the target RNA of interest ("trigger" or "target"), but with an editing-enhancing C:A mismatch at a central UAG stop codon (alternative pairings could be used); and an output coding sequence. The stop codon prevents the translation of the output CDS so that only the marker (e.g., mCherry) is expressed. In the presence of the trigger, double-stranded RNA (dsRNA) is formed, which recruits ADAR to edit the adenosine (A) in the UAG to an inosine (I), enabling the translation of the downstream CDS (e.g., EGFP). "Self-cleaving" 2A sequences (Loughran, G. et al. (2017) *RNA N. Y. N* 23, 1285-1289) insulate the flanking CDSs from the variable sensing sequence. We first focused our efforts on 3' untranslated regions (UTRs) for finding trigger sequences, because, compared to those in CDS, they do not encounter translating ribosomes which may affect or be affected by the dsRNA, and any changes that occur in the 3' UTR as a result of unintentional ADAR editing are less likely to cause detrimental outcomes. Most human (57%) and mouse (73%) genes have a 90 bp trigger candidate for at least one reported Y UTR variant.

Figure 1B:
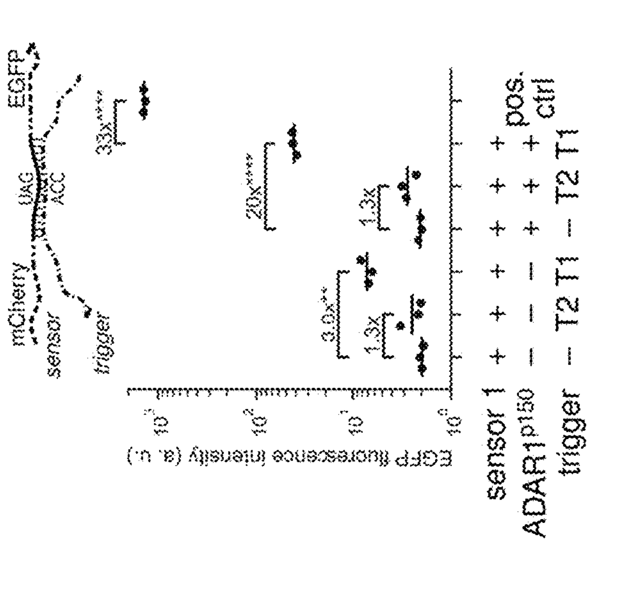
Figure 1C:
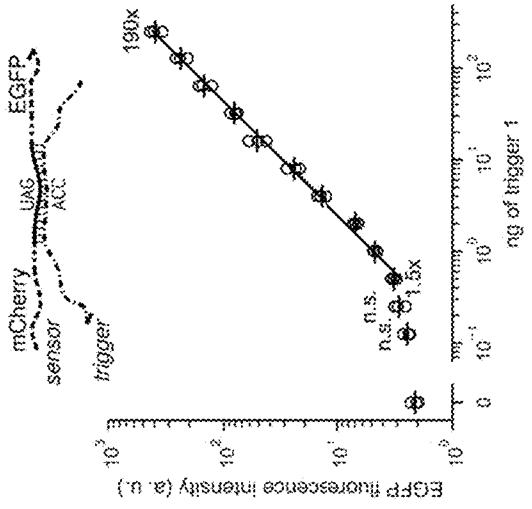
Figure 1D:
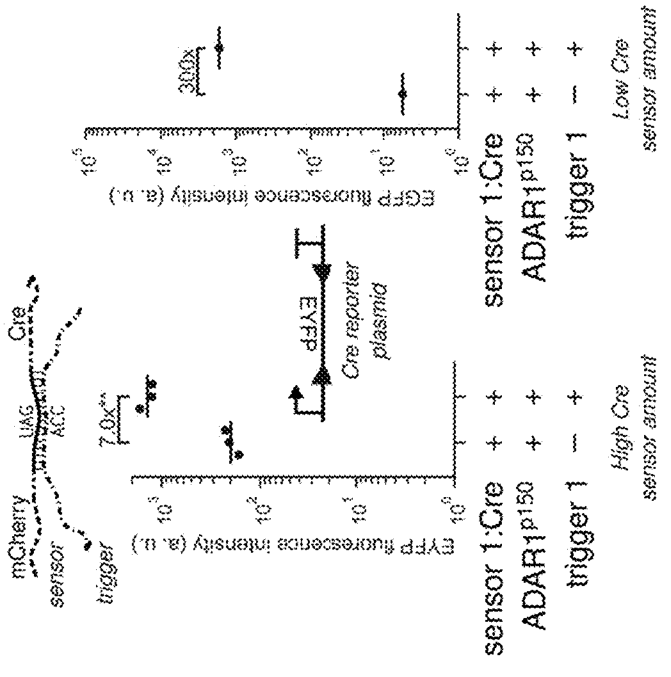

We first verified RADAR in human embryonic kidney (HEK) cells using a de novo designed trigger, T1, embedded in the 3' UTR of a cotransfected gene (FIG. 1B). Corresponding sensor S1 output depends on ADAR, and is enhanced the most by the p150 isoform of ADAR1 (FIG. 1B, FIGS. 3D-3G). We determined that S1 output is a strongly correlated, approximately linear function of T1 plasmid input across two orders of magnitude (FIG. 1C). RADAR output is modular, as we could utilize the Cre recombinase, a useful tool in neurobiology (Luo, L. et al. (2018) *Neuron* 98, 256-281), as an alternative output (FIG. 1D).

Figures 1E, 1F:
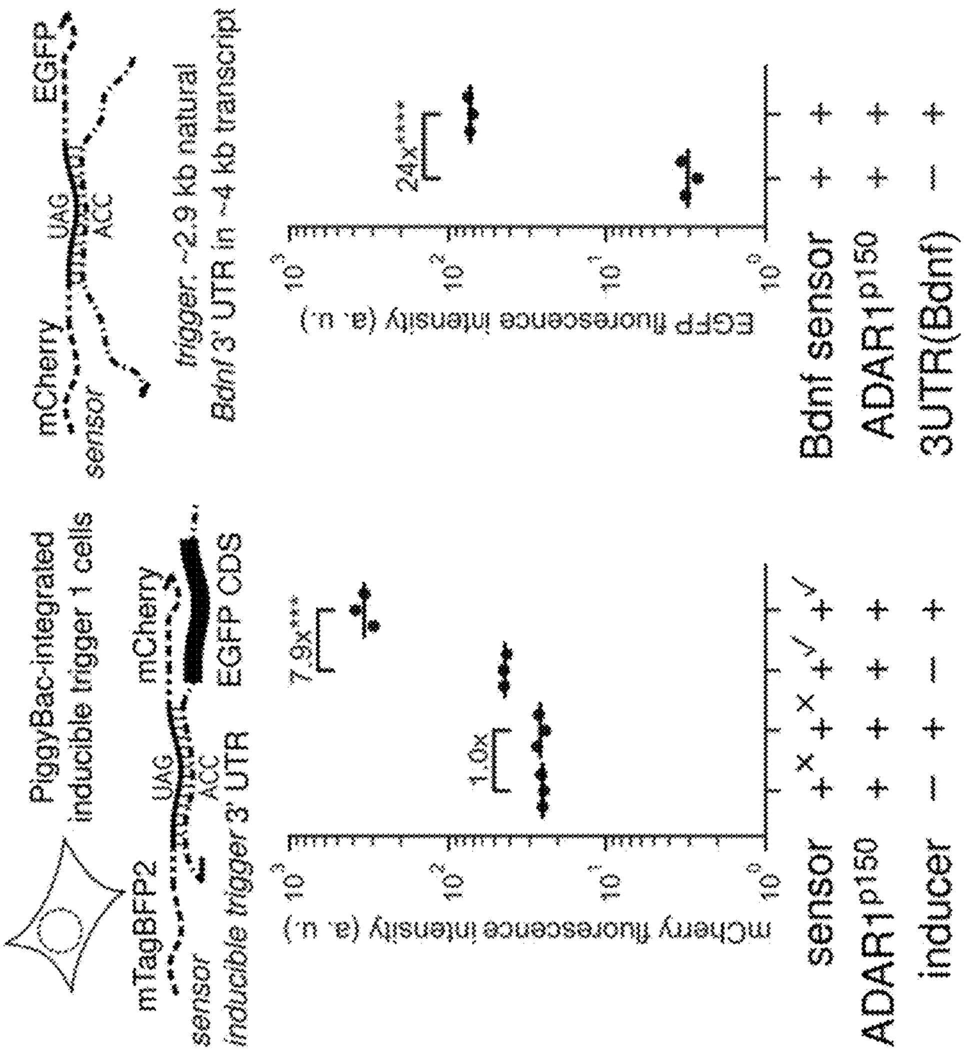
Figure 1G:
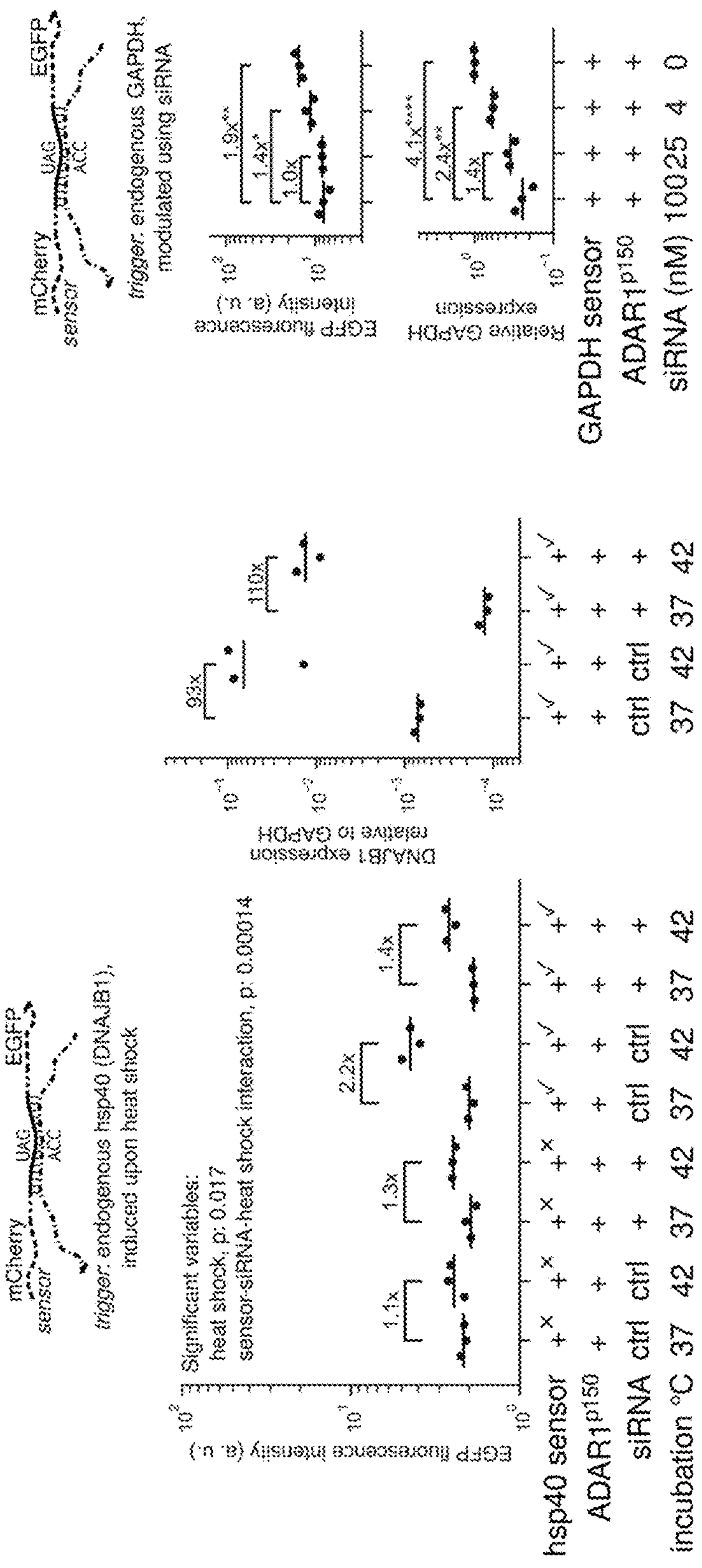
Figure 4E:
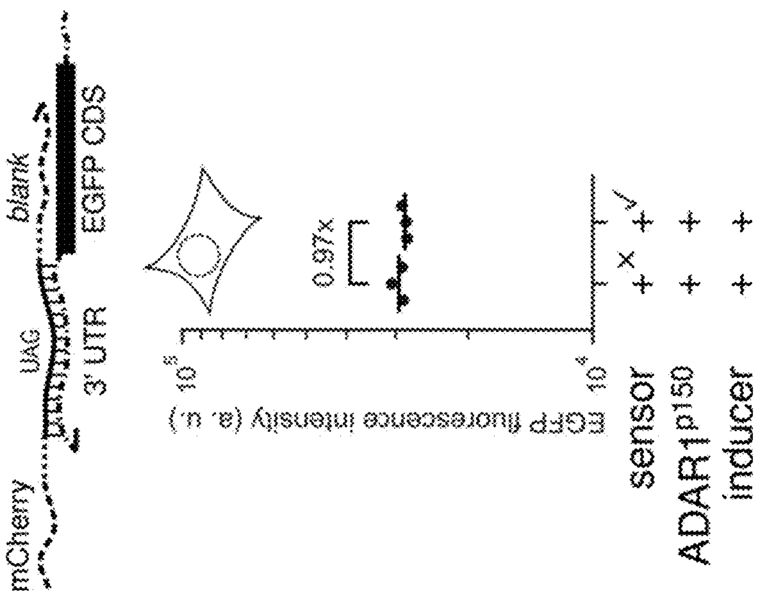

We then validated RADAR in scenarios closer to eventual use cases. First, in addition to transiently delivered trigger plasmids, we saw increased output in response to doxycyclineinduced expression of T1 embedded in the 3' UTR of a genomically integrated EGFP (FIG. 1E). EGFP levels were not negatively impacted by the presence of S1 (FIG. 4E). Second, to test whether our design functions in the complex context of a natural 3' UTR, we designed a sensor SBdnf for a subsequence within the 2.9 kb 3' UTR of murine Bdnf, taking advantage of the mouse-human orthogonality for unambiguous testing. We observed a significant response from SBdnf to the Bdnf 3' UTR expressed in HEK cells (FIG. 1F). Finally, we investigated a sensor for the 3' UTR of DNAJB1, a member of the hsp40 heat shock response protein family. While the sensor for T1 was unaffected, the SDNAJB1 output significantly increased upon heat shock (FIG. 1G), suggesting that SDNAJB1 specifically detects endogenous DNAJB1 expression. We further evaluated a sensor for GAPDH, showing how the sensor for it can detect changes to GAPDH levels upon siRNA knockdown (FIG. 1G).

Figure 1H:
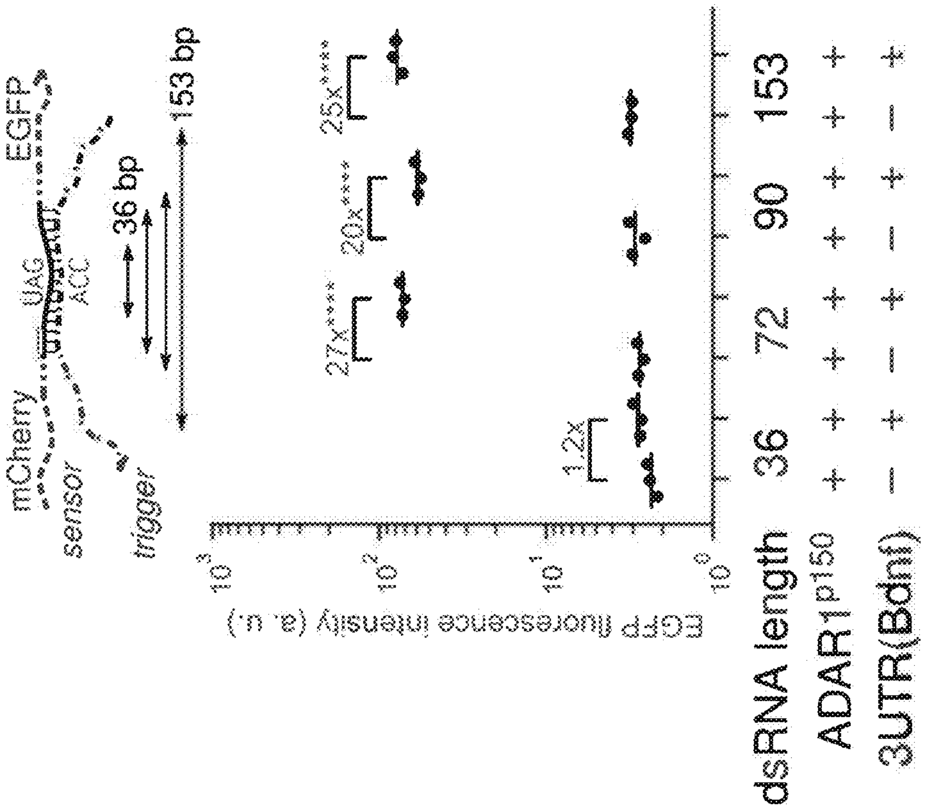
Figure 1J:
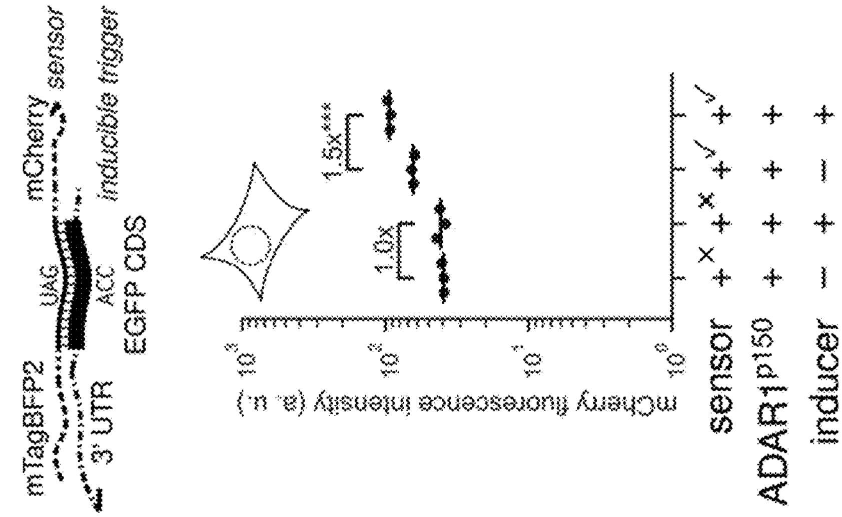
Figure 1I:
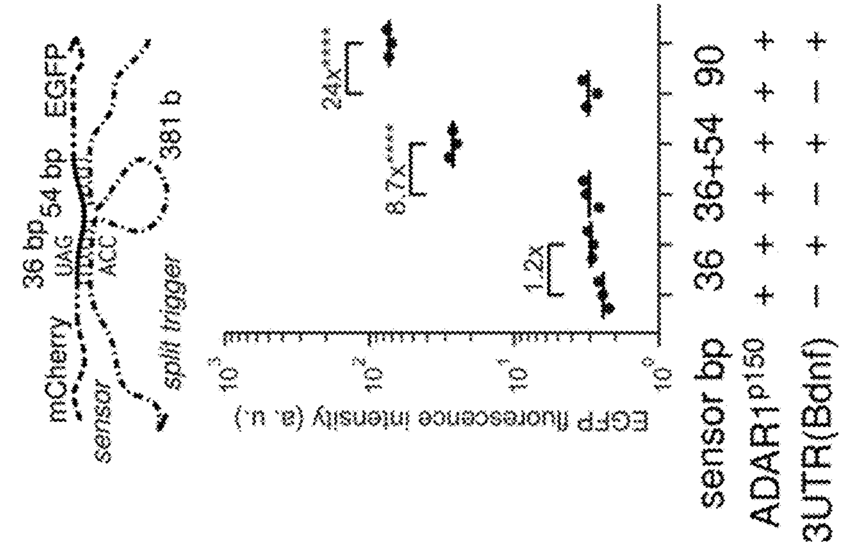
Figure 4F:
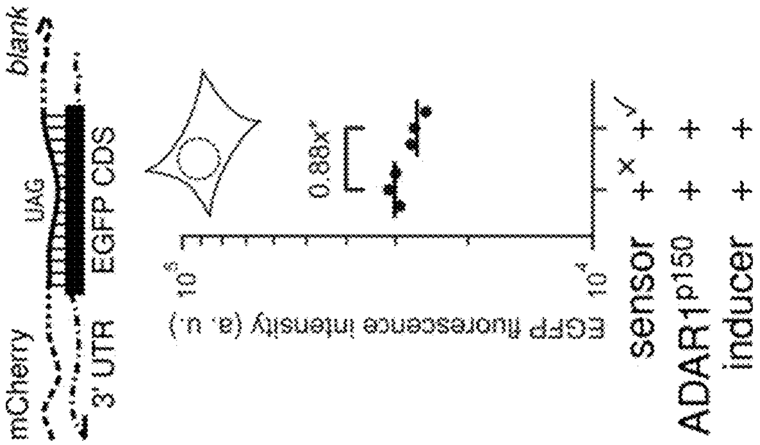

We then explored strategies for expanding the coverage of the human/mouse transcriptome. First, using the 3' UTR of Bdnf, we observed that RADAR performance was largely maintained down to 72 bp dsRNA (FIG. 1H). Second, inspired by work showing that ADAR enzymes are tolerant of or even benefited by disruptions in the target dsRNA (Uzonyi, A. et al. (2021) *Mol. Cell*), we validated that we could rescue the signal from the non-functional 36 bp sensor if we introduced an additional 54 bp sequence complementary to another part of the long Bdnf 3' UTR, constituting a "split" design (FIG. 1I). Such a split design offers great flexibility for several scenarios: to skip over undesired reverse-complement stop codons, to skip over complex secondary structures, miRNA binding sites, or other functional features of the trigger RNA, to distinguish between homologs where the sequence containing CCA is shared, but unique regions exist elsewhere, and to detect gene fusions and alternatively spliced transcripts where the unique junction is not amenable to direct sensing (no CCA within the proximity of the junction). Finally, we validated that a sensor for the CDS of EGFP (SEGFP) showed a significant response to trigger induction (FIG. 1J), albeit less ideal than 3' UTR sensors (FIGS. 4D-4F), offering an alternative when necessary but also reaffirming our initial prioritization of 3' UTRs.

Figure 1K:
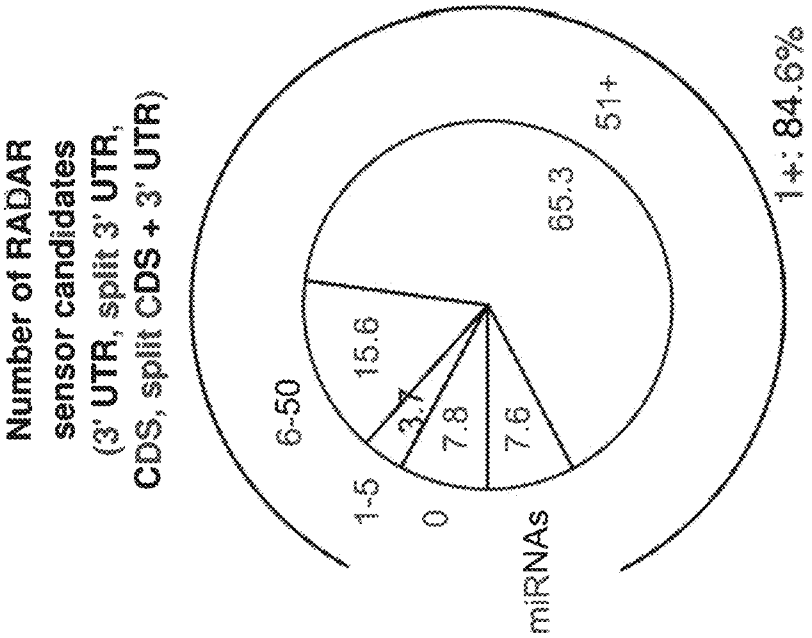
Figure 4G:
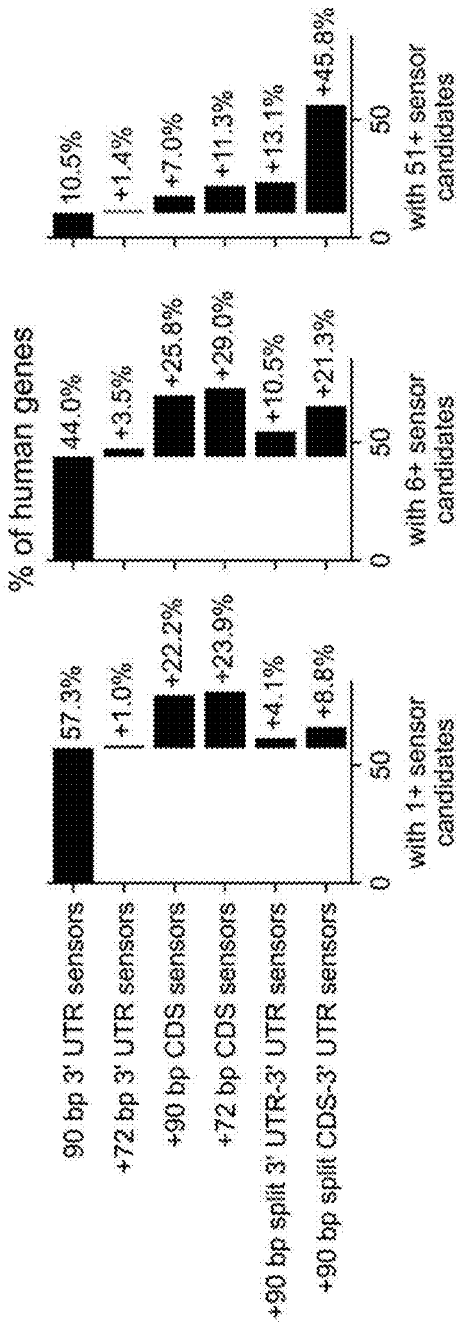
Figure 4H:
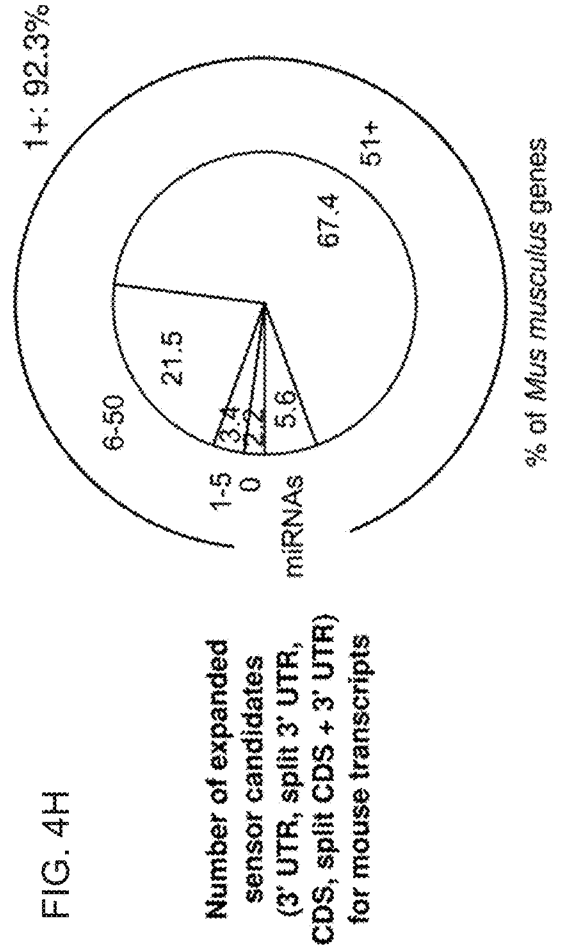

Combining the ability of shortening the sensor, using a split design, and sensing CDSs, >85% of human (FIG. 1K, FIG. 4G) and mouse (FIG. 4H) genes have at least one candidate trigger sequence compatible with RADAR.

Figure 1L:
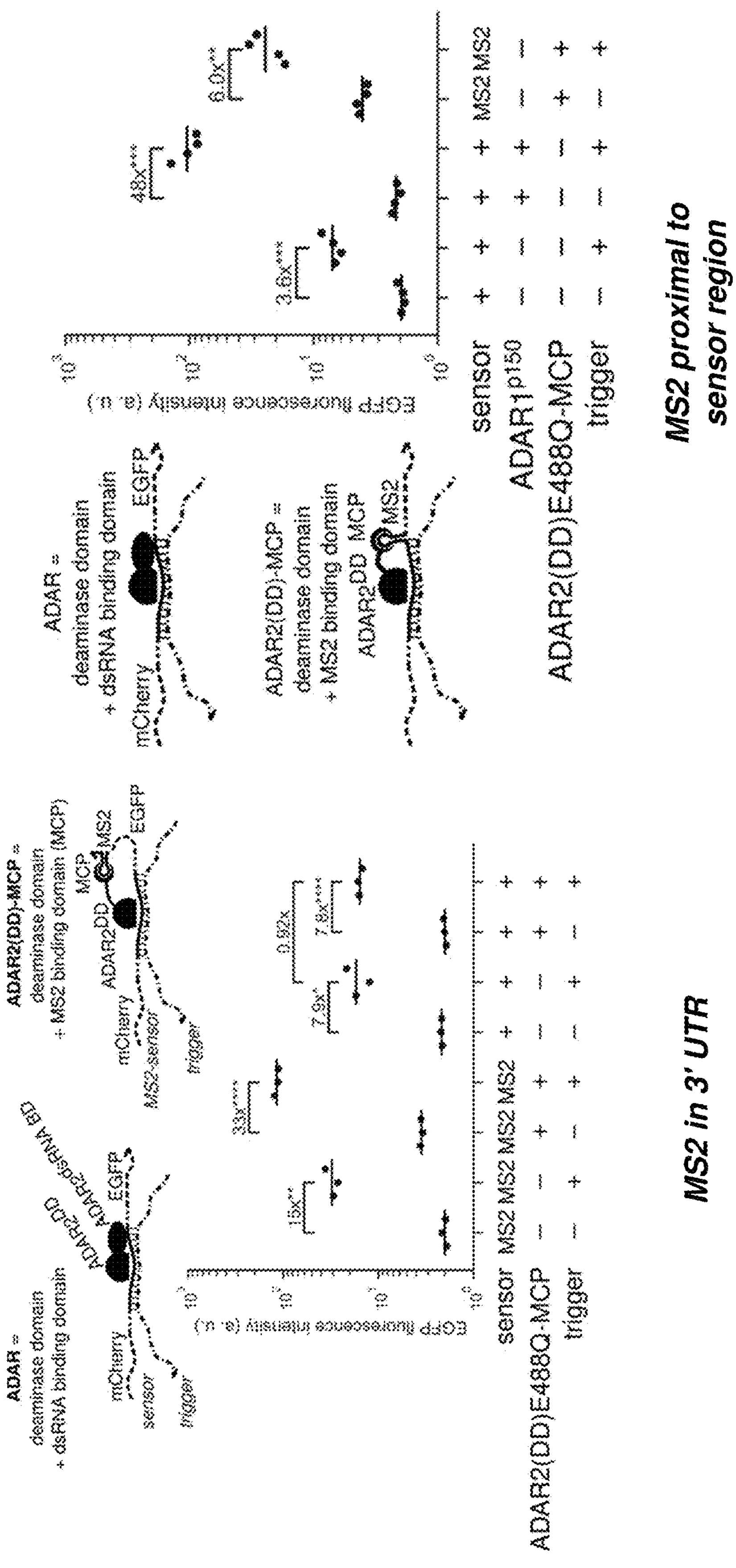

While ADAR over-expression greatly improves RADAR's dynamic range, it may have detrimental side effects. To ameliorate this potential problem, we utilized an engineered version of ADAR, containing only a mutant deaminase domain of ADAR2 and the MS2 RNA binding protein MCP ("ADAR(DD)-MCP")(Katrekar, D. et al. (2019) *Nat. Methods* 16, 239-242; Biswas, J. et al. (2020) *iScience* 23, 101318). Combining this enzyme with MS2-bearing sensors, we achieved a dynamic range similar to ADAR1p150 over-expression (FIG. 1L). Crucially, ADAR (DD)-MCP did not affect the original MS2-lacking sensor (FIG. 1L), suggesting that this "orthogonal" ADAR is less likely to edit endogenous dsRNA structures.

Figures 2A, 2B, 2C:
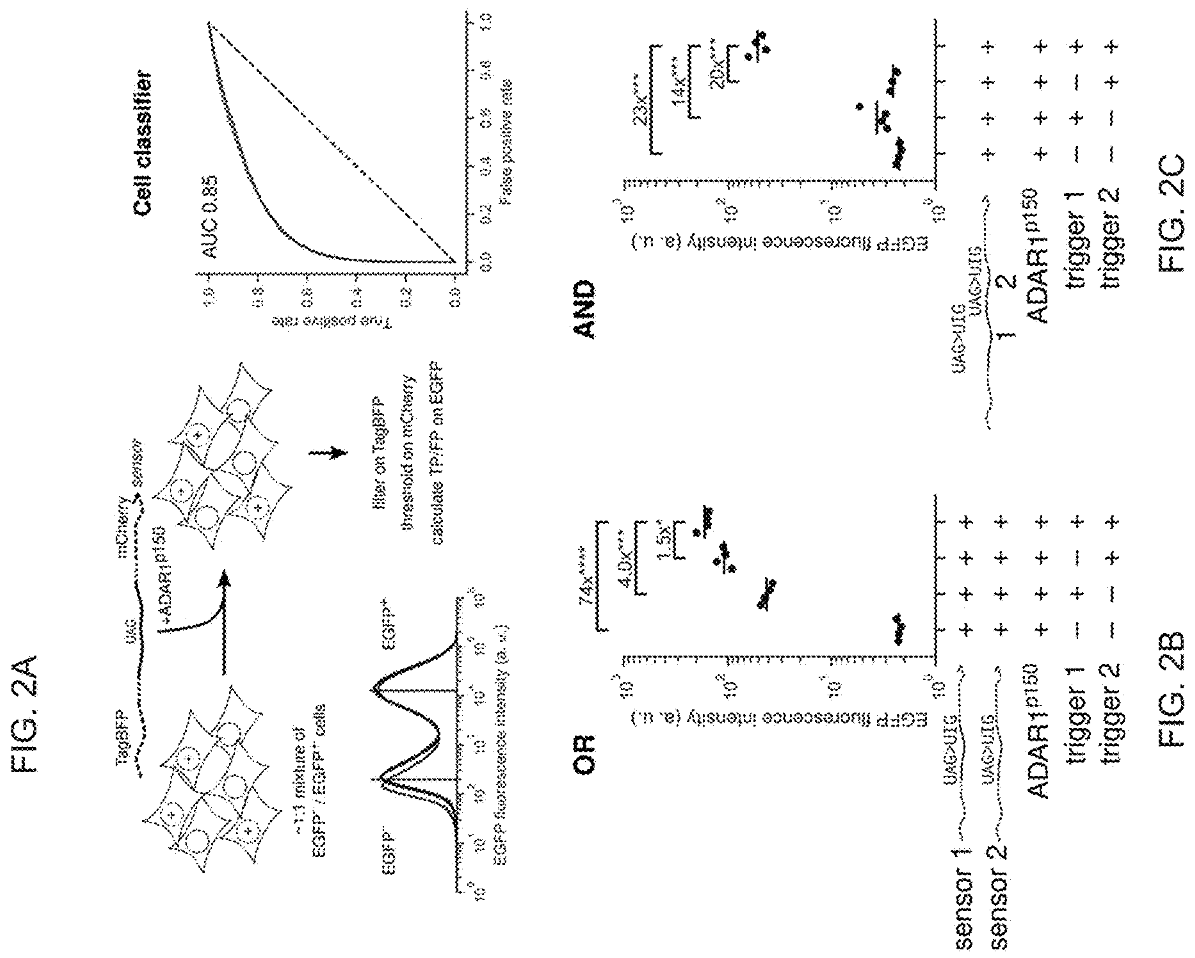
FIGS. 2A-2E. Unique features and potential applications of RADAR. 2A) A cell classifier that performs consistently in triplicates. 2B) OR logic. 2C) AND logic. 2D) RADAR distinguishes dinucleotide and single nucleotide variants. 2E) RADAR functions in plants. Images from a representative plant.

RADAR has several unique features and potential applications. For example, RADAR can be used for cell classification (FIG. 2A). RADAR can also integrate multiple inputs using OR and logic (FIGS. 2B-2C); for the latter, two sensor sequences can be straightforwardly concatenated such that both stop codons have to be edited for output expression.

Figure 4I:
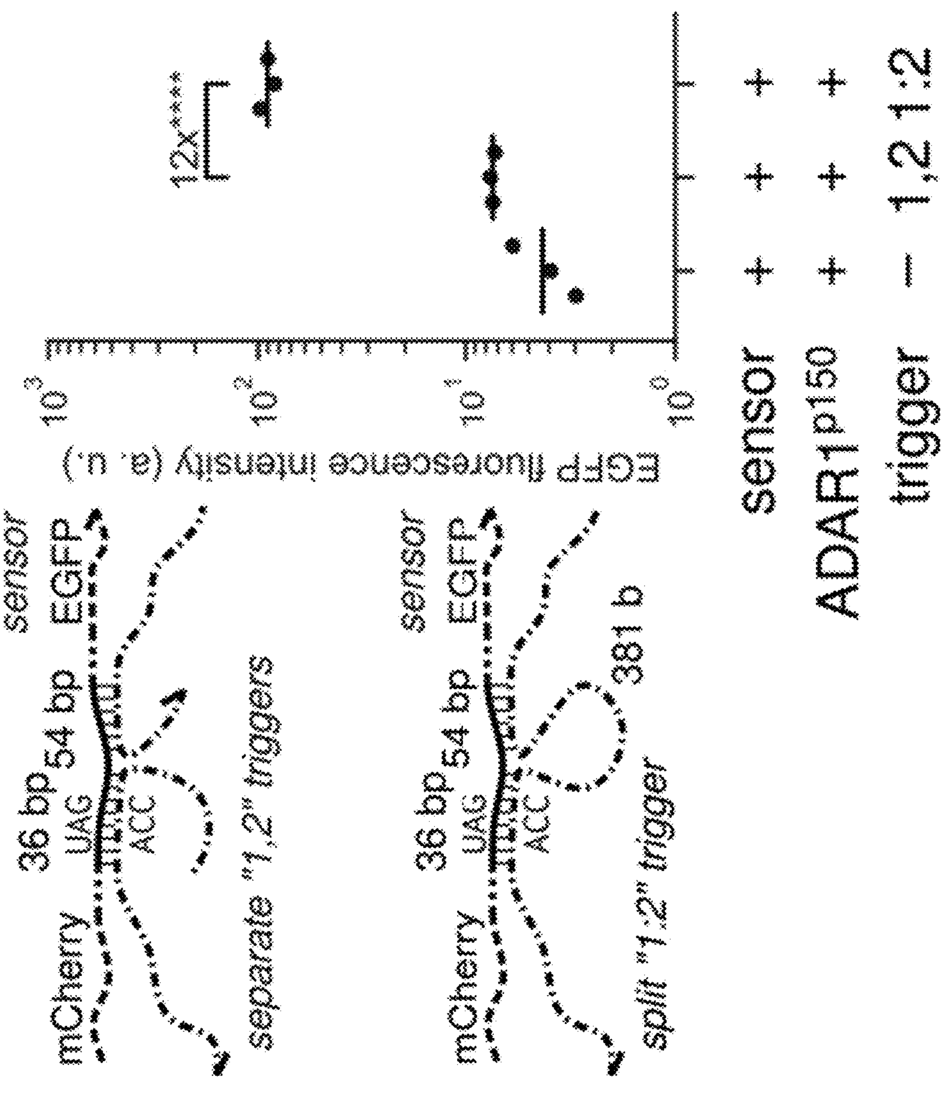
Figure 5:
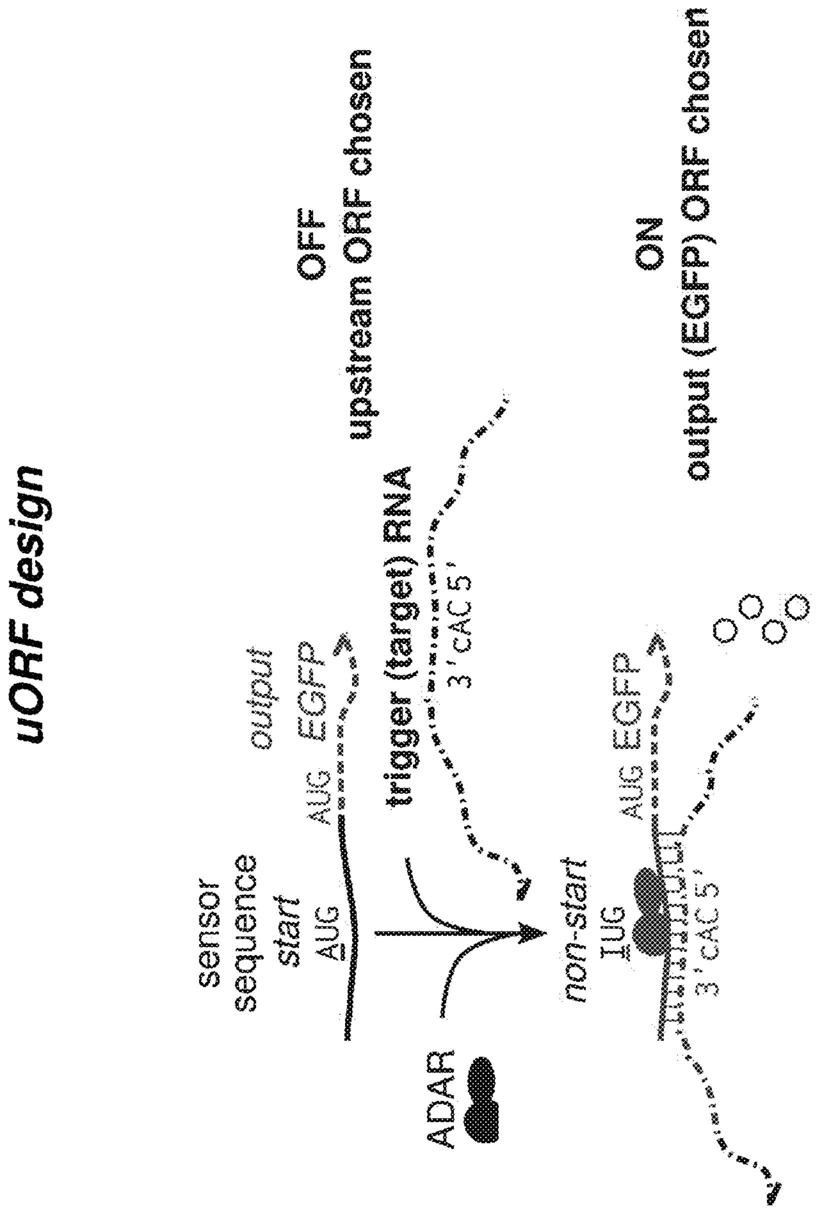
FIG. 5 depicts an exemplary sensor RNA containing an editable start codon.

Cell states, especially in medical contexts, are often defined by not only the expression level of RNAs but also the presence of new RNA sequences. We leveraged RADAR's unique features to sense the latter. First, as ADAR is sensitive to the base identities surrounding the edited adenosine (Qu, L. et al. (2019) *Nat. Biotechnol.* 37, 1059-1069), RADAR is uniquely suitable for distinguishing certain short genetic variants. As a demonstration, we validated a sensor that distinguishes two common oncogenic mutations of TP53 associated with different invasive traits in cancer cells (Yoshikawa, K. et al. (2010) *Biomed. Res.* 31, 401-411) (FIG. 2D) as well as a single base distinguisher (FIG. 2D). ~5% of known or likely pathogenic variants reported in ClinVar can potentially be distinguished from their wild type alleles using RADAR. Second, as gene fusions drive many cancers (Gao, Q. et al. (2018) *Cell Rep.* 23, 227-238.e3), the split design provides a method to sense such fusions. We verified that the sensor is more responsive to split trigger sequences present on the same transcript compared to the same trigger sequences on separate transcripts (FIG. 4I), suggesting the feasibility of fusion-specific sensors.

TABLE 2

Figure 2D:
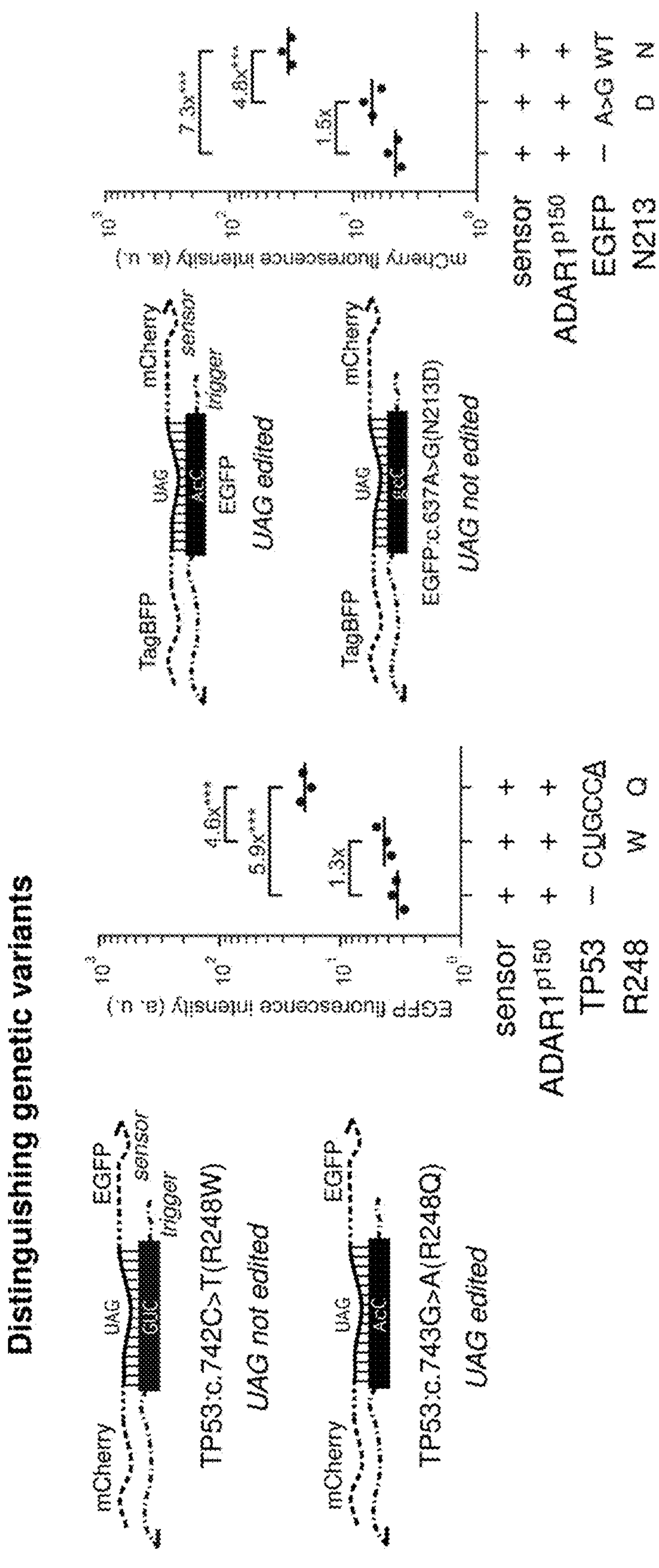

Variant pairs that have an on/off ratio of 10 shown in FIG. 2D

| on | off | pair | ratio | edit_distance |
|---|---|---|---|---|
| GCA | CGG | GCA/CGG | 191.4 | 3 |
| TCA | CGG | TCA/CGG | 186.48 | 3 |
| TTA | CGG | TTA/CGG | 176.7 | 3 |
| GTA | CGG | GTA/CGG | 171.53 | 3 |
| GCA | AAG | GCA/AAG | 171.3 | 3 |
| GAA | CGG | GAA/CGG | 169.02 | 3 |
| TAA | CGG | TAA/CGG | 168.92 | 3 |
| GCA | AAC | GCA/AAC | 168.02 | 3 |
| TCA | AAG | TCA/AAG | 166.9 | 3 |
| TCA | AAC | TCA/AAC | 163.7 | 3 |
| TTA | AAG | TTA/AAG | 158.15 | 3 |
| TTA | AAC | TTA/AAC | 155.12 | 3 |
| GTA | AAG | GTA/AAG | 153.51 | 3 |

TABLE 2-continued

Variant pairs that have an on/off ratio of 10 shown in FIG. 2D

| on | off | pair | ratio | edit_distance |
|---|---|---|---|---|
| GAA | AAG | GAA/AAG | 151.27 | 2 |
| TAA | AAG | TAA/AAG | 151.18 | 2 |
| GTA | AAC | GTA/AAC | 150.58 | 3 |
| CAA | CGG | CAA/CGG | 150.48 | 2 |
| GAA | AAC | GAA/AAC | 148.38 | 2 |
| TAA | AAC | TAA/AAC | 148.29 | 2 |
| GCA | TGC | GCA/TGC | 147.23 | 3 |
| GCA | ATC | GCA/ATC | 144.31 | 3 |
| TCA | TGC | TCA/TGC | 143.44 | 2 |
| GCA | AGG | GCA/AGG | 143.21 | 3 |
| GCA | ATG | GCA/ATG | 140.94 | 3 |
| TCA | ATC | TCA/ATC | 140.6 | 3 |
| TCA | AGG | TCA/AGG | 139.53 | 3 |
| TCA | ATG | TCA/ATG | 137.31 | 3 |
| GCA | TGG | GCA/TGG | 136.03 | 3 |
| TTA | TGC | TTA/TGC | 135.92 | 2 |
| CAA | AAG | CAA/AAG | 134.68 | 2 |
| TTA | ATC | TTA/ATC | 133.23 | 2 |
| GCA | CGT | GCA/CGT | 132.75 | 3 |
| TCA | TGG | TCA/TGG | 132.53 | 2 |
| TTA | AGG | TTA/AGG | 132.22 | 3 |
| CAA | AAC | CAA/AAC | 132.1 | 2 |
| GTA | TGC | GTA/TGC | 131.94 | 3 |
| GCA | TAG | GCA/TAG | 131.44 | 3 |
| TTA | ATG | TTA/ATG | 130.12 | 2 |
| GAA | TGC | GAA/TGC | 130.01 | 3 |
| TAA | TGC | TAA/TGC | 129.93 | 2 |
| TCA | CGT | TCA/CGT | 129.33 | 3 |
| GTA | ATC | GTA/ATC | 129.32 | 2 |
| GTA | AGG | GTA/AGG | 128.34 | 3 |
| TCA | TAG | TCA/TAG | 128.06 | 2 |
| GAA | ATC | GAA/ATC | 127.43 | 3 |
| TAA | ATC | TAA/ATC | 127.36 | 3 |
| GAA | AGG | GAA/AGG | 126.47 | 3 |
| TAA | AGG | TAA/AGG | 126.39 | 3 |
| GTA | ATG | GTA/ATG | 126.3 | 2 |
| TTA | TGG | TTA/TGG | 125.59 | 2 |
| GGA | CGG | GGA/CGG | 124.47 | 2 |
| GAA | ATG | GAA/ATG | 124.46 | 3 |
| TAA | ATG | TAA/ATG | 124.38 | 3 |
| TTA | CGT | TTA/CGT | 122.55 | 3 |
| CCA | CGG | CCA/CGG | 122.45 | 2 |
| GCA | ACG | GCA/ACG | 122.45 | 2 |
| GTA | TGG | GTA/TGG | 121.91 | 3 |
| TTA | TAG | TTA/TAG | 121.35 | 2 |
| GAA | TGG | GAA/TGG | 120.13 | 3 |
| TAA | TGG | TAA/TGG | 120.05 | 2 |
| TCA | ACG | TCA/ACG | 119.3 | 2 |
| GTA | CGT | GTA/CGT | 118.96 | 3 |
| CGA | CGG | CGA/CGG | 118.44 | 1 |
| GTA | TAG | GTA/TAG | 117.79 | 3 |
| GAA | CGT | GAA/CGT | 117.22 | 3 |
| TAA | CGT | TAA/CGT | 117.15 | 3 |
| GAA | TAG | GAA/TAG | 116.07 | 2 |
| TAA | TAG | TAA/TAG | 116 | 1 |
| CAA | TGC | CAA/TGC | 115.75 | 3 |
| CAA | ATC | CAA/ATC | 113.46 | 3 |
| TTT | CGG | TTT/CGG | 113.3 | 3 |
| TTA | ACG | TTA/ACG | 113.05 | 3 |
| CAA | AGG | CAA/AGG | 112.6 | 3 |
| GGA | AAG | GGA/AAG | 111.4 | 3 |
| CAA | ATG | CAA/ATG | 110.81 | 3 |
| GTA | ACG | GTA/ACG | 109.73 | 3 |
| CCA | AAG | CCA/AAG | 109.59 | 3 |
| GGA | AAC | GGA/AAC | 109.27 | 3 |
| GAA | ACG | GAA/ACG | 108.13 | 3 |
| TAA | ACG | TAA/ACG | 108.07 | 3 |
| CCA | AAC | CCA/AAC | 107.49 | 3 |
| CAA | TGG | CAA/TGG | 106.95 | 3 |
| CGA | AAG | CGA/AAG | 106 | 3 |
| CAA | CGT | CAA/CGT | 104.37 | 2 |
| GCA | TAC | GCA/TAC | 104.09 | 3 |
| CGA | AAC | CGA/AAC | 103.97 | 3 |
| CAA | TAG | CAA/TAG | 103.34 | 2 |
| GCA | TAT | GCA/TAT | 102.76 | 3 |
| TTT | AAG | TTT/AAG | 101.41 | 3 |

TABLE 2-continued

Variant pairs that have an on/off ratio of 10 shown in FIG. 2D

| on | off | pair | ratio | edit_distance |
|---|---|---|---|---|
| TCA | TAC | TCA/TAC | 101.41 | 2 |
| TCA | TAT | TCA/TAT | 100.11 | 2 |
| TTT | AAC | TTT/AAC | 99.47 | 3 |
| CAA | ACG | CAA/ACG | 96.27 | 3 |
| TTA | TAC | TTA/TAC | 96.1 | 2 |
| GGA | TGC | GGA/TGC | 95.74 | 2 |
| TTA | TAT | TTA/TAT | 94.87 | 2 |
| CCA | TGC | CCA/TGC | 94.19 | 3 |
| GCA | AAT | GCA/AAT | 93.87 | 3 |
| GGA | ATC | GGA/ATC | 93.85 | 3 |
| GTA | TAC | GTA/TAC | 93.28 | 3 |
| GGA | AGG | GGA/AGG | 93.13 | 2 |
| CTA | CGG | CTA/CGG | 92.65 | 2 |
| GCA | CGC | GCA/CGC | 92.61 | 3 |
| CCA | ATC | CCA/ATC | 92.32 | 3 |
| GTA | TAT | GTA/TAT | 92.09 | 3 |
| GAA | TAC | GAA/TAC | 91.92 | 2 |
| TAA | TAC | TAA/TAC | 91.86 | 1 |
| GGA | ATG | GGA/ATG | 91.65 | 3 |
| CCA | AGG | CCA/AGG | 91.62 | 3 |
| TGA | CGG | TGA/CGG | 91.53 | 2 |
| TCA | AAT | TCA/AAT | 91.45 | 3 |
| CGA | TGC | CGA/TGC | 91.1 | 2 |
| GAA | TAT | GAA/TAT | 90.74 | 2 |
| TAA | TAT | TAA/TAT | 90.69 | 1 |
| TCA | CGC | TCA/CGC | 90.23 | 3 |
| CCA | ATG | CCA/ATG | 90.16 | 3 |
| CGA | ATC | CGA/ATC | 89.3 | 3 |
| GCA | GGG | GCA/GGG | 88.98 | 2 |
| CGA | AGG | CGA/AGG | 88.62 | 2 |
| GGA | TGG | GGA/TGG | 88.46 | 2 |
| CGA | ATG | CGA/ATG | 87.21 | 3 |
| TTT | TGC | TTT/TGC | 87.16 | 2 |
| CCA | TGG | CCA/TGG | 87.03 | 3 |
| TCA | GGG | TCA/GGG | 86.69 | 3 |
| TTA | AAT | TTA/AAT | 86.66 | 3 |
| GGA | CGT | GGA/CGT | 86.33 | 2 |
| TTA | CGC | TTA/CGC | 85.5 | 3 |
| GGA | TAG | GGA/TAG | 85.48 | 3 |
| TTT | ATC | TTT/ATC | 85.43 | 2 |
| CCA | CGT | CCA/CGT | 84.92 | 2 |
| TTT | AGG | TTT/AGG | 84.78 | 3 |
| GCA | TGT | GCA/TGT | 84.2 | 3 |
| CGA | TGG | CGA/TGG | 84.18 | 2 |
| GTA | AAT | GTA/AAT | 84.12 | 3 |
| CCA | TAG | CCA/TAG | 84.09 | 3 |
| TTT | ATG | TTT/ATG | 83.43 | 2 |
| GTA | CGC | GTA/CGC | 82.99 | 3 |
| CTA | AAG | CTA/AAG | 82.92 | 3 |
| GAA | AAT | GAA/AAT | 82.89 | 2 |
| TAA | AAT | TAA/AAT | 82.84 | 2 |
| TTA | GGG | TTA/GGG | 82.15 | 3 |
| CGA | CGT | CGA/CGT | 82.14 | 1 |
| TCA | TGT | TCA/TGT | 82.04 | 2 |
| TGA | AAG | TGA/AAG | 81.92 | 3 |
| CAA | TAC | CAA/TAC | 81.84 | 2 |
| GAA | CGC | GAA/CGC | 81.78 | 3 |
| TAA | CGC | TAA/CGC | 81.73 | 3 |
| CGA | TAG | CGA/TAG | 81.33 | 3 |
| CTA | AAC | CTA/AAC | 81.33 | 3 |
| CAA | TAT | CAA/TAT | 80.79 | 2 |
| TTT | TGG | TTT/TGG | 80.53 | 2 |
| TGA | AAC | TGA/AAC | 80.35 | 3 |
| GTA | GGG | GTA/GGG | 79.74 | 2 |
| GGA | ACG | GGA/ACG | 79.63 | 3 |
| TTT | CGT | TTT/CGT | 78.58 | 2 |
| GAA | GGG | GAA/GGG | 78.58 | 2 |
| TAA | GGG | TAA/GGG | 78.53 | 3 |
| CCA | ACG | CCA/ACG | 78.33 | 2 |
| TTT | TAG | TTT/TAG | 77.81 | 2 |
| TTA | TGT | TTA/TGT | 77.74 | 2 |
| GTT | CGG | GTT/CGG | 75.83 | 3 |
| CGA | ACG | CGA/ACG | 75.77 | 3 |
| GTA | TGT | GTA/TGT | 75.46 | 3 |
| GCA | ATT | GCA/ATT | 74.55 | 3 |
| CCT | CGG | CCT/CGG | 74.51 | 2 |

TABLE 2-continued

Variant pairs that have an on/off ratio of 10 shown in FIG. 2D

| on | off | pair | ratio | edit_distance |
|---|---|---|---|---|
| GAA | TGT | GAA/TGT | 74.36 | 3 |
| TAA | TGT | TAA/TGT | 74.31 | 2 |
| CAA | AAT | CAA/AAT | 73.8 | 2 |
| CAA | CGC | CAA/CGC | 72.81 | 2 |
| GCA | AGC | GCA/AGC | 72.66 | 3 |
| TCA | ATT | TCA/ATT | 72.63 | 3 |
| TTT | ACG | TTT/ACG | 72.49 | 3 |
| CTA | TGC | CTA/TGC | 71.27 | 3 |
| TCA | AGC | TCA/AGC | 70.79 | 3 |
| TGA | TGC | TGA/TGC | 70.41 | 1 |
| CAA | GGG | CAA/GGG | 69.96 | 3 |
| CTA | ATC | CTA/ATC | 69.86 | 2 |
| CTA | AGG | CTA/AGG | 69.32 | 3 |
| TGA | ATC | TGA/ATC | 69.01 | 3 |
| TTA | ATT | TTA/ATT | 68.83 | 2 |
| TGA | AGG | TGA/AGG | 68.48 | 2 |
| CTA | ATG | CTA/ATG | 68.22 | 2 |
| GTT | AAG | GTT/AAG | 67.87 | 3 |
| GGA | TAC | GGA/TAC | 67.69 | 3 |
| TGA | ATG | TGA/ATG | 67.4 | 3 |
| TTA | AGC | TTA/AGC | 67.08 | 3 |
| GGA | TAT | GGA/TAT | 66.82 | 3 |
| GTA | ATT | GTA/ATT | 66.81 | 2 |
| CCT | AAG | CCT/AAG | 66.68 | 3 |
| CCA | TAC | CCA/TAC | 66.59 | 3 |
| GTT | AAC | GTT/AAC | 66.57 | 3 |
| CAA | TGT | CAA/TGT | 66.2 | 3 |
| CTA | TGG | CTA/TGG | 65.85 | 3 |
| GAA | ATT | GAA/ATT | 65.83 | 3 |
| TAA | ATT | TAA/ATT | 65.8 | 3 |
| CCA | TAT | CCA/TAT | 65.74 | 3 |
| CCT | AAC | CCT/AAC | 65.41 | 3 |
| GTA | AGC | GTA/AGC | 65.11 | 3 |
| TGA | TGG | TGA/TGG | 65.05 | 1 |
| CGA | TAC | CGA/TAC | 64.41 | 3 |
| CTA | CGT | CTA/CGT | 64.26 | 2 |
| GAA | AGC | GAA/AGC | 64.16 | 3 |
| TAA | AGC | TAA/AGC | 64.12 | 3 |
| CTA | TAG | CTA/TAG | 63.63 | 3 |
| CGA | TAT | CGA/TAT | 63.59 | 3 |
| TGA | CGT | TGA/CGT | 63.48 | 2 |
| TGA | TAG | TGA/TAG | 62.86 | 2 |
| TTT | TAC | TTT/TAC | 61.62 | 2 |
| GGA | AAT | GGA/AAT | 61.04 | 3 |
| TTT | TAT | TTT/TAT | 60.83 | 1 |
| GGA | CGC | GGA/CGC | 60.22 | 2 |
| CCA | AAT | CCA/AAT | 60.05 | 3 |
| CTA | ACG | CTA/ACG | 59.27 | 3 |
| CCA | CGC | CCA/CGC | 59.24 | 2 |
| CAA | ATT | CAA/ATT | 58.61 | 3 |
| TGA | ACG | TGA/ACG | 58.56 | 3 |
| CTT | CGG | CTT/CGG | 58.54 | 2 |
| GTT | TGC | GTT/TGC | 58.33 | 3 |
| CGA | AAT | CGA/AAT | 58.08 | 3 |
| GGA | GGG | GGA/GGG | 57.87 | 1 |
| CCT | TGC | CCT/TGC | 57.31 | 3 |
| CGA | CGC | CGA/CGC | 57.3 | 1 |
| GTT | ATC | GTT/ATC | 57.17 | 2 |
| CAA | AGC | CAA/AGC | 57.13 | 3 |
| CCA | GGG | CCA/GGG | 56.93 | 3 |
| GTT | AGG | GTT/AGG | 56.74 | 3 |
| CCT | ATC | CCT/ATC | 56.18 | 3 |
| GTT | ATG | GTT/ATG | 55.84 | 2 |
| CCT | AGG | CCT/AGG | 55.75 | 3 |
| TTT | AAT | TTT/AAT | 55.57 | 2 |
| CGA | GGG | CGA/GGG | 55.06 | 2 |
| CCT | ATG | CCT/ATG | 54.86 | 3 |
| TTT | CGC | TTT/CGC | 54.82 | 3 |
| GGA | TGT | GGA/TGT | 54.76 | 2 |
| GTT | TGG | GTT/TGG | 53.89 | 3 |
| CCA | TGT | CCA/TGT | 53.87 | 3 |
| ACA | CGG | ACA/CGG | 53.03 | 3 |
| CCT | TGG | CCT/TGG | 52.95 | 3 |
| TTT | GGG | TTT/GGG | 52.68 | 3 |
| GTT | CGT | GTT/CGT | 52.59 | 2 |
| CTT | AAG | CTT/AAG | 52.39 | 3 |

TABLE 2-continued

Variant pairs that have an on/off ratio of 10 shown in FIG. 2D

| on | off | pair | ratio | edit_distance |
|---|---|---|---|---|
| CGA | TGT | CGA/TGT | 52.1 | 2 |
| GTT | TAG | GTT/TAG | 52.08 | 3 |
| GCA | CTG | GCA/CTG | 51.85 | 3 |
| CCT | CGT | CCT/CGT | 51.67 | 1 |
| CTT | AAC | CTT/AAC | 51.39 | 3 |
| CCT | TAG | CCT/TAG | 51.17 | 3 |
| TCA | CTG | TCA/CTG | 50.51 | 3 |
| CTA | TAC | CTA/TAC | 50.38 | 3 |
| TTT | TGT | TTT/TGT | 49.85 | 1 |
| TGA | TAC | TGA/TAC | 49.77 | 2 |
| CTA | TAT | CTA/TAT | 49.74 | 3 |
| GGT | CGG | GGT/CGG | 49.41 | 2 |
| TGA | TAT | TGA/TAT | 49.14 | 2 |
| GTT | ACG | GTT/ACG | 48.51 | 3 |
| GGA | ATT | GGA/ATT | 48.48 | 3 |
| TTA | CTG | TTA/CTG | 47.86 | 2 |
| CCA | ATT | CCA/ATT | 47.69 | 3 |
| CCT | ACG | CCT/ACG | 47.67 | 2 |
| ACA | AAG | ACA/AAG | 47.46 | 2 |
| GGA | AGC | GGA/AGC | 47.25 | 2 |
| ACA | AAC | ACA/AAC | 46.56 | 2 |
| CCA | AGC | CCA/AGC | 46.48 | 3 |
| GTA | CTG | GTA/CTG | 46.46 | 2 |
| CGA | ATT | CGA/ATT | 46.13 | 3 |
| GAA | CTG | GAA/CTG | 45.78 | 3 |
| TAA | CTG | TAA/CTG | 45.76 | 3 |
| GCA | ACT | GCA/ACT | 45.58 | 2 |
| CTA | AAT | CTA/AAT | 45.44 | 3 |
| GCA | GAG | GCA/GAG | 45.24 | 2 |
| CTT | TGC | CTT/TGC | 45.03 | 3 |
| CGA | AGC | CGA/AGC | 44.96 | 2 |
| TGA | AAT | TGA/AAT | 44.89 | 3 |
| CTA | CGC | CTA/CGC | 44.83 | 2 |
| TCA | ACT | TCA/ACT | 44.41 | 2 |
| TGA | CGC | TGA/CGC | 44.29 | 2 |
| GGT | AAG | GGT/AAG | 44.22 | 3 |
| CTT | ATC | CTT/ATC | 44.14 | 2 |
| TTT | ATT | TTT/ATT | 44.13 | 1 |
| TCA | GAG | TCA/GAG | 44.07 | 3 |
| GCA | CAT | GCA/CAT | 43.94 | 3 |
| CTT | AGG | CTT/AGG | 43.8 | 3 |
| GGT | AAC | GGT/AAC | 43.38 | 3 |
| CTT | ATG | CTT/ATG | 43.11 | 2 |
| CTA | GGG | CTA/GGG | 43.07 | 3 |
| TTT | AGC | TTT/AGC | 43.01 | 3 |
| TCA | CAT | TCA/CAT | 42.81 | 3 |
| TGA | GGG | TGA/GGG | 42.55 | 2 |
| TTA | ACT | TTA/ACT | 42.08 | 3 |
| TTA | GAG | TTA/GAG | 41.76 | 3 |
| GCC | CGG | GCC/CGG | 41.68 | 3 |
| CTT | TGG | CTT/TGG | 41.61 | 3 |
| GTT | TAC | GTT/TAC | 41.24 | 3 |
| GTA | ACT | GTA/ACT | 40.85 | 3 |
| ACA | TGC | ACA/TGC | 40.79 | 3 |
| CTA | TGT | CTA/TGT | 40.76 | 3 |
| CAA | CTG | CAA/CTG | 40.76 | 2 |
| GTT | TAT | GTT/TAT | 40.71 | 2 |
| GCA | CAC | GCA/CAC | 40.65 | 3 |
| CTT | CGT | CTT/CGT | 40.6 | 1 |
| TTA | CAT | TTA/CAT | 40.57 | 3 |
| GTA | GAG | GTA/GAG | 40.54 | 2 |
| CCT | TAC | CCT/TAC | 40.52 | 3 |
| TGA | TGT | TGA/TGT | 40.27 | 1 |
| GAA | ACT | GAA/ACT | 40.25 | 3 |
| TAA | ACT | TAA/ACT | 40.22 | 3 |
| CTT | TAG | CTT/TAG | 40.2 | 3 |
| CCC | CGG | CCC/CGG | 40.12 | 2 |
| CCT | TAT | CCT/TAT | 40 | 2 |
| ACA | ATC | ACA/ATC | 39.98 | 2 |
| GAA | GAG | GAA/GAG | 39.95 | 1 |
| TAA | GAG | TAA/GAG | 39.92 | 2 |
| ACA | AGG | ACA/AGG | 39.68 | 2 |
| TCA | CAC | TCA/CAC | 39.61 | 3 |
| GTA | CAT | GTA/CAT | 39.38 | 3 |
| ACA | ATG | ACA/ATG | 39.05 | 2 |
| GAA | CAT | GAA/CAT | 38.81 | 2 |

TABLE 2-continued

Variant pairs that have an on/off ratio of 10 shown in FIG. 2D

| on | off | pair | ratio | edit_distance |
|---|---|---|---|---|
| TAA | CAT | TAA/CAT | 38.78 | 2 |
| GGT | TGC | GGT/TGC | 38.01 | 2 |
| ACA | TGG | ACA/TGG | 37.69 | 3 |
| ATA | CGG | ATA/CGG | 37.59 | 3 |
| TTA | CAC | TTA/CAC | 37.53 | 3 |
| CTT | ACG | CTT/ACG | 37.45 | 3 |
| GCC | AAG | GCC/AAG | 37.3 | 3 |
| GGT | ATC | GGT/ATC | 37.26 | 3 |
| GTT | AAT | GTT/AAT | 37.19 | 2 |
| GGT | AGG | GGT/AGG | 36.97 | 2 |
| ACA | CGT | ACA/CGT | 36.78 | 3 |
| GTT | CGC | GTT/CGC | 36.69 | 3 |
| GCC | AAC | GCC/AAC | 36.59 | 2 |
| CCT | AAT | CCT/AAT | 36.54 | 2 |
| GTA | CAC | GTA/CAC | 36.43 | 3 |
| ACA | TAG | ACA/TAG | 36.42 | 3 |
| GGT | ATG | GGT/ATG | 36.39 | 3 |
| CTA | ATT | CTA/ATT | 36.09 | 2 |
| CCT | CGC | CCT/CGC | 36.05 | 2 |
| CCC | AAG | CCC/AAG | 35.91 | 3 |
| GAA | CAC | GAA/CAC | 35.9 | 2 |
| TAA | CAC | TAA/CAC | 35.88 | 2 |
| CAA | ACT | CAA/ACT | 35.83 | 3 |
| TGA | ATT | TGA/ATT | 35.65 | 3 |
| CAA | GAG | CAA/GAG | 35.57 | 2 |
| GTT | GGG | GTT/GGG | 35.25 | 2 |
| CCC | AAC | CCC/AAC | 35.22 | 2 |
| CTA | AGC | CTA/AGC | 35.17 | 3 |
| GGT | TGG | GGT/TGG | 35.12 | 2 |
| TGA | AGC | TGA/AGC | 34.75 | 2 |
| CCT | GGG | CCT/GGG | 34.64 | 3 |
| GCA | GAC | GCA/GAC | 34.59 | 2 |
| CAA | CAT | CAA/CAT | 34.55 | 1 |
| GCA | CAG | GCA/CAG | 34.54 | 3 |
| GGT | CGT | GGT/CGT | 34.27 | 1 |
| ACA | ACG | ACA/ACG | 33.93 | 1 |
| GGT | TAG | GGT/TAG | 33.93 | 3 |
| GGA | CTG | GGA/CTG | 33.72 | 3 |
| TCA | GAC | TCA/GAC | 33.7 | 3 |
| TCA | CAG | TCA/CAG | 33.65 | 3 |
| ATA | AAG | ATA/AAG | 33.64 | 2 |
| GTT | TGT | GTT/TGT | 33.36 | 2 |
| CCA | CTG | CCA/CTG | 33.17 | 2 |
| GCA | GCG | GCA/GCG | 33.1 | 1 |
| ATA | AAC | ATA/AAC | 33 | 2 |
| CCT | TGT | CCT/TGT | 32.78 | 2 |
| TCA | GCG | TCA/GCG | 32.24 | 2 |
| CGA | CTG | CGA/CTG | 32.08 | 2 |
| GCC | TGC | GCC/TGC | 32.06 | 2 |
| CAA | CAC | CAA/CAC | 31.96 | 1 |
| TTA | GAC | TTA/GAC | 31.94 | 3 |
| TTA | CAG | TTA/CAG | 31.88 | 3 |
| CTT | TAC | CTT/TAC | 31.84 | 3 |
| GGT | ACG | GGT/ACG | 31.61 | 3 |
| GCC | ATC | GCC/ATC | 31.43 | 2 |
| CTT | TAT | CTT/TAT | 31.43 | 2 |
| GCC | AGG | GCC/AGG | 31.19 | 3 |
| GTA | GAC | GTA/GAC | 31 | 2 |
| GTA | CAG | GTA/CAG | 30.95 | 3 |
| CCC | TGC | CCC/TGC | 30.86 | 2 |
| TTT | CTG | TTT/CTG | 30.69 | 2 |
| GCC | ATG | GCC/ATG | 30.69 | 3 |
| TTA | GCG | TTA/GCG | 30.55 | 3 |
| GAA | GAC | GAA/GAC | 30.55 | 1 |
| TAA | GAC | TAA/GAC | 30.53 | 2 |
| GAA | CAG | GAA/CAG | 30.5 | 2 |
| TAA | CAG | TAA/CAG | 30.48 | 2 |
| CCC | ATC | CCC/ATC | 30.25 | 2 |
| CCC | AGG | CCC/AGG | 30.02 | 3 |
| GTA | GCG | GTA/GCG | 29.66 | 2 |
| GGA | ACT | GGA/ACT | 29.64 | 3 |
| GCC | TGG | GCC/TGG | 29.62 | 3 |
| CCC | ATG | CCC/ATG | 29.54 | 3 |
| GTT | ATT | GTT/ATT | 29.54 | 1 |
| GGA | GAG | GGA/GAG | 29.42 | 2 |
| GAA | GCG | GAA/GCG | 29.23 | 2 |

TABLE 2-continued

Variant pairs that have an on/off ratio of 10 shown in FIG. 2D

| on | off | pair | ratio | edit_distance |
|---|---|---|---|---|
| TAA | GCG | TAA/GCG | 29.21 | 3 |
| CCA | ACT | CCA/ACT | 29.16 | 2 |
| CCT | ATT | CCT/ATT | 29.02 | 2 |
| GCA | GGC | GCA/GGC | 29 | 2 |
| CCA | GAG | CCA/GAG | 28.94 | 3 |
| ATA | TGC | ATA/TGC | 28.91 | 3 |
| GCC | CGT | GCC/CGT | 28.91 | 3 |
| ACA | TAC | ACA/TAC | 28.84 | 3 |
| GTT | AGC | GTT/AGC | 28.79 | 3 |
| CTT | AAT | CTT/AAT | 28.71 | 2 |
| GCC | TAG | GCC/TAG | 28.62 | 3 |
| GGA | CAT | GGA/CAT | 28.58 | 3 |
| CCC | TGG | CCC/TGG | 28.51 | 3 |
| ACA | TAT | ACA/TAT | 28.47 | 3 |
| ATA | ATC | ATA/ATC | 28.34 | 1 |
| CCG | CGG | CCG/CGG | 28.34 | 1 |
| CTT | CGC | CTT/CGC | 28.33 | 2 |
| CCT | AGC | CCT/AGC | 28.28 | 3 |
| TCA | GGC | TCA/GGC | 28.26 | 3 |
| CGA | ACT | CGA/ACT | 28.2 | 3 |
| ATA | AGG | ATA/AGG | 28.12 | 2 |
| CCA | CAT | CCA/CAT | 28.11 | 2 |
| CGA | GAG | CGA/GAG | 27.99 | 3 |
| CCC | CGT | CCC/CGT | 27.83 | 2 |
| ATA | ATG | ATA/ATG | 27.68 | 1 |
| GCA | TCG | GCA/TCG | 27.63 | 2 |
| CCC | TAG | CCC/TAG | 27.55 | 3 |
| CTT | GGG | CTT/GGG | 27.22 | 3 |
| CAA | GAC | CAA/GAC | 27.2 | 2 |
| CGA | CAT | CGA/CAT | 27.19 | 2 |
| CAA | CAG | CAA/CAG | 27.15 | 1 |
| TTT | ACT | TTT/ACT | 26.98 | 2 |
| TCA | TCG | TCA/TCG | 26.92 | 1 |
| GGT | TAC | GGT/TAC | 26.87 | 3 |
| TTA | GGC | TTA/GGC | 26.78 | 3 |
| TTT | GAG | TTT/GAG | 26.78 | 3 |
| ATA | TGG | ATA/TGG | 26.71 | 3 |
| GCC | ACG | GCC/ACG | 26.67 | 2 |
| GGT | TAT | GGT/TAT | 26.53 | 2 |
| GGA | CAC | GGA/CAC | 26.44 | 3 |
| ATA | CGT | ATA/CGT | 26.07 | 3 |
| CAA | GCG | CAA/GCG | 26.02 | 3 |
| ACA | AAT | ACA/AAT | 26.01 | 2 |
| CCA | CAC | CCA/CAC | 26.01 | 2 |
| TTT | CAT | TTT/CAT | 26.01 | 2 |
| GTA | GGC | GTA/GGC | 25.99 | 2 |
| ATA | TAG | ATA/TAG | 25.81 | 3 |
| CTT | TGT | CTT/TGT | 25.75 | 2 |
| CCC | ACG | CCC/ACG | 25.67 | 2 |
| ACA | CGC | ACA/CGC | 25.66 | 3 |
| GAA | GGC | GAA/GGC | 25.61 | 2 |
| TAA | GGC | TAA/GGC | 25.6 | 3 |
| TTA | TCG | TTA/TCG | 25.5 | 2 |
| CCG | AAG | CCG/AAG | 25.36 | 2 |
| CGA | CAC | CGA/CAC | 25.15 | 2 |
| CTA | CTG | CTA/CTG | 25.1 | 1 |
| CCG | AAC | CCG/AAC | 24.88 | 3 |
| TGA | CTG | TGA/CTG | 24.79 | 3 |
| GTA | TCG | GTA/TCG | 24.76 | 3 |
| ACA | GGG | ACA/GGG | 24.65 | 3 |
| GAA | TCG | GAA/TCG | 24.4 | 3 |
| TAA | TCG | TAA/TCG | 24.38 | 2 |
| GGT | AAT | GGT/AAT | 24.23 | 2 |
| TTT | CAC | TTT/CAC | 24.06 | 3 |
| ATA | ACG | ATA/ACG | 24.05 | 2 |
| GCT | CGG | GCT/CGG | 23.95 | 3 |
| GGT | CGC | GGT/CGC | 23.91 | 2 |
| ACA | TGT | ACA/TGT | 23.33 | 3 |
| GAT | CGG | GAT/CGG | 23.02 | 3 |
| GGT | GGG | GGT/GGG | 22.97 | 1 |
| CTT | ATT | CTT/ATT | 22.8 | 1 |
| CAA | GGC | CAA/GGC | 22.8 | 3 |
| GCC | TAC | GCC/TAC | 22.67 | 2 |
| GGA | GAC | GGA/GAC | 22.5 | 2 |
| GGA | CAG | GGA/CAG | 22.46 | 3 |
| GCC | TAT | GCC/TAT | 22.38 | 3 |

TABLE 2-continued

Variant pairs that have an on/off ratio of 10 shown in FIG. 2D

| on | off | pair | ratio | edit_distance |
|---|---|---|---|---|
| CTT | AGC | CTT/AGC | 22.22 | 3 |
| CCA | GAC | CCA/GAC | 22.13 | 3 |
| CCA | CAG | CCA/CAG | 22.09 | 2 |
| CTA | ACT | CTA/ACT | 22.06 | 3 |
| CTA | GAG | CTA/GAG | 21.9 | 3 |
| CCC | TAC | CCC/TAC | 21.82 | 2 |
| CCG | TGC | CCG/TGC | 21.8 | 3 |
| TGA | ACT | TGA/ACT | 21.8 | 3 |
| GGT | TGT | GGT/TGT | 21.74 | 1 |
| CAA | TCG | CAA/TCG | 21.72 | 3 |
| TGA | GAG | TGA/GAG | 21.63 | 3 |
| CCC | TAT | CCC/TAT | 21.54 | 3 |
| GGA | GCG | GGA/GCG | 21.52 | 2 |
| GCT | AAG | GCT/AAG | 21.44 | 3 |
| CGA | GAC | CGA/GAC | 21.41 | 3 |
| CCG | ATC | CCG/ATC | 21.37 | 3 |
| CGA | CAG | CGA/CAG | 21.37 | 2 |
| CTA | CAT | CTA/CAT | 21.27 | 2 |
| CCG | AGG | CCG/AGG | 21.2 | 2 |
| CCA | GCG | CCA/GCG | 21.17 | 2 |
| GCT | AAC | GCT/AAC | 21.03 | 3 |
| TGA | CAT | TGA/CAT | 21.01 | 3 |
| CCG | ATG | CCG/ATG | 20.87 | 2 |
| GCA | AGA | GCA/AGA | 20.72 | 2 |
| ACA | ATT | ACA/ATT | 20.66 | 2 |
| GAT | AAG | GAT/AAG | 20.6 | 2 |
| GTT | CTG | GTT/CTG | 20.54 | 2 |
| CGA | GCG | CGA/GCG | 20.48 | 3 |
| TTT | GAC | TTT/GAC | 20.48 | 3 |
| GCC | AAT | GCC/AAT | 20.44 | 3 |
| ATA | TAC | ATA/TAC | 20.44 | 3 |
| TTT | CAG | TTT/CAG | 20.44 | 3 |
| GAT | AAC | GAT/AAC | 20.21 | 2 |
| TCA | AGA | TCA/AGA | 20.19 | 2 |
| ATA | TAT | ATA/TAT | 20.18 | 3 |
| CCT | CTG | CCT/CTG | 20.18 | 2 |
| GCC | CGC | GCC/CGC | 20.17 | 2 |
| CCG | TGG | CCG/TGG | 20.14 | 2 |
| ACA | AGC | ACA/AGC | 20.13 | 2 |
| GCA | ACC | GCA/ACC | 19.92 | 2 |
| CTA | CAC | CTA/CAC | 19.68 | 2 |
| CCC | AAT | CCC/AAT | 19.68 | 3 |
| CCG | CGT | CCG/CGT | 19.65 | 2 |
| TTT | GCG | TTT/GCG | 19.59 | 3 |
| CCG | TAG | CCG/TAG | 19.46 | 2 |
| TGA | CAC | TGA/CAC | 19.44 | 3 |
| CCC | CGC | CCC/CGC | 19.41 | 1 |
| TCA | ACC | TCA/ACC | 19.41 | 2 |
| GCC | GGG | GCC/GGG | 19.38 | 2 |
| GGT | ATT | GGT/ATT | 19.25 | 2 |
| TTA | AGA | TTA/AGA | 19.13 | 2 |
| GGA | GGC | GGA/GGC | 18.86 | 1 |
| GGT | AGC | GGT/AGC | 18.76 | 2 |
| CCC | GGG | CCC/GGG | 18.65 | 3 |
| GTA | AGA | GTA/AGA | 18.57 | 2 |
| CCA | GGC | CCA/GGC | 18.55 | 3 |
| GCT | TGC | GCT/TGC | 18.43 | 3 |
| ATA | AAT | ATA/AAT | 18.43 | 2 |
| TTA | ACC | TTA/ACC | 18.4 | 3 |
| GCC | TGT | GCC/TGT | 18.34 | 3 |
| GAA | AGA | GAA/AGA | 18.3 | 2 |
| TAA | AGA | TAA/AGA | 18.29 | 2 |
| ATA | CGC | ATA/CGC | 18.19 | 3 |
| CCG | ACG | CCG/ACG | 18.13 | 1 |
| GTT | ACT | GTT/ACT | 18.06 | 2 |
| GCT | ATC | GCT/ATC | 18.06 | 3 |
| GGA | TCG | GGA/TCG | 17.97 | 3 |
| CGA | GGC | CGA/GGC | 17.95 | 2 |
| GTT | GAG | GTT/GAG | 17.92 | 2 |
| GCT | AGG | GCT/AGG | 17.92 | 3 |
| GTA | ACC | GTA/ACC | 17.86 | 3 |
| CCT | ACT | CCT/ACT | 17.74 | 1 |
| GAT | TGC | GAT/TGC | 17.71 | 3 |
| TTC | CGG | TTC/CGG | 17.68 | 3 |
| CCA | TCG | CCA/TCG | 17.67 | 2 |
| CCC | TGT | CCC/TGT | 17.65 | 3 |

TABLE 2-continued

Variant pairs that have an on/off ratio of 10 shown in FIG. 2D

| on | off | pair | ratio | edit_distance |
|---|---|---|---|---|
| GCT | ATG | GCT/ATG | 17.64 | 3 |
| CCT | GAG | CCT/GAG | 17.61 | 3 |
| GAA | ACC | GAA/ACC | 17.6 | 3 |
| TAA | ACC | TAA/ACC | 17.58 | 3 |
| ATA | GGG | ATA/GGG | 17.47 | 3 |
| GTT | CAT | GTT/CAT | 17.41 | 2 |
| GAT | ATC | GAT/ATC | 17.35 | 3 |
| GAT | AGG | GAT/AGG | 17.22 | 3 |
| TTT | GGC | TTT/GGC | 17.17 | 3 |
| CCT | CAT | CCT/CAT | 17.11 | 1 |
| CGA | TCG | CGA/TCG | 17.09 | 3 |
| GCT | TGG | GCT/TGG | 17.03 | 3 |
| GAT | ATG | GAT/ATG | 16.95 | 3 |
| CTA | GAC | CTA/GAC | 16.75 | 3 |
| CTA | CAG | CTA/CAG | 16.72 | 2 |
| GCT | CGT | GCT/CGT | 16.61 | 2 |
| TGA | GAC | TGA/GAC | 16.54 | 3 |
| ATA | TGT | ATA/TGT | 16.54 | 3 |
| TGA | CAG | TGA/CAG | 16.52 | 3 |
| GCT | TAG | GCT/TAG | 16.45 | 3 |
| GAT | TGG | GAT/TGG | 16.36 | 3 |
| TTT | TCG | TTT/TCG | 16.35 | 2 |
| CAA | AGA | CAA/AGA | 16.29 | 2 |
| GCC | ATT | GCC/ATT | 16.24 | 3 |
| GTT | CAC | GTT/CAC | 16.11 | 3 |
| GCA | GTG | GCA/GTG | 16.06 | 2 |
| CTA | GCG | CTA/GCG | 16.02 | 3 |
| GAT | CGT | GAT/CGT | 15.96 | 2 |
| CTT | CTG | CTT/CTG | 15.86 | 1 |
| TTC | AAG | TTC/AAG | 15.83 | 3 |
| TGA | GCG | TGA/GCG | 15.83 | 3 |
| CCT | CAC | CCT/CAC | 15.82 | 2 |
| GCC | AGC | GCC/AGC | 15.82 | 2 |
| GAT | TAG | GAT/TAG | 15.81 | 2 |
| CAA | ACC | CAA/ACC | 15.67 | 3 |
| TCA | GTG | TCA/GTG | 15.65 | 3 |
| CCC | ATT | CCC/ATT | 15.63 | 3 |
| GCA | AGT | GCA/AGT | 15.61 | 3 |
| TCT | CGG | TCT/CGG | 15.57 | 3 |
| TTC | AAC | TTC/AAC | 15.52 | 2 |
| CTC | CGG | CTC/CGG | 15.46 | 2 |
| AAA | CGG | AAA/CGG | 15.45 | 3 |
| CCG | TAC | CCG/TAC | 15.41 | 3 |
| GCT | ACG | GCT/ACG | 15.32 | 2 |
| CCC | AGC | CCC/AGC | 15.23 | 2 |
| CCG | TAT | CCG/TAT | 15.21 | 3 |
| TCA | AGT | TCA/AGT | 15.21 | 3 |
| TTA | GTG | TTA/GTG | 14.83 | 2 |
| GAT | ACG | GAT/ACG | 14.73 | 3 |
| ATA | ATT | ATA/ATT | 14.64 | 1 |
| TTA | AGT | TTA/AGT | 14.41 | 3 |
| GTA | GTG | GTA/GTG | 14.4 | 1 |
| ACA | CTG | ACA/CTG | 14.37 | 3 |
| TTG | CGG | TTG/CGG | 14.35 | 2 |
| ATA | AGC | ATA/AGC | 14.27 | 2 |
| TAA | GTG | TAA/GTG | 14.18 | 3 |
| GAA | GTG | GAA/GTG | 14.18 | 2 |
| CTA | GGC | CTA/GGC | 14.04 | 3 |
| GTA | AGT | GTA/AGT | 13.99 | 3 |
| TCC | CGG | TCC/CGG | 13.95 | 3 |
| CTT | ACT | CTT/ACT | 13.94 | 2 |
| TCT | AAG | TCT/AAG | 13.93 | 3 |
| CCG | AAT | CCG/AAT | 13.9 | 3 |
| GTC | CGG | GTC/CGG | 13.88 | 3 |
| TGA | GGC | TGA/GGC | 13.87 | 2 |
| CTC | AAG | CTC/AAG | 13.84 | 3 |
| CTT | GAG | CTT/GAG | 13.84 | 3 |
| AAA | AAG | AAA/AAG | 13.83 | 1 |
| GAA | AGT | GAA/AGT | 13.79 | 3 |
| GCA | GTC | GCA/GTC | 13.79 | 2 |
| TAA | AGT | TAA/AGT | 13.78 | 3 |
| GCA | TCC | GCA/TCC | 13.72 | 2 |
| CCG | CGC | CCG/CGC | 13.71 | 2 |
| GTT | GAC | GTT/GAC | 13.71 | 2 |
| GTT | CAG | GTT/CAG | 13.68 | 3 |
| TCT | AAC | TCT/AAC | 13.67 | 3 |

TABLE 2-continued

Variant pairs that have an on/off ratio of 10 shown in FIG. 2D

| on | off | pair | ratio | edit_distance |
|---|---|---|---|---|
| TTC | TGC | TTC/TGC | 13.6 | 1 |
| AAA | AAC | AAA/AAC | 13.57 | 1 |
| CTC | AAC | CTC/AAC | 13.57 | 2 |
| GGA | AGA | GGA/AGA | 13.48 | 1 |
| CCT | GAC | CCT/GAC | 13.47 | 3 |
| CTT | CAT | CTT/CAT | 13.44 | 1 |
| CCT | CAG | CCT/CAG | 13.44 | 2 |
| TCA | GTC | TCA/GTC | 13.44 | 3 |
| GGT | CTG | GGT/CTG | 13.38 | 3 |
| CTA | TCG | CTA/TCG | 13.37 | 3 |
| TCA | TCC | TCA/TCC | 13.37 | 1 |
| GCA | TTG | GCA/TTG | 13.34 | 3 |
| TTC | ATC | TTC/ATC | 13.33 | 1 |
| CCA | AGA | CCA/AGA | 13.26 | 2 |
| TTC | AGG | TTC/AGG | 13.23 | 3 |
| TGA | TCG | TGA/TCG | 13.21 | 2 |
| CCG | GGG | CCG/GGG | 13.17 | 2 |
| GTT | GCG | GTT/GCG | 13.11 | 2 |
| GCT | TAC | GCT/TAC | 13.03 | 3 |
| TTC | ATG | TTC/ATG | 13.02 | 2 |
| TCA | TTG | TCA/TTG | 13 | 2 |
| GGA | ACC | GGA/ACC | 12.96 | 3 |
| CCT | GCG | CCT/GCG | 12.88 | 2 |
| GCT | TAT | GCT/TAT | 12.86 | 2 |
| TTG | AAG | TTG/AAG | 12.84 | 2 |
| CGA | AGA | CGA/AGA | 12.82 | 1 |
| CCA | ACC | CCA/ACC | 12.75 | 2 |
| TTA | GTC | TTA/GTC | 12.73 | 2 |
| TTA | TCC | TTA/TCC | 12.67 | 2 |
| ACA | ACT | ACA/ACT | 12.63 | 1 |
| CAA | GTG | CAA/GTG | 12.63 | 3 |
| TTG | AAC | TTG/AAC | 12.6 | 3 |
| TTC | TGG | TTC/TGG | 12.57 | 2 |
| ACA | GAG | ACA/GAG | 12.53 | 3 |
| GAT | TAC | GAT/TAC | 12.52 | 2 |
| TCC | AAG | TCC/AAG | 12.48 | 3 |
| CCG | TGT | CCG/TGT | 12.47 | 3 |
| CTT | CAC | CTT/CAC | 12.43 | 2 |
| GTC | AAG | GTC/AAG | 12.42 | 3 |
| GCA | AAA | GCA/AAA | 12.39 | 2 |
| GCA | CTC | GCA/CTC | 12.38 | 3 |
| GAT | TAT | GAT/TAT | 12.36 | 1 |
| GTA | GTC | GTA/GTC | 12.36 | 1 |
| CGA | ACC | CGA/ACC | 12.33 | 3 |
| TTA | TTG | TTA/TTG | 12.31 | 1 |
| GTA | TCC | GTA/TCC | 12.3 | 3 |
| GCA | TCT | GCA/TCT | 12.29 | 2 |
| CAA | AGT | CAA/AGT | 12.28 | 3 |
| TTC | CGT | TTC/CGT | 12.27 | 3 |
| TTT | AGA | TTT/AGA | 12.27 | 3 |
| AGT | CGG | AGT/CGG | 12.26 | 2 |
| TCC | AAC | TCC/AAC | 12.24 | 2 |
| ACA | CAT | ACA/CAT | 12.18 | 3 |
| GTC | AAC | GTC/AAC | 12.18 | 2 |
| GAA | GTC | GAA/GTC | 12.18 | 2 |
| TAA | GTC | TAA/GTC | 12.17 | 3 |
| TTC | TAG | TTC/TAG | 12.14 | 2 |
| GAA | TCC | GAA/TCC | 12.12 | 3 |
| TAA | TCC | TAA/TCC | 12.11 | 2 |
| TCA | AAA | TCA/AAA | 12.07 | 2 |
| TCA | CTC | TCA/CTC | 12.06 | 3 |
| TCT | TGC | TCT/TGC | 11.98 | 2 |
| TCA | TCT | TCA/TCT | 11.98 | 1 |
| GTA | TTG | GTA/TTG | 11.95 | 2 |
| GTG | CGG | GTG/CGG | 11.92 | 2 |
| AAA | TGC | AAA/TGC | 11.89 | 3 |
| CTC | TGC | CTC/TGC | 11.89 | 2 |
| TTT | ACC | TTT/ACC | 11.8 | 3 |
| GAA | TTG | GAA/TTG | 11.78 | 3 |
| GGT | ACT | GGT/ACT | 11.77 | 2 |
| TAA | TTG | TAA/TTG | 11.77 | 2 |
| GCT | AAT | GCT/AAT | 11.75 | 2 |
| TCT | ATC | TCT/ATC | 11.74 | 3 |
| GGT | GAG | GGT/GAG | 11.68 | 2 |
| CTC | ATC | CTC/ATC | 11.66 | 1 |
| TCT | AGG | TCT/AGG | 11.65 | 3 |

TABLE 2-continued

Variant pairs that have an on/off ratio of 10 shown in FIG. 2D

| on | off | pair | ratio | edit_distance |
|---|---|---|---|---|
| AAA | ATC | AAA/ATC | 11.65 | 2 |
| GCT | CGC | GCT/CGC | 11.59 | 3 |
| CTC | AGG | CTC/AGG | 11.57 | 3 |
| AAA | AGG | AAA/AGG | 11.56 | 2 |
| GTT | GGC | GTT/GGC | 11.49 | 2 |
| TCT | ATG | TCT/ATG | 11.46 | 3 |
| TTA | CTC | TTA/CTC | 11.43 | 2 |
| TTA | AAA | TTA/AAA | 11.43 | 2 |
| CTC | ATG | CTC/ATG | 11.39 | 2 |
| AAA | ATG | AAA/ATG | 11.38 | 2 |
| TTA | TCT | TTA/TCT | 11.35 | 2 |
| GGT | CAT | GGT/CAT | 11.34 | 2 |
| TTC | ACG | TTC/ACG | 11.31 | 3 |
| CCT | GGC | CCT/GGC | 11.29 | 3 |
| GCC | CTG | GCC/CTG | 11.29 | 3 |
| GAT | AAT | GAT/AAT | 11.29 | 1 |
| ACA | CAC | ACA/CAC | 11.26 | 3 |
| GAT | CGC | GAT/CGC | 11.14 | 3 |
| GCT | GGG | GCT/GGG | 11.14 | 2 |
| GTA | AAA | GTA/AAA | 11.1 | 2 |
| GTA | CTC | GTA/CTC | 11.09 | 2 |
| TCT | TGG | TCT/TGG | 11.07 | 2 |
| CCG | ATT | CCG/ATT | 11.04 | 3 |
| TTG | TGC | TTG/TGC | 11.04 | 2 |
| GTA | TCT | GTA/TCT | 11.02 | 3 |
| CTC | TGG | CTC/TGG | 10.99 | 3 |
| AAA | TGG | AAA/TGG | 10.98 | 3 |
| AGT | AAG | AGT/AAG | 10.97 | 2 |
| GTT | TCG | GTT/TCG | 10.94 | 3 |
| GAA | AAA | GAA/AAA | 10.94 | 1 |
| TAA | CTC | TAA/CTC | 10.93 | 3 |
| TAA | AAA | TAA/AAA | 10.93 | 1 |
| GAA | CTC | GAA/CTC | 10.93 | 3 |
| CCC | CTG | CCC/CTG | 10.87 | 2 |
| GAA | TCT | GAA/TCT | 10.86 | 3 |
| TAA | TCT | TAA/TCT | 10.85 | 2 |
| CAA | GTC | CAA/GTC | 10.84 | 3 |
| GCA | TTC | GCA/TTC | 10.82 | 3 |
| TTG | ATC | TTG/ATC | 10.82 | 2 |
| TCT | CGT | TCT/CGT | 10.8 | 2 |
| CAA | TCC | CAA/TCC | 10.79 | 3 |
| CCG | AGC | CCG/AGC | 10.76 | 3 |
| AGT | AAC | AGT/AAC | 10.76 | 2 |
| CCT | TCG | CCT/TCG | 10.75 | 2 |
| TTG | AGG | TTG/AGG | 10.74 | 2 |
| TCC | TGC | TCC/TGC | 10.73 | 1 |
| AAA | CGT | AAA/CGT | 10.72 | 3 |
| CTC | CGT | CTC/CGT | 10.72 | 2 |
| GAT | GGG | GAT/GGG | 10.7 | 2 |
| TCT | TAG | TCT/TAG | 10.69 | 2 |
| GTC | TGC | GTC/TGC | 10.67 | 2 |
| GTG | AAG | GTG/AAG | 10.66 | 2 |
| CTC | TAG | CTC/TAG | 10.62 | 3 |
| AAA | TAG | AAA/TAG | 10.61 | 2 |
| CTT | GAC | CTT/GAC | 10.58 | 3 |
| TTG | ATG | TTG/ATG | 10.57 | 1 |
| CTT | CAG | CTT/CAG | 10.56 | 2 |
| TCA | TTC | TCA/TTC | 10.54 | 2 |
| GCT | TGT | GCT/TGT | 10.54 | 2 |
| TCC | ATC | TCC/ATC | 10.52 | 2 |
| GGT | CAC | GGT/CAC | 10.49 | 3 |
| CAA | TTG | CAA/TTG | 10.49 | 3 |
| GTC | ATC | GTC/ATC | 10.46 | 1 |
| GTG | AAC | GTG/AAC | 10.46 | 3 |
| GGA | GTG | GGA/GTG | 10.45 | 2 |
| TCC | AGG | TCC/AGG | 10.44 | 3 |
| GTC | AGG | GTC/AGG | 10.38 | 3 |
| CCA | GTG | CCA/GTG | 10.28 | 3 |
| TCC | ATG | TCC/ATG | 10.27 | 3 |
| GTC | ATG | GTC/ATG | 10.22 | 2 |
| TTG | TGG | TTG/TGG | 10.2 | 1 |
| ATA | CTG | ATA/CTG | 10.18 | 2 |
| GGA | AGT | GGA/AGT | 10.15 | 2 |
| GAT | TGT | GAT/TGT | 10.13 | 2 |

TABLE 2-continued

Variant pairs that have an on/off ratio of 10 shown in FIG. 2D

| on | off | pair | ratio | edit_distance |
|---|---|---|---|---|
| CTT | GCG | CTT/GCG | 10.12 | 3 |
| CTA | AGA | CTA/AGA | 10.03 | 2 |

Figure 2E:
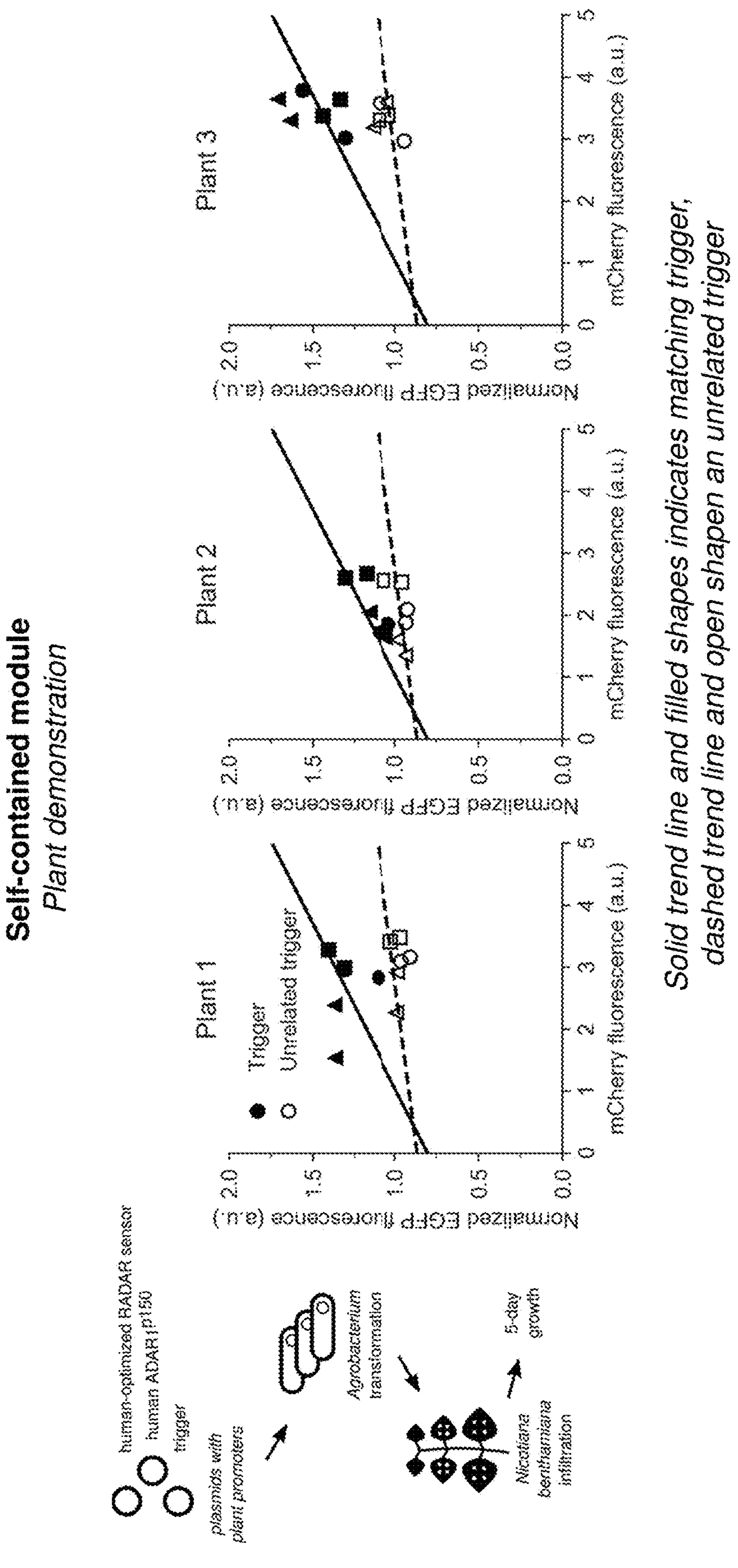

Finally, to show that RADAR is a self-contained module, we assessed RADAR in plants, organisms lacking endogenous ADAR. Without any optimization other than switching to plant promoters and vectors, we observed elevated fluorescent output in response to the matching T1 trigger compared to a non-matching trigger in a *Nicotiana benthamiana* model system (FIG. 2E), indicating that RADAR still operates as intended in a heterologous context, and is therefore potentially useful in a wide range of species, even those lacking native ADAR machinery.

Here we demonstrated leveraging ADAR editing to create a modular, programmable molecular device capable of sensing a broad variety of RNAs. One key direction of future improvements to RADAR is increasing input sensitivity (FIGS. 4A-4C) to accommodate the expression level of more endogenous RNAs. Designing new sensors is straightforward thanks to base pairing rules; a plasmid encoding a new sensor can be generated using standard techniques in two days of receiving short oligonucleotides. Since all RADAR components can be delivered via mRNA, the wide range of existing RNA synthetic biology tools (Dykstra, P. B. et al. (2022) *Nat. Rev. Genet.* 1-14) as well as RNA nanotechnology advances (Groves, B. et al. (2016) *Nat. Nanotechnol.* 11, 287-294) could be combined with RADAR to produce cell classifiers, research tools, and smart dynamic therapies. For example, RADAR sensors could be used to track cells as they become infected with a virus, as they transition from normal to pre-cancerous to cancerous to metastatic, or as they become senescent to study these processes, create smart therapies that can dynamically detect these state changes, and stop or even reverse the processes driving them. By integrating multiple inputs, RADAR can enable high specificity and low off-target effects of the downstream interventions. It is especially suitable for increasing the specificity of RNA-based vaccination and gene therapies, the power of which was recently demonstrated during the pandemic. As RADAR can be delivered on viral or other genetic vectors and achieve cell type-specific expression, it removes the need for promoter identification, which has remained a major hurdle in onboarding new organisms for bioengineering or genetics-driven research.

The methods herein have numerous applications. RADARs can be used for feedback gene editing where gene editing enzymes may be turned off once a desired mutation is detected to reduce off-target editing. RADARs can be used for feedback gene expression for gene therapy where a transcription factor could be produced in response to the gene that it regulates, either positively or negatively. This enables precise control over the expression levels of that gene. RADARs can be used for markerless cell therapy screening where in cell therapies, cells must be edited/engineered with high fidelity, but this is often hard to achieve without having a selectable marker (which most of the time is undesirable to use). RADAR could be used to transiently select for cells that have the intended. RADARs can be used to detect plant pathogens such as viruses. RADARs can be used for the delivery of oncolytics and senolytics to kill diseased cells. RADARs can be used for manipulating cells based on their type or state: e.g., sensing a marker of T cell exhaustion to then modify T cell therapy behavior; detecting whether a cell is the right dendritic cell to express an antigen for a "tolerogenic vaccine" (antigens expressed by certain dendritic cells will make the body become tolerant to it, so this is kind of treatment for allergies). RADARs can be used for regulating engineered RNA viruses (e.g., alphaviruses and the rabies virus have been engineered for various purposes, including therapeutics such as self-amplifying RNA vaccines or cancer treatments, and our system could be used to control that, e.g. by negative feedback, to regulate dosage and lifetime). Our system could a part of the RNA virus package or a separate, co-delivered module. RADARs can be used for safety devices other than feedback for engineered viruses; e.g., one may not want to express an RNA-based therapy in cells infected with a retrovirus such as HIV, so our system could detect the presence of HIV RNA, and shut down so that the RNA wouldn't get integrated into the genome. (It could of course also try to deliver a treatment/inhibitor to the latent HIV). RADARs can also be used for IVF screening of eggs for certain mutations before fertilization (non-destructive, non-modifying).

Methods

Plasmid generation. Plasmids were generated using standard molecular cloning practices, including InFusion of linearized plasmids and PCR fragments and restriction-ligation of linearized fragments and annealed phosphorylated oligonucleotides. A complete list of plasmids and associated maps is found in Table 3. Plasmids are available upon request from the corresponding author and will be deposited to Addgene. Human ADAR plasmids as well as the ADAR1 knockout cell line were generously provided by prof. Billy Li. Cre and Cre reporter plasmids were kindly gifted by prof. Liqun Luo. pUBC_stdMCP_serinemod_E488QADAR_p2A_yGFP ("ADAR(DD)-MCP") was a gift from Robert Singer (Addgene plasmid #154787).

TABLE 3

List of plasmids used

| Plasmid | Description | Source |
|---|---|---|
| EK0208 CMV-TO-BFPmut-stop-t70587 (FLP-IN) | trigger in 3' UTR | this work |
| EK0211 CMV-TO-BFPmut-stop-t17d9b (FLP-IN) | orthogonal trigger in 3' UTR. used as second input in OR, AND gates | this work |
| EK0285 SFFV-mCherry-SG(s70587)SG-EGFP (FLP-IN) | sensor for EK0208; mCherry marker, EGFP output | this work |
| EK0289 SFFV-mCherry-SG(s17d9b)SG-EGFP (FLP-IN) | sensor for EK0211; mCherry marker, EGFP output | this work |

TABLE 3-continued

List of plasmids used

| Plasmid | Description | Source |
|---|---|---|
| EK0290 SFFV-mCherry-SG(s70587-AND-s17d9b)SG-EGFP (FLP-IN) | sensor for "EK0208 AND EK0211"; mCherry marker, EGFP output | this work |
| EK0301 SFFV-mCherry-SG(Bdnf.s1)SG-EGFP (FLP-IN) | sensor for murine Bdnf 3' UTR; mCherry marker, EGFP output; 90 bp long | this work |
| EK0307 CMV-TO-BFPmut-stop-3UTR(Bdnf) (FLP-IN) | synthetic construct with 3' UTR of murine Bdnf | this work |
| EK0312 pAAV-EF1a-DIO-EYFP-WPRE-HGHpA | reporter for Cre with EYFP output; derived from a gift from prof. Liqun Luo | this work |
| EK0313 SFFV-mCherry-SG(s70587)SG-Cre (FLP-IN) | sensor for EK0208; mCherry marker, Cre output derived from a gift from prof. Liqun Luo | this work |
| EK0341 SFFV-mCherry-SG(Bdnf.s1L153)SG-EGFP (FLP-IN) | 153 bp long sensor for murine Bdnf 3' UTR | this work |
| EK0354 SFFV-mCherry-SG(Bdnf.s1L72)SG-EGFP (FLP-IN) | 72 bp long sensor for murine Bdnf 3' UTR | this work |
| EK0358 SFFV-mCherry-SG(Bdnf.s1L36)SG-EGFP (FLP-IN) | 36 bp long sensor for murine Bdnf 3' UTR | this work |
| EK0362 SFFV-mCherry-SG(Bdnf.s1L36 + 54@202)SG-EGFP (FLP-IN) | 36 + 54 = 90 bp long sensor for murine Bdnf 3' UTR where the trigger sequence is split | this work |
| EK0379 CMV-TO-EGFP-stop-t70587 (PB) | trigger in 3' UTR; used to make a cell line to study sensors for integrated 3' UTR or CDS triggers; expression is inducible with doxycycline | this work |
| EK0445 SFFV-mCherry-SGc(DNAJB1.s1)cSG-EGFP-(3xMS2) (FLP-IN) | sensor for human DNAJB1 (hsp40) 3' UTR; mCherry marker, EGFP output, three MS2 sequences in 3' UTR | this work |
| EK0387 SFFV-mTagBFP2-SGc(Bdnf.s1)cSG-mCherry (FLP-IN) | sensor for murine Bdnf 3' UTR; mTagBFP2 marker, mCherry output; 90 bp long | this work |
| EK0344 SFFV-mCherry-SG(Bdnf.s1)SG-Cre (FLP-IN) | sensor for murine Bdnf 3' UTR; mCherry marker, Cre output; 90 bp long | this work |
| EK0393 SFFV-mTagBFP2-SGc(EGFP.s2)cSG-mCherry (FLP-IN) | sensor for EGFP CDS; mTagBFP2 marker, mCherry output | this work |
| EK0325 SFFV-mCherry-SG(EGFP.s2)SG-Cre (FLP-IN) | EGFP CDS sensor; mCherry marker, Cre output | this work |
| EK0441 CMV-TO-BFPmut-stop-EGFP.t2 (FLP-IN) | trigger sequence from EGFP CDS in 3' UTR context | this work |
| EK0423 SFFV-mTagBFP2-SGc(s70587)cSG-mCherry (FLP-IN) | sensor for synthetic sequence (EK0208); mTagBFP2 marker, mCherry output | this work |
| EK0438 SFFV-mCherry-SGc(s70587)cSG-EGFP-(3xMS2) (FLP-IN) | sensor for synthetic sequence (EK0208) with three MS2 sequences in the 3' UTR. compared to EK0285, also has additional restriction sites around the sensor sequence. recommended for the basis for cloning new sensors for use with MCP-ADAR(DD) | this work |
| EK0409 SFFV-mCherry-SGc(s70587)cSG-EGFP (FLP-IN) | compared to EK0285, also has additional restriction sites around the sensor sequence, and is recommended for the basis for cloning new sensors | this work |
| NK10 mCherry-SG(s70587-3xMS2)SG-EGFP (FLP-IN) | similar to EK0438, but with MS2 sequences directly after the sensor sequence | this work |
| NSK025 CMV-TO-EGFP: c.637A > G(N213D; CCA > CCG)-stop-t70587 (PB) | EGFP mutant N213D derived from EK0379 | this work |
| NSK021 CMV-TO-p53R248Q (FLP-IN) | p53 mutant R248Q | this work |
| NSK026 CMV-TO-p53R248W | p53 mutant R248W | this work |
| NSK024 SFFV-mCherry-SG(p53R248Q.s2)SG-EGFP (FLP-IN) | sensor for p53 mutant R248Q; mCherry marker, EGFP output | this work |

TABLE 3-continued

List of plasmids used

| Plasmid | Description | Source |
|---|---|---|
| pUBC__stdMCP__serinemod__E488QADAR__p2A__yGFP | ADAR2 hyperactive mutant E488Q deaminase domain fused with MCP | Biswas et al iScience 2020 |
| EK0395 Che-SG(s70587)SG-GFP (PEAQ) | EK0285 in plant-expressable format | this work |
| EK0396 BFPmut-stop-t70587 (PEAQ) | EK0208 in plant-expressable format | this work |
| EK0397 3FLAG-ADAR1-p150-HIS (PEAQ) | human ADAR1, p150 isoform in plant-expressable format | this work |
| CC0101 BFPmut-stop-Bdnf.t1 (PEAQ) | an orthogonal trigger sequence used in plant experiments, derived from the 3' UTR of murine Bdnf | this work |

Tissue culture. Flp-In T-REx Human Embryonic Kidney (HEK) 293 cells were purchased from Thermo Scientific (catalog #R78007). Cells were cultured in a humidity-controlled incubator under standard culture conditions (37° C. with 5% C02) in Dulbecco's Modified Eagle Medium, supplemented with 10% fetal bovine serum (Fisher Scientific catalog #FB 12999102), 1 mM sodium pyruvate (EMD Millipore catalog #TMS-005-C), Ix penicillin-streptomycin (Genesee catalog #25-512), 2 mM Lglutamine (Genesee catalog #25-509) and 1×MEM non-essential amino acids (Genesee catalog #25-536). To induce expression of certain constructs, 100 ng/mL of doxycycline was added at the time of transfection. The inducible-trigger containing cell line was generated by transfecting the construct in a PiggyBac backbone along with PiggyBac integrase (4:1), with 50 μg/mL hygromycin added for selection when reseeding into 10 cm dishes two days after transfection.

Transient transfections. HEK 293 cells were cultured in either 24-well or 96-well tissue culture-treated plates under standard culture conditions. When cells were 70-90% confluent, the cells were transiently transfected with plasmid constructs using the jetOPTIMUSR DNA transfection Reagent (Polyplus catalog #117-15), as per manufacturer's instructions using 0.375 uL of reagent per 50 uL of jetOPTIMUS buffer for 500 ng total DNA transfections in the 24-well format and 0.13 uL of reagent per 12.5 uL of buffer for 130 ng total DNA in the 96-well format. All transfections are detailed in Table 4.

TABLE 4

Transfections preformed.

| FIG. | Experiment ID | Cell line | Condition | Plasmid | Amount (ng) | Format |
|---|---|---|---|---|---|---|
| 1B, 3A, 3B | 1 | HEK293 Flp-In T-Rex | sensor | EK0285 SFFV-mCherry-SG(s70587)SG-EGFP (FLP-IN) | 200 | 24-well |
| | | | sensor + non-matching trigger | EK0285 SFFV-mCherry-SG(s70587)SG-EGFP (FLP-IN) | 200 | |
| | | | | EK0211 CMV-TO-BFPmut-stop-t17d9b (FLP-IN) | 250 | |
| | | | sensor + matching trigger | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | sensor + ADAR1-p150 | EK0285 SFFV-mCherry-SG(s70587)SG-EGFP (FLP-IN) | 200 | |
| | | | | pCDH 3FLAG-ADAR1-p150-HIS | 50 | |
| | | | sensor + non-matching trigger + ADAR1-p150 | EK0285 SFFV-mCherry-SG(s70587)SG-EGFP (FLP-IN) | 200 | |
| | | | | EK0211 CMV-TO-BFPmut-stop-t17d9b (FLP-IN) | 250 | |
| | | | | pCDH 3FLAG-ADAR1-p150-HIS | 50 | |
| | | | sensor + matching trigger + ADAR1-p150 | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | | pCDH 3FLAG-ADAR1-p150-HIS | 50 | |
| 1C | 2 | HEK293 Flp-In T-Rex | sensor + trigger + ADAR1-p150 | EK0285 SFFV-mCherry-SG(s70587)SG-EGFP (FLP-IN) | 200 | 24-well |
| | | | | EK0208 CMV-TO-BFPmut-stop-t70587 (FLP-IN) | 0-250 | |
| | | | | pCDH 3FLAG-ADAR1-p150-HIS | 50 | |
| 1D | 3 | HEK293 Flp-In T-Rex | sensor + ADAR1-p150 | EK0313 SFFV-mCherry-SG(s70587)SG-Cre (FLP-IN) | 100 | 24-well |
| | | | | EK0312 pAAV-EF1a-DIO-EYFP- | 100 | |

TABLE 4-continued

Transfections preformed.

| FIG. | Experiment ID | Cell line | Condition | Plasmid | Amount (ng) | Format |
|---|---|---|---|---|---|---|
| | | | | WPRE-HGHpA | | |
| | | | | pCDH 3FLAG-ADAR1-p150-HIS | 50 | |
| | | | sensor + trigger + ADAR1-p150 | EK0313 SFFV-mCherry-SG(s70587)SG-Cre (FLP-IN) | 100 | |
| | | | | EK0312 pAAV-EF1a-DIO-EYFP-WPRE-HGHpA | 100 | |
| | | | | EK0208 CMV-TO-BFPmut-stop-t70587 (FLP-IN) | 250 | |
| | | | | pCDH 3FLAG-ADAR1-p150-HIS | 50 | |
| 1E | 4 | PiggyBac of HEK293 Flp-In T-Rex with EK0379 CMV-TO-EGFP-stop-t70587 (PB) | non-matched sensor + ADAR1-p150 | EK0387 SFFV-mTagBFP2-SGc(Bdnf.s1)cSG-mCherry (FLP-IN) | 450 | 24-well |
| | | | | pCDH 3FLAG-ADAR1-p150-HIS | 50 | |
| | | | sensor + ADAR1-p150 | EK0423 SFFV-mTagBFP2-SGc(s70587)cSG-mCherry (FLP-IN) | 450 | |
| | | | | pCDH 3FLAG-ADAR1-p150-HIS | 50 | |
| 1F | 5 | HEK293 Flp-In T-Rex | sensor + ADAR1-p150 | EK0301 SFFV-mCherry-SG(Bdnf.s1)SG-EGFP (FLP-IN) | 200 | 24-well |
| | | | | pCDH 3FLAG-ADAR1-p150-HIS | 50 | |
| | | | sensor + 3UTR(Bdnf) + ADAR1-p150 | EK0301 SFFV-mCherry-SG(Bdnf.s1)SG-EGFP (FLP-IN) | 200 | |
| | | | | EK0307 CMV-TO-BFPmut-stop-3UTR(Bdnf) (FLP-IN) | 250 | |
| | | | | pCDH 3FLAG-ADAR1-p150-HIS | 50 | |
| 1G | 6 | HEK293 | non-matched sensor + ADAR1-p150, no heat shock | EK0285 SFFV-mCherry-SG(s70587)SG-EGFP (FLP-IN) | 450 | 24-well |
| | | | | pCDH 3FLAG-ADAR1-p150-HIS | 50 | |
| | | | hsp40 sensor + ADAR1-p150, no heat shock | EK0445 SFFV-mCherry-SGc(DNAJB1.s1)cSG-EGFP-(3xMS2) (FLP-IN) | 450 | |
| | | | | pCDH 3FLAG-ADAR1-p150-HIS | 50 | |
| | | | non-matched sensor + ADAR1-p150, no heat shock | EK0285 SFFV-mCherry-SG(s70587)SG-EGFP (FLP-IN) | 450 | |
| | | | | pCDH 3FLAG-ADAR1-p150-HIS | 50 | |
| | | | hsp40 sensor + ADAR1-p150, no heat shock | EK0445 SFFV-mCherry-SGc(DNAJB1.s1)cSG-EGFP-(3xMS2) (FLP-IN) | 450 | |
| | | | | pCDH 3FLAG-ADAR1-p150-HIS | 50 | |
| 1H | 5 | HEK293 Flp-In T-Rex | dsRNA length 36 + ADAR1-p150 | EK0358 SFFV-mCherry-SG(Bdnf.s1L36)SG-EGFP (FLP-IN) | 200 | 24-well |
| | | | | pCDH 3FLAG-ADAR1-p150-HIS | 50 | |
| | | | dsRNA length 36 + ADAR1-p150 + 3UTR(Bdnf) | EK0358 SFFV-mCherry-SG(Bdnf.s1L36)SG-EGFP (FLP-IN) | 200 | |
| | | | | pCDH 3FLAG-ADAR1-p150-HIS | 50 | |
| | | | | EK0307 CMV-TO-BFPmut-stop-3UTR(Bdnf) (FLP-IN) | 250 | |
| | | | dsRNA length 72 + ADAR1-p150 | EK0354 SFFV-mCherry-SG(Bdnf.s1L72)SG-EGFP (FLP-IN) | 200 | |
| | | | | pCDH 3FLAG-ADAR1-p150-HIS | 50 | |
| | | | dsRNA length 72 + ADAR1-p150 + 3UTR(Bdnf) | EK0354 SFFV-mCherry-SG(Bdnf.s1L72)SG-EGFP (FLP-IN) | 200 | |
| | | | | pCDH 3FLAG-ADAR1-p150-HIS | 50 | |
| | | | | EK0307 CMV-TO-BFPmut-stop-3UTR(Bdnf) (FLP-IN) | 250 | |
| | | | dsRNA length 90 + ADAR1-p150 | EK0301 SFFV-mCherry-SG(Bdnf.s1)SG-EGFP (FLP-IN) | 200 | |
| | | | | pCDH 3FLAG-ADAR1-p150-HIS | 50 | |
| | | | dsRNA length 90 + ADAR1-p150 + 3UTR(Bdnf) | EK0301 SFFV-mCherry-SG(Bdnf.s1)SG-EGFP (FLP-IN) | 200 | |
| | | | | EK0307 CMV-TO-BFPmut-stop-3UTR(Bdnf) (FLP-IN) | 250 | |
| | | | | pCDH 3FLAG-ADAR1-p150-HIS | 50 | |
| | | | dsRNA length 153 + ADAR1-p150 | EK0341 SFFV-mCherry-SG(Bdnf.s1L153)SG-EGFP (FLP-IN) | 200 | |
| | | | | pCDH 3FLAG-ADAR1-p150-HIS | 50 | |
| | | | dsRNA length 153 + ADAR1-p150 + | EK0341 SFFV-mCherry-SG(Bdnf.s1L153)SG-EGFP (FLP-IN) | 200 | |

TABLE 4-continued

Transfections preformed.

| FIG. | Experiment ID | Cell line | Condition | Plasmid | Amount (ng) | Format |
|---|---|---|---|---|---|---|
| | | | 3UTR(Bdnf) | pCDH 3FLAG-ADAR1-p150-HIS | 50 | |
| | | | | EK0307 CMV-TO-BFPmut-stop-3UTR(Bdnf) (FLP-IN) | 250 | |
| 1I | 5 | HEK293 Flp-In T-Rex | dsRNA length 36 + ADAR1-p150 | EK0358 SFFV-mCherry-SG(Bdnf.s1L36)SG-EGFP (FLP-IN) | 200 | 24-well |
| | | | | pCDH 3FLAG-ADAR1-p150-HIS | 50 | |
| | | | dsRNA length 36 + ADAR1-p150 + 3UTR(Bdnf) | EK0358 SFFV-mCherry-SG(Bdnf.s1L36)SG-EGFP (FLP-IN) | 200 | |
| | | | | pCDH 3FLAG-ADAR1-p150-HIS | 50 | |
| | | | | EK0307 CMV-TO-BFPmut-stop-3UTR(Bdnf) (FLP-IN) | 250 | |
| | | | dsRNA length 36 + 54 + ADAR1-p150 | EK0362 SFFV-mCherry-SG(Bdnf.s1L36 + 54@202)SG-EGFP (FLP-IN) | 200 | |
| | | | | pCDH 3FLAG-ADAR1-p150-HIS | 50 | |
| | | | dsRNA length 36 + 54 + ADAR1-p150 + 3UTR(Bdnf) | EK0362 SFFV-mCherry-SG(Bdnf.s1L36 + 54@202)SG-EGFP (FLP-IN) | 200 | |
| | | | | pCDH 3FLAG-ADAR1-p150-HIS | 50 | |
| | | | | EK0307 CMV-TO-BFPmut-stop-3UTR(Bdnf) (FLP-IN) | 250 | |
| | | | dsRNA length 90 + ADAR1-p150 | EK0301 SFFV-mCherry-SG(Bdnf.s1)SG-EGFP (FLP-IN) | 200 | |
| | | | | pCDH 3FLAG-ADAR1-p150-HIS | 50 | |
| | | | dsRNA length 90 + ADAR1-p150 + 3UTR(Bdnf) | EK0301 SFFV-mCherry-SG(Bdnf.s1)SG-EGFP (FLP-IN) | 200 | |
| | | | | EK0307 CMV-TO-BFPmut-stop-3UTR(Bdnf) (FLP-IN) | 250 | |
| | | | | pCDH 3FLAG-ADAR1-p150-HIS | 50 | |
| 1J | 4 | PiggyBac of HEK293 Flp-In T-Rex with EK0379 CMV-TO-EGFP-stop-t70587 (PB) | non-matched sensor + ADAR1-p150 | EK0387 SFFV-mTagBFP2-SGc(Bdnf.s1)cSG-mCherry (FLP-IN) | 450 | 24-well |
| | | | | pCDH 3FLAG-ADAR1-p150-HIS | 50 | |
| | | | sensor + ADAR1-p150 | EK0393 SFFV-mTagBFP2-SGc(EGFP.s2)cSG-mCherry (FLP-IN) | 450 | |
| | | | | pCDH 3FLAG-ADAR1-p150-HIS | 50 | |
| 1L | 8 | HEK293 Flp-In T-Rex | MS2 sensor | EK0438 SFFV-mCherry-SGc(s70587)cSG-EGFP-(3xMS2) (FLP-IN) | 200 | 24-well |
| | | | MS2 sensor + trigger | EK0438 SFFV-mCherry-SGc(s70587)cSG-EGFP-(3xMS2) (FLP-IN) | 200 | |
| | | | | EK0208 CMV-TO-BFPmut-stop-t70587 (FLP-IN) | 250 | |
| | | | MS2 sensor + ADAR(DD)-MCP | EK0438 SFFV-mCherry-SGc(s70587)cSG-EGFP-(3xMS2) (FLP-IN) | 200 | |
| | | | | pUBC__stdMCP__serinemod__E488QADAR__p2A__yGFP | 50 | |
| | | | MS2 sensor + ADAR(DD)-MCP + trigger | EK0438 SFFV-mCherry-SGc(s70587)cSG-EGFP-(3xMS2) (FLP-IN) | 200 | |
| | | | | pUBC__stdMCP__serinemod__E488QADAR__p2A__yGFP | 50 | |
| | | | | EK0208 CMV-TO-BFPmut-stop-t70587 (FLP-IN) | 250 | |
| | | | sensor | EK0285 SFFV-mCherry-SG(s70587)SG-EGFP (FLP-IN) | 200 | |
| | | | sensor + trigger | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | sensor + ADAR(DD)-MCP | EK0285 SFFV-mCherry-SG(s70587)SG-EGFP (FLP-IN) | 200 | |
| | | | | pUBC__stdMCP__serinemod__E488QADAR__p2A__yGFP | 50 | |
| | | | sensor + ADAR(DD)- | EK0285 SFFV-mCherry-SG(s70587)SG-EGFP (FLP-IN) | 200 | |

TABLE 4-continued

Transfections preformed.

| FIG. | Experiment ID | Cell line | Condition | Plasmid | Amount (ng) | Format |
|---|---|---|---|---|---|---|
| | | | MCP + trigger | pUBC__stdMCP__serinemod__E488QA DAR__p2A__yGFP | 50 | |
| | | | | EK0208 CMV-TO-BFPmut-stop-t70587 (FLP-IN) | 250 | |
| 2A | 9 | ~50% PiggyBac of HEK293 Flp-In T-Rex with EK0379 CMV-TO-EGFP-stop-t70587 (PB) ~50% HEK293 Flp-In T-Rex | 3' UTR sensor | EK0423 SFFV-mTagBFP2-SGc(s70587)cSG-mCherry (FLP-IN) | 450 | 24-well |
| | | | | pCDH 3FLAG-ADAR1-p150-HIS | 50 | |
| 2B | 10 | HEK293 Flp-In T-Rex | sensor 1 + sensor 2 + ADAR1-p150 | EK0285 SFFV-mCherry-SG(s70587)SG-EGFP (FLP-IN) | 25 | 96-well |
| | | | | EK0289 SFFV-mCherry-SG(s17d9b)SG-EGFP (FLP-IN) | 25 | |
| | | | | pCDH 3FLAG-ADAR1-p150-HIS | 12.5 | |
| | | | sensor 1 + sensor 2 + ADAR1-p150 + trigger 1 | EK0285 SFFV-mCherry-SG(s70587)SG-EGFP (FLP-IN) | 25 | |
| | | | | EK0289 SFFV-mCherry-SG(s17d9b)SG-EGFP (FLP-IN) | 25 | |
| | | | | pCDH 3FLAG-ADAR1-p150-HIS | 12.5 | |
| | | | | EK0208 CMV-TO-BFPmut-stop-t70587 (FLP-IN) | 31.25 | |
| | | | sensor 1 + sensor 2 + ADAR1-p150 + trigger 2 | EK0285 SFFV-mCherry-SG(s70587)SG-EGFP (FLP-IN) | 25 | |
| | | | | EK0289 SFFV-mCherry-SG(s17d9b)SG-EGFP (FLP-IN) | 25 | |
| | | | | pCDH 3FLAG-ADAR1-p150-HIS | 12.5 | |
| | | | | EK0211 CMV-TO-BFPmut-stop-t17d9b (FLP-IN) | 31.25 | |
| | | | sensor 1 + sensor 2 + ADAR1-p150 + trigger 1 + trigger 2 | EK0285 SFFV-mCherry-SG(s70587)SG-EGFP (FLP-IN) | 25 | |
| | | | | EK0289 SFFV-mCherry-SG(s17d9b)SG-EGFP (FLP-IN) | 25 | |
| | | | | pCDH 3FLAG-ADAR1-p150-HIS | 12.5 | |
| | | | | EK0208 CMV-TO-BFPmut-stop-t70587 (FLP-IN) | 31.25 | |
| | | | | EK0211 CMV-TO-BFPmut-stop-t17d9b (FLP-IN) | 31.25 | |
| 2C | 10 | HEK293 Flp-In T-Rex | AND sensor + ADAR1-p150 | EK0290 SFFV-mCherry-SG(s70587-AND-s17d9b)SG-EGFP (FLP-IN) | 50 | 96-well |
| | | | | pCDH 3FLAG-ADAR1-p150-HIS | 12.5 | |
| | | | AND sensor + ADAR1-p150 + trigger 1 | EK0290 SFFV-mCherry-SG(s70587-AND-s17d9b)SG-EGFP (FLP-IN) | 50 | |
| | | | | pCDH 3FLAG-ADAR1-p150-HIS | 12.5 | |
| | | | | EK0208 CMV-TO-BFPmut-stop-t70587 (FLP-IN) | 31.25 | |
| | | | AND sensor + ADAR1-p150 + trigger 2 | EK0290 SFFV-mCherry-SG(s70587-AND-s17d9b)SG-EGFP (FLP-IN) | 50 | |
| | | | | pCDH 3FLAG-ADAR1-p150-HIS | 12.5 | |
| | | | | EK0211 CMV-TO-BFPmut-stop-t17d9b (FLP-IN) | 31.25 | |
| | | | AND sensor + ADAR1-p150 + trigger 1 + trigger 2 | EK0290 SFFV-mCherry-SG(s70587-AND-s17d9b)SG-EGFP (FLP-IN) | 50 | |
| | | | | pCDH 3FLAG-ADAR1-p150-HIS | 12.5 | |
| | | | | EK0208 CMV-TO-BFPmut-stop-t70587 (FLP-IN) | 31.25 | |
| | | | | EK0211 CMV-TO-BFPmut-stop-t17d9b (FLP-IN) | 31.25 | |
| 2D | 12 | HEK293 Flp-In T-Rex | sensor + ADAR1-p150 | NSK024 SFFV-mCherry-SG(p53R248Q.s2)SG-EGFP (FLP-IN) | 200 | 24-well |
| | | | | pCDH 3FLAG-ADAR1-p150-HIS | 50 | |
| | | | sensor + ADAR1-p150 + | NSK024 SFFV-mCherry-SG(p53R248Q.s2)SG-EGFP (FLP-IN) | 200 | |

TABLE 4-continued

Transfections preformed.

| FIG. | Experiment ID | Cell line | Condition | Plasmid | Amount (ng) | Format |
|---|---|---|---|---|---|---|
| | | | p53 (R248W) | pCDH 3FLAG-ADAR1-p150-HIS | 50 | |
| | | | | NSK026 CMV-TO-p53R248W | 250 | |
| | | | sensor + ADAR1-p150 + p53 (R248Q) | NSK024 SFFV-mCherry-SG(p53R248Q.s2)SG-EGFP (FLP-IN) | 200 | |
| | | | | pCDH 3FLAG-ADAR1-p150-HIS | 50 | |
| | | | | NSK021 CMV-TO-p53R248Q (FLP-IN) | 250 | |
| 2E | 13 | Agrobacterium infiltration of *Nicotiana benthamiana* | trigger | EK0395 Che-SG(s70587)SG-GFP (pEAQ) | ⅓ of 0.9 OD | plant infiltration |
| | | | | EK0396 BFPmut-stop-t70587 (pEAQ) | ⅓ of 0.9 OD | |
| | | | | EK0397 3FLAG-ADAR1-p150-HIS (pEAQ) | ⅓ of 0.9 OD | |
| | | | unrelated trigger | EK0395 Che-SG(s70587)SG-GFP (pEAQ) | ⅓ of 0.9 OD | |
| | | | | CC0101 BFPmut-stop-Bdnf.t1 (pEAQ) | ⅓ of 0.9 OD | |
| | | | | EK0397 3FLAG-ADAR1-p150-HIS (pEAQ) | ⅓ of 0.9 OD | |
| 3C | 14 | HEK293 Flp-In T-Rex | SFFV | PCR of SFFV promoter and mCherry-SG(s70587)SG-EGFP | 402 | 24-well |
| | | | EF1a | PCR of EF1a promoter and mCherry-SG(s70587)SG-EGFP | 497 | |
| | | | CMV | PCR of CMV promoter and mCherry-SG(s70587)SG-EGFP | 425 | |
| | | | CMV344 | PCR of CMV promoter (344 bp variant) and mCherry-SG(s70587)SG-EGFP | 378 | |
| | | | CMVa | PCR of CMV-tetO promoter (508 bp CMV 5' truncation) | 420 | |
| | | | CMVb | PCR of CMV-tetO promoter (432 bp CMV 5' truncation) | 409 | |
| | | | CMVc | PCR of CMV-tetO promoter (356 bp CMV 5' truncation) | 398 | |
| | | | CMVd | PCR of CMV-tetO promoter (280 bp CMV 5' truncation) | 387 | |
| | | | CMVe | PCR of CMV-tetO promoter (204 bp CMV 5' truncation) | 375 | |
| | | | CMV-tetO | PCR of CMV-tetO promoter and mCherry-SG(s70587)SG-EGFP | 444 | |
| 3D | 15 | HEK293 Flp-In T-Rex | sensor | EK0285 SFFV-mCherry-SG(s70587)SG-EGFP (FLP-IN) | 200 | 24-well |
| | | | sensor + orthogonal trigger | EK0285 SFFV-mCherry-SG(s70587)SG-EGFP (FLP-IN) | 200 | |
| | | | | EK0211 CMV-TO-BFPmut-stop-t17d9b (FLP-IN) | 250 | |
| | | | sensor + trigger | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | sensor + trigger + ADAR1-p150 | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | | pCDH 3FLAG-ADAR1-p150-HIS | 50 | |
| 3E | 16 | HEK293 ADAR1 K/O | sensor | EK0285 SFFV-mCherry-SG(s70587)SG-EGFP (FLP-IN) | 200 | 24-well |
| | | | sensor + trigger | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | sensor + trigger + ADAR1-p150 | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | | pCDH 3FLAG-ADAR1-p150-HIS | 50 | |
| 3F | 1 | HEK293 Flp-In T-Rex | sensor | EK0285 SFFV-mCherry-SG(s70587)SG-EGFP (FLP-IN) | 200 | 24-well |
| | | | sensor + non-matching trigger | EK0285 SFFV-mCherry-SG(s70587)SG-EGFP (FLP-IN) | 200 | |
| | | | | EK0211 CMV-TO-BFPmut-stop-t17d9b (FLP-IN) | 250 | |
| | | | sensor + matching trigger | EK0285 SFFV-mCherry-SG(s70587)SG-EGFP (FLP-IN) | 200 | |

TABLE 4-continued

Transfections preformed.

| FIG. | Experiment ID | Cell line | Condition | Plasmid | Amount (ng) | Format |
|---|---|---|---|---|---|---|
| | | | | EK0208 CMV-TO-BFPmut-stop-t70587 (FLP-IN) | 250 | |
| | | | sensor + ADAR1-p110 | EK0285 SFFV-mCherry-SG(s70587)SG-EGFP (FLP-IN) | 200 | |
| | | | | pCDH 3FLAG-ADAR1-p110-HIS | 50 | |
| | | | sensor + non-matching trigger + ADAR1-p110 | EK0285 SFFV-mCherry-SG(s70587)SG-EGFP (FLP-IN) | 200 | |
| | | | | EK0211 CMV-TO-BFPmut-stop-t17d9b (FLP-IN) | 250 | |
| | | | | pCDH 3FLAG-ADAR1-p110-HIS | 50 | |
| | | | sensor + matching trigger + ADAR1-p110 | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | | pCDH 3FLAG-ADAR1-p110-HIS | 50 | |
| | | | sensor + ADAR1-p150 | EK0285 SFFV-mCherry-SG(s70587)SG-EGFP (FLP-IN) | 200 | |
| | | | | pCDH 3FLAG-ADAR1-p150-HIS | 50 | |
| | | | sensor + non-matching trigger + ADAR1-p150 | EK0285 SFFV-mCherry-SG(s70587)SG-EGFP (FLP-IN) | 200 | |
| | | | | EK0211 CMV-TO-BFPmut-stop-t17d9b (FLP-IN) | 250 | |
| | | | | pCDH 3FLAG-ADAR1-p150-HIS | 50 | |
| | | | sensor + matching trigger + ADAR1-p150 | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | | pCDH 3FLAG-ADAR1-p150-HIS | 50 | |
| | | | sensor + ADAR2 | EK0285 SFFV-mCherry-SG(s70587)SG-EGFP (FLP-IN) | 200 | |
| | | | | pCDH 3FLAG-ADAR2-HIS | 50 | |
| | | | sensor + non-matching trigger + ADAR2 | EK0285 SFFV-mCherry-SG(s70587)SG-EGFP (FLP-IN) | 200 | |
| | | | | EK0211 CMV-TO-BFPmut-stop-t17d9b (FLP-IN) | 250 | |
| | | | | pCDH 3FLAG-ADAR2-HIS | 50 | |
| | | | sensor + matching trigger + ADAR2 | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | | pCDH 3FLAG-ADAR2-HIS | 50 | |
| 3G | 18 | HEK293 Flp-In T-Rex | sensor + ADAR1-p150 | EK0285 SFFV-mCherry-SG(s70587)SG-EGFP (FLP-IN) | 200 | 24-well |
| | | | | pCDH 3FLAG-ADAR1-p150-HIS | 0-50 | |
| | | | sensor + trigger + ADAR1-p150 | EK0285 SFFV-mCherry-SG(s70587)SG-EGFP (FLP-IN) | 200 | |
| | | | | EK0208 CMV-TO-BFPmut-stop-t70587 (FLP-IN) | 250 | |
| | | | | pCDH 3FLAG-ADAR1-p150-HIS | 0-50 | |
| 4A | 19 | HEK293 Flp-In T-Rex | cells: blank | EK0387 SFFV-mTagBFP2-SGc(Bdnf.s1)cSG-mCherry (FLP-IN) | 450 | 24-well |
| | | | | pCDH 3FLAG-ADAR1-p150-HIS | 50 | |
| | | PiggyBac of HEK293 Flp-In T-Rex with EK0379 CMV-TO-EGFP-stop-t70587 (PB) | cells: no inducer | EK0387 SFFV-mTagBFP2-SGc(Bdnf.s1)cSG-mCherry (FLP-IN) | 450 | |
| | | | | pCDH 3FLAG-ADAR1-p150-HIS | 50 | |
| | | | cells: inducer | EK0387 SFFV-mTagBFP2-SGc(Bdnf.s1)cSG-mCherry (FLP-IN) | 450 | |
| | | | | pCDH 3FLAG-ADAR1-p150-HIS | 50 | |
| 4B | 20 | N/A | plasmid titration | EK0379 CMV-TO-EGFP-stop-t70587 (PB) | varied | N/A |
| 4C | 21 | PiggyBac of HEK293 Flp-In T-Rex with EK0379 CMV-TO-EGFP-stop- | no inducer | N/A | N/A | 24-well |
| | | | inducer | N/A | N/A | |

TABLE 4-continued

| Transfections preformed. | | | | | | |
|---|---|---|---|---|---|---|
| FIG. | Experiment ID | Cell line | Condition | Plasmid | Amount (ng) | Format |
| | | t70587 (PB) | | | | |
| 4D | 22 | HEK293 Flp-In T-Rex | sensor + ADAR1-p150 | EK0393 SFFV-mTagBFP2-SGc(EGFP.s2)cSG-mCherry (FLP-IN) | 200 | 24-well |
| | | | | pCDH 3FLAG-ADAR1-p150-HIS | 50 | |
| | | | sensor + trigger in CDS + ADAR1-p150 | EK0393 SFFV-mTagBFP2-SGc(EGFP.s2)cSG-mCherry (FLP-IN) | 200 | |
| | | | | EK0379 CMV-TO-EGFP-stop-t70587 (PB) | 250 | |
| | | | | pCDH 3FLAG-ADAR1-p150-HIS | 50 | |
| | | | sensor + trigger in 3' UTR + ADAR1-p150 | EK0393 SFFV-mTagBFP2-SGc(EGFP.s2)cSG-mCherry (FLP-IN) | 200 | |
| | | | | EK0441 CMV-TO-BFPmut-stop-EGFP.t2 (FLP-IN) | 250 | |
| | | | | pCDH 3FLAG-ADAR1-p150-HIS | 50 | |
| 4E | 23 | PiggyBac of HEK293 Flp-In T-Rex with EK0379 CMV-TO-EGFP-stop-t70587 (PB) | non-matching sensor + ADAR1-p150 + inducer | EK0344 SFFV-mCherry-SG(Bdnf.s1)SG-Cre (FLP-IN) | 450 | 24-well |
| | | | | pCDH 3FLAG-ADAR1-p150-HIS | 50 | |
| | | | sensor (3' UTR) + ADAR1-p150 + inducer | EK0313 SFFV-mCherry-SG(s70587)SG-Cre (FLP-IN) | 450 | |
| | | | | pCDH 3FLAG-ADAR1-p150-HIS | 50 | |
| 4F | 23 | PiggyBac of HEK293 Flp-In T-Rex with EK0379 CMV-TO-EGFP-stop-t70587 (PB) | non-matching sensor + ADAR1-p150 + inducer | EK0344 SFFV-mCherry-SG(Bdnf.s1)SG-Cre (FLP-IN) | 450 | |
| | | | | pCDH 3FLAG-ADAR1-p150-HIS | 50 | |
| | | | sensor (CDS) + ADAR1-p150 + inducer | EK0325 SFFV-mCherry-SG(EGFP.s2)SG-Cre (FLP-IN) | 450 | |
| | | | | pCDH 3FLAG-ADAR1-p150-HIS | 50 | |
| 4I | 24 | HEK293 Flp-In T-Rex | sensor | EK0285 SFFV-mCherry-SG(s70587)SG-EGFP (FLP-IN) | 52 | 96-well |
| | | | sensor + trigger | EK0285 SFFV-mCherry-SG(s70587)SG-EGFP (FLP-IN) | 52 | |
| | | | | EK0208 CMV-TO-BFPmut-stop-t70587 (FLP-IN) | 65 | |
| | | | sensor + ADAR1-p150 | EK0285 SFFV-mCherry-SG(s70587)SG-EGFP (FLP-IN) | 52 | |
| | | | | pCDH 3FLAG-ADAR1-p150-HIS | 13 | |
| | | | sensor + trigger + ADAR1-p150 | EK0285 SFFV-mCherry-SG(s70587)SG-EGFP (FLP-IN) | 52 | |
| | | | | EK0208 CMV-TO-BFPmut-stop-t70587 (FLP-IN) | 65 | |
| | | | | pCDH 3FLAG-ADAR1-p150-HIS | 13 | |
| | | | MS2-sensor + ADAR(DD)-MCP | NK10 mCherry-SG(s70587-3xMS2)SG-EGFP (FLP-IN) | 52 | |
| | | | | pUBC__stdMCP__serinemod__E488QADAR__p2A__yGFP | 13 | |
| | | | MS2-sensor + trigger + ADAR(DD)-MCP | NK10 mCherry-SG(s70587-3xMS2)SG-EGFP (FLP-IN) | 52 | |
| | | | | EK0208 CMV-TO-BFPmut-stop-t70587 (FLP-IN) | 65 | |
| | | | | pUBC__stdMCP__serinemod__E488QADAR__p2A__yGFP | 13 | |
| 2D | 25 | HEK293 Flp-In T-Rex | sensor + ADAR1-p150 | EK0393 SFFV-mTagBFP2-SGc(EGFP.s2)cSG-mCherry (FLP-IN) | 200 | 24-well |
| | | | | pCDH 3FLAG-ADAR1-p150-HIS | 50 | |
| | | | sensor + ADAR1-p150 + EGFP (A > G) | EK0393 SFFV-mTagBFP2-SGc(EGFP.s2)cSG-mCherry (FLP-IN) | 200 | |
| | | | | pCDH 3FLAG-ADAR1-p150-HIS | 50 | |
| | | | | NSK025 CMV-TO-EGFP: c.637A > G(N213D; CCA > CCG)-stop-t70587 (PB) | 250 | |
| | | | sensor + ADAR1-p150 + | EK0393 SFFV-mTagBFP2-SGc(EGFP.s2)cSG-mCherry (FLP-IN) | 200 | |

TABLE 4-continued

| Transfections preformed. | | | | | | |
|---|---|---|---|---|---|---|
| FIG. | Experiment ID | Cell line | Condition | Plasmid | Amount (ng) | Format |
| | | | EGFP (WT) | pCDH 3FLAG-ADAR1-p150-HIS | 50 | |
| | | | | EK0379 CMV-TO-EGFP-stop-t70587 (PB) | 250 | |

24-well format: approximately 100,000 cells seeded. 0.375 uL of jetOptimus reagent in 50 uL jetOptimus buffer per condition for transfection on the following day. 500 ng total DNA for each condition, with remainder adjusted with filler plasmid. 96-well format: approximately 25,000 cells seeded. 0.13 uL of jetOptimus reagent in 12.5 uL jetOptimus buffer per condition for transfection on the following day. 130 ng total DNA for each condition, with remainder adjusted with filler plasmid. plant infiltration: Agrobacteria were electroporated with each plasmid separately. Overnight inoculates were verified with colony PCR. Cultures were diluted to an GD of 0.9 and combined in equal volumes for infiltration.

Figure 3A:
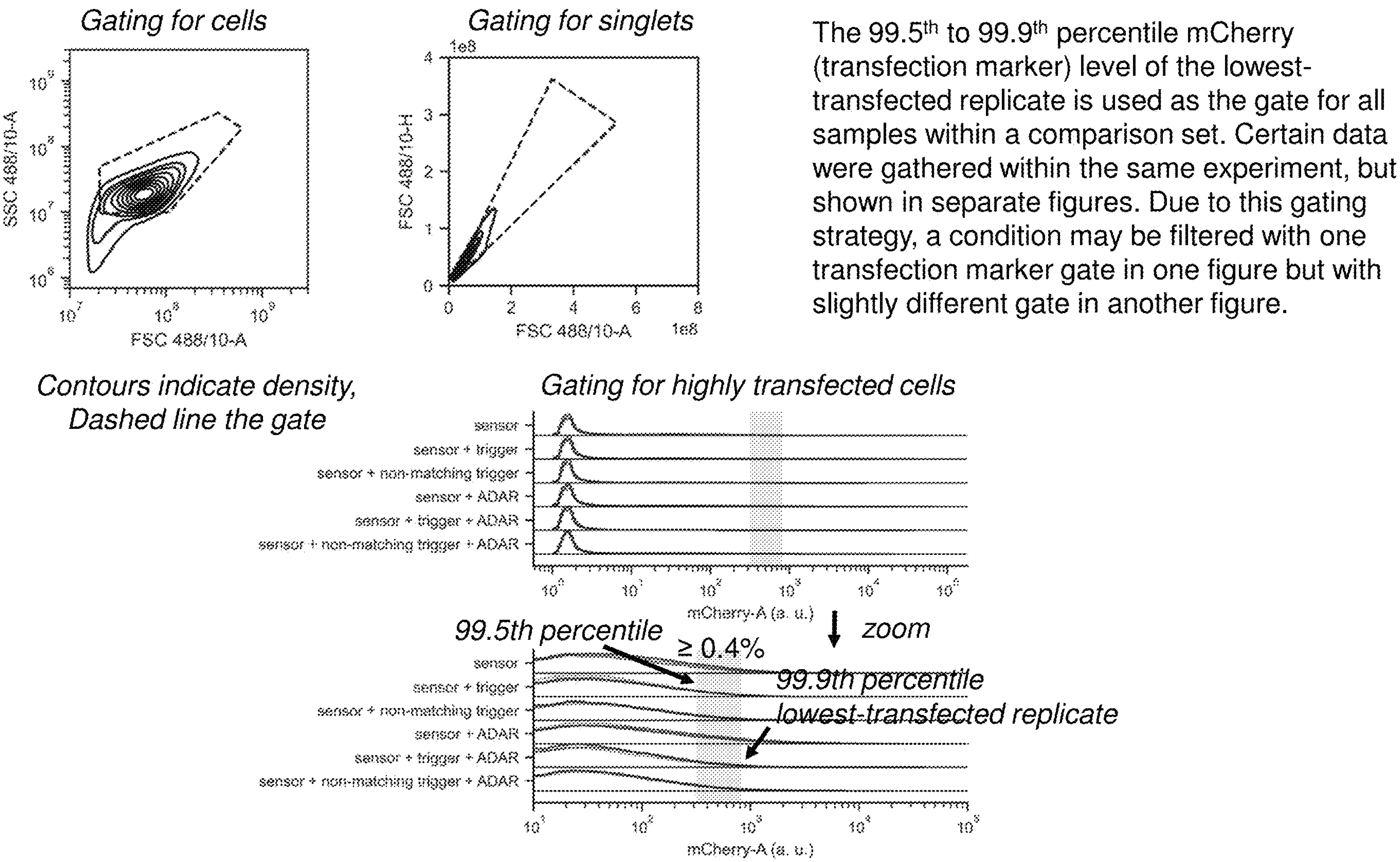
FIGS. 3A-3G. 3A) Flow cytometry gating overview. 3B) The ratio between the mean output fluorescence of the triggered and untriggered conditions depends on the chosen marker gate. Two-dimensional density plot showing the output (EGFP fluorescence, GFP-A) as a function of transfection marker levels (mCherry fluorescence, mCherry-A). The grey band indicates the chosen gate, as in subplot a. Traces indicate mean of EGFP fluorescence in small mCherry fluorescence bins. Points indicate mean in the chosen gate. Each replicate is a separate trace, but the 2D histogram combines all replicates. Rightmost column overlays all replicates. Black lines indicate the average of means across replicates, with the width indicating the gate. The means match those shown in main FIG. 1C. 3C) Enhancer choice affects baseline signaling, with SFFV giving the lowest baseline signal (EGFP fluorescence in the absence of trigger). Promoter variants were combined with the sensor using overlap extension PCR and transfected as linear fragments. 3D) Sanger sequencing confirmation of ADAR editing. 3E) RADAR does not function in ADAR-deficient cells, unless ADAR is supplied. 3F) The p150 isoform of ADAR1 was the best ADAR at improving the dynamic range of RADAR output. 3G) ADAR levels modulate sensor output. Purple numbers indicate the fold difference of the triggered case without ADAR, pink numbers indicate the fold difference to the untriggered case without ADAR, and black numbers indicate the fold activation upon adding trigger.
Figure 3B:
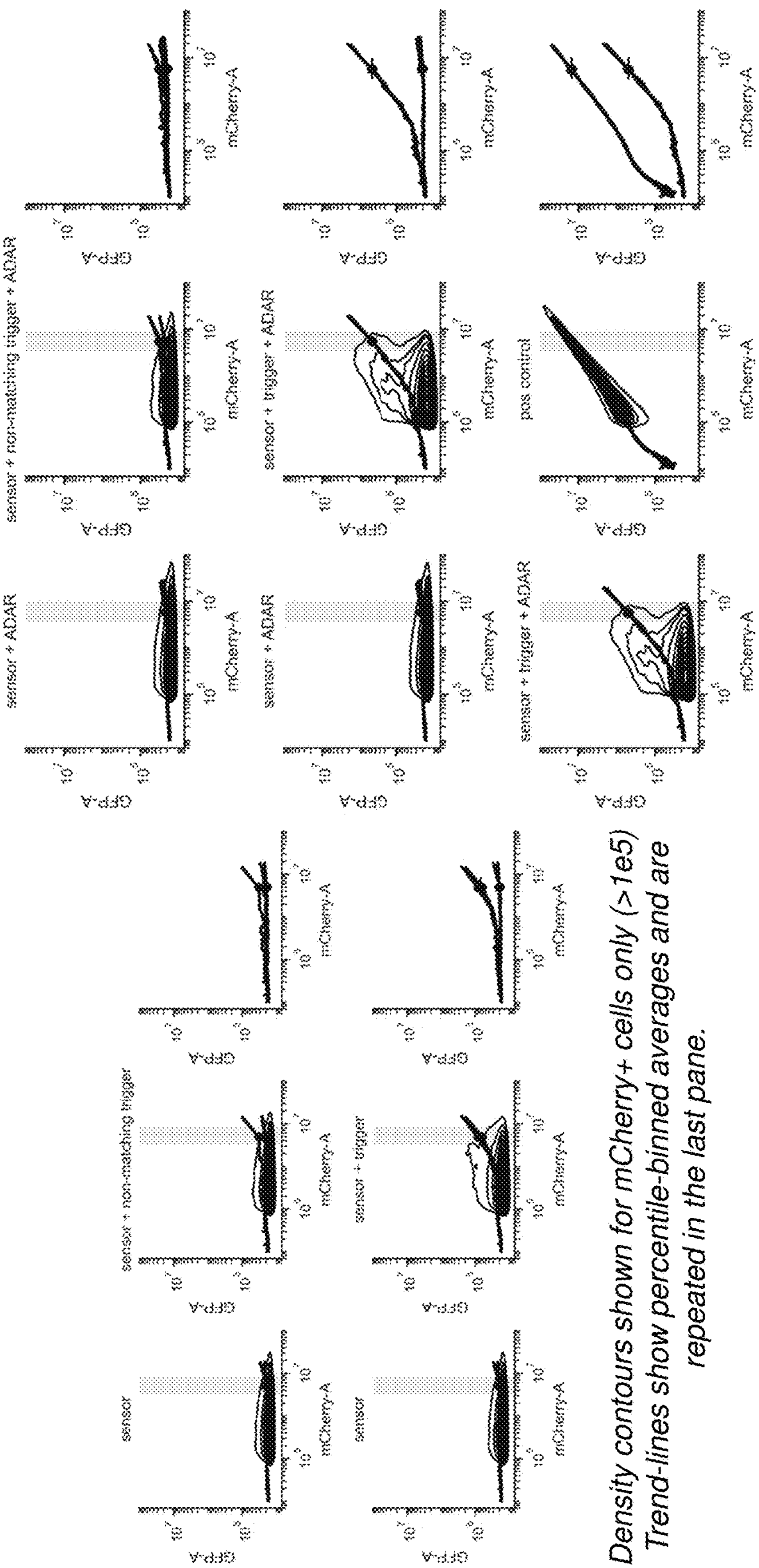
Figures 3C, 3D, 3E, 3F, 3G:
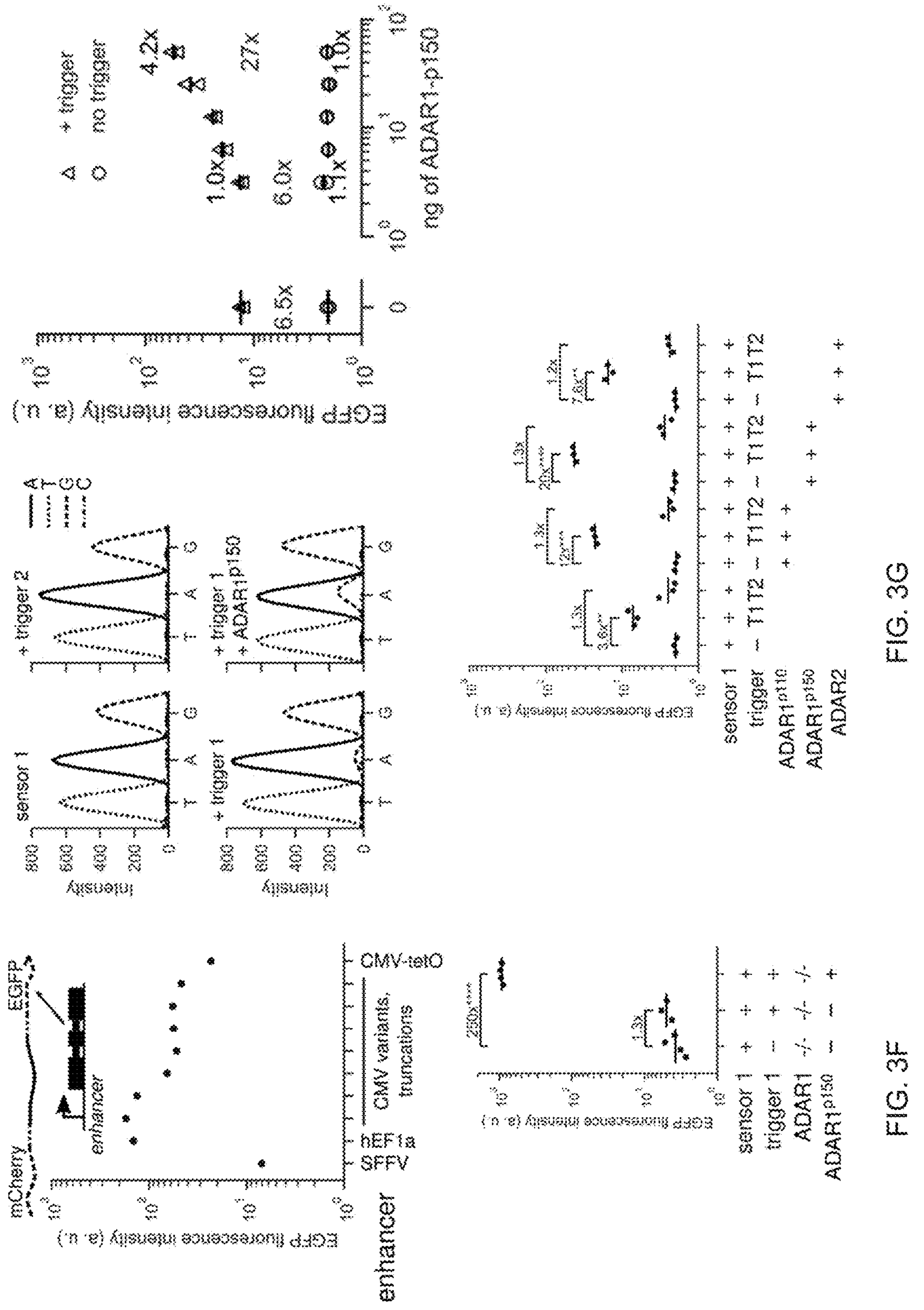

Flow cytometry and data analysis. Cells were harvested approximately 48 hours after transfection by trypsinization and resuspended in flow buffer (HBSS+2.5 mg/mL bovine serum albumin). Post 40 um straining, cells were analyzed by flow cytometry (Biorad ZE5 Cell Analyzer), and data was processed with the cytoflow Python package. An overview of gating and analysis is given in FIGS. 3A-3B.

RNA extraction and reverse-transcription. HEK293T cells grown in 24-plates were spun down and RNA was extracted using the following kits: RNAasy mini kit (Qiagen), RNase-Free DNase Set (Qiagen), and QIAshredder (Qiagen). After extraction RNA quality was assessed by running 500 ng on 1% agarose gel. 500 ng of purified RNA was then reverse-transcribed using iScript cDNA synthesis (Biorad). For Sanger sequencing, cDNA was sent to Genewiez/Azenta with matching primers.

qPCR Measurements. qPCR was carried out on a QuantStudio3 (Applied Biosystems) using SYBR-Green. RNA estimation was calculated based on the calibration curve of purified plasmid and normalized by the Ct threshold. The following primer pair sequences for GFP (Signagen) and normalizing gene (β-actin) were used: GFP-F AAGCAGAAGAACGGCATCAA (SEQ ID NO: 10), GFP-r TCCAGCAGGACCATGTGATC (SEQ ID NO:11), β-actin-F CGTCCACCGCAAATGCTT (SEQ ID NO: 12), β-actin-R GTTTTCTGCGCAAGTTAGGTTTTGT (SEQ ID NO: 13).

Leaf infiltration and analysis. Three leaves in three *Nicotiana benthamiana* plants were infiltrated with *Agrobacterium* separately transformed with RADAR components (sensor and human ADAR1p150), and a matching or unrelated trigger, with two infiltrations of either trigger per leaf. Quantification based on averages of average fluorescence intensities from six rectangular regions per infiltration spot. EGFP (output) fluorescence was normalized using the mCherry (marker) fluorescent intensity.

Statistical analysis. Values are reported as the means from at least three biological replicates, representative of two independent biological experiments. For experiments comparing two groups, a Bonferroni-corrected two-tailed Student t-test was used to assess significance.

Bioinformatics. We analyzed all genes with annotated 3' UTRs in the human genome in search of trigger sequences compatible with the RADAR design. Later, we also considered all genes with a CDS annotation. 3' UTR and CDS sequences were obtained from Ensembl Biomart. Candidates must have a 5' CCA 3' sequence (which is paired with the 5' UAG 3' in the sensor) flanked by a sufficiently long stretch of sequence; the reverse complement of the trigger sequence should not create an in-frame stop codon in the sensor. Furthermore, the trigger sequences should be unique (assessed by mapping to the genome), and the sensor sequence easily synthesizable (lacking homopolymer runs and with 35-80% GC content). The hg38 genome build was used for human transcriptome analysis and the GRCm39 build for murine transcriptome analysis. The blastn tool version 2.9.0+ was used with the -task blastn -evalue 1 arguments, and further filtering was done on the alignment length (minimum 30 matches) and position (must overlap the central CCA or alternative sequence). Results from alternative chromosomes duplicative in nature were removed. A single hit—the target sequence—was allowed, with sensors having more hits discarded from analysis; this means that some designs were discarded due to pseudogenes and other repetitive regions that may or may not be expressed as RNA. As sequences other than the UAG:CCA pairing can efficiently be edited, we also analyzed candidate trigger sequences with a central GCA, UCA, or CAA sequence.

The 20211025 release of ClinVar was used to analyze the potential for detecting known and likely pathogenic variants, assuming that UAG can be edited when paired by one of CAA, CUA, CGA, ACA, UCA, GCA, CCA, CCU, CCC (Qu, L. et al. (2019) *Nat. Biotechnol.* 37, 1059-1069). Alternative and reference alleles were padded based on the hg38 reference genome by one base on either side. A variant was considered distinguishable by RADAR if the padded alternate allele contained one of the edit-triggering variants, but the padded reference did not contain any.

Example 2

Standard RADAR

In vitro transcribed mRNA and pseudouridine incorporation. While the RADAR design does not require special modifications (i.e., the mRNA can be made by the cell from a DNA plasmid, or it could be made in vitro with standard nucleotides), it can in some cases be hindered by modifications.

One such modification is pseudouridine (Ψ), particularly N1-methyl-pseudouridine, used for synthetic mRNA to reduce its immunogenicity. Typically, all uridine (U) bases are replaced by pseudouridine in IVT mRNA by supplying the modified nucleoside triphosphate instead of UTP in the reaction. However, Ψ affects ADAR editing negatively. Furthermore, it increases stop-codon readthrough, and is thus particularly not good for RADAR—the off state looks less "off" due to increased readthrough, and the on state looks less "on" due to decreased editing.

If the UAG stop codon is used, ΨAG may be particularly affected in terms of editing, due to the increased base stacking between Ψ and A that prevents the necessary flipping out of the A base. The UGA stop codon, particularly when followed by G (UGAg) may be helpful in this case, as ΨGAg does not directly put the modified base next to A, although a 5' G also decreases editing of an A. In addition to affecting the catalytic part of ADAR editing, Ψ can affect the dsRNA binding ability of ADAR.

To generate IVT mRNA, a sensor or trigger plasmid containing the T7 promoter, a TEV 5' leader UTR and a hybrid 3' UTR was amplified, adding a 120-base poly A tail. The PCR amplicon was purified and used as the template in an IVT reaction with the CleanCap AG reagent, ATP, GTP, CTP, and T7 polymerase in the presence of murine RNase inhibitor; the amount of UTP vs N1 mΨ was varied 0-100%. IVT mRNA fidelity was verified on a gel, DNA removed with DNase I, and mRNA purified using the QIAgen RNeasy mini kit. mRNA was transfected with the TransIT-mRNA kit, with 500 ng of total mRNA per well in 24-well format, with flow cytometry after 20 hours. ADAR was not over-expressed in the mRNA experiments, relying only on the wild-type expression levels of ADAR1 in HEK293 cells. Trigger was in the 3' UTR of BFP, with a control sequence used in the "no-input" case so that both conditions received 200 ng of sensor and 300 ng of a BFP mRNA (with matching or non-matching trigger sequence).

Figure 8:
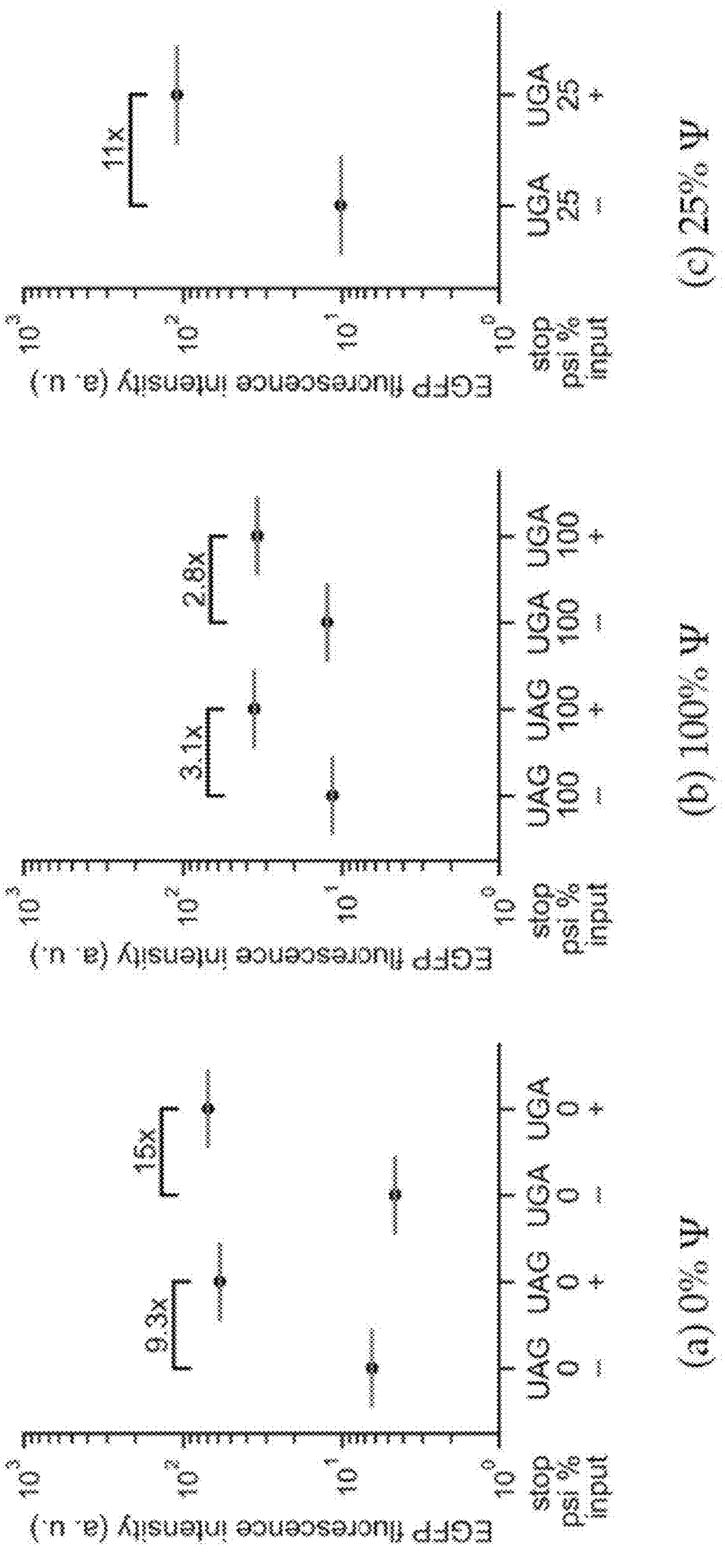
FIG. 8 Varying Ψ% (pseudouridine percentage) in sensor IVT mRNA with UAG or UGA stop codon used in sensor. Using 100% Ψ greatly diminishes fold-activation; an intermediate level of pseudouridine incorporation is acceptable. Analysis at high transfection marker levels (mCherry, part of sensor mRNA) and for trigger-positive cells (BFP).
Figure 9:
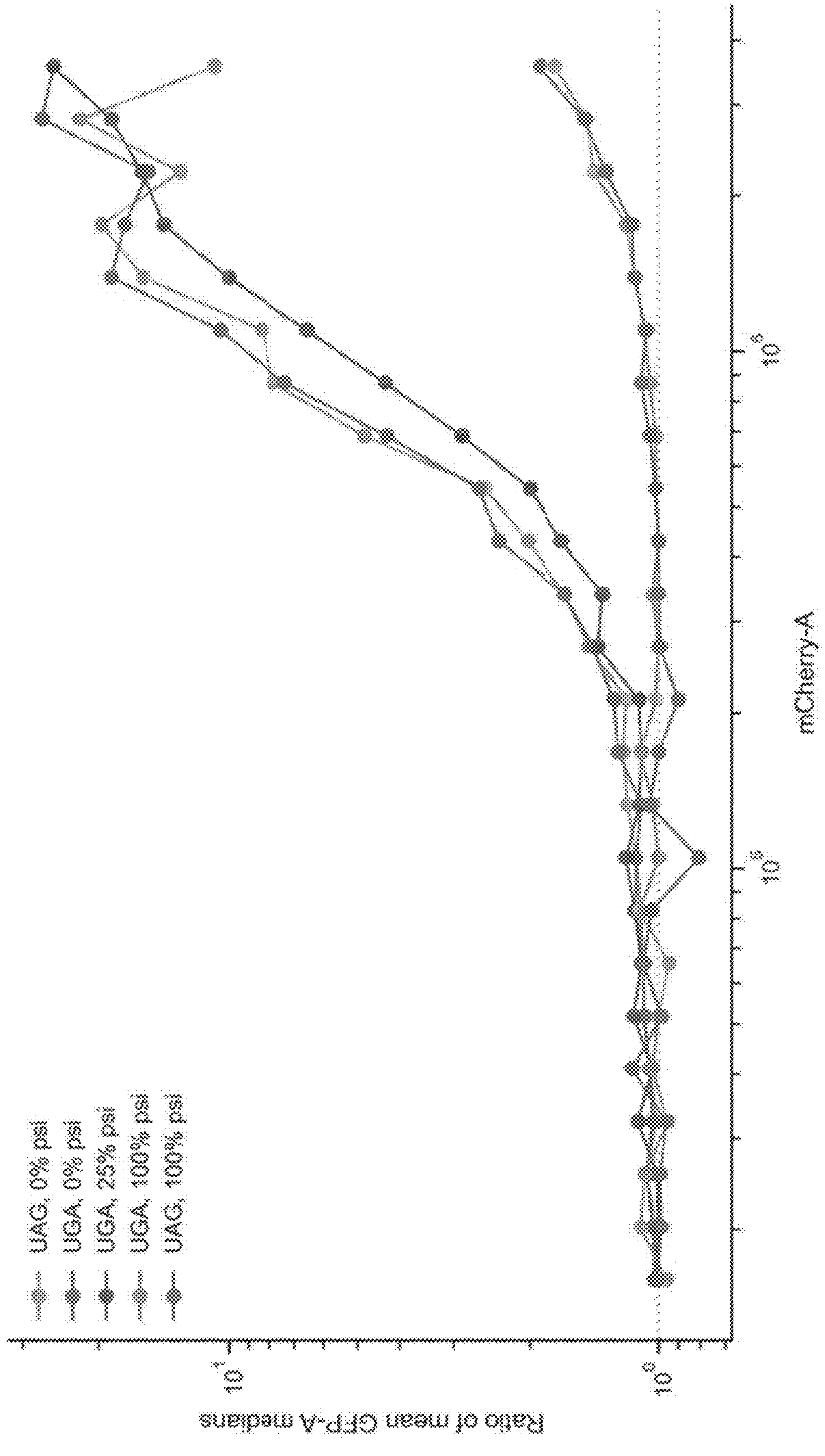
FIG. 9 Sensor performance as function of mCherry (sensor) levels from same dataset as FIG. 8.
Figure 10:
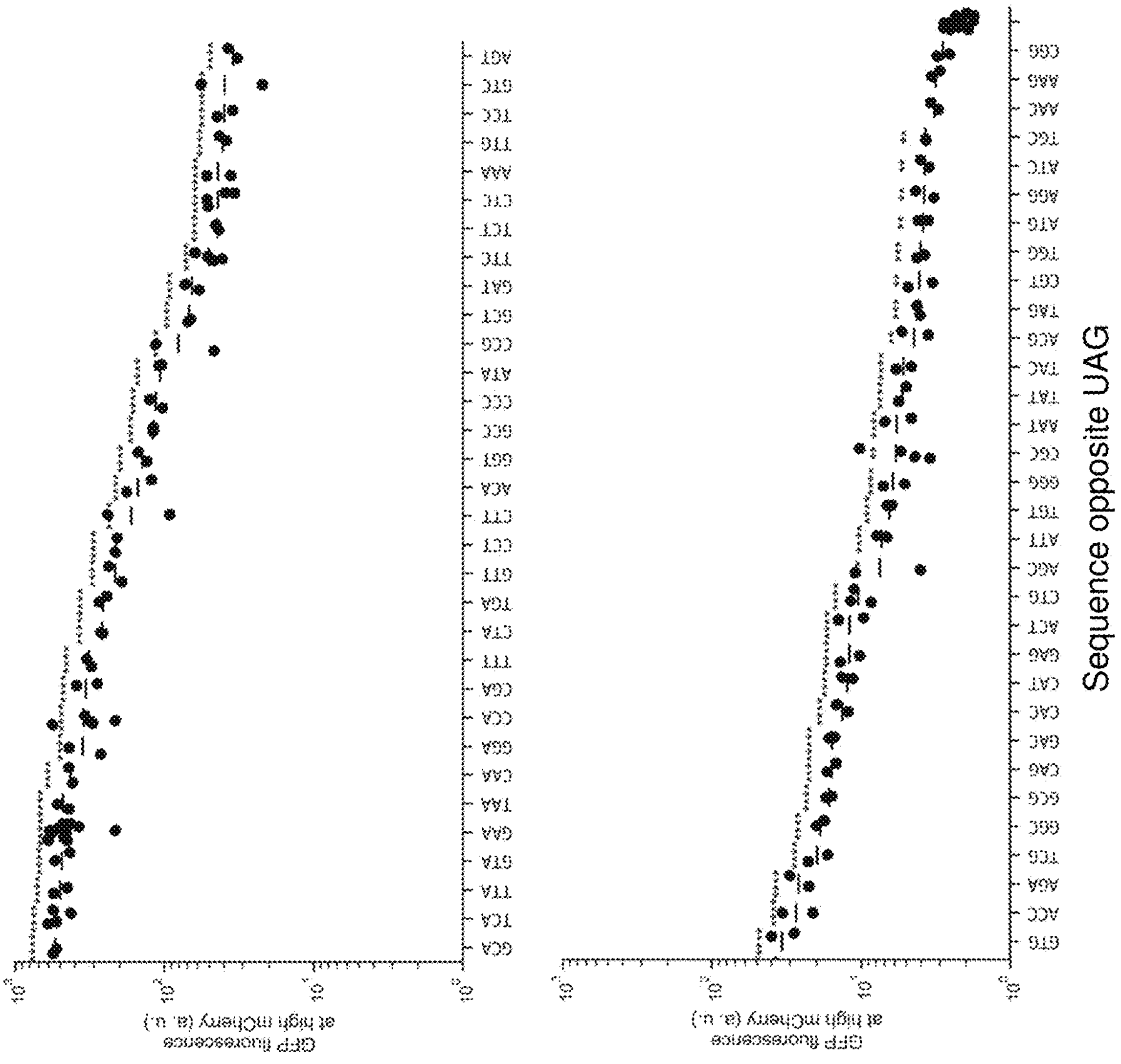
FIG. 10 Average output fluorescence at high sensor levels for all 64 NNN sequences in the trigger that are opposite the sensor's UAG stop codon. "-" indicates the negative control.

Full pseudouridine incorporation indeed greatly diminished, but did not fully abrogate sensor functionality, both by increasing baseline and reducing trigger-dependent activation (FIGS. 8 and 10). However, using an intermediate level of random pseudouridine incorporation enabled satisfactory performance.

UAG:NNN analysis. To understand the capability for nucleotide variant detection (single-nucleotide and multi-nucleotide variants, SNVs and MNVs), all 5' NNN 3' trigger sequences opposite the UAG stop codon were interrogated.

Figure 6:
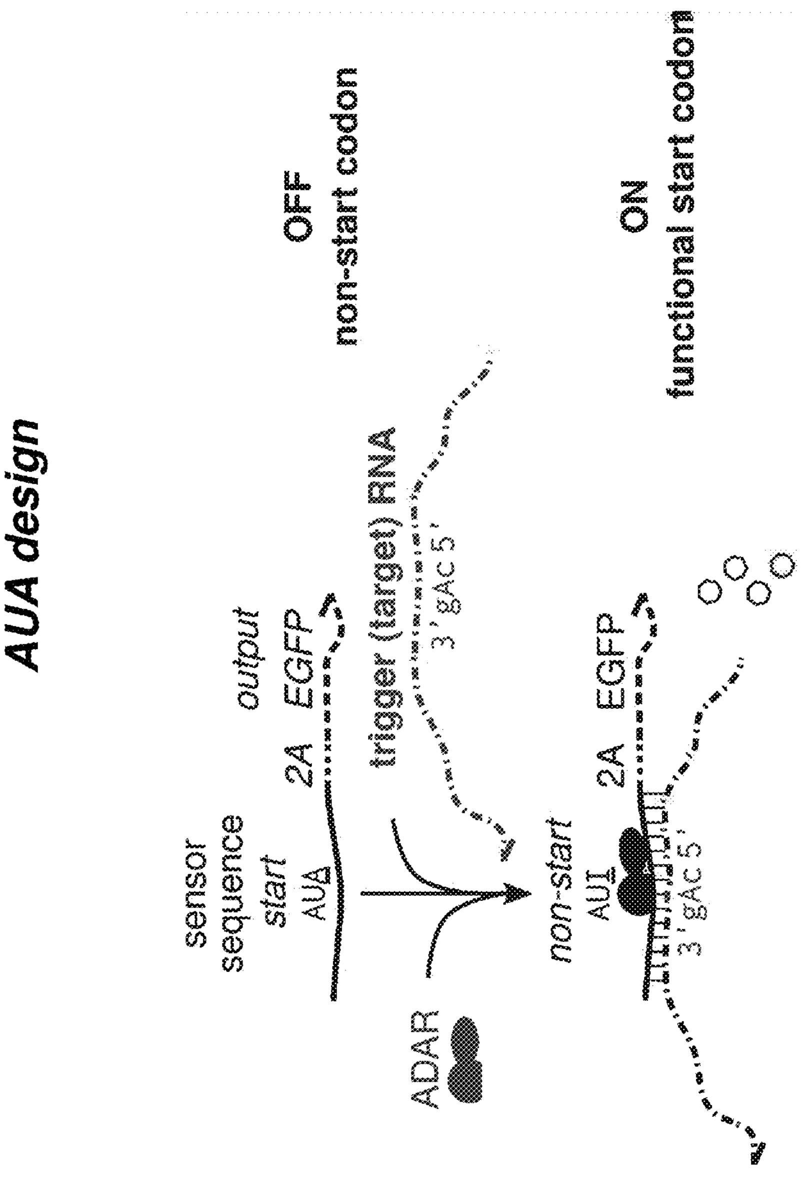
FIG. 6 depicts an exemplary sensor RNA containing an editable non-start (AUA) codon.
Figure 7:
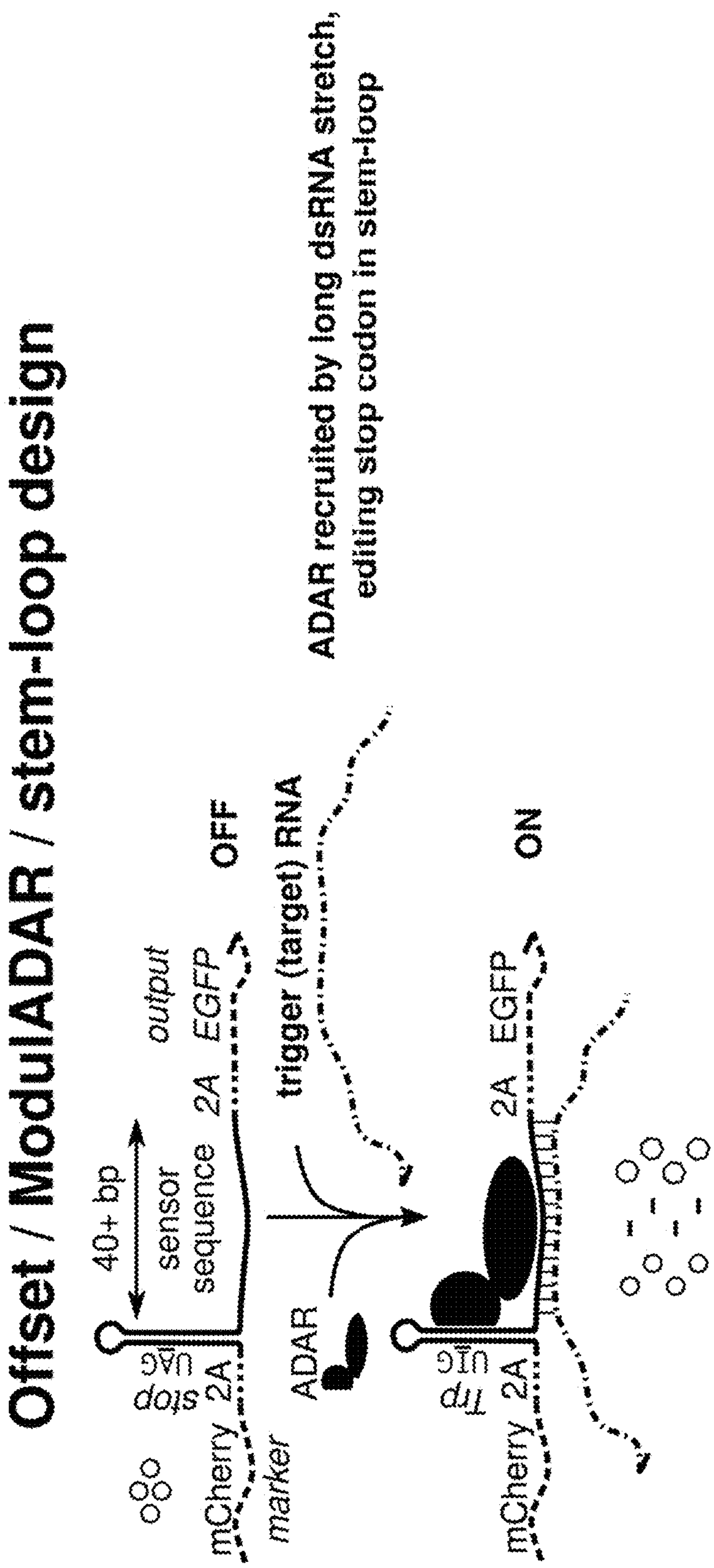
FIG. 7 depicts an exemplary sensor RNA containing a stem-loop with an editable codon.
Figure 11:
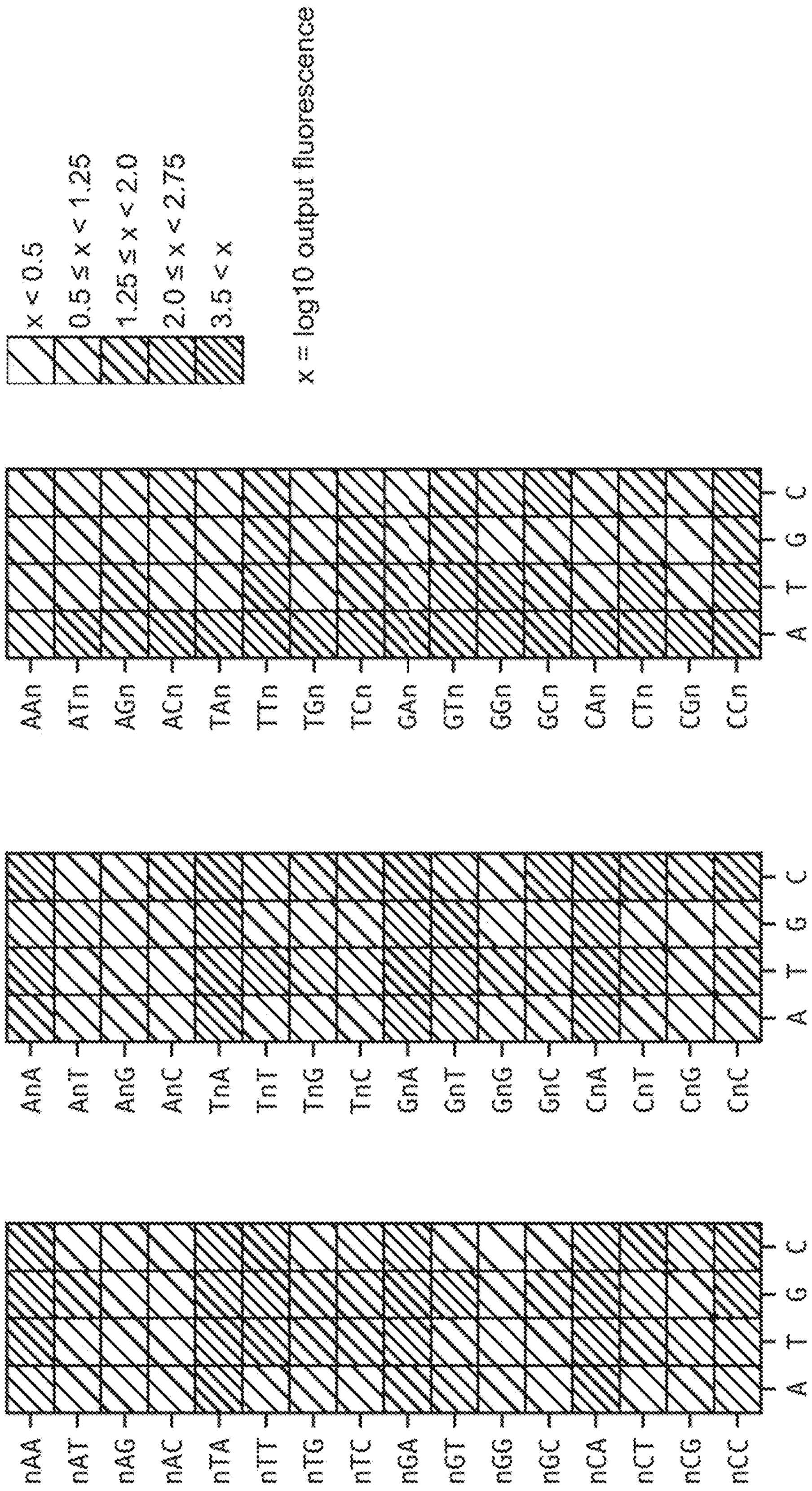
FIG. 11 Data from FIG. 10 represented in different ways, varying which position ("n") is shown across rows. Log average output fluorescence at high sensor levels for all 64 NNN sequences in the trigger that are opposite the sensor's UAG stop codon.
Figure 12:
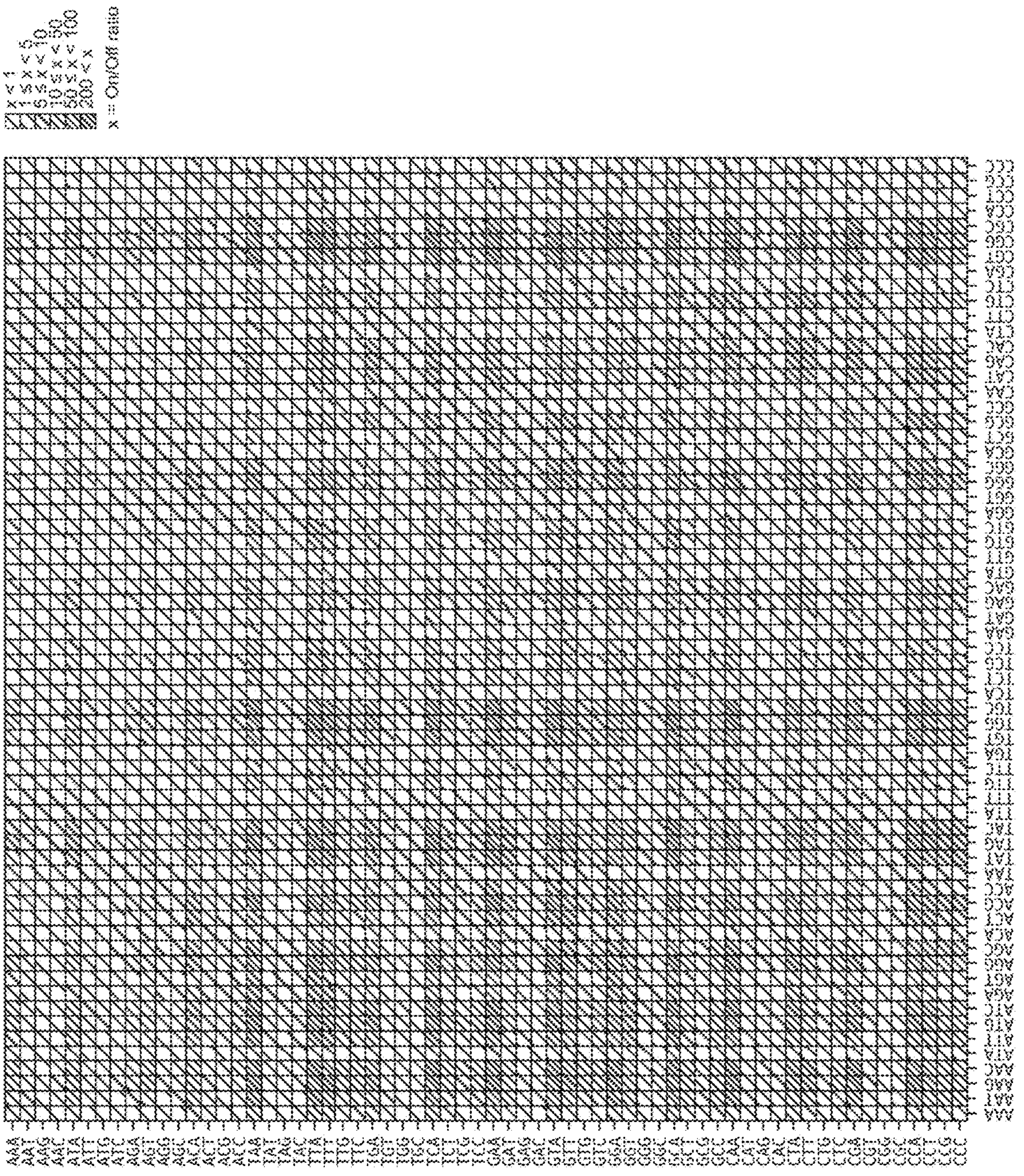
FIG. 12 Fold-expression differences between two triggering sequences.
Figure 13:
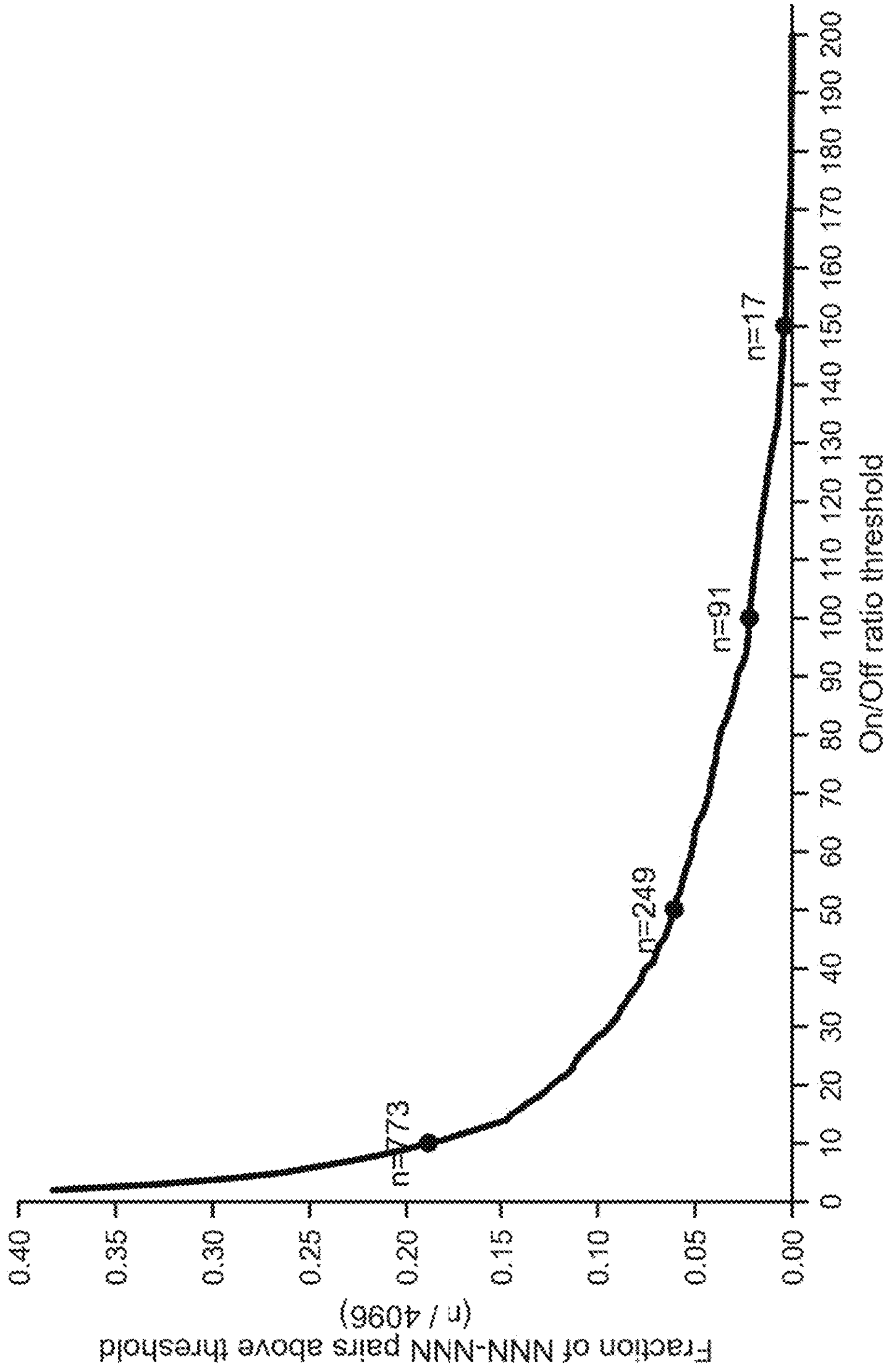
FIG. 13 Fraction of NNN-NNN pairs that have an on/off ratio above a given threshold. For example, 249 pairs of NNN (on)-NNN (off) triggers can be distinguished with the "on" state being at least 50-fold higher than the "off" state.
Figure 14:
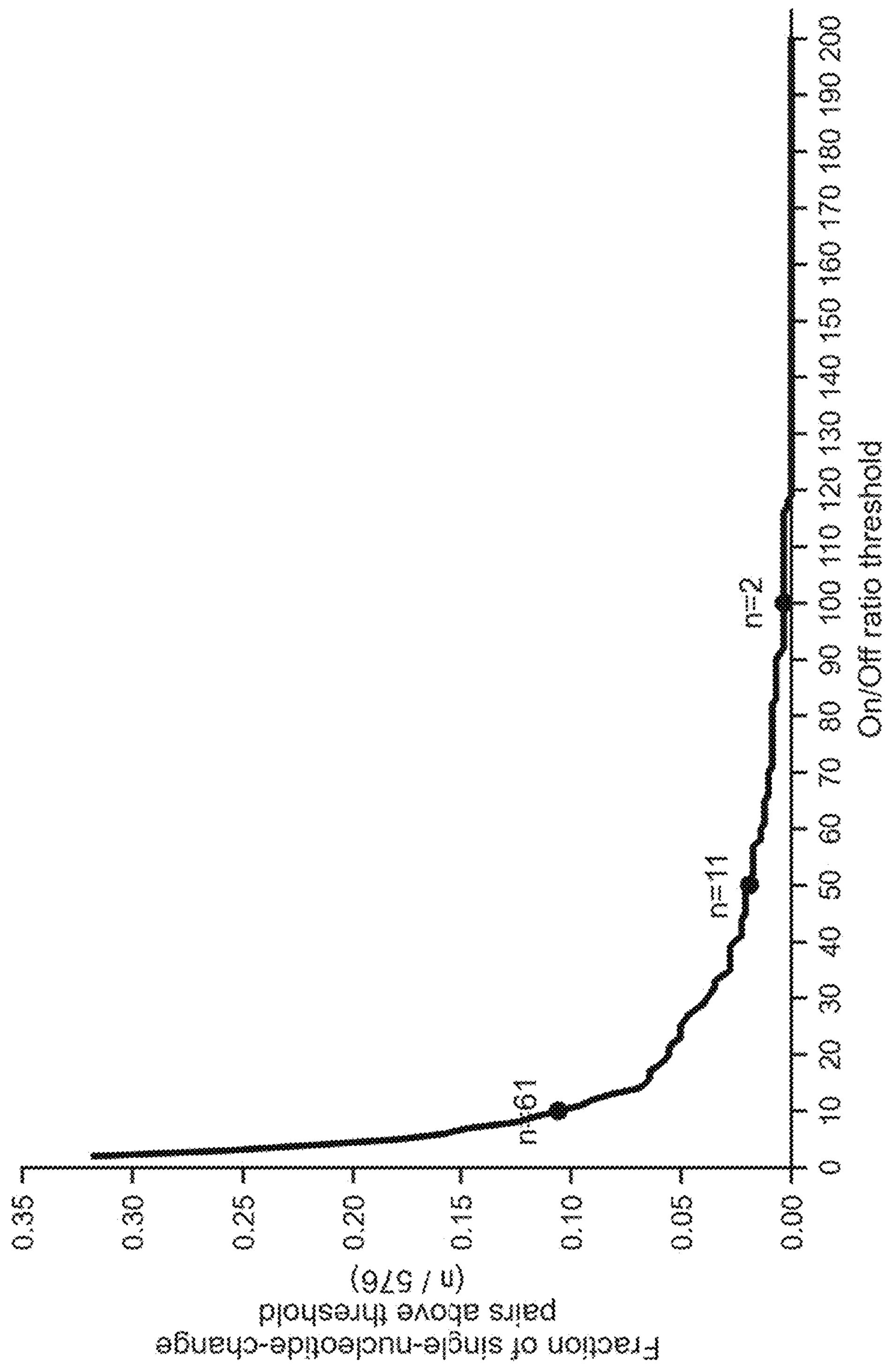
FIG. 14 Fraction of NNN-NNN pairs that have an on/off ratio above a given threshold and are different in only a single nucleotide. For example, 11 pairs of NNN (on)-NNN (off) triggers can be distinguished with the "on" state being at least 50-fold higher than the "off" state and the triggering sequences differing in only one position.

The triggering ability of the 64 5' NNN 3' sequences vary across around two logs (FIGS. 10 and 11). The 64-by-64 matrix of NNN-NNN pairings can be compared, where one of these would be the "off" state and the other the "on" state. To distinguish between the two states, the output fluorescent levels should be sufficiently different. The difference with the on-off activation ratio (FIG. 12) was characterized. Many of the 4,096 NNN-NNN pairs can be distinguished with high on-off ratios (FIG. 6). Specifically, many of the 576 NNN-NNN pairs that differ only in a single position (are thus SNVs) can also be distinguished with high on-off ratios (FIG. 13).

Figure 15:
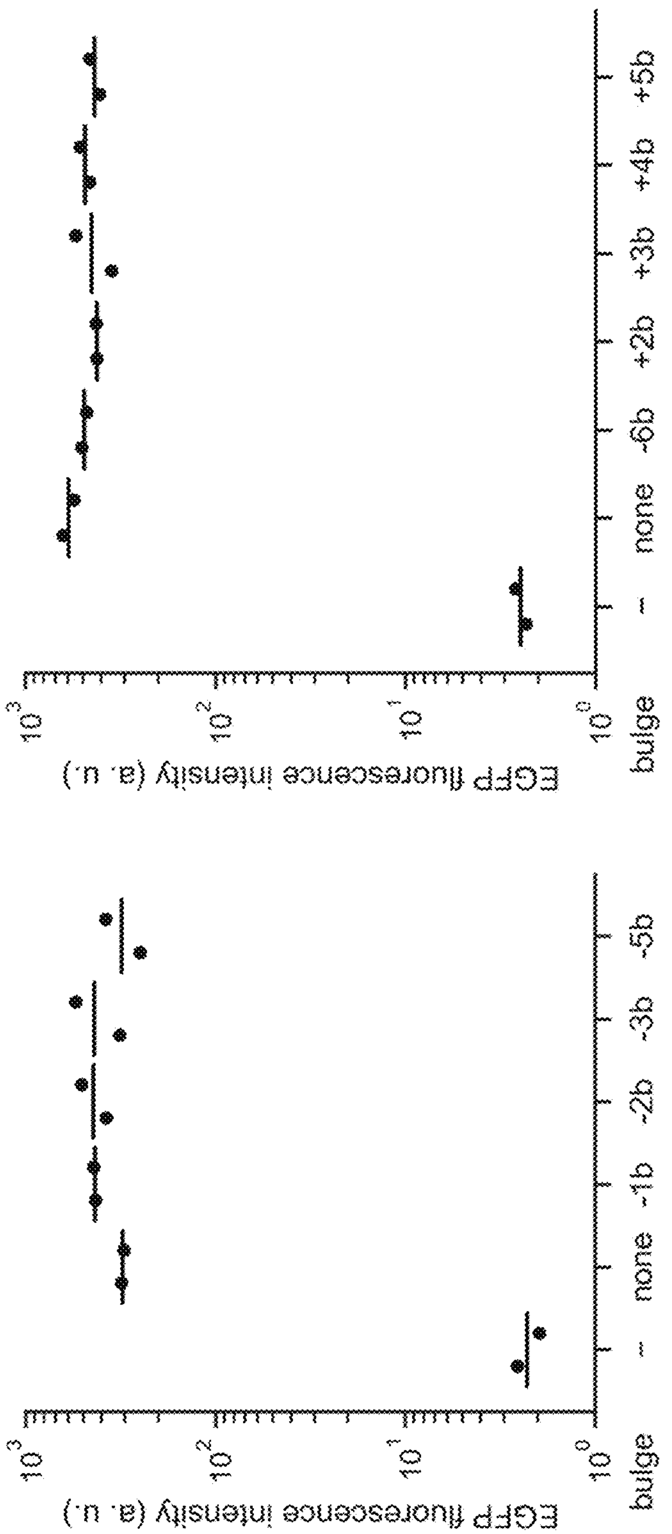
FIG. 15 Mismatches near the 5' CCA 3' sequence in the trigger RNA do not affect sensor performance. "none"—perfect complementarity; "-"—no input; "-1b"—mismatch immediately 5' of CCA; "+2b"—mismatch after one matching base, 3' of CCA.
Figure 16:
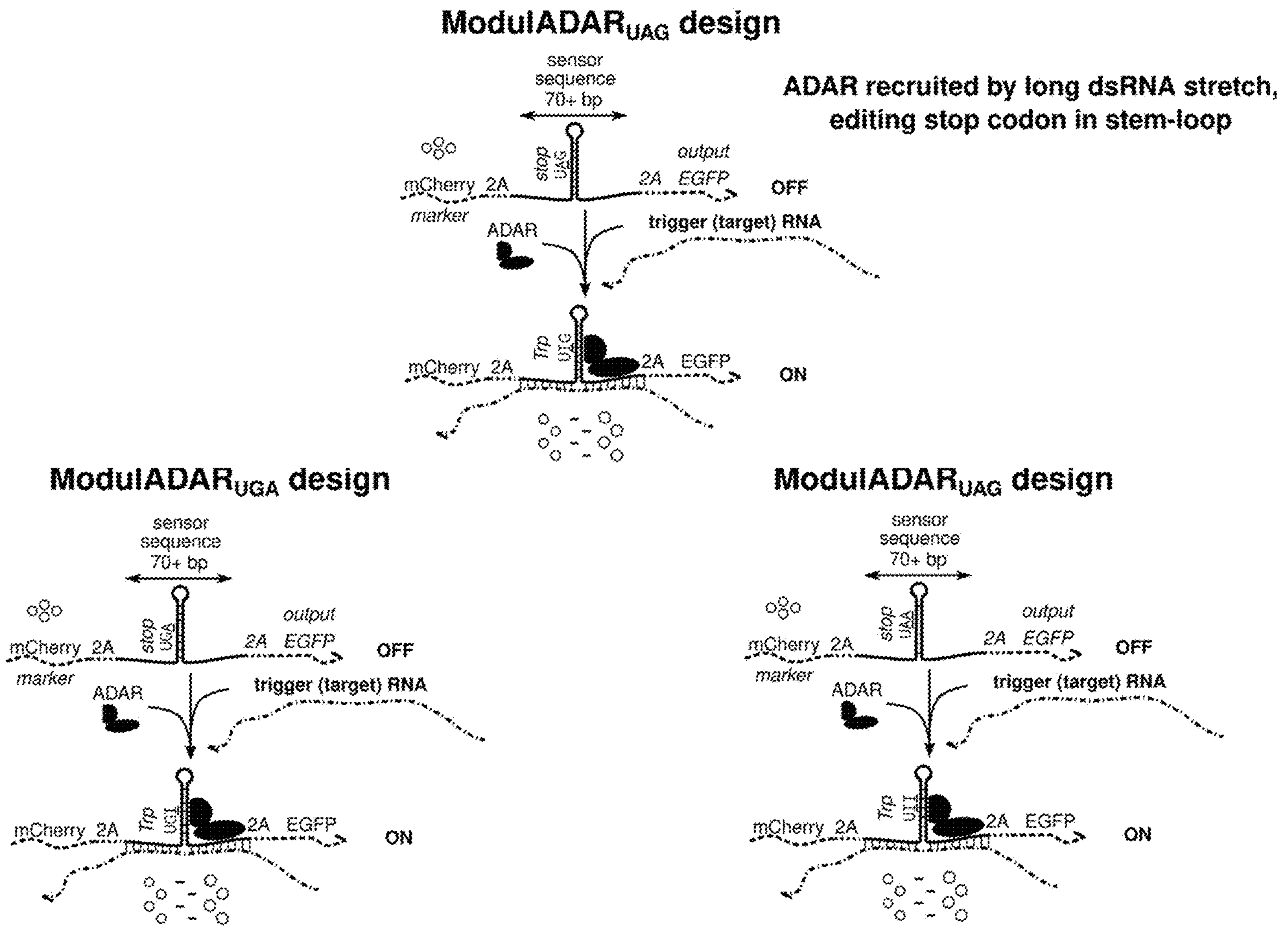
FIG. 16 Exemplary ModulADAR mechanism with UAG stop codon and alternatives with UGA and UAA stop codons.

Effect of bulges near UAG/CCA. Mismatches near the CCA:UAG pairing on the triggering strand were inserted. None of the tested mismatches, neither 5' nor 3' strongly affected sensor performance (FIG. 15).

ModulADAR/"Offset RADAR"

Previously called "Offset RADAR". This mechanism takes the standard RADAR and separates out the RNA binding from the RNA editing.

Sensor composition: (1) UAG/UGA/UAA stop codon within a stem-loop, sur-rounded by sequence complementary to the trigger RNA, (2) a 2A tag and (3) the output protein. An optional marker+2A tag can precede the sensor RNA.

Mechanism: The sensor and trigger form dsRNA around the stem-loop, which recruits ADAR. ADAR is then able to edit the stop codon within the stem-loop and remove it, allowing translation of the downstream output.

The stem-loop can be selected from naturally occurring ADAR editing sites, or selected from a library screen. Crucially, the stem-loop should not be edited without the extended dsRNA formation. For natural sites, this means the stem loop should likely be shortened, otherwise it is edited by ADAR without the dsRNA formation. The stem-loop is typically placed in the middle of the sequence complementary to the trigger RNA, but this position can be altered (e.g., 5' of the complementary region, 3' of the complementary region, or somewhere in between; it should be in the vicinity of the complementary region).

They key aspect is that the editing substrate is the stem-loop formed by the sensor, not the sensor:trigger dsRNA duplex—this is key to its novelty, as such a design has not been envisioned by International Application PCT/US2022/033459 or Qian et al. Nature 2022.

Portions of natural ADAR editing substrate stem-loops have previously been incorporated into guide RNAs for the purposes of editing endogenous RNAs (as opposed to editing an exogenous RNA such as the sensor RNAs described here), for example Fukuda et al., Scientific Reports 2017. However, the stem-loops in those examples have been truncated to contain the portion of the stem-loop that interacts with the ADAR dsRNA binding domains, whereas here the stem-loops are truncated to the portions that interact with and are edited by the ADAR catalytic domain. Other types of stem-loops that are not the targets of ADAR editing have also been introduced to other guide RNAs for the purposes of recruiting engineered ADAR enzymes for editing endogenous RNAs; such stem-loops include MS2 hairpins for recruiting MCP-ADAR(DD) (e.g., Azad et al. Gene Therapy 2017 and International Application PCT/US2022/033459), or Cas13-binding hairpins for recruiting dCas13b-ADAR (DD) (e.g., Cox et al. Science 2017 and WO2019071048). However, in those applications, the stem-loop does not serve as the editing substrate containing an editable codon as it does here, but is used for recruiting an engineered ADAR, while in ModulADAR, the dsRNA formed by the sensor and trigger RNA recruit native ADAR.

A major advantage of changing the editing substrate is that this allows deep optimization of the editing, separate from the binding. ADAR enzymes have dsRNA binding domains that have little substrate specificity and a separate catalytic deaminase domain, which does have some substrate preferences. In the standard RADAR setup, the sensor dsRNA around the editing site is determined by the sequence of the triggering RNA so the optimization of ADAR binding and editing is done jointly; here either can be freely chosen. In the standard setup, the UAG stop codon is chosen because it is the most robust, particularly if immediately paired with CCA; in the ModulADAR design other stop codons can be leveraged, which can be advantageous, e.g. because the UAA stop codon typically allows for less readthrough than UAG, or UGA (particularly if followed by G, so UGAG) may be less affected by uridine modifications than UAG since in the former the A is not surrounded by modified bases while in the latter it is (the commonly used pseudouridine modification inhibits ADAR editing).

Another advantage and aspect of novelty is that now more sequences can be chosen as candidate triggers; in the standard design each sequence should have a CCA (or some small number of alternatives) that can basepair with UAG to efficiently edit it, while here there's no such requirement.

In principle, this kind of approach (separating the ADAR binding and editing) can be applied to the "uORF," "AUA,"

and "AUG" approaches described in the present disclosure as well. Lists of natural editing targets with suitable motifs that could be used in each case are prioritized. By having the editing substrate in a separate, stand-alone and trigger-independent sequence, motifs larger than the three bases of a stop codon could be used, for example a strong Kozak sequence can be included in front of a non-start (AUA) or start codon (AUG), without needing to find the reverse complement of such a sequence within the trigger RNA, as would be required if the editing happened in the duplex formed by the sensor and trigger RNAs.

Stem-loop choice. The stop-codon-containing stem-loop choice is critical. It should be well-edited when ADAR is localized by dsRNA formation, but should not be edited without the presence of additional dsRNA formed by the sensor and trigger.

One source of stem-loops is natural editing sites, which are often in a stem-loop. These stem-loops generally have a stem that is long enough to be bound by the dsRNA binding domains of ADAR enzymes. For use in ModulADAR, the stem should be shortened to just the part bound by the catalytic domain of ADAR.

Natural editing sites often contain UAG sequences; the stem-loop should be inserted into the sensor such that the UAG is in-frame with the coding sequences. Natural editing sites containing UGA or UAA also exist. For sequences containing UAA, both As should be naturally edited. Any other in-frame stop codons should be removed; they can be kept if they are also efficiently edited upon ADAR co-localization.

Natural editing sites in the human genome have been cataloged (Gabay et al., Nature Communications 2022). A handful of these sites are tested; specifically, ones derived from the GLURB, CAPS1, GLI1, GABRA3, and HT2RC genes.

Stem-loops are generated in a library and evaluated for performance. The contact area of ADAR2 deaminase domain based on available structures is around 12 bp, so stems tested in this way should be about 9-30 bp, with the size of the stem referring to the basepaired portion of the stem-loop.

Results

Figure 17:
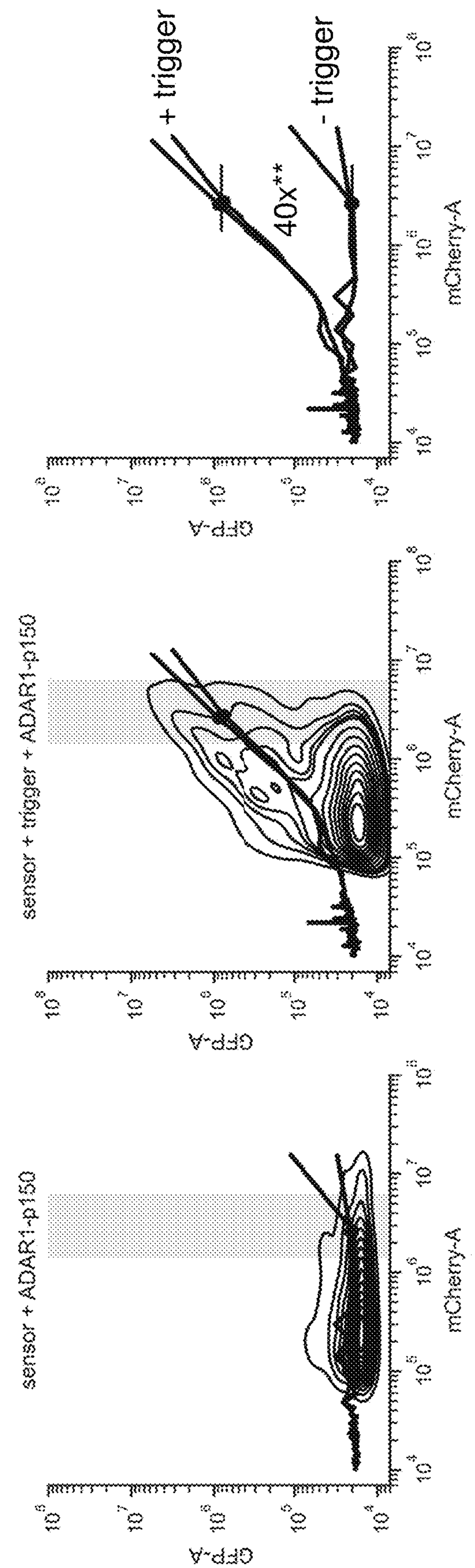
FIG. 17 ModulADAR effectively detects an mRNA input with 40-fold increase in mean fluorescence in highly-transfected cells.
Figure 27:
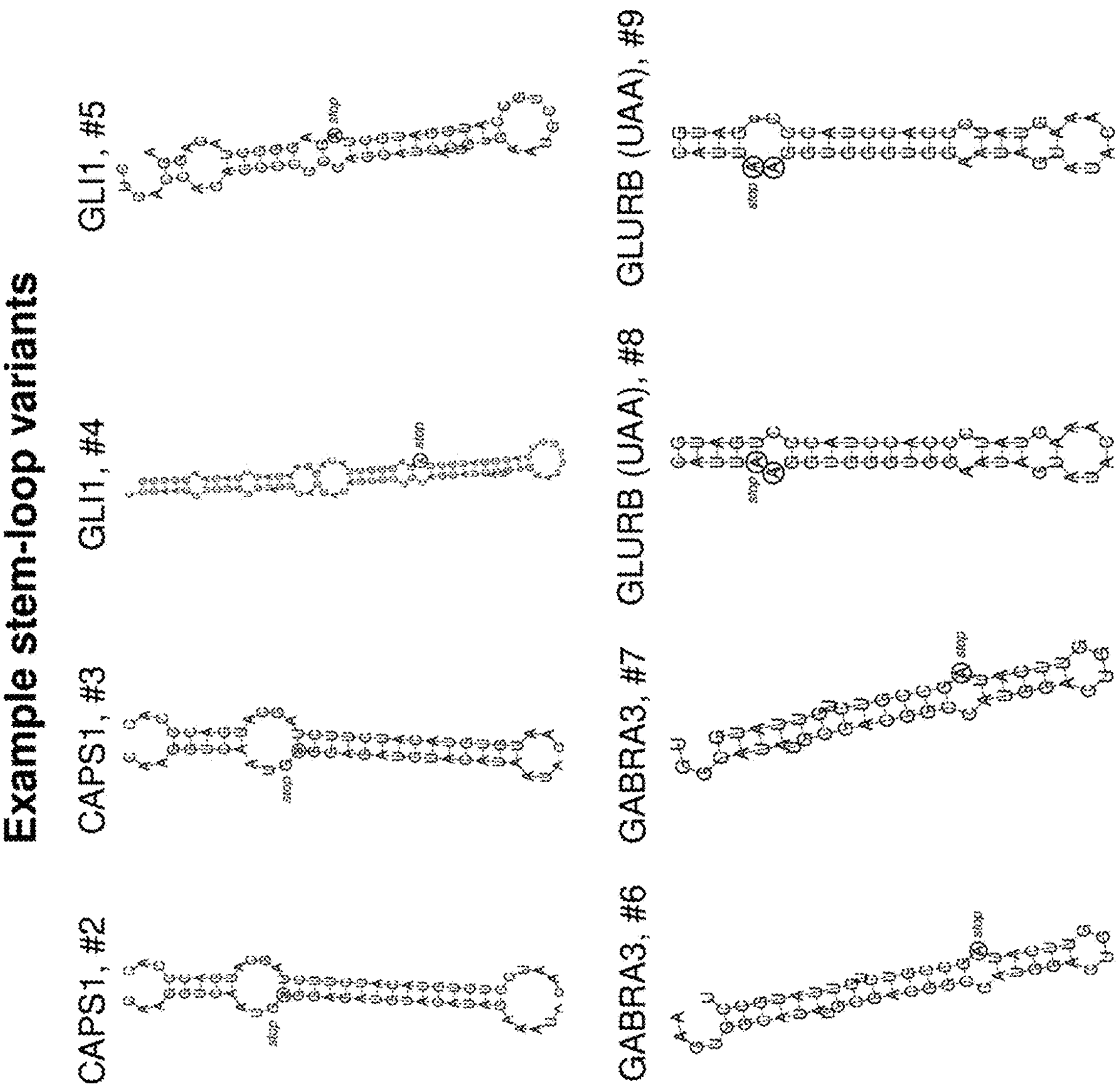
FIG. 27 Example ModulADAR stem-loop variants derived from natural ADAR editing sites with modifications, including but not limited to removing unedited in-frame stop codons, shortening the stem of the stem-loop, or changing the identity of the editable stop codon and the mismatches opposite it. From left to right and top to bottom SEQ ID NO:1-8
Figure 28:
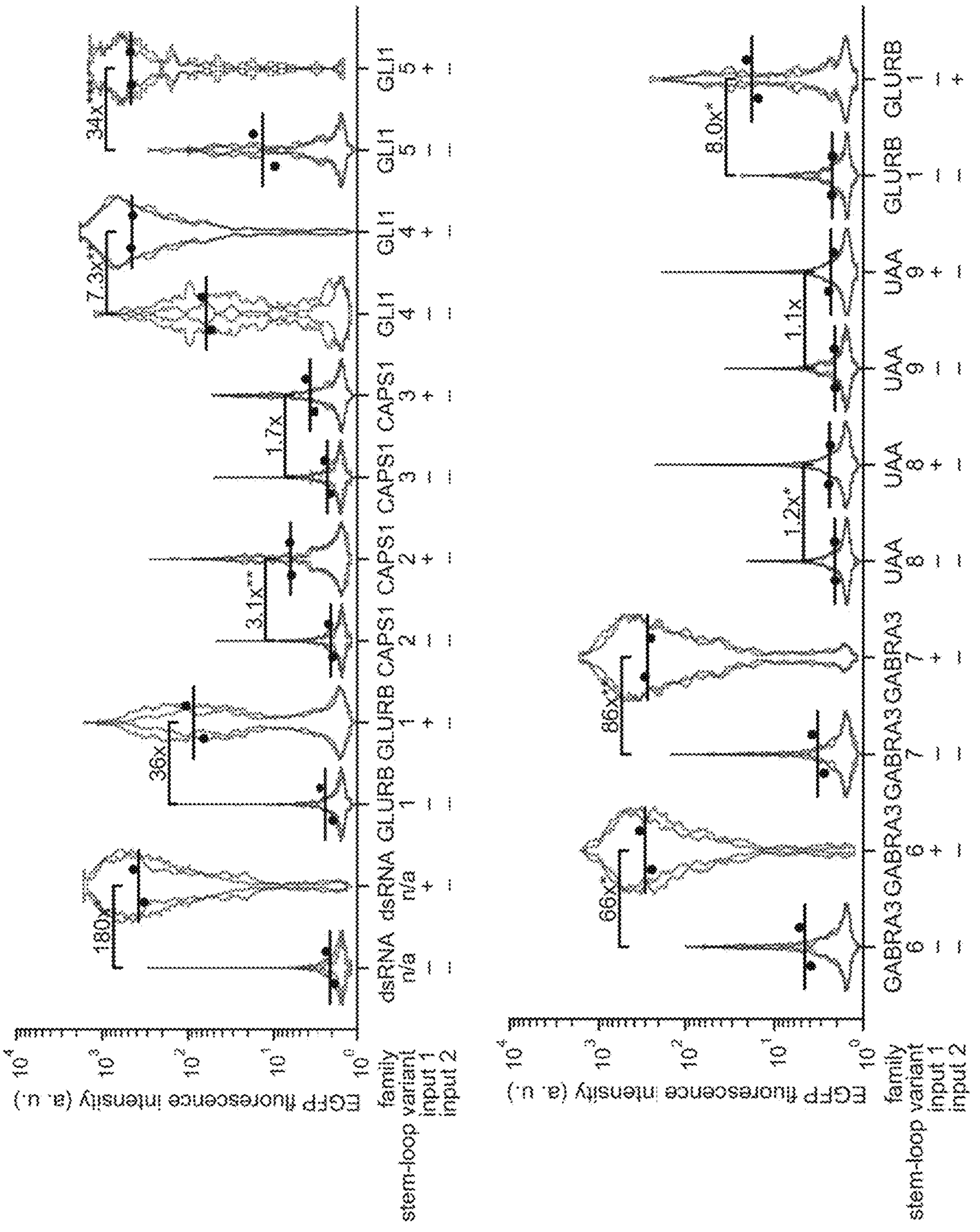
FIG. 28 Evaluation of example ModulADAR stem-loop variants derived from natural ADAR editing sites.
Figure 29:
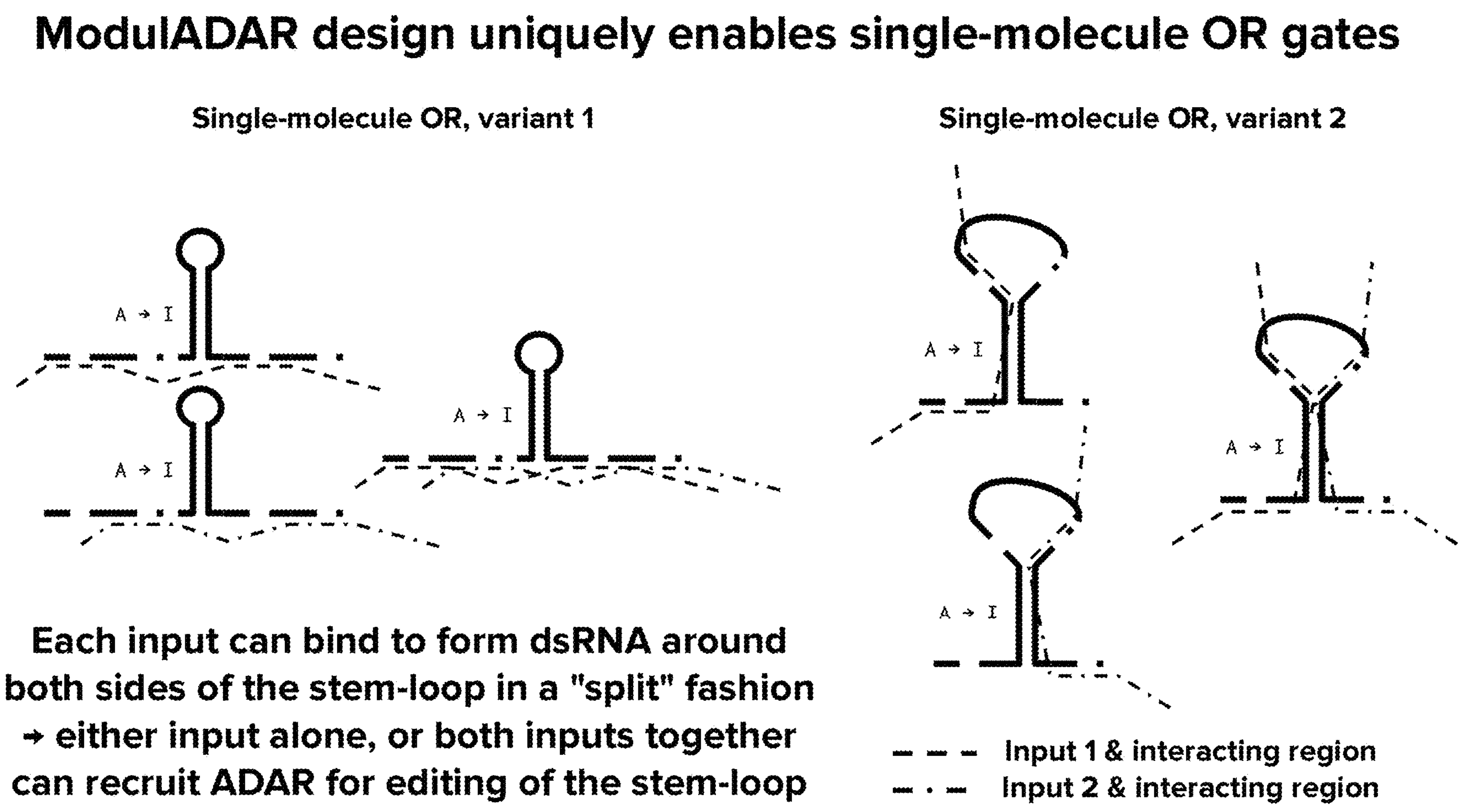
FIG. 29 Exemplary ModulADAR design for single molecule OR gates.

Basic Characterization. When a stem-loop derived from GLURB (aka GLUR2, GRIA2) is placed in the middle of the complementarity region, the ModulADAR design works well (FIG. 17). Further improvements were made by exploring other natural editing sites from genes including CAPS1, GLI1, and GABRA3 (FIG. 27 and FIG. 28), placed within the sensor nucleotide sequence. A very long stem-loop incorporating most of the natural editing site may not perform as well as a truncated stem, e.g. stem-loop variant #4 (full GLI1) vs stem-loop variant #5 (truncated GLI1), with the loss in performance attributable to an increase in trigger-independent signaling (FIG. 28), which is expected, as the full editing site should be well-edited by ADAR, even without additional dsRNA, as it contains a long enough stem to recruit ADAR. By shortening the stem, editing becomes conditional on the dsRNA formed by the sensor and trigger, as envisioned in the ModulADAR design. A similar, albeit smaller trend was observed for two variants derived from GABRA3, where the longer stem-loop variant #6 showed a higher baseline than the shorter variant #7 (FIG. 28). Importantly, the conditions when the trigger is present are similar in these comparisons, again supporting the mechanism by which dsRNA formed by the sensor and trigger (which is the same across these comparisons) recruits ADAR, followed by editing of the substrate, which is a part of the stem-loop. Changing the stop codon in a GLURB-derived stem-loop to UAA did not perform well (FIG. 28), likely due to requiring two adenosines to be edited; adding an additional mismatch so that both adenosines in the UAA codon are opposite a cytosine did not improve performance. Natural sites with UAA sequences could be used instead, e.g. as occurring in HT2RC. The CAPS1 gene contains a natural editing site with a UGA subsequence, which was used here to evaluate the third stop codon option (FIG. 28).

OR logic. OR logic in the standard case (no editable stem-loop) is achieved by co-delivering two separate RNAs with different inputs. This means that if you have two inputs, A and B, the output dose from just "A" will be ≈50%, just "B" will be ≈50% and from both "A" and "B" together will be 100%.

Figure 25:
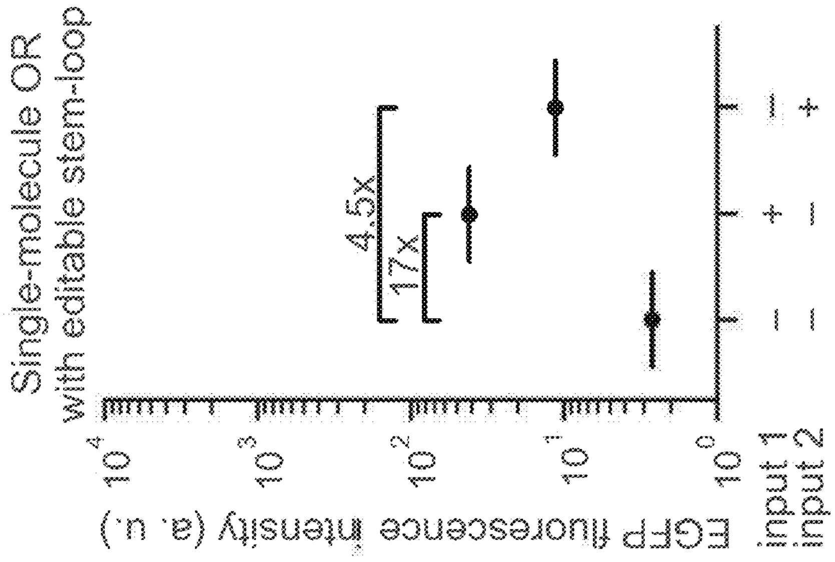
FIG. 25 ModulADAR with an editable stem-loop enables a two-input OR gate comprised of a single molecule that can separately bind two different inputs.
Figure 26:
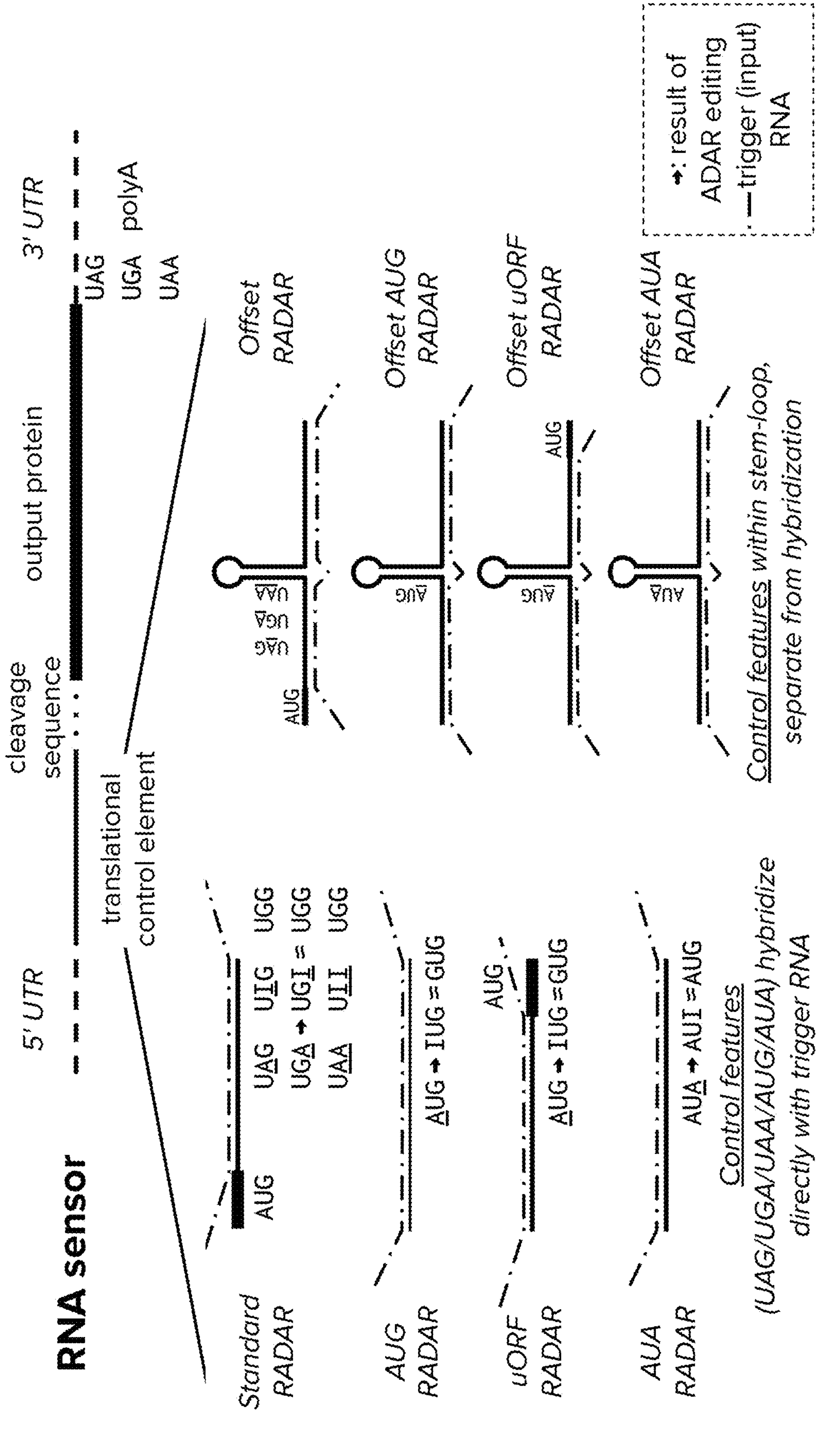
FIG. 26 Exemplary sensor RNA designs.

A single-molecule OR gate can be made with the ModulADAR technique such that the output from all cases (just "A", just "B", or both "A" and "B" together) will be approximately the same (FIG. 25). This is another aspect of novelty, as this is not possible when editing occurs in a dsRNA duplex, requiring the use of two different molecules as outlined above.

uORF RADAR

Sensor composition: (1) AUG surrounded by sequence complementary to the trigger RNA, (2) output (with an AUG). The first AUG is crucially out of frame from the output AUG so that the first reading frame functions as an "upstream open reading frame," repressing translation from the output AUG start codon.

Mechanism: The first AUG is set up to be edited to IUG upon dsRNA formation; IUG (GUG) is no longer a start codon and turns off the upstream reading frame, allowing the downstream frame to be translated.

Ideally the upstream reading frame is long, almost as long as the correct downstream reading frame. There should not be any other AUGs within the sensor sequence.

Two uORFs can be placed in series for an AND gate (both inputs have to be present in order to remove both uORFs).

Results

Figure 18:
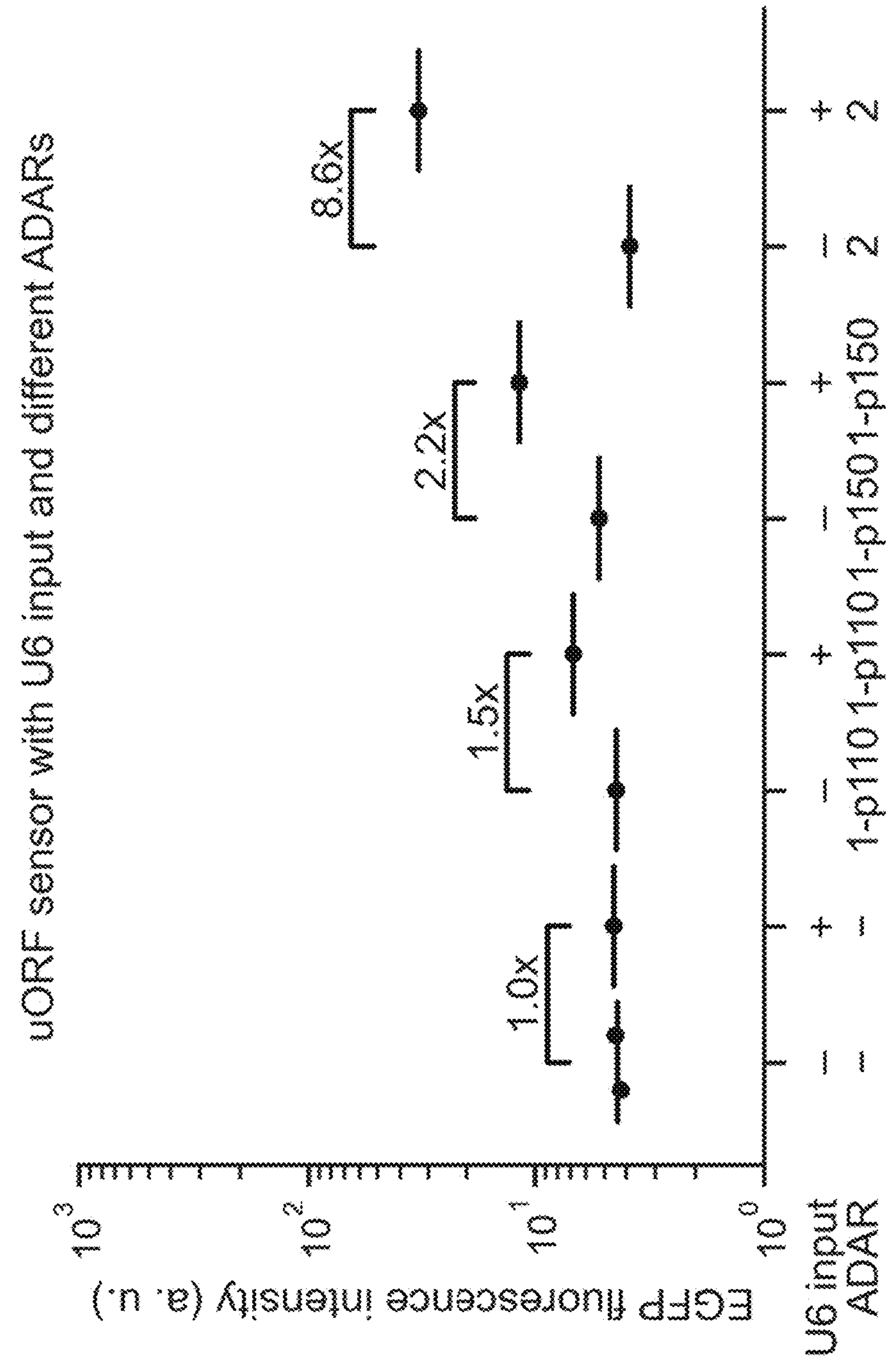
FIG. 18 uORF works best with ADAR2 over-expression.
Figure 19:
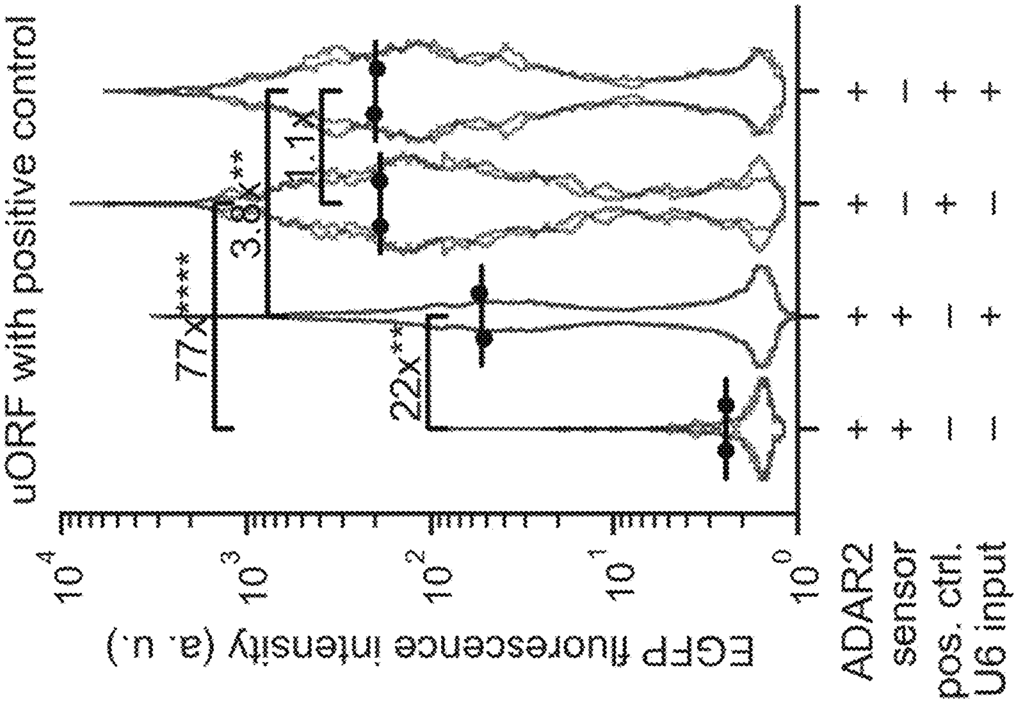
FIG. 19 uORF detecting a U6-driven RNA, along with a positive control (AUG mutated to GUG in the uORF).
Figure 20:
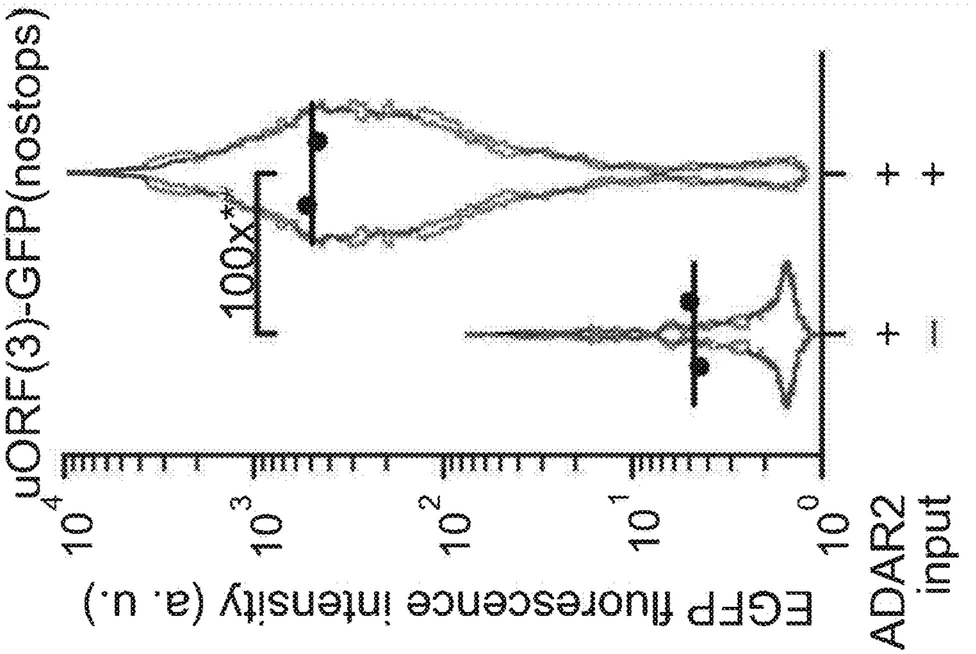
FIG. 20 Improving uORF performance by removing stops in the output that are in the uORF's frame to produce a long uORF.
Figure 21:
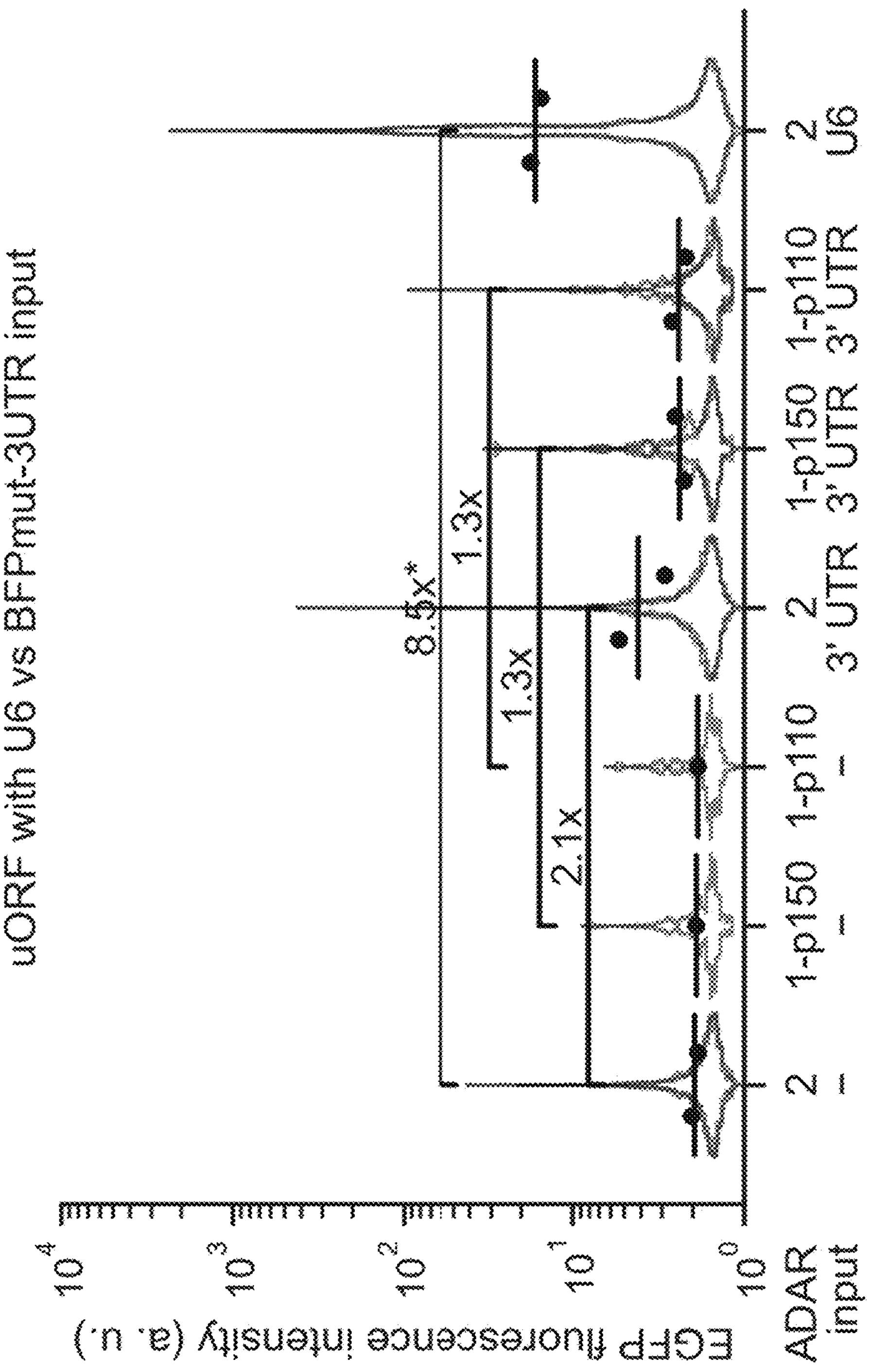
FIG. 21 Exemplary uORF design where the input RNA is expressed from a normal promoter (resulting in an mRNA).
Figure 22:
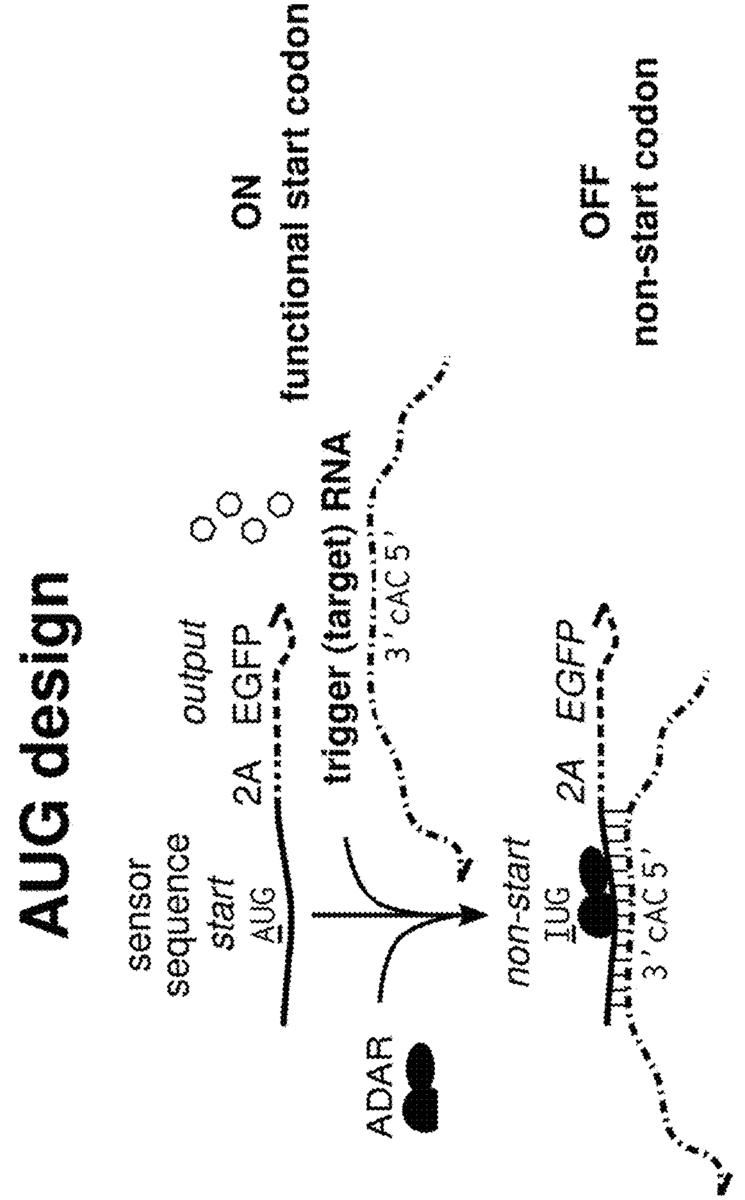
FIG. 22 Exemplary AUG RADAR mechanism
Figure 23:
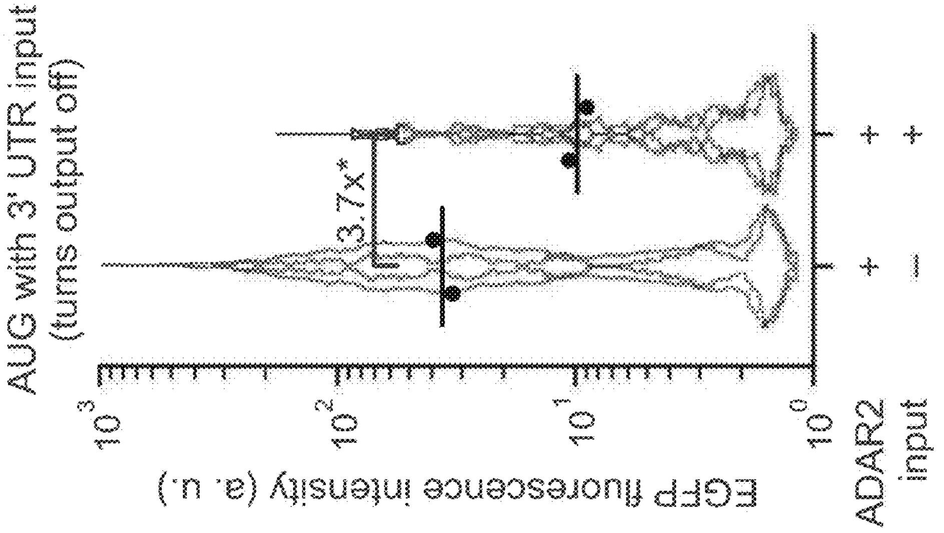
FIG. 23 AUG RADAR with a typical mRNA input.

Basic characterization with nuclearly localized trigger RNAs. The uORF mechanism works best with ADAR2 over-expression (FIG. 18). The uORF mechanism achieves ≈29% of the positive control levels (FIG. 19). The uORF mechanism output is greatly improved by removing stop codons from the output protein that are in-frame with the uORF so that the uORF produces a long reading frame (FIG. 20). Two uORFs in series can form an AND gate.

AUG RADAR

This design is derived from the "uORF" design, but rather than editing an upstream reading frame, the AUG of the output reading frame is edited directly.

Sensor composition: (1) AUG start codon surrounded by sequence complementary to the trigger RNA, (2) 2A tag, (3) output. All of the components are in frame with each other.

Mechanism: The AUG is set up to be edited to IUG upon dsRNA formation; IUG (GUG) is no longer a start codon, disabling the translation of the output protein.

Here the output is turned off in response to an input ("NOT X" type logic) as opposed to all other designs where the output is turned on in response to an input.

There should not be any in-frame AUG sequences within the sensor that could enable functional production of the output protein. The sensor should not have in-frame stop codons downstream of the AUG.

The AUG RADAR is similar to the uORF RADAR, it's just that there is no second, downstream reading frame; the "upstream" reading frame contains the desired output.

Results

Basic Characterization. The AUG mechanism works with a cytosolic triggering mRNA (i.e., the typical mRNA).

AUA RADAR

Sensor composition: (1) AUA surrounded by sequence complementary to the trigger RNA, (2) 2A tag, (3) output (without AUG). All of the components are in frame with each other.

Mechanism: The AUA is set up to be edited to AUI upon dsRNA formation; AUI (AUG) can function as a start codon and enable translation of the otherwise not translated output protein.

There should not be any in-frame AUG sequences within the sensor that could enable functional production of the output protein. The sensor should not have in-frame stop codons downstream of AUA.

It helps to have a separate, long, overlapping reading frame in a different frame than the main one; this stabilizes the RNA when it is in the "off" state.

When two AUA sensors are in series, one would achieve OR logic on a single RNA strand (as opposed to two RNAs with the standard RADAR design).

Results

Figure 24:
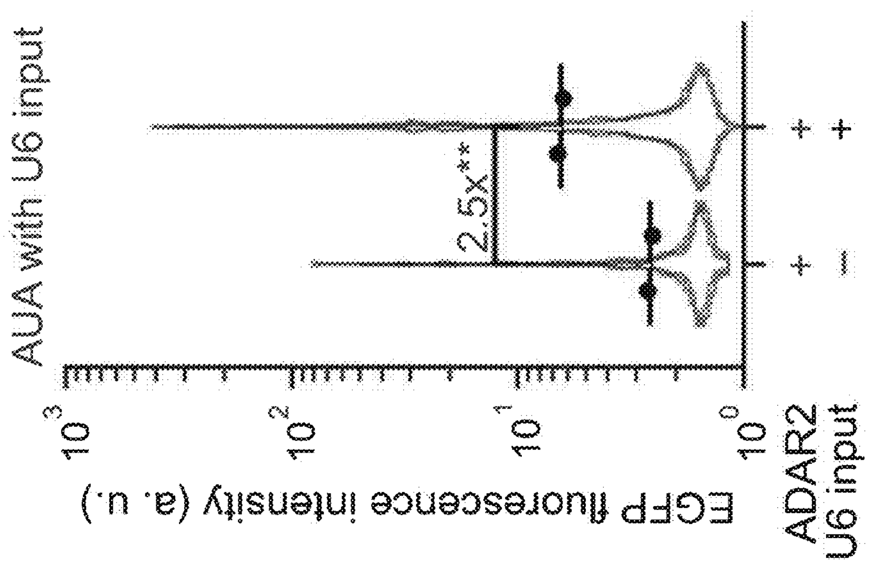
FIG. 24 AUA RADAR sensor for U6-expressed RNA with ADAR2 over-expression.

Basic characterization. The AUA mechanism works best with ADAR2 over-expression (FIG. 24).

Combinations

It is possible to combine the different varieties together for different logic functions. Below RADAR is either the standard RADAR or the ModulADAR variety.

TABLE 4

Sensor architecture combination.

| Start Codon, input A | Stop Codon, input B | no input | A only | B only | A and B | function |
|---|---|---|---|---|---|---|
| uORF | RADAR | off | off | off | on | A AND B |
| uORF | AUG | off | on | off | off | A NIMPLY B |
| uORF | AUA | off | off | off | on | A AND B |
| AUA | RADAR | off | off | off | on | A AND B |

REFERENCES

1. Kulkarni, A., Anderson, A. G., Merullo, D. P. & Konopka, G. *Curr. Opin. Biotechnol.* 58, 129-136 (2019).
2. Xie, Z., Liu, S. J., Bleris, L. & Benenson, Y. *Nucleic Acids Res.* 38, 2692-2701 (2010).
3. Xie, Z., Wroblewska, L., Prochazka, L., Weiss, R. & Benenson, Y. *Science* 333, 1307-1311 (2011).
4. Han, S. et al. *Mol. Ther.—Nucleic Acids* 27, 797-809 (2022).
5. Ying, Z.-M., Wang, F., Chu, X., Yu, R.-Q. & Jiang, J.-H. *Angew. Chem. Int. Ed.* 59, 18599-18604 (2020).
6. Lin, J., Wang, W.-J., Wang, Y., Liu, Y. & Xu, L. *J. Am. Chem. Soc.* 143, 19834-19843 (2021).
7. Hochrein, L. M., Li, H. & Pierce, N. A. *ACS Synth. Biol.* (2021).doi:10.1021/acssynbio.1c00037
8. Zhao, E. M. et al. *Nat. Biotechnol.* 1-7 (2021).doi: 10.1038/s41587-021-01068-2
9. Hur, S. *Annu. Rev. Immunol.* 37, 349-375 (2019).
10. Gatsiou, A., Vlachogiannis, N., Lunella, F. F., Sachse, M. & Stellos, K. *Antioxid. Redox Signal.* 29, 846-863 (2017).
11. Goodman, R. A., Macbeth, M. R. & Beal, P. A. *Adenosine Deaminases Act. RNA ADARs—Ed.* 1-33 (2012).doi: 10.1007/82_2011_144
12. Gallo, A., Vukic, D., Michalik, D., O'Connell, M. A. & Keegan, L. P. *Hum. Genet.* 136, 1265-1278 (2017).
13. Wang, Y., Zheng, Y. & Beal, P. A. *The Enzymes* 41, 215-268 (2017).
14. Katrekar, D. et al. *Nat. Methods* 16, 239-242 (2019).
15. Qu, L. et al. *Nat. Biotechnol.* 37, 1059-1069 (2019).
16. Merkle, T. et al. *Nat. Biotechnol.* 37, 133-138 (2019).
17. Reautschnig, P. et al. *Nat. Biotechnol.* 1-10 (2022).doi: 10.1038/s41587-021-01105-0
18. Loughran, G., Howard, M. T., Firth, A. E. & Atkins, J. F. *RNA N. Y. N* 23, 1285-1289 (2017).
19. Luo, L., Callaway, E. M. & Svoboda, K. *Neuron* 98, 256-281 (2018).
20. Uzonyi, A. et al. *Mol. Cell* (2021).doi:10.1016/j.molcel.2021.03.024
21. Biswas, J., Rahman, R., Gupta, V., Rosbash, M. & Singer, R. H. *iScience* 23, 101318 (2020).
22. Yoshikawa, K. et al. *Biomed. Res.* 31, 401-411 (2010).
23. Gao, Q. et al. *Cell Rep.* 23, 227-238.e3 (2018).
24. Dykstra, P. B., Kaplan, M. & Smolke, C. D. *Nat. Rev. Genet.* 1-14 (2022).doi:10.1038/s41576-021-00436-7
25. Groves, B. et al. *Nat. Nanotechnol.* 11, 287-294 (2016).

Notwithstanding the appended claims, the disclosure set forth herein is also described by the following clauses:

1. A method for detecting a target RNA in a biological sample, the method comprising:
   (a) combining the biological sample with a sensor RNA comprising the following:
      (i) a first nucleotide sequence comprising a stem-loop sequence comprising one or more stop codons,
      (ii) a second nucleotide sequence comprising a sensor nucleotide sequence that is reverse complementary to the target RNA,
      (iii) a third nucleotide sequence encoding a first cleavage domain, and
      (iv) a fourth nucleotide sequence encoding an output protein; and
   (b) assaying for the presence of the output protein in the biological sample.
2. The method of clause 1, wherein the one or more stop codons comprises at least 1 base that is mismatched with a sequence within the stem loop opposite the one or more stop codons.
3. The method of clauses 1 or 2, further comprising:
   (i) a fifth nucleotide sequence comprising a second cleavage domain wherein the fifth nucleotide sequence precedes the first nucleotide sequence and
   (ii) a sixth nucleotide sequence comprising a nucleotide sequence encoding a marker protein wherein the sixth nucleotide sequence precedes the fifth nucleotide sequence.
4. The method of any of clauses 1-3, wherein the cleavage domain is a 2A self-cleaving domain.
5. The method of clause 4, wherein the 2A self-cleaving domain is selected from the group of T2A, P2A, E2A and F2A.
6. The method of any of clauses 1-5, wherein the stem loop is a GluR-B stem loop or modified variant thereof.
7. The method of any of clauses 1-6, wherein the stem loop is 18 to 60 base pairs in length.
8. The method of any of clauses 1-7, wherein the sensor nucleotide sequence is 60 or more nucleotides in length.

9. The method of any of clauses 1-8, wherein the target RNA is encoded by a gene fusion, a splice variant or a gene variant comprising a single nucleotide polymorphism.
10. The method of any of clauses 1-9, wherein the sensor nucleotide is reverse complementary to the 3' UTR of the target RNA.
11. The method of any of clauses 1-10, wherein the marker protein is a fluorescent protein or a luminescent protein
12. The method of any of clauses 1-11, wherein the output protein is selected from a fluorescent protein, a genomic modification protein, a transcription factor, a killing factor, a toxin, an antigen, a T cell receptor, a therapeutic protein and an enzyme.
13. The method of any of clauses 1-12, wherein the detecting is quantitative or qualitative.
14. The method of any of clauses 1-13, wherein the biological sample is a cell.
15. The method of any of clauses 1-14, wherein the combining with the biological sample comprises contacting the biological sample with a lipid nanoparticle comprising the sensor RNA or an adeno-associated virus (AAV) comprising the sensor RNA wherein the sensor RNA in contained with a AAV vector.
16. The method of any of clauses 1-14, wherein the combining with the biological sample comprises transfecting the biological sample with a recombinant vector comprising the sensor RNA.
17. The method of clause 16, wherein the recombinant vector is selected from the group of a plasmid, a viral vector, a cosmid, and an artificial chromosome.
18. The method of any of clauses 1-17, wherein assaying for the presence of the output protein comprises using immunoblotting.
19. The method of any of clauses 1-17, wherein assaying for the presence of the output protein comprises using microscopy.
20. The method of any of clauses 1-17, wherein assaying for the presence of the output protein comprises using flow cytometry.
21. The method of any of clauses 1-20, wherein the sensor RNA comprises one or more MS2 hairpins.
22. The method of any of clauses 1-21, wherein the sensor nucleotide sequence is reverse complementary to two or more non-contiguous sequences within a single target RNA.
23. The method of any of clauses 1-22, wherein the sensor nucleotide sequence is reverse complementary to two or more distinct target RNAs.
24. The method of any of clauses 1-23, wherein the sensor RNA further comprises a nucleotide sequence encoding a second sensor nucleotide sequence that is reverse complementary to a second target RNA wherein the sequences of the first and second target RNAs are different.
25. The method of clause 24, wherein the second sensor nucleotide sequence comprises a second stop codon.
26. The method of clause 24, wherein the second sensor nucleotide sequence comprises a stem-loop sequence comprising one or more stop or start codons.
27. The method of any of clauses 1-26, further comprising combining the biological sample with an adenosine deaminase acting on RNA (ADAR) protein or coding sequence thereof.
28. The method of clause 27, wherein the ADAR protein is ADAR2, $ADAR^{p110}$ or $ADAR^{p150}$.
29. The method of clause 27, wherein the ADAR protein is a modified ADAR comprising an ADAR deaminase domain and a MS2 binding domain.
30. The method of any of clauses 1-29, wherein the biological sample is combined with two or more sensor RNAs that detect two or more target RNAs.
31. The method of any of clauses 1-20, wherein the sensor RNA comprises one or more pseudouridines.
32. The method of clause 31, wherein 75% or less of the uridines in the sensor RNA are pseudouridine.
33. The method of any of clauses 31-32, wherein the pseudouridine is N1-methyl-pseudouridine.
34. The method of any of clauses 1-33, wherein the stop codon is UGA.
35. The method of clause 34, wherein there is a guanosine following the adenosine in the UGA stop codon.
36. The method of any of clauses 31-35, wherein the pseudouridine is not adjacent to the adenosine in the stop codon of the sensor nucleotide sequence.
37. A method for detecting a target RNA in a biological sample, the method comprising:
   (a) combining the biological sample with a sensor RNA comprising the following:
      (i) a first nucleotide sequence comprising a sensor nucleotide sequence that is reverse complementary to the target RNA wherein the sensor nucleotide sequence comprises a stem-loop sequence comprising one or more stop codons,
      (ii) a second nucleotide sequence encoding a first cleavage domain, and
      (iii) a third nucleotide sequence encoding an output protein; and
   (b) assaying for the presence of the output protein in the biological sample.
38. The method of clause 37, further comprising:
   (i) a fourth nucleotide sequence comprising a second cleavage domain wherein the fourth nucleotide sequence precedes the first nucleotide sequence and
   (ii) a fifth nucleotide sequence comprising a nucleotide sequence encoding a marker protein wherein the fifth nucleotide sequence precedes the fourth nucleotide sequence.
39. The method of clauses 37-38, wherein the one or more stop codons comprises at least 1 base that is mismatched with a sequence within the stem loop opposite the one or more stop codons.
40. The method of any of clauses 37-39, wherein the cleavage domain is a 2A self-cleaving domain.
41. The method of clause 40, wherein the 2A self-cleaving domain is selected from the group of T2A, P2A, E2A and F2A.
42. The method of any of clauses 37-41, wherein the stem loop is a GluR-B stem loop or modified variant thereof.
43. The method of any of clauses 37-42, wherein the stem loop is 9 to 24 base pairs in length.
44. The method of any of clauses 37-43, wherein the sensor nucleotide sequence is 60 or more nucleotides in length.
45. The method of any of clauses 37-44, wherein the target RNA is encoded by a gene fusion, a splice variant or a gene variant comprising a single nucleotide polymorphism.
46. The method of any of clauses 37-45, wherein the sensor nucleotide is reverse complementary to the 3' UTR of the target RNA.

47. The method of any of clauses 37-46, wherein the marker protein is a fluorescent protein or a luminescent protein
48. The method of any of clauses 37-47, wherein the output protein is selected from a fluorescent protein, a genomic modification protein, a transcription factor, a killing factor, a toxin, an antigen, a T cell receptor, a therapeutic protein and an enzyme.
49. The method of any of clauses 37-48, wherein the detecting is quantitative or qualitative.
50. The method of any of clauses 37-49, wherein the biological sample is a cell.
51. The method of any of clauses 37-50, wherein the combining with the biological sample comprises contacting the biological sample with a lipid nanoparticle comprising the sensor RNA or an adeno-associated virus (AAV) comprising the sensor RNA wherein the sensor RNA in contained with a AAV vector.
52. The method of any of clauses 37-51, wherein the combining with the biological sample comprises transfecting the biological sample with a recombinant vector comprising the sensor RNA.
53. The method of clause 52, wherein the recombinant vector is selected from the group of a plasmid, a viral vector, a cosmid, and an artificial chromosome.
54. The method of any of clauses 37-53, wherein assaying for the presence of the output protein comprises using immunoblotting.
55. The method of any of clauses 37-54, wherein assaying for the presence of the output protein comprises using microscopy.
56. The method of any of clauses 37-55, wherein assaying for the presence of the output protein comprises using flow cytometry.
57. The method of any of clauses 37-56, wherein the sensor RNA comprises one or more MS2 hairpins.
58. The method of any of clauses 37-57, wherein the sensor nucleotide sequence is reverse complementary to two or more non-contiguous sequences within a single target RNA.
59. The method of any of clauses 37-58, wherein the sensor nucleotide sequence is reverse complementary to two or more distinct target RNAs.
60. The method of any of clauses 37-59, wherein the sensor RNA further comprises a nucleotide sequence encoding a second sensor nucleotide sequence that is reverse complementary to a second target RNA wherein the sequences of the first and second target RNAs are different.
61. The method of clause 60, wherein the second sensor nucleotide sequence comprises a second stop codon or a first start codon.
62. The method of clause 60, wherein the second sensor nucleotide sequence comprises a stem-loop sequence comprising one or more stop or start codons.
63. The method of any of clauses 37-62, further comprising combining the biological sample with an adenosine deaminase acting on RNA (ADAR) protein or coding sequence thereof.
64. The method of clause 63, wherein the ADAR protein is ADAR2 or $ADAR^{p150}$.
65. The method of clause 63, wherein the ADAR protein is a modified ADAR comprising an ADAR deaminase domain and a MS2 binding domain.
66. The method of any of clauses 37-65, wherein the biological sample is combined with two or more sensor RNAs that detect two or more target RNAs.
67. The method of any of clauses 37-66, wherein the sensor RNA comprises one or more pseudouridines.
68. The method of clause 67, wherein 75% or less of the uridines in the sensor RNA are pseudouridine.
69. The method of any of clauses 37-68, wherein the pseudouridine is N1-methyl-pseudouridine.
70. The method of any of clauses 37-69, wherein the stop codon is UGA.
71. The method of clause 70, wherein there is a guanosine following the adenosine in the UGA stop codon.
72. The method of any of clauses 67 to 71, wherein the pseudouridine is not adjacent to the adenosine in the stop codon of the sensor nucleotide sequence.
73. A method for detecting a target RNA in a biological sample, the method comprising:
    (a) combining the biological sample with a sensor RNA comprising the following:
        (i) a first nucleotide sequence comprising a sensor nucleotide sequence that is reverse complementary to the 3' UTR of the target RNA, wherein the sensor nucleotide sequence comprises one or more stop codons,
        (ii) a second nucleotide sequence encoding a first cleavage domain, and
        (iii) a third nucleotide sequence encoding an output protein; and
    (b) assaying for the presence of the output protein in the biological sample.
74. The method of clause 73, further comprising:
    (i) a fourth nucleotide sequence comprising a second cleavage domain wherein the fourth nucleotide sequence precedes the first nucleotide sequence and
    (ii) a fifth nucleotide sequence comprising a nucleotide sequence encoding a marker protein wherein the fifth nucleotide sequence precedes the fourth nucleotide sequence.
75. The method of any of clauses 73-74, wherein the one or more stop codons comprises at least 1 base that is mismatched with the 3' UTR of the target mRNA sequence.
76. The method of any of clauses 73-75, wherein the cleavage domain is a 2A self-cleaving domain.
77. The method of clause 76, wherein the 2A self-cleaving domain is selected from the group of T2A, P2A, E2A and F2A.
78. The method of any of clauses 73-77, further comprising fifth nucleotide sequence comprising a second cleavage domain, wherein the fifth nucleotide sequence precedes the second nucleotide sequence.
79. The method of any of clauses 73-78, wherein the sensor nucleotide sequence is 60 or more nucleotides in length.
80. The method of any of clauses 73-79, wherein the target RNA is encoded by a gene fusion, a splice variant or a gene variant comprising a single nucleotide polymorphism.
81. The method of any of clauses 73-80, wherein the marker protein is a fluorescent protein or a luminescent protein
82. The method of any of clauses 73-81, wherein the output protein is selected from a fluorescent protein, a genomic modification protein, a transcription factor, a killing factor, a toxin, an antigen, a T cell receptor, a therapeutic protein and an enzyme.
83. The method of any of clauses 73-82, wherein the detecting is quantitative or qualitative.

84. The method of any of clauses 73-83, wherein the biological sample is a cell.

85. The method of any of clauses 73-84, wherein the combining with the biological sample comprises contacting the biological sample with a lipid nanoparticle comprising the sensor RNA or an adeno-associated virus (AAV) comprising the sensor RNA wherein the sensor RNA in contained with a AAV vector.

86. The method of any of clauses 73-85, wherein the combining with the biological sample comprises transfecting the biological sample with a recombinant vector comprising the sensor RNA.

87. The method of clause 86, wherein the recombinant vector is selected from the group of a plasmid, a viral vector, a cosmid, and an artificial chromosome.

88. The method of any of clauses 73-87, wherein assaying for the presence of the output protein comprises using immunoblotting.

89. The method of any of clauses 73-88, wherein assaying for the presence of the output protein comprises using microscopy.

90. The method of any of clauses 73-89, wherein assaying for the presence of the output protein comprises using flow cytometry.

91. The method of any of clauses 73-90, wherein the sensor RNA comprises one or more MS2 hairpins.

92. The method of any of clauses 73-91, wherein the sensor nucleotide sequence is reverse complementary to two or more non-contiguous sequences within a single target RNA.

93. The method of any of clauses 73-92, wherein the sensor nucleotide sequence is reverse complementary to two or more distinct target RNAs.

94. The method of any of clauses 73-93, wherein the sensor RNA further comprises a nucleotide sequence encoding a second sensor nucleotide sequence that is reverse complementary to a second target RNA wherein the sequences of the first and second target RNAs are different.

95. The method of clause 94, wherein the second senor nucleotide sequence comprises a second stop codon or a first start codon.

96. The method of clause 94, wherein the second sensor nucleotide sequence comprises a stem-loop sequence comprising one or more stop or start codons.

97. The method of any of clauses 73-96, further comprising combining the biological sample with an adenosine deaminase acting on RNA (ADAR) protein or coding sequence thereof.

98. The method of clause 97, wherein the ADAR protein is ADAR2 or $ADAR^{p150}$.

99. The method of clause 98, wherein the ADAR protein is a modified ADAR comprising an ADAR deaminase domain and a MS2 binding domain.

100. The method of any of clauses 73-99, wherein the biological sample is combined with two or more sensor RNAs that detect two or more target RNAs.

101. The method of any of clauses 73-100, wherein the sensor RNA comprises one or more pseudouridines.

102. The method of clause 101, wherein 75% or less of the uridines in the sensor RNA are pseudouridine.

103. The method of any of clauses 101-102, wherein the pseudouridine is N1-methyl-pseudouridine.

104. The method of any of clauses 73-103, wherein the stop codon is UGA.

105. The method of clause 104, wherein there is a guanosine following the adenosine in the UGA stop codon.

106. The method of any of clauses 104-105, wherein the pseudouridine is not adjacent to the adenosine in the stop codon of the sensor nucleotide sequence.

107. A method for detecting a target RNA in a biological sample, the method comprising:

(a) combining the biological sample with a sensor RNA comprising the following:

(i) a first nucleotide sequence comprising a sensor nucleotide sequence that is reverse complementary to the target RNA, wherein the sensor nucleotide sequence comprises a start codon and (ii) a second nucleotide sequence encoding an output protein; and (b) assaying for the presence of the output protein in the biological sample.

108. The method of clause 107, wherein the sequence encoding the output protein comprises a start codon.

109. The method of any of clauses 107-108, wherein the start codon in the sensor sequence comprises at least 1 base that is mismatched with the target RNA sequence.

110. The method any of clauses 107-109, further comprising:

(i) a third nucleotide sequence comprising a first cleavage domain wherein the third nucleotide sequence is between the first and the second nucleotide sequence.

112. The method of any of clauses 107-110, wherein the sensor nucleotide sequence is 70 or more nucleotides in length.

113. The method of any of clauses 107-112, wherein the target RNA is encoded by a gene fusion, a splice variant or a gene variant comprising a single nucleotide polymorphism.

114. The method of any of clauses 107-113, wherein the output protein is selected from a fluorescent protein, a genomic modification protein, a transcription factor, a killing factor, a toxin, an antigen, a T cell receptor, a therapeutic protein and an enzyme.

115. The method of any of clauses 107-114, wherein the detecting is quantitative or qualitative.

116. The method of any of clauses 107-115, wherein the biological sample is a cell.

117. The method of any of clauses 107-116, wherein the combining with the biological sample comprises contacting the biological sample with a lipid nanoparticle comprising the sensor RNA or an adeno-associated virus (AAV) comprising the sensor RNA wherein the sensor RNA in contained with a AAV vector.

118. The method of any of clauses 107-117, wherein the combining with the biological sample comprises transfecting the biological sample with a recombinant vector comprising the sensor RNA.

119. The method of clause 118, wherein the recombinant vector is selected from the group of a plasmid, a viral vector, a cosmid, and an artificial chromosome.

120. The method of any of clauses 107-119, wherein assaying for the presence of the output protein comprises using immunoblotting.

121. The method of any of clauses 107-120, wherein assaying for the presence of the output protein comprises using microscopy.

122. The method of any of clauses 107-121, wherein assaying for the presence of the output protein comprises using flow cytometry.

123. The method of any of clauses 107-122, wherein the sensor RNA comprises one or more MS2 hairpins.
124. The method of any of clauses 107-123, wherein the sensor nucleotide sequence is reverse complementary to two or more non-contiguous sequences within a single target RNA.
125. The method of any of clauses 107-124, wherein the sensor nucleotide sequence is reverse complementary to two or more distinct target RNAs.
126. The method of any of clauses 107-125, wherein the sensor RNA further comprises a nucleotide sequence encoding a second sensor nucleotide sequence that is reverse complementary to a second target RNA wherein the sequences of the first and second target RNAs are different.
127. The method of clause 126, wherein the second sensor nucleotide sequence comprises a second stop codon or a first start codon.
128. The method of clause 126, wherein the second sensor nucleotide sequence comprises a stem-loop sequence comprising one or more stop or start codons.
129. The method of any of clauses 107-128, further comprising combining the biological sample with an adenosine deaminase acting on RNA (ADAR) protein or coding sequence thereof.
130. The method of clause 129, wherein the ADAR protein is ADAR2 or $ADAR^{p150}$.
131. The method of clause 130, wherein the ADAR protein is a modified ADAR comprising an ADAR deaminase domain and a MS2 binding domain.
132. The method of any of clauses 107-131, wherein the biological sample is combined with two or more sensor RNAs that detect two or more target RNAs.
133. A method for detecting a target RNA in a biological sample, the method comprising:
  (a) combining the biological sample with a sensor RNA comprising the following:
    (i) a first nucleotide sequence comprising a sensor nucleotide sequence that is reverse complementary to the target RNA, wherein the sensor nucleotide sequence comprises an AUA sequence and
    (ii) a second nucleotide sequence encoding an output protein; and
  (b) assaying for the presence of the output protein in the biological sample.
134. The method of clause 133, wherein the AUA sequence comprises at least 1 base that is mismatched with the target RNA sequence.
135. The method any of clauses 133-134, further comprising:
  (i) a third nucleotide sequence comprising a first cleavage domain wherein the third nucleotide sequence is between the first and the second nucleotide sequence.
137. The method of any of clauses 133-135, wherein the sensor nucleotide sequence is 70 or more nucleotides in length.
138. The method of any of clauses 133-137, wherein the target RNA is encoded by a gene fusion, a splice variant or a gene variant comprising a single nucleotide polymorphism.
139. The method of any of clauses 133-138, wherein the output protein is selected from a fluorescent protein, a genomic modification protein, a transcription factor, a killing factor, a toxin, an antigen, a T cell receptor, a therapeutic protein and an enzyme.
140. The method of any of clauses 133-139, wherein the detecting is quantitative or qualitative.
141. The method of any of clauses 133-140, wherein the biological sample is a cell.
142. The method of any of clauses 133-141, wherein the combining with the biological sample comprises contacting the biological sample with a lipid nanoparticle comprising the sensor RNA or an adeno-associated virus (AAV) comprising the sensor RNA wherein the sensor RNA in contained with a AAV vector.
143. The method of any of clauses 133-142, wherein the combining with the biological sample comprises transfecting the biological sample with a recombinant vector comprising the sensor RNA.
144. The method of clause 143, wherein the recombinant vector is selected from the group of a plasmid, a viral vector, a cosmid, and an artificial chromosome.
145. The method of any of clauses 133-144, wherein assaying for the presence of the output protein comprises using immunoblotting.
146. The method of any of clauses 133-145, wherein assaying for the presence of the output protein comprises using microscopy.
147. The method of any of clauses 133-146, wherein assaying for the presence of the output protein comprises using flow cytometry.
148. The method of any of clauses 133-147, wherein the sensor RNA comprises one or more MS2 hairpins.
149. The method of any of clauses 133-148, wherein the sensor nucleotide sequence is reverse complementary to two or more non-contiguous sequences within a single target RNA.
150. The method of any of clauses 133-149, wherein the sensor nucleotide sequence is reverse complementary to two or more distinct target RNAs.
151. The method of any of clauses 133-150, wherein the sensor RNA further comprises a nucleotide sequence encoding a second sensor nucleotide sequence that is reverse complementary to a second target RNA the sequences of the first and second target RNAs are different.
152. The method of clause 151, wherein the second senor nucleotide sequence comprises a stop codon or a start codon.
153. The method of clause 151, wherein the second sensor nucleotide sequence comprises a stem-loop sequence comprising one or more stop or start codons.
154. The method of any of clauses 133-153, further comprising combining the biological sample with an adenosine deaminase acting on RNA (ADAR) protein or coding sequence thereof.
155. The method of clause 154, wherein the ADAR protein is ADAR2 or $ADAR^{p150}$.
156. The method of clause 155, wherein the ADAR protein is a modified ADAR comprising an ADAR deaminase domain and a MS2 binding domain.
157. The method of any of clauses 133-156, wherein the biological sample is combined with two or more sensor RNAs that detect two or more target RNAs.
158. A method of expressing a protein in a target cell, the method comprising combining a cell with the sensor RNA of any of the preceding clauses, wherein the target RNA is present in the target cell.
159. The method of clause 158, further comprising combining the cell with an ADAR protein or a coding sequence thereof.

160. The method of clauses 158 or 159, wherein the ADAR protein is $ADAR^{p150}$.
161. The method of clause 158, wherein the ADAR protein is a modified ADAR protein comprising an ADAR deaminase domain and a MS2 binding domain.
162. The method of any of clauses 158-161, wherein the combining with the cell comprises contacting the cell with a lipid nanoparticle comprising the sensor RNA or an adeno-associated virus (AAV) comprising the sensor RNA wherein the sensor RNA in contained with a AAV vector.
163. The method of any of clauses 158-162, wherein the combining with the cell comprises transfecting the cell with a recombinant vector comprising the sensor RNA.
164. The method of any of clauses 158-163, wherein the target RNA is associated with a disease or condition.
165. The method of any of clauses 158-164, wherein the output protein treats the disease or condition.
166. The method of any of clauses 158-165, wherein the target RNA is encoded by a gene fusion, a splice variant or a gene variant comprising a single nucleotide polymorphism.
167. The method of clause 166, wherein the recombinant vector is selected from the group of a plasmid, a viral vector, a cosmid and an artificial chromosome.
168. A recombinant vector comprising the sensor RNA of any of the preceding clauses.
169. The recombinant vector of clause 168, wherein the recombinant vector is selected from the group of a plasmid, a viral vector, a cosmid and an artificial chromosome.
170. A kit, the kit comprising the sensor RNA of any of the preceding clauses.
171. The kit of clause 170, further comprising an ADAR protein or a coding sequence thereof.
172. The kit of clause 171, wherein the ADAR protein is $ADAR^{p150}$.
173. The kit of clause 171, wherein the ADAR protein is a modified ADAR protein comprising an ADAR deaminase domain and a MS2 binding domain.
174. The kit of any of clauses 170-173, further comprising a biological sample with the target RNA and a biological sample without the target RNA.
175. The method of any of clauses 1-36, wherein combining comprises administering to a patient.
176. The method of any of clauses 37-72, wherein combining comprises administering the sensor RNA to a patient.
177. The method of any of clauses 73-107, wherein combining comprises administering the sensor RNA to a patient.
178. The method of any of clauses 107-132, wherein combining comprises administering the sensor RNA to a patient.
179. The method of any of clauses 133-167, wherein combining comprises administering the sensor RNA to a patient.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112(f) or 35 U.S.C. § 112(6) is not invoked.

What is claimed is:

1. A single-stranded ribonucleic acid (ssRNA) sensor, comprising:
   (a) a first region comprising: (i) a nucleotide sequence configured to hybridize to a target ribonucleic acid (RNA); and (ii) a stem-loop sequence comprising one or more editable codons; and
   (b) a second region comprising a sequence encoding a protein.

2. The ssRNA sensor of claim 1, wherein said one or more editable codons comprises a stop codon.

3. The ssRNA sensor of claim 2, wherein said stop codon further comprises 5'-UGA-3', 5'-UAA-3', or 5'-UAG-3'.

4. A composition comprising the ssRNA sensor of claim 1 and a cell comprising said target RNA.

5. The ssRNA sensor of claim 1, wherein said one or more editable codons comprises a start codon.

6. The ssRNA sensor of claim 5, wherein said stem-loop sequence further comprises a Kozak sequence operably linked to said start codon.

7. The ssRNA sensor of claim 1, wherein said one or more editable codons comprises a non-stop, non-start codon that is editable to become a start codon.

8. The ssRNA sensor of claim 7, wherein said stem-loop sequence further comprises a Kozak sequence operably linked to said non-stop, non-start codon.

9. The ssRNA sensor of claim 7, wherein said non-stop, non-start codon comprises 5'-AUA-3'.

10. The ssRNA sensor of claim 1, wherein said nucleotide sequence is configured to hybridize to said target RNA in an untranslated region (UTR) of said target RNA.

11. The ssRNA sensor of claim 1, wherein said protein comprises a toxin, a killing factor, a T-cell receptor, a chimeric antigen receptor, or any combination thereof.

12. The ssRNA sensor of claim 1, wherein said protein comprises a fluorescent protein, a genomic modification protein, a transcription factor, an antigen, a therapeutic protein, an enzyme, or any combination thereof.

13. The ssRNA sensor of claim 1, wherein said target RNA is a messenger RNA (mRNA), a long non-coding RNA (lncRNA), a transfer RNA (tRNA), a ribosomal RNA (rRNA), a microRNA (miRNA), or a small nucleolar RNA (snoRNA).

14. The ssRNA sensor of claim 1, wherein said nucleotide sequence configured to hybridize to said target RNA in (a) (i) and said stem-loop sequence comprising one or more editable codons in (a) (ii) are non-overlapping.

15. The ssRNA sensor of claim 1, wherein said one or more editable codons is in a stem sequence of said stem-loop sequence.

16. The ssRNA sensor of claim 1, wherein said one or more editable codons comprises at least one base that is mismatched with a sequence within said stem-loop sequence opposite said one or more editable codons.

17. The ssRNA sensor of claim 1, wherein said sequence encoding said protein is in frame with said one or more editable codons.

18. The ssRNA sensor of claim 1, wherein said nucleotide sequence configured to hybridize to said target RNA in (a) (i) comprises at least 60% complementarity to said target RNA.

19. The ssRNA sensor of claim 1, wherein a stem of said stem-loop sequence is at least 12 base pairs in length.

20. The ssRNA sensor of claim 1, wherein said target RNA comprises an encoded gene fusion.

21. The ssRNA sensor of claim 1, wherein said nucleotide sequence that is configured to hybridize to said target RNA in (a) (i) is configured to hybridize to two or more non-contiguous sequences within said target RNA.

22. A method, comprising:

(a) combining a target cell with a sensor ribonucleic acid (RNA) comprising:
  (A) a first region comprising: (i) a nucleotide sequence configured to hybridize to a target RNA of said target cell; and (ii) a stem-loop sequence comprising one or more editable codons; and
  (B) a second region comprising a sequence encoding a protein; and
(b) subjecting said sensor RNA to conditions sufficient: (i) for said first region of said sensor RNA to hybridize to said target RNA; and (ii) for editing of said one or more editable codons to occur.

23. The method of claim 22, further comprising, in (b), subjecting said sensor RNA to conditions sufficient for editing said one or more editable codons to occur, such that editing of said one or more editable codons impairs expression of said second region of said sensor RNA.

24. The method of claim 22, further comprising, in (b), subjecting said sensor RNA to conditions sufficient for editing said one or more editable codons to occur, such that editing of said one or more editable codons promotes expression of said second region of said sensor RNA.

25. The method of claim 22, wherein said combining said target cell with said sensor RNA comprises combining said target cell with a lipid nanoparticle comprising said sensor RNA.

26. The method of claim 22, further comprising, prior to (a), subjecting an adeno-associated viral vector (AAV) encoding said sensor RNA to conditions sufficient to transcribe said sensor RNA from said AAV encoding said sensor RNA.

27. The method of claim 22, further comprising, in (b), subjecting said sensor RNA to conditions sufficient for editing said one or more editable codons with an adenosine deaminase acting on RNA (ADAR) protein to occur.

28. The method of claim 22, wherein said combining said target cell with said sensor RNA comprises administering said sensor RNA to a patient.

* * * * *

SEQUENCE LISTING

```
Sequence total quantity: 13
SEQ ID NO: 1            moltype = RNA  length = 63
FEATURE                 Location/Qualifiers
source                  1..63
                        mol_type = other RNA
                        organism = synthetic construct
SEQUENCE: 1
caaggtcaat gaggagatgt acatagaaat acaatcctgt gtacatcttc tagcatgacc  60
cac                                                                63

SEQ ID NO: 2            moltype = RNA  length = 57
FEATURE                 Location/Qualifiers
source                  1..57
                        mol_type = other RNA
                        organism = synthetic construct
SEQUENCE: 2
caaggtcaat gaggagatgt acataataca atgtgtacat cttctagcat gacccac     57

SEQ ID NO: 3            moltype = RNA  length = 89
FEATURE                 Location/Qualifiers
source                  1..89
                        mol_type = other RNA
                        organism = synthetic construct
SEQUENCE: 3
cccaacctct gtctatcacc acagcccccc agcatcactg tgaatgctgc catggatgct  60
agagggctac aggaagagcc agaagttgg                                    89

SEQ ID NO: 4            moltype = RNA  length = 60
FEATURE                 Location/Qualifiers
source                  1..60
                        mol_type = other RNA
                        organism = synthetic construct
SEQUENCE: 4
ctcaccacag ccccccagca tcactgtgaa tgctgccatg gatgctagag ggctacagga  60

SEQ ID NO: 5            moltype = RNA  length = 51
FEATURE                 Location/Qualifiers
source                  1..51
                        mol_type = other RNA
                        organism = synthetic construct
SEQUENCE: 5
aagtggcata tgcgacggcc atggactggt tcatagccgt ctgttatgcc t           51

SEQ ID NO: 6            moltype = RNA  length = 45
FEATURE                 Location/Qualifiers
source                  1..45
```

-continued

```
                      mol_type = other RNA
                      organism = synthetic construct
SEQUENCE: 6
tggcatatgc gacggccatg gactggttca tagccgtctg ttatg                 45

SEQ ID NO: 7          moltype = RNA  length = 48
FEATURE               Location/Qualifiers
source                1..48
                      mol_type = other RNA
                      organism = synthetic construct
SEQUENCE: 7
cattaaggtg ggtggaatag tatacaaagt atcccaccta ccctgatg              48

SEQ ID NO: 8          moltype = RNA  length = 47
FEATURE               Location/Qualifiers
source                1..47
                      mol_type = other RNA
                      organism = synthetic construct
SEQUENCE: 8
cattaaggtg ggtggaatag tatacaaata tcccacctac cccgatg               47

SEQ ID NO: 9          moltype = RNA  length = 51
FEATURE               Location/Qualifiers
source                1..51
                      mol_type = other RNA
                      organism = synthetic construct
SEQUENCE: 9
tccgtttagg tgggtggaat agtaatacaa agtatcccac ctacccagac g          51

SEQ ID NO: 10         moltype = DNA  length = 20
FEATURE               Location/Qualifiers
source                1..20
                      mol_type = other DNA
                      organism = synthetic construct
SEQUENCE: 10
aagcagaaga acggcatcaa                                             20

SEQ ID NO: 11         moltype = DNA  length = 20
FEATURE               Location/Qualifiers
source                1..20
                      mol_type = other DNA
                      organism = synthetic construct
SEQUENCE: 11
tccagcagga ccatgtgatc                                             20

SEQ ID NO: 12         moltype = DNA  length = 18
FEATURE               Location/Qualifiers
source                1..18
                      mol_type = other DNA
                      organism = synthetic construct
SEQUENCE: 12
cgtccaccgc aaatgctt                                               18

SEQ ID NO: 13         moltype = DNA  length = 25
FEATURE               Location/Qualifiers
source                1..25
                      mol_type = other DNA
                      organism = synthetic construct
SEQUENCE: 13
gttttctgcg caagttaggt tttgt                                       25
```